United States Patent
Toettcher et al.

(10) Patent No.: US 11,746,131 B2
(45) Date of Patent: Sep. 5, 2023

(54) LIGHT-RESPONSIVE FUSION PROTEINS FOR CONTROLLING BINDING TO TARGETS

(71) Applicant: The Trustees of Princeton University, Princeton, NJ (US)

(72) Inventors: Jared Toettcher, Princeton, NJ (US); Jose Avalos, Princeton, NJ (US); Maxwell Wilson, Princeton, NJ (US); Alexander Goglia, Hopewell, NJ (US); Evan M. Zhao, Clarence Center, NY (US); Agnieszka Gil, Bound Brook, NJ (US); Cesar Carrasco-Lopez, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 316 days.

(21) Appl. No.: 16/889,690

(22) Filed: Jun. 1, 2020

(65) Prior Publication Data
US 2020/0291075 A1    Sep. 17, 2020

Related U.S. Application Data

(63) Continuation-in-part of application No. PCT/US2018/063447, filed on Nov. 30, 2018.

(60) Provisional application No. 62/593,750, filed on Dec. 1, 2017, provisional application No. 62/962,517, filed on Jan. 17, 2020.

(51) Int. Cl.
*C07K 14/415*    (2006.01)
*C07K 19/00*    (2006.01)
*C07K 1/16*    (2006.01)
*C07K 1/36*    (2006.01)

(52) U.S. Cl.
CPC .............. *C07K 14/415* (2013.01); *C07K 1/16* (2013.01); *C07K 1/36* (2013.01); *C07K 19/00* (2013.01); *C07K 2319/80* (2013.01)

(58) Field of Classification Search
CPC ... C07K 14/415; C07K 19/00; C07K 2319/00
See application file for complete search history.

(56) References Cited

U.S. PATENT DOCUMENTS 9,115,184 B2 * 8/2015 Bonger ............... C07K 14/001
9,163,094 B2 * 10/2015 Schmidt .............. C07K 14/415

FOREIGN PATENT DOCUMENTS

WO    WO 2011/002977 A2    1/2011
WO    WO 2019/109017 A1    6/2019

OTHER PUBLICATIONS

Aihara, Y. et al., "Mutations in N-terminal flanking region of blue light-sensing light-oxygen and voltage 2 (LOV2) domain disrupt its repressive activity on kinase domain in the Chlamydomonas phototropin," The Journal of biological chemistry, vol. 287; No. 13; 9901-9909 (2012).
Bothma, J. P. et al., "LlamaTags: A Versatile Tool to Image Transcription Factor Dynamics in Live Embryos," Cell, vol. 173; No. 7; 1810-1822 (2018).
Boyden, E. S. et al., "Millisecond-timescale, genetically targeted optical control of neural activity," Nat Neurosci, vol. 8; No. 9; 1263-1268 (2005).
Carrasco-Lopez, C. et al., "Light-responsive monobodies for dynamic control of customizable protein binding." bioRxiv; 36 pages (2019).
Carrasco-Lopez, C. et al., "Development of light-responsive protein binding in the monobody non-immunoglobulin scaffold," Nature Communications, vol. 11; No. 4045; 13 pages (2020).
Dagliyan, O. et al., "Engineering extrinsic disorder to control protein activity in living cells," Science, vol. 354; No. 6318; 1441-1444 (2016).
Dagliyan, O. et al., "Rational design of a ligand-controlled protein conformational switch," PNAS, vol. 110; No. 17; 6800-6804 (2013).
De Meyer, T., Muyldermans, S. & Depicker, A. Nanobody-based products as research and diagnostic tools. Trends Biotechnol 32, 263-270, doi:10.1016/j.tibtech.2014.03.001 (2014).
Dine, E. et al., "Protein phase separation provides long-term memory of transient spatial stimuli," Cell Syst., vol. 6; No. 6; 655-663 (2018).
Fridy, P. C. et al., "A robust pipeline for rapid production of versatile nanobody repertoires," Nature methods, vol. 11; No. 12; 1253-1260 (2014).
Gil, A.A. et al., "Femtosecond to Millisecond Dynamics of Light Induced Allostery in the Avena Sativa Lov Domain," J. Phys. Chem. B., vol. 121; No. 5; 1010-1019 (2017).
Gil, A.A. et al., "Optogenetic Control of Protein Binding Using Light-Switchable Nanobodies," BioRxiv, 29 pages (2019).
Gil, A.A. et al., "Optogenetic Control of Protein Binding Using Light-Switchable Nanobodies," Nature Communications, 12 pages (2020).
Grusch, M. et al., "Spatio-temporally precise activation of engineered receptor tyrosine kinases by light," The EMBO journal, vol. 33; 1713-1726 (2014).
Guntas. G. et al., "Engineering an improved light-induced dimer (iLID) for controlling the localization and activity of signaling proteins," PNAS, vol. 112; No. 1; 112-117 (2015).
Gureasko, J. et al., "Membrane-dependent signal integration by the Ras activator Son of sevenless," Nature structural & molecular biology, vol. 15; No. 5; 452-461 (2008).

(Continued)

*Primary Examiner* — Jeffrey E. Russel
(74) *Attorney, Agent, or Firm* — Hamilton, Brook, Smith & Reynolds, P.C.

(57) ABSTRACT

Provided herein is an isolated fusion protein comprising a light-responsive domain and a heterologous peptide component. Exposure of the fusion protein to light induces a conformational change in the fusion protein that alters an activity of the fusion protein and the activity is a binding activity selected from an in vitro binding activity, an in vivo extracellular binding activity and an in vivo intracellular binding activity. Also provided are methods of using and identifying the fusion proteins.

20 Claims, 61 Drawing Sheets
(3 of 61 Drawing Sheet(s) Filed in Color)

Specification includes a Sequence Listing.

(56) References Cited

OTHER PUBLICATIONS

Kennedy, M. J. et al., "Rapid blue-light induction of protein interactions in living cells," Nature methods, vol. 7; No. 12; 973-975 (2010).

Levskaya, A. et al., "Spatiotemporal control of cell signalling using a light-switchable protein interaction," Nature, vol. 461; No. 7266; 997-1001 (2009).

Lungu, O. I. et al., "Designing photoswitchable peptides using the AsLOV2 domain," Chemistry & biology, vol. 19; No. 4; 507-517 (2012).

Motta-Mena, L. B. et al., "An optogenetic gene expression system with rapid activation and deactivation kinetics," Nat Chem Biol, vol. 10; No. 3; 196-202 (2014).

Muyldermans, S., "Nanobodies: natural single-domain antibodies," Annual review of biochemistry, vol. 82; 17.1-17.23 (2013).

Niopek, D. et al., "Engineering light-inducible nuclear localization signals for precise spatiotemporal control of protein dynamics in living cells," Nature communications, vol. 5; 4404; 11 pages (2014).

Niopek, D et al., "Optogenetic control of nuclear protein export," Nature communications, vol. 7; 10624; 9 pages (2016).

Pleiner, T., Bates, M. & Gorlich, D., "A toolbox of anti-mouse and anti-rabbit IgG secondary nanobodies," The Journal of cell biology, vol. 217; No. 3; 1143-1154 (2018).

Regot, S. et al., "High-sensitivity measurements of multiple kinase activities in live single cells," Cell. vol. 157; No. 7; 1724-1734 (2014).

Reis, J. M. et al., "Discovering Selective Binders for Photoswitchable Proteins Using Phage Display," ACS synthetic biology 7, 2355-2364, doi:10.1021/acssynbio.8b00123 (2018).

Renicke, C et al., "A LOV2 domain-based optogenetic tool to control protein degradation and cellular function," Chemistry & biology, vol. 20; 619-626 (2013).

Roovers, R. C. et al., "Efficient inhibition of EGFR signaling and of tumour growth by antagonistic anti-EFGR Nanobodies," Cancer Immunol Immunother, vol. 56; 303-317 (2007).

Rothbauer, U. et al., "Targeting and tracing antigens in live cells with fluorescent nanobodies," Nature methods, vol. 3; No. 11; 887-889 (2006).

Roybal, K. T. et al., "Engineering T Cells with Customized Therapeutic Response Programs Using Synthetic Notch Receptors," Cell, vol. 167; No. 2; 419-432 (2016).

Salomon, M. et al., "Photochemical and mutational analysis of the FMN-binding domains of the plant blue light receptor, phototropin," Biochemistry, vol. 39; 9401-9410 (2000).

Schuck, P. and Zhao, H., "The role of mass transport limitation and surface heterogeneity in the biophysical characterization of macromolecular binding processes by SPR biosensing," Methods in molecular biology, vol. 627; 15-54 (2010).

Shimizu-Sato, S. et al., "A light-switchable gene promoter system." Nature biotechnology, vol. 20; 1041-1044 (2002).

Shin, Y. et al. Spatiotemporal Control of Intracellular Phase Transitions Using Light-Activated optoDroplets. Cell, vol. 168; No. 1-2; 159-171 (2017).

Song, S. et al., "Modulating LOV Domain Photodynamics with a Residue Alteration Outside the Chromophore Binding Site," Biochemistry, vol. 50; No. 13; 2411-2423 (2011).

Strickland, D. et al., "Rationally Improving LOV Domain-Based Photoswitches." Nat. Methods, vol. 7; No. 8; 623-626 (2010).

Strickland, D. et al., "TULIPs: tunable, light-controlled interacting protein tags for cell biology," Nature methods, vol. 9; No. 4; 379-384 (2012).

Tischer, D. K. & Weiner, O. D., "Light-based tuning of ligand half-life supports kinetic proofreading model of T cell signaling," eLife, vol. 8; 25 pages (2019).

Toettcher, J.E. et al., "Light-based feedback for controlling intracellular signaling dynamics," Nature Methods, vol. 8; No. 10; 837-839 (2011).

Toettcher, J.E. et al., "Using Optogenetics to Interrogate the Dynamic Control of Signal Transmission by the Ras/Erk Module," Cell. vol. 155; No. 6; 1422-1434 (2013).

Wang, H. et al., "LOVTRAP: an optogenetic system for photoinduced protein dissociation," Nature methods, vol. 13; No. 9; 755-758 (2016).

Yumerefendi, H. et al., "Control of Protein Activity and Cell Fate Specification via Light-Mediated Nuclear Translocation," PloS one, vol. 10; No. 6; e0128443; 19 pages (2015).

Yumerefendi, H. et al., "Light-induced nuclear export reveals rapid dynamics of epigenetic modifications," Nat Chem Biol, vol. 12; No. 6; 399-401 (2016). (2016).

Zhao, E.M. et al., "Light-based control of metabolic flux through assembly of synthetic organelles," Nat. Chem. Biol., vol. 15; No. 6; 589-597 (2019).

Zhao, E.M. et al., "Optogenetic regulation of engineered cellular metabolism for microbial chemical production," Nature, vol. 555; No. 7698; 683-687 (2018).

Zhou. X. X. et al., "Optical control of cell signaling by single-chain photoswitchable kinases," Science, vol. 355; No. 6327; 836-842 (2017).

Zoltowski, B.D. et al., "Mechanism Based Tuning of a LOV Domain Photoreceptor," Nat Chem Biol, vol. 5; No. 11; 827-834 (2009).

Notification Concerning Transmittal of International Preliminary Report on Patentability for International Application No. PCT/US2018/063447, entitled: "Light-Responsive Fusion Proteins For Controlling Binding To Targets," dated Jun. 11, 2020.

Notification of Transmittal of The International Search Report and The Written Opinion for International Application No. PCT/US2018/063447, entitled: "Light-Responsive Fusion Proteins For Controlling Binding To Targets?" dated May 6, 2019.

Bubeck, F. et al., "Engineered anti-CRISPR proteins for optogenetic control of CRISPR-Cas9," Nature Methods, vol. 15; 924-927 (2018).

Chen, X. et al., "Spatiotemporal Control of Gene Expression in Mammalian Cells and in Mice Using the LightOn System," Curr. Protoc. Chem. Biol., vol. 5; 111-129 (2013).

Harper, S.M. et al., "Disruption of the LOV-Jα Helix Interaction Activates Phototropin Kinase Activity," Biochemistry, vol. 43; 16184-16192 (2004).

* cited by examiner

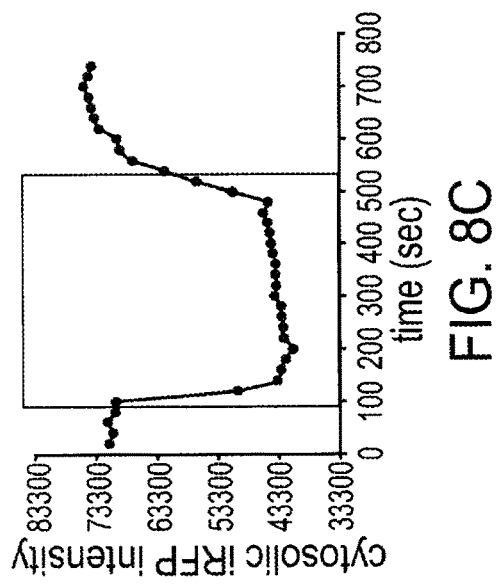
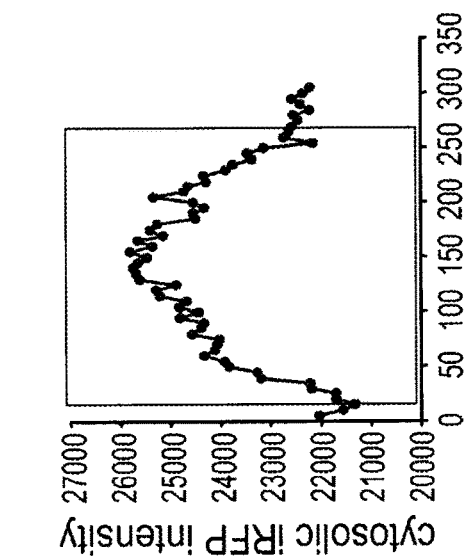
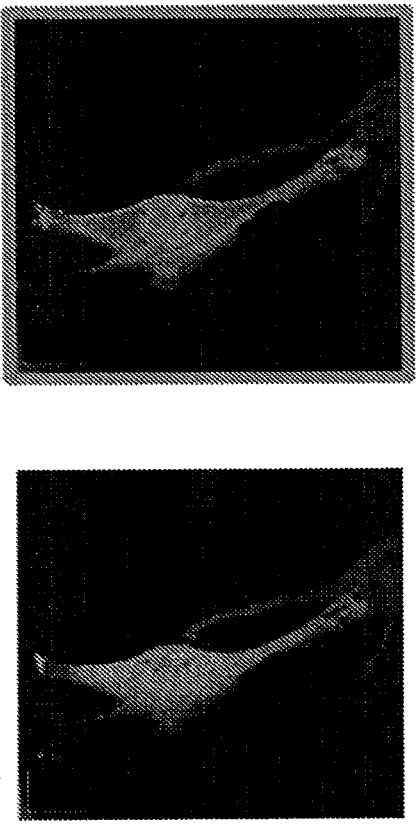
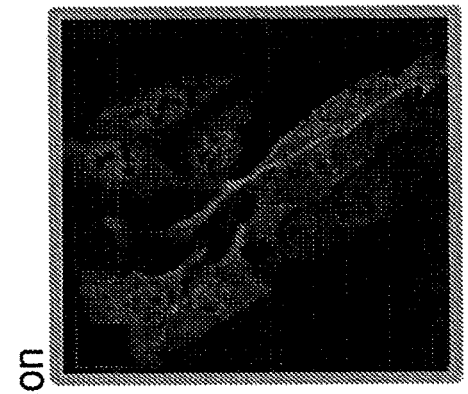
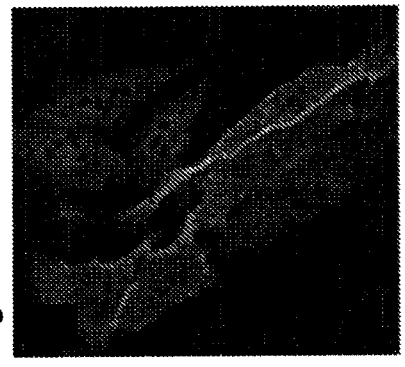

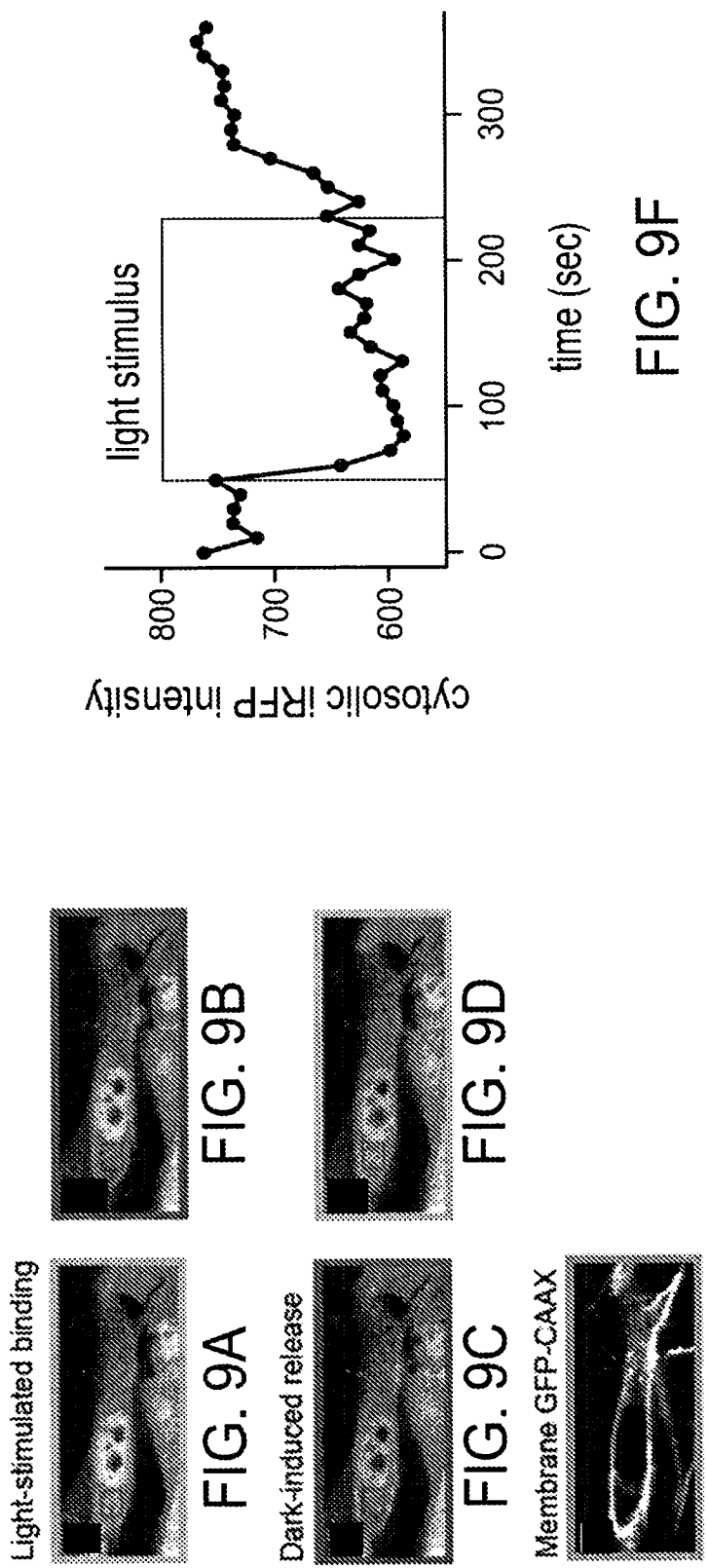

Light Induced Dissociation

FIG. 11A Light Induced Binding

FIG. 11D Light Induced Dissociation

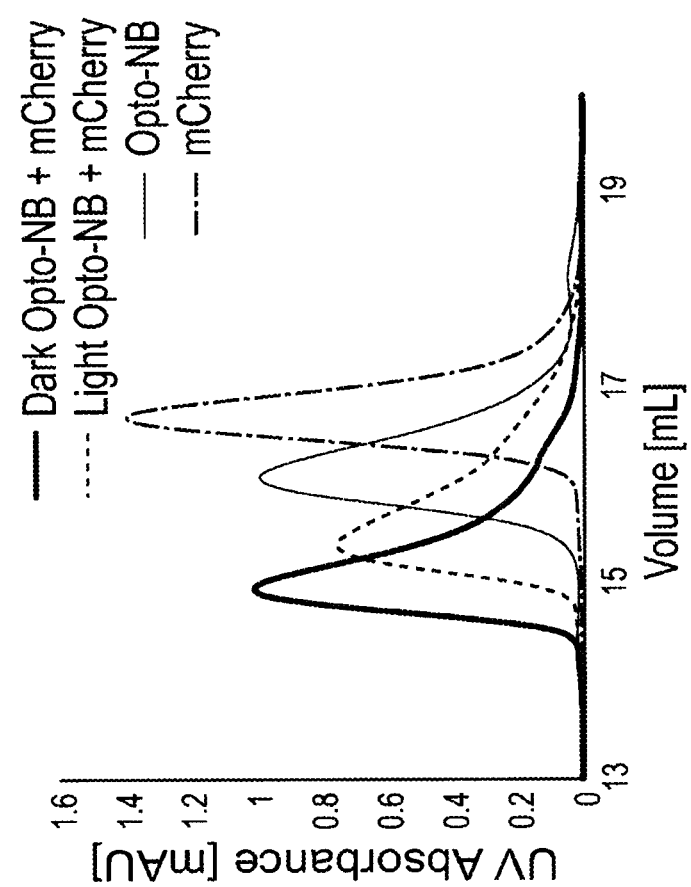
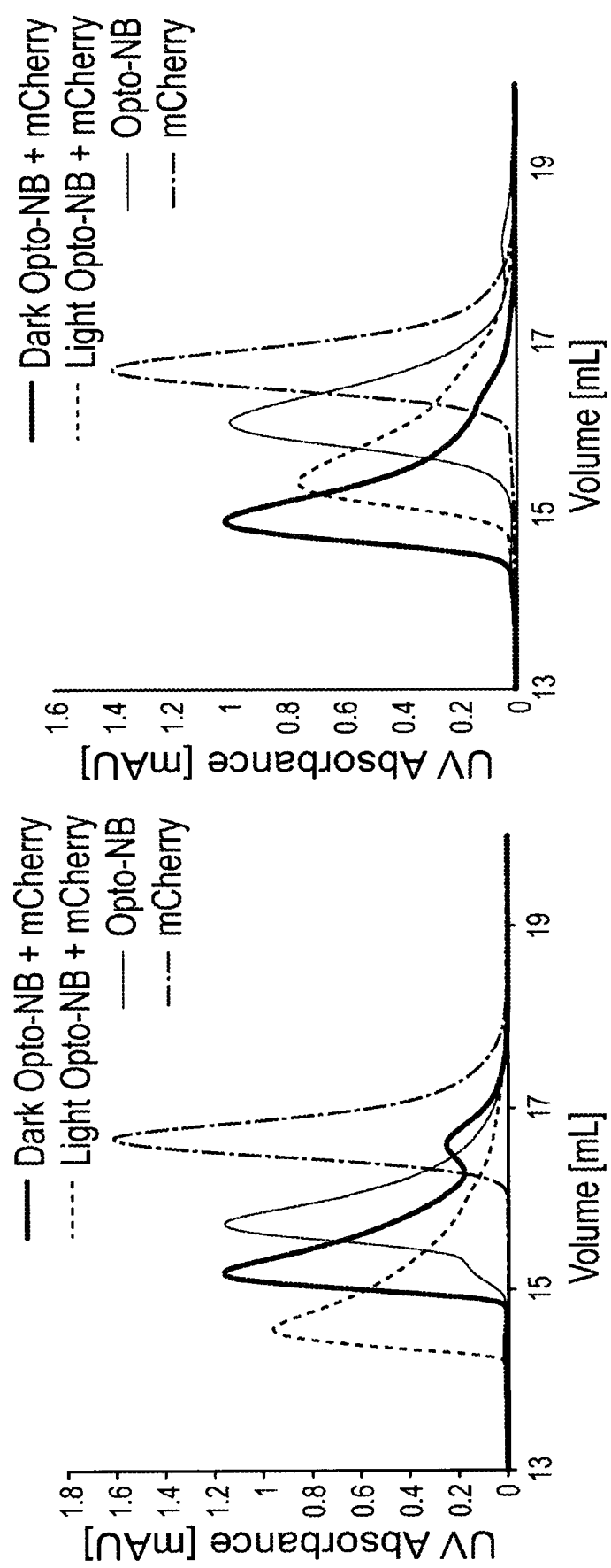
FIG. 13A
FIG. 13B

Light Induced Binding

Light Induced Dissociation

FIG. 20A     FIG. 20B     FIG. 20C
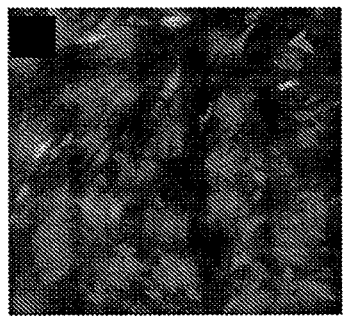 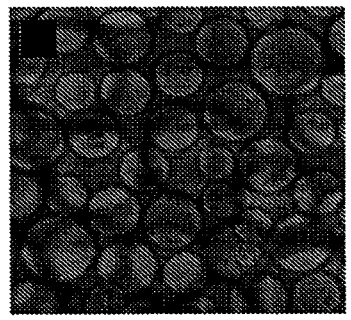 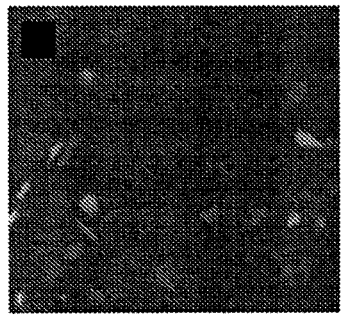
 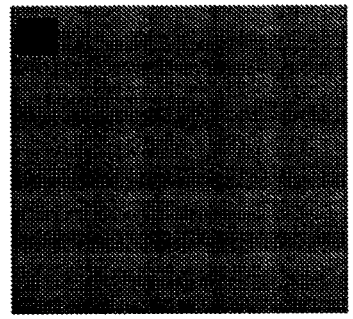
Cells containing:
Gal4_UAS_tBFP_PGK_iRFP
+
NB_synNotch_Gal4VP64
+/ mCherry Beads    incubate→ check tBFP expression
FIG. 20D     FIG. 20E     FIG. 20F

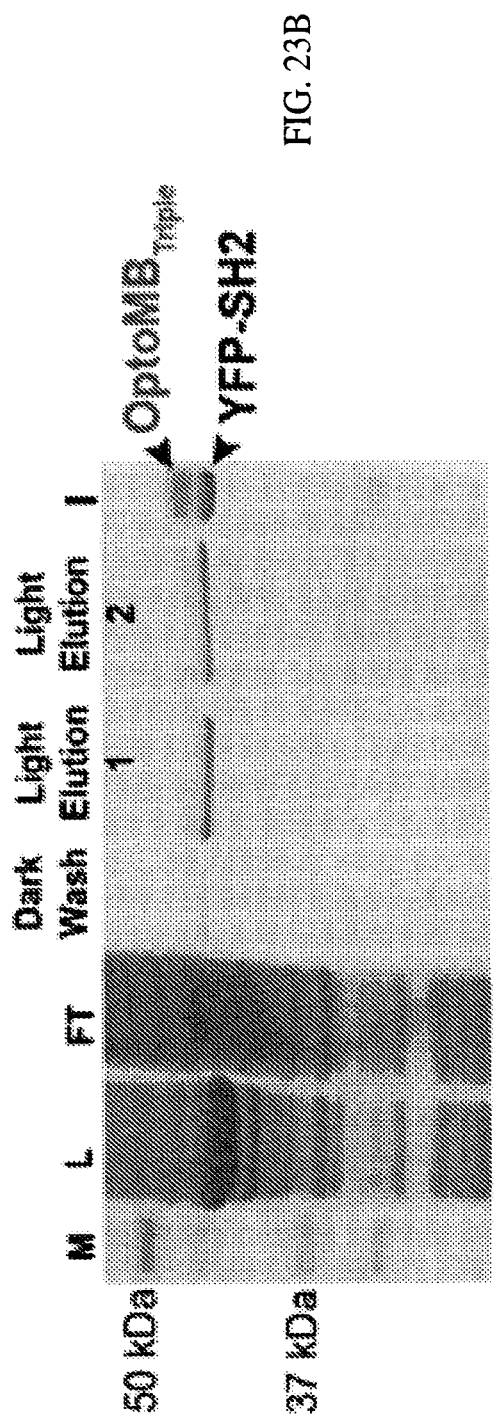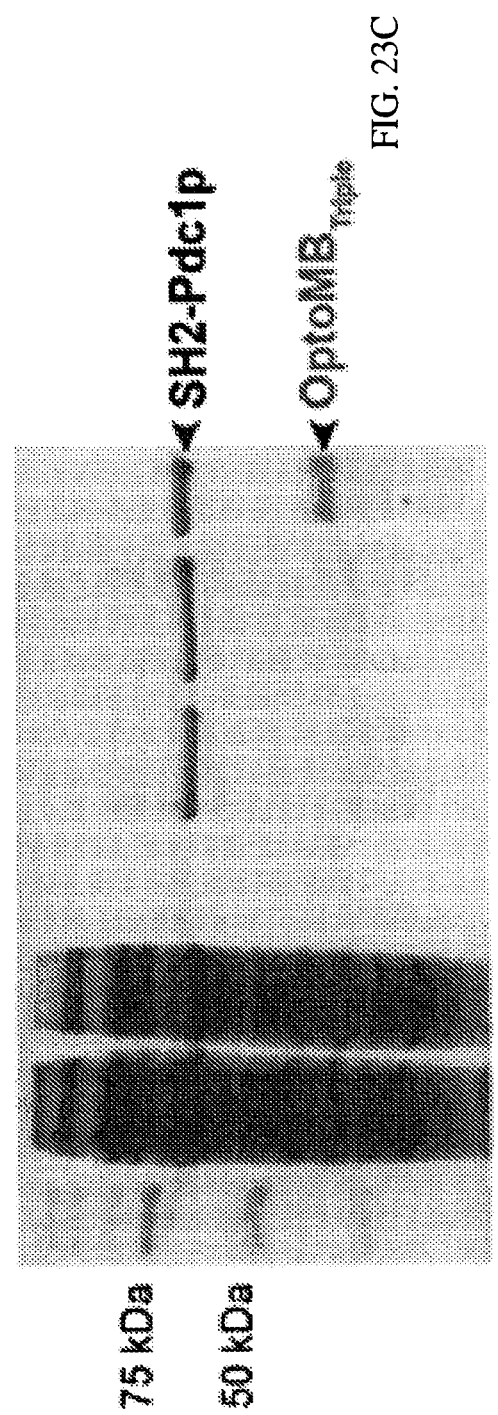

SEQUENCE LISTING

<160> NUMBER OF SEQ ID NOS: 50

<210> SEQ ID NO 1
<211> LENGTH: 923
<212> TYPE: PRT
<213> ORGANISM: Avena sativa

<400> SEQUENCE: 1

```
Met Ala Ser Lys Gly Ala Gly Gly Gly Gly His Glu Glu Pro
1               5                   10                  15

Gln Arg Pro Lys Gln Gln Leu Pro Arg Asp Ser Arg Gly Ser Leu Glu
                20                  25                  30

Val Phe Asn Pro Ser Ser Ser Ser Ala Ala Val Glu Pro Pro Ser Ala
            35                  40                  45

Phe Arg Pro Ala Ala Arg Ser Ala Ser Pro Phe Ile Glu Glu Ala Thr
    50                  55                  60

Gly Gly Ile Glu Asp Val Gly Lys Ala Thr Gln Arg Ala Ala Glu Trp
65                  70                  75                  80

Gly Leu Val Leu Gln Thr Asn Glu Gln Thr Gly Arg Pro Gln Gly Val
                85                  90                  95

Ser Ala Arg Ser Ser Gly Gly Gly Ser Ala Arg Ser Ser Ser Asp
                100                 105                 110

Asp Lys Ala Val Ala Gly Ala Ile Pro Arg Val Ser Glu Glu Leu Arg
        115                 120                 125

Ala Ala Leu Ser Ala Phe Gln Gln Thr Phe Val Val Ser Asp Ala Ser
    130                 135                 140

Arg Pro Gly His Pro Ile Met Tyr Ala Ser Ala Gly Phe Phe Asn Met
145                 150                 155                 160

Thr Gly Tyr Thr Ser Lys Glu Val Val Gly Arg Asn Cys Arg Phe Leu
                165                 170                 175

Gln Gly Ser Gly Thr Asp Pro Ala Glu Ile Ala Lys Ile Arg Gln Ala
            180                 185                 190

Leu Ala Asn Gly Ser Asn Tyr Cys Gly Arg Val Leu Asn Tyr Lys Lys
        195                 200                 205
```

```
Asp Gly Thr Ala Phe Trp Asn Leu Leu Thr Ile Ala Pro Ile Lys Asp
    210                 215                 220
Glu Glu Gly Arg Val Leu Lys Phe Ile Gly Met Gln Val Glu Val Ser
225                 230                 235                 240
Lys Tyr Thr Glu Gly Asn Lys Asp Thr Val Val Arg Pro Asn Gly Leu
                245                 250                 255
Pro Glu Ser Leu Ile Lys Tyr Asp Ala Arg Gln Lys Asp Gln Ala Arg
            260                 265                 270
Ser Ser Val Ser Glu Leu Leu Ala Ile Lys Asn Pro Arg Ser Leu
        275                 280                 285
Ser Glu Ser Thr Asn Ser Thr Phe Lys Arg Lys Ser Gln Glu Ser Val
    290                 295                 300
Gly Ala Leu Thr Gly Asp Arg Pro Gly Lys Arg Ser Ser Glu Ser Gly
305                 310                 315                 320
Ser Arg Arg Asn Ser Lys Ser Gly Ala Arg Thr Ser Leu Gln Lys Ile
                325                 330                 335
Ser Glu Val Pro Glu Arg Gly Ser Lys Ser Arg Lys Ser Gly Leu Tyr
            340                 345                 350
Ser Leu Met Ser Leu Leu Gly Met Gly Pro Gly Asn Ile Glu Lys Asp
        355                 360                 365
Met Leu Lys Pro Arg Asp Glu Asp Pro Leu Leu Asp Ser Asp Asp Glu
    370                 375                 380
Arg Pro Glu Ser Phe Asp Asp Glu Leu Arg Arg Lys Glu Met Arg Arg
385                 390                 395                 400
Gly Ile Asp Leu Ala Thr Thr Leu Glu Arg Ile Glu Lys Asn Phe Val
                405                 410                 415
Ile Thr Asp Pro Arg Leu Pro Asp Asn Pro Ile Ile Phe Ala Ser Asp
            420                 425                 430
Ser Phe Leu Gln Leu Thr Glu Tyr Ser Arg Glu Glu Ile Leu Gly Arg
        435                 440                 445
Asn Cys Arg Phe Leu Gln Gly Pro Glu Thr Asp Arg Ala Thr Val Arg
    450                 455                 460
Lys Ile Arg Asp Ala Ile Asp Asn Gln Thr Glu Val Thr Val Gln Leu
465                 470                 475                 480
Ile Asn Tyr Thr Lys Ser Gly Lys Lys Phe Trp Asn Leu Phe His Leu
                485                 490                 495
Gln Pro Met Arg Asp Gln Lys Gly Asp Val Gln Tyr Phe Ile Gly Val
            500                 505                 510
Gln Leu Asp Gly Thr Glu His Val Arg Asp Ala Ala Glu Arg Glu Gly
        515                 520                 525
Val Met Leu Ile Lys Lys Thr Ala Glu Asn Ile Asp Glu Ala Ala Lys
    530                 535                 540
Glu Leu Pro Asp Ala Asn Leu Arg Pro Glu Asp Leu Trp Ala Asn His
545                 550                 555                 560
Ser Lys Val Val Leu Pro Lys Pro His Met Lys Asp Ser Ala Ser Trp
                565                 570                 575
Arg Ala Ile Gln Lys Val Leu Glu Gly Gly Glu Asn Ile Asp Leu Lys
            580                 585                 590
His Phe Arg Pro Val Lys Pro Leu Gly Ser Gly Asp Thr Gly Ser Val
        595                 600                 605
His Leu Val Glu Leu Leu Asn Thr Gly Glu Tyr Phe Ala Met Lys Ala
    610                 615                 620
Met Asp Lys Asn Val Met Leu Asn Arg Asn Lys Val His Arg Ala Asn
```

```
                625                 630                 635                 640
Ala Glu Arg Glu Ile Leu Asp Met Leu Asp His Pro Phe Leu Pro Thr
                    645                 650                 655
Leu Tyr Ala Ser Phe Gln Thr Lys Thr His Ile Cys Leu Ile Thr Asp
                660                 665                 670
Tyr Tyr Pro Gly Gly Glu Leu Phe Leu Leu Asp Arg Gln Pro Leu
            675                 680                 685
Lys Val Leu Arg Glu Asp Ala Val Arg Phe Tyr Ala Ala Glu Val Val
            690                 695                 700
Ile Ala Leu Glu Tyr Leu His Cys Gln Gly Ile Ile Tyr Arg Asp Leu
705                 710                 715                 720
Lys Pro Glu Asn Ile Leu Leu His Arg Asp Gly His Ile Ser Leu Thr
                    725                 730                 735
Asp Phe Asp Leu Ser Cys Leu Thr Ser Cys Arg Pro Gln Val Phe Leu
                740                 745                 750
Pro Glu Glu Ala Asn Lys Lys Ser Arg Arg Lys Ser Arg Ser Ser Pro
            755                 760                 765
Ile Phe Phe Ala Glu Pro Met Arg Ala Ser Asn Ser Phe Val Gly Thr
            770                 775                 780
Glu Glu Tyr Ile Ala Pro Glu Ile Ile Thr Gly Ala Gly His Thr Ser
785                 790                 795                 800
Ala Val Asp Trp Trp Ala Leu Gly Ile Leu Leu Tyr Glu Met Leu Tyr
                    805                 810                 815
Gly Tyr Thr Pro Phe Arg Gly Lys Thr Arg Gln Arg Thr Phe Ala Asn
                820                 825                 830
Ile Leu His Lys Asp Ile Arg Phe Pro Ala Ser Ile Ser Val Ser Leu
            835                 840                 845
Pro Ala Arg Gln Leu Ile Tyr Arg Leu Leu His Arg Asp Pro Ser Asn
            850                 855                 860
Arg Leu Gly Ser Tyr Glu Gly Ser Asn Glu Ile Lys Glu His Pro Phe
865                 870                 875                 880
Phe Arg Gly Ile Asn Trp Ala Leu Val Arg Gly Thr Ala Pro Pro Lys
                    885                 890                 895
Leu Asp Ala Pro Leu Phe Pro Asp Asp Thr Asp Lys Gly Met Gly Asp
                900                 905                 910
Ala Ala Ala Ala Asp Thr His Thr Asp Met Phe
            915                 920

<210> SEQ ID NO 2
<211> LENGTH: 239
<212> TYPE: PRT
<213> ORGANISM: Artificial Sequence
<220> FEATURE:
<223> OTHER INFORMATION: HA4-AsLOV2 (SS58 insertion)

<400> SEQUENCE: 2

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser Ser
                20                  25                  30

Ser Val Tyr Tyr Tyr Arg Ile Thr Tyr Gly Glu Thr Gly Gly Asn Ser
            35                  40                  45

Pro Val Gln Glu Phe Thr Val Pro Tyr Ser Gly Leu Glu Arg Ile Glu
        50                  55                  60

Lys Asn Phe Val Ile Thr Asp Pro Arg Leu Pro Asp Asn Pro Ile Ile
```

```
                65                  70                  75                  80
        Phe Ala Ser Asp Ser Phe Leu Gln Leu Thr Glu Tyr Ser Arg Glu Glu
                        85                  90                  95

Ile Leu Gly Arg Asn Cys Arg Phe Leu Gln Gly Pro Glu Thr Asp Arg
                        100                 105                 110

Ala Thr Val Arg Lys Ile Arg Asp Ala Ile Asp Asn Gln Thr Glu Val
                        115                 120                 125

Thr Val Gln Leu Ile Asn Tyr Thr Lys Ser Gly Lys Lys Phe Trp Asn
                        130                 135                 140

Leu Phe His Leu Gln Pro Met Arg Asp Gln Lys Gly Asp Val Gln Tyr
        145                 150                 155                 160

Phe Ile Gly Val Gln Leu Asp Gly Thr Glu His Val Arg Asp Ala Ala
                        165                 170                 175

Glu Arg Glu Gly Val Met Leu Ile Lys Lys Thr Ala Glu Asn Ile Asp
                        180                 185                 190

Glu Ala Ala Gly Ser Ser Thr Ala Thr Ile Ser Gly Leu Ser Pro Gly
                        195                 200                 205

Val Asp Tyr Thr Ile Thr Val Tyr Ala Trp Gly Glu Asp Ser Ala Gly
                        210                 215                 220

Tyr Met Phe Met Tyr Ser Pro Ile Ser Ile Asn Tyr Arg Thr Cys
        225                 230                 235
```

<210> SEQ ID NO 3
<211> LENGTH: 236
<212> TYPE: PRT
<213> ORGANISM: Artificial Sequence
<220> FEATURE:
<223> OTHER INFORMATION: HA4-AsLOV2 (MS29 insertion with residues
      removed from L1)

<400> SEQUENCE: 3

```
        Gly Ser Ser Val Ser Val Pro Thr Lys Leu Glu Val Val Ala Ala
        1               5                   10                  15

Thr Pro Thr Ser Leu Leu Ile Ser Trp Asp Ala Pro Met Gly Leu Glu
                        20                  25                  30

Arg Ile Glu Lys Asn Phe Val Ile Thr Asp Pro Arg Leu Pro Asp Asn
                        35                  40                  45

Pro Ile Ile Phe Ala Ser Asp Ser Phe Leu Gln Leu Thr Glu Tyr Ser
                        50                  55                  60

Arg Glu Glu Ile Leu Gly Arg Asn Cys Arg Phe Leu Gln Gly Pro Glu
        65                  70                  75                  80

Thr Asp Arg Ala Thr Val Arg Lys Ile Arg Asp Ala Ile Asp Asn Gln
                        85                  90                  95

Thr Glu Val Thr Val Gln Leu Ile Asn Tyr Thr Lys Ser Gly Lys Lys
                        100                 105                 110

Phe Trp Asn Leu Phe His Leu Gln Pro Met Arg Asp Gln Lys Gly Asp
                        115                 120                 125

Val Gln Tyr Phe Ile Gly Val Gln Leu Asp Gly Thr Glu His Val Arg
                        130                 135                 140

Asp Ala Ala Glu Arg Glu Gly Val Met Leu Ile Lys Lys Thr Ala Glu
        145                 150                 155                 160

Asn Ile Asp Glu Ala Ala Gly Ser Val Tyr Tyr Tyr Arg Ile Thr Tyr
                        165                 170                 175

Gly Glu Thr Gly Gly Asn Ser Pro Val Gln Glu Phe Thr Val Pro Tyr
                        180                 185                 190
```

```
Ser Ser Ser Thr Ala Thr Ile Ser Gly Leu Ser Pro Gly Val Asp Tyr
            195                 200                 205

Thr Ile Thr Val Tyr Ala Trp Gly Glu Asp Ser Ala Gly Tyr Met Phe
            210                 215                 220

Met Tyr Ser Pro Ile Ser Ile Asn Tyr Arg Thr Cys
225                 230                 235

<210> SEQ ID NO 4
<211> LENGTH: 239
<212> TYPE: PRT
<213> ORGANISM: Artificial Sequence
<220> FEATURE:
<223> OTHER INFORMATION: HA4-AsLOV2 (MS29 insertion)

<400> SEQUENCE: 4

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Gly Leu Glu
            20                  25                  30

Arg Ile Glu Lys Asn Phe Val Ile Thr Asp Pro Arg Leu Pro Asp Asn
            35                  40                  45

Pro Ile Ile Phe Ala Ser Asp Ser Phe Leu Gln Leu Thr Glu Tyr Ser
        50                  55                  60

Arg Glu Glu Ile Leu Gly Arg Asn Cys Arg Phe Leu Gln Gly Pro Glu
65                  70                  75                  80

Thr Asp Arg Ala Thr Val Arg Lys Ile Arg Asp Ala Ile Asp Asn Gln
            85                  90                  95

Thr Glu Val Thr Val Gln Leu Ile Asn Tyr Thr Lys Ser Gly Lys Lys
            100                 105                 110

Phe Trp Asn Leu Phe His Leu Gln Pro Met Arg Asp Gln Lys Gly Asp
            115                 120                 125

Val Gln Tyr Phe Ile Gly Val Gln Leu Asp Gly Thr Glu His Val Arg
        130                 135                 140

Asp Ala Ala Glu Arg Glu Gly Val Met Leu Ile Lys Lys Thr Ala Glu
145                 150                 155                 160

Asn Ile Asp Glu Ala Ala Gly Ser Ser Ser Val Tyr Tyr Tyr Arg
            165                 170                 175

Ile Thr Tyr Gly Glu Thr Gly Gly Asn Ser Pro Val Gln Glu Phe Thr
            180                 185                 190

Val Pro Tyr Ser Ser Ser Thr Ala Thr Ile Ser Gly Leu Ser Pro Gly
            195                 200                 205

Val Asp Tyr Thr Ile Thr Val Tyr Ala Trp Gly Glu Asp Ser Ala Gly
            210                 215                 220

Tyr Met Phe Met Tyr Ser Pro Ile Ser Ile Asn Tyr Arg Thr Cys
225                 230                 235

<210> SEQ ID NO 5
<211> LENGTH: 238
<212> TYPE: PRT
<213> ORGANISM: Artificial Sequence
<220> FEATURE:
<223> OTHER INFORMATION: HA4-AsLOV2 (GN46 insertion with residues
      removed from L3)

<400> SEQUENCE: 5

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser Ser
```

```
            20                  25                  30
Ser Val Tyr Tyr Tyr Arg Ile Thr Tyr Gly Glu Thr Gly Gly Leu Glu
        35                  40                  45

Arg Ile Glu Lys Asn Phe Val Ile Thr Asp Pro Arg Leu Pro Asp Asn
 50                  55                  60

Pro Ile Ile Phe Ala Ser Asp Ser Phe Leu Gln Leu Thr Glu Tyr Ser
 65                  70                  75                  80

Arg Glu Glu Ile Leu Gly Arg Asn Cys Arg Phe Leu Gln Gly Pro Glu
                85                  90                  95

Thr Asp Arg Ala Thr Val Arg Lys Ile Arg Asp Ala Ile Asp Asn Gln
            100                 105                 110

Thr Glu Val Thr Val Gln Leu Ile Asn Tyr Thr Lys Ser Gly Lys Lys
        115                 120                 125

Phe Trp Asn Leu Phe His Leu Gln Pro Met Arg Asp Gln Lys Gly Asp
130                 135                 140

Val Gln Tyr Phe Ile Gly Val Gln Leu Asp Gly Thr Glu His Val Arg
145                 150                 155                 160

Asp Ala Ala Glu Arg Glu Gly Val Met Leu Ile Lys Lys Thr Ala Glu
                165                 170                 175

Asn Ile Asp Glu Ala Ala Gly Asn Ser Pro Val Gln Glu Phe Thr Val
            180                 185                 190

Pro Tyr Ser Ser Ser Thr Ala Thr Ile Ser Gly Leu Ser Pro Gly Val
        195                 200                 205

Asp Tyr Thr Ile Thr Val Tyr Ala Trp Gly Glu Asp Ser Ala Gly Tyr
    210                 215                 220

Met Phe Met Tyr Ser Pro Ile Ser Ile Asn Tyr Arg Thr Cys
225                 230                 235

<210> SEQ ID NO 6
<211> LENGTH: 237
<212> TYPE: PRT
<213> ORGANISM: Artificial Sequence
<220> FEATURE:
<223> OTHER INFORMATION: HA4-AsLOV2 (TN45 insertion with residues
      removed from L3)

<400> SEQUENCE: 6

Gly Ser Ser Val Ser Ser Val Pro Thr Lys Leu Glu Val Val Ala Ala
 1               5                  10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Leu Glu Arg
        35                  40                  45

Ile Glu Lys Asn Phe Val Ile Thr Asp Pro Arg Leu Pro Asp Asn Pro
 50                  55                  60

Ile Ile Phe Ala Ser Asp Ser Phe Leu Gln Leu Thr Glu Tyr Ser Arg
 65                  70                  75                  80

Glu Glu Ile Leu Gly Arg Asn Cys Arg Phe Leu Gln Gly Pro Glu Thr
                85                  90                  95

Asp Arg Ala Thr Val Arg Lys Ile Arg Asp Ala Ile Asp Asn Gln Thr
            100                 105                 110

Glu Val Thr Val Gln Leu Ile Asn Tyr Thr Lys Ser Gly Lys Lys Phe
        115                 120                 125

Trp Asn Leu Phe His Leu Gln Pro Met Arg Asp Gln Lys Gly Asp Val
    130                 135                 140
```

-continued

Gln Tyr Phe Ile Gly Val Gln Leu Asp Gly Thr Glu His Val Arg Asp
145                 150                 155                 160

Ala Ala Glu Arg Glu Gly Val Met Leu Ile Lys Lys Thr Ala Glu Asn
                165                 170                 175

Ile Asp Glu Ala Ala Gly Asn Ser Pro Val Gln Glu Phe Thr Val Pro
            180                 185                 190

Tyr Ser Ser Ser Thr Ala Thr Ile Ser Gly Leu Ser Pro Gly Val Asp
        195                 200                 205

Tyr Thr Ile Thr Val Tyr Ala Trp Gly Glu Asp Ser Ala Gly Tyr Met
    210                 215                 220

Phe Met Tyr Ser Pro Ile Ser Ile Asn Tyr Arg Thr Cys
225                 230                 235

<210> SEQ ID NO 7
<211> LENGTH: 237
<212> TYPE: PRT
<213> ORGANISM: Artificial Sequence
<220> FEATURE:
<223> OTHER INFORMATION: HA4-AsLOV2 (SP68 insertion with residues
      removed from L5)

<400> SEQUENCE: 7

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser Ser
                20                  25                  30

Ser Val Tyr Tyr Tyr Arg Ile Thr Tyr Gly Glu Thr Gly Gly Asn Ser
            35                  40                  45

Pro Val Gln Glu Phe Thr Val Pro Tyr Ser Ser Ser Thr Ala Thr Ile
50                  55                  60

Ser Gly Ser Gly Leu Glu Arg Ile Glu Lys Asn Phe Val Ile Thr Asp
65                  70                  75                  80

Pro Arg Leu Pro Asp Asn Pro Ile Ile Phe Ala Ser Asp Ser Phe Leu
                85                  90                  95

Gln Leu Thr Glu Tyr Ser Arg Glu Glu Ile Leu Gly Arg Asn Cys Arg
            100                 105                 110

Phe Leu Gln Gly Pro Glu Thr Asp Arg Ala Thr Val Arg Lys Ile Arg
        115                 120                 125

Asp Ala Ile Asp Asn Gln Thr Glu Val Thr Val Gln Leu Ile Asn Tyr
    130                 135                 140

Thr Lys Ser Gly Lys Lys Phe Trp Asn Leu Phe His Leu Gln Pro Met
145                 150                 155                 160

Arg Asp Gln Lys Gly Asp Val Gln Tyr Phe Ile Gly Val Gln Leu Asp
                165                 170                 175

Gly Thr Glu His Val Arg Asp Ala Ala Glu Arg Glu Gly Val Met Leu
            180                 185                 190

Ile Lys Lys Thr Ala Glu Asn Ile Asp Glu Ala Ala Gly Pro Val Asp
        195                 200                 205

Tyr Thr Ile Thr Val Tyr Ala Trp Gly Glu Asp Ser Ala Gly Tyr Met
    210                 215                 220

Phe Met Tyr Ser Pro Ile Ser Ile Asn Tyr Arg Thr Cys
225                 230                 235

<210> SEQ ID NO 8
<211> LENGTH: 238
<212> TYPE: PRT
<213> ORGANISM: Artificial Sequence
<220> FEATURE:
<223> OTHER INFORMATION: HA4-AsLOV2 (PT18 insertion with residues
      removed from L1)

<400> SEQUENCE: 8

Gly Ser Ser Val Ser Val Pro Thr Lys Leu Glu Val Val Ala Ala
1               5                   10                  15

Pro Gly Leu Glu Arg Ile Glu Lys Asn Phe Val Ile Thr Asp Pro Arg
            20                  25                  30

Leu Pro Asp Asn Pro Ile Ile Phe Ala Ser Asp Ser Phe Leu Gln Leu
        35                  40                  45

Thr Glu Tyr Ser Arg Glu Glu Ile Leu Gly Arg Asn Cys Arg Phe Leu
50                  55                  60

Gln Gly Pro Glu Thr Asp Arg Ala Thr Val Arg Lys Ile Arg Asp Ala
65                  70                  75                  80

Ile Asp Asn Gln Thr Glu Val Thr Val Gln Leu Ile Asn Tyr Thr Lys
                85                  90                  95

Ser Gly Lys Lys Phe Trp Asn Leu Phe His Leu Gln Pro Met Arg Asp
            100                 105                 110

Gln Lys Gly Asp Val Gln Tyr Phe Ile Gly Val Gln Leu Asp Gly Thr
        115                 120                 125

Glu His Val Arg Asp Ala Ala Glu Arg Glu Gly Val Met Leu Ile Lys
    130                 135                 140

Lys Thr Ala Glu Asn Ile Asp Glu Ala Ala Gly Thr Ser Leu Leu Ile
145                 150                 155                 160

Ser Trp Asp Ala Pro Met Ser Ser Ser Val Tyr Tyr Tyr Arg Ile
                165                 170                 175

Thr Tyr Gly Glu Thr Gly Gly Asn Ser Pro Val Gln Glu Phe Thr Val
            180                 185                 190

Pro Tyr Ser Ser Ser Thr Ala Thr Ile Ser Gly Leu Ser Pro Gly Val
        195                 200                 205

Asp Tyr Thr Ile Thr Val Tyr Ala Trp Gly Glu Asp Ser Ala Gly Tyr
    210                 215                 220

Met Phe Met Tyr Ser Pro Ile Ser Ile Asn Tyr Arg Thr Cys
225                 230                 235

<210> SEQ ID NO 9
<211> LENGTH: 138
<212> TYPE: PRT
<213> ORGANISM: Artificial Sequence
<220> FEATURE:
<223> OTHER INFORMATION: Truncated AsLOV2

<400> SEQUENCE: 9

Gly Leu Glu Arg Ile Glu Lys Asn Phe Val Ile Thr Asp Pro Arg Leu
1               5                   10                  15

Pro Asp Asn Pro Ile Ile Phe Ala Ser Asp Ser Phe Leu Gln Leu Thr
            20                  25                  30

Glu Tyr Ser Arg Glu Glu Ile Leu Gly Arg Asn Cys Arg Phe Leu Gln
        35                  40                  45

Gly Pro Glu Thr Asp Arg Ala Thr Val Arg Lys Ile Arg Asp Ala Ile
    50                  55                  60

Asp Asn Gln Thr Glu Val Thr Val Gln Leu Ile Asn Tyr Thr Lys Ser
65                  70                  75                  80

Gly Lys Lys Phe Trp Asn Leu Phe His Leu Gln Pro Met Arg Asp Gln
                85                  90                  95

Lys Gly Asp Val Gln Tyr Phe Ile Gly Val Gln Leu Asp Gly Thr Glu
            100                 105                 110

His Val Arg Asp Ala Ala Glu Arg Glu Gly Val Met Leu Ile Lys Lys
        115                 120                 125

Thr Ala Glu Asn Ile Asp Glu Ala Ala Gly
        130                 135

<210> SEQ ID NO 10
<211> LENGTH: 101
<212> TYPE: PRT
<213> ORGANISM: Artificial Sequence
<220> FEATURE:
<223> OTHER INFORMATION: Monobody HA4

<400> SEQUENCE: 10

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Thr Ala Thr Ile
    50                  55                  60

Ser Gly Leu Ser Pro Gly Val Asp Tyr Thr Ile Thr Val Tyr Ala Trp
65                  70                  75                  80

Gly Glu Asp Ser Ala Gly Tyr Met Phe Met Tyr Ser Pro Ile Ser Ile
                85                  90                  95

Asn Tyr Arg Thr Cys
            100

<210> SEQ ID NO 11
<211> LENGTH: 371
<212> TYPE: PRT
<213> ORGANISM: Artificial Sequence
<220> FEATURE:
<223> OTHER INFORMATION: His6-YFP-SH2

<400> SEQUENCE: 11

His His His His His His Ser Ser Gly Glu Asn Leu Tyr Phe Gln Gly
1               5                   10                  15

His Met Ala Ser Lys Val Ser Lys Gly Glu Glu Leu Phe Thr Gly Val
            20                  25                  30

Val Pro Ile Leu Val Glu Leu Asp Gly Asp Val Asn Gly His Lys Phe
        35                  40                  45

Ser Val Ser Gly Glu Gly Glu Gly Asp Ala Thr Tyr Gly Lys Leu Thr
    50                  55                  60

Leu Lys Phe Ile Cys Thr Thr Gly Lys Leu Pro Val Pro Trp Pro Thr
65                  70                  75                  80

Leu Val Thr Thr Phe Gly Tyr Gly Leu Gln Cys Phe Ala Arg Tyr Pro
                85                  90                  95

Asp His Met Lys Gln His Asp Phe Phe Lys Ser Ala Met Pro Glu Gly
            100                 105                 110

Tyr Val Gln Glu Arg Thr Ile Phe Phe Lys Asp Asp Gly Asn Tyr Lys
        115                 120                 125

Thr Arg Ala Glu Val Lys Phe Glu Gly Asp Thr Leu Val Asn Arg Ile
    130                 135                 140

Glu Leu Lys Gly Ile Asp Phe Lys Glu Asp Gly Asn Ile Leu Gly His
145                 150                 155                 160

Lys Leu Glu Tyr Asn Tyr Asn Ser His Asn Val Tyr Ile Met Ala Asp
                165                 170                 175

Lys Gln Lys Asn Gly Ile Lys Val Asn Phe Lys Ile Arg His Asn Ile
            180                 185                 190

Glu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
    210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr Leu Gly Met Asp Glu
                245                 250                 255

Leu Tyr Lys Ser Leu Glu Lys His Ser Trp Tyr His Gly Pro Val Ser
            260                 265                 270

Arg Asn Ala Ala Glu Tyr Leu Leu Ser Ser Gly Ile Asn Gly Ser Phe
        275                 280                 285

Leu Val Arg Glu Ser Glu Ser Ser Pro Gly Gln Arg Ser Ile Ser Leu
    290                 295                 300

Arg Tyr Glu Gly Arg Val Tyr His Tyr Arg Ile Asn Thr Ala Ser Asp
305                 310                 315                 320

Gly Lys Leu Tyr Val Ser Ser Glu Ser Arg Phe Asn Thr Leu Ala Glu
                325                 330                 335

Leu Val His His His Ser Thr Val Ala Asp Gly Leu Ile Thr Thr Leu
            340                 345                 350

His Tyr Pro Ala Pro Lys Arg Asn Lys Pro Thr Val Tyr Gly Val Ser
        355                 360                 365

Pro Asn Tyr
    370

<210> SEQ ID NO 12
<211> LENGTH: 239
<212> TYPE: PRT
<213> ORGANISM: Artificial Sequence
<220> FEATURE:
<223> OTHER INFORMATION: HA4-AsLOV2 (SS30 insertion)

<400> SEQUENCE: 12

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Gly Leu
            20                  25                  30

Glu Arg Ile Glu Lys Asn Phe Val Ile Thr Asp Pro Arg Leu Pro Asp
        35                  40                  45

Asn Pro Ile Ile Phe Ala Ser Asp Ser Phe Leu Gln Leu Thr Glu Tyr
    50                  55                  60

Ser Arg Glu Glu Ile Leu Gly Arg Asn Cys Arg Phe Leu Gln Gly Pro
65                  70                  75                  80

Glu Thr Asp Arg Ala Thr Val Arg Lys Ile Arg Asp Ala Ile Asp Asn
                85                  90                  95

Gln Thr Glu Val Thr Val Gln Leu Ile Asn Tyr Thr Lys Ser Gly Lys
            100                 105                 110

Lys Phe Trp Asn Leu Phe His Leu Gln Pro Met Arg Asp Gln Lys Gly
        115                 120                 125

Asp Val Gln Tyr Phe Ile Gly Val Gln Leu Asp Gly Thr Glu His Val
    130                 135                 140

Arg Asp Ala Ala Glu Arg Glu Gly Val Met Leu Ile Lys Lys Thr Ala
145                 150                 155                 160

Glu Asn Ile Asp Glu Ala Ala Gly Ser Ser Ser Val Tyr Tyr Tyr Arg
                165                 170                 175

Ile Thr Tyr Gly Glu Thr Gly Gly Asn Ser Pro Val Gln Glu Phe Thr
            180                 185                 190

Val Pro Tyr Ser Ser Ser Thr Ala Thr Ile Ser Gly Leu Ser Pro Gly
            195                 200                 205

Val Asp Tyr Thr Ile Thr Val Tyr Ala Trp Gly Glu Asp Ser Ala Gly
            210                 215                 220

Tyr Met Phe Met Tyr Ser Pro Ile Ser Ile Asn Tyr Arg Thr Cys
225                 230                 235

<210> SEQ ID NO 13
<211> LENGTH: 239
<212> TYPE: PRT
<213> ORGANISM: Artificial Sequence
<220> FEATURE:
<223> OTHER INFORMATION: HA4-AsLOV2 (NS47 insertion)

<400> SEQUENCE: 13

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser Ser
                20                  25                  30

Ser Val Tyr Tyr Tyr Arg Ile Thr Tyr Gly Glu Thr Gly Gly Asn Gly
            35                  40                  45

Leu Glu Arg Ile Glu Lys Asn Phe Val Ile Thr Asp Pro Arg Leu Pro
50                  55                  60

Asp Asn Pro Ile Ile Phe Ala Ser Asp Ser Phe Leu Gln Leu Thr Glu
65                  70                  75                  80

Tyr Ser Arg Glu Glu Ile Leu Gly Arg Asn Cys Arg Phe Leu Gln Gly
                85                  90                  95

Pro Glu Thr Asp Arg Ala Thr Val Arg Lys Ile Arg Asp Ala Ile Asp
            100                 105                 110

Asn Gln Thr Glu Val Thr Val Gln Leu Ile Asn Tyr Thr Lys Ser Gly
            115                 120                 125

Lys Lys Phe Trp Asn Leu Phe His Leu Gln Pro Met Arg Asp Gln Lys
        130                 135                 140

Gly Asp Val Gln Tyr Phe Ile Gly Val Gln Leu Asp Gly Thr Glu His
145                 150                 155                 160

Val Arg Asp Ala Ala Glu Arg Glu Gly Val Met Leu Ile Lys Lys Thr
                165                 170                 175

Ala Glu Asn Ile Asp Glu Ala Ala Gly Ser Pro Val Gln Glu Phe Thr
            180                 185                 190

Val Pro Tyr Ser Ser Ser Thr Ala Thr Ile Ser Gly Leu Ser Pro Gly
            195                 200                 205

Val Asp Tyr Thr Ile Thr Val Tyr Ala Trp Gly Glu Asp Ser Ala Gly
            210                 215                 220

Tyr Met Phe Met Tyr Ser Pro Ile Ser Ile Asn Tyr Arg Thr Cys
225                 230                 235

<210> SEQ ID NO 14
<211> LENGTH: 239
<212> TYPE: PRT
<213> ORGANISM: Artificial Sequence
<220> FEATURE:
<223> OTHER INFORMATION: HA4-AsLOV2 (SA84 insertion)

<400> SEQUENCE: 14

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Thr Ala Thr Ile
    50                  55                  60

Ser Gly Leu Ser Pro Gly Val Asp Tyr Thr Ile Thr Val Tyr Ala Trp
65              70                  75                  80

Gly Glu Asp Ser Gly Leu Glu Arg Ile Glu Lys Asn Phe Val Ile Thr
                85                  90                  95

Asp Pro Arg Leu Pro Asp Asn Pro Ile Ile Phe Ala Ser Asp Ser Phe
                100                 105                 110

Leu Gln Leu Thr Glu Tyr Ser Arg Glu Glu Ile Leu Gly Arg Asn Cys
            115                 120                 125

Arg Phe Leu Gln Gly Pro Glu Thr Asp Arg Ala Thr Val Arg Lys Ile
130             135                 140

Arg Asp Ala Ile Asp Asn Gln Thr Glu Val Thr Val Gln Leu Ile Asn
145                 150                 155                 160

Tyr Thr Lys Ser Gly Lys Lys Phe Trp Asn Leu Phe His Leu Gln Pro
                165                 170                 175

Met Arg Asp Gln Lys Gly Asp Val Gln Tyr Phe Ile Gly Val Gln Leu
            180                 185                 190

Asp Gly Thr Glu His Val Arg Asp Ala Ala Glu Arg Gln Gly Val Met
            195                 200                 205

Leu Ile Lys Lys Thr Ala Glu Asn Ile Asp Glu Ala Ala Gly Ala Gly
    210                 215                 220

Tyr Met Phe Met Tyr Ser Pro Ile Ser Ile Asn Tyr Arg Thr Cys
225                 230                 235

<210> SEQ ID NO 15
<211> LENGTH: 354
<212> TYPE: PRT
<213> ORGANISM: Artificial Sequence
<220> FEATURE:
<223> OTHER INFORMATION: YFP-SH2

<400> SEQUENCE: 15

Met Ala Ser Lys Val Ser Lys Gly Glu Glu Leu Phe Thr Gly Val Val
1               5                   10                  15

Pro Ile Leu Val Glu Leu Asp Gly Asp Val Asn Gly His Lys Phe Ser
            20                  25                  30

Val Ser Gly Glu Gly Glu Gly Asp Ala Thr Tyr Gly Lys Leu Thr Leu
        35                  40                  45

Lys Phe Ile Cys Thr Thr Gly Lys Leu Pro Val Pro Trp Pro Thr Leu
    50                  55                  60

Val Thr Thr Phe Gly Tyr Gly Leu Gln Cys Phe Ala Arg Tyr Pro Asp
65              70                  75                  80

His Met Lys Gln His Asp Phe Phe Lys Ser Ala Met Pro Glu Gly Tyr
                85                  90                  95

Val Gln Glu Arg Thr Ile Phe Phe Lys Asp Asp Gly Asn Tyr Lys Thr

```
                    100                 105                 110
Arg Ala Glu Val Lys Phe Glu Gly Asp Thr Leu Val Asn Arg Ile Glu
            115                 120                 125

Leu Lys Gly Ile Asp Phe Lys Glu Asp Gly Asn Ile Leu Gly His Lys
            130                 135             140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
            195                 200                 205

Ser Ala Leu Ser Lys Asp Pro Asn Glu Lys Arg Asp His Met Val Leu
210                 215                 220

Leu Glu Phe Val Thr Ala Ala Gly Ile Thr Leu Gly Met Asp Glu Leu
225                 230                 235                 240

Tyr Lys Ser Leu Glu Lys His Ser Trp Tyr His Gly Pro Val Ser Arg
                245                 250                 255

Asn Ala Ala Glu Tyr Leu Leu Ser Ser Gly Ile Asn Gly Ser Phe Leu
            260                 265                 270

Val Arg Glu Ser Glu Ser Ser Pro Gly Gln Arg Ser Ile Ser Leu Arg
            275                 280                 285

Tyr Glu Gly Arg Val Tyr His Tyr Arg Ile Asn Thr Ala Ser Asp Gly
            290                 295                 300

Lys Leu Tyr Val Ser Ser Glu Ser Arg Phe Asn Thr Leu Ala Glu Leu
305                 310                 315                 320

Val His His His Ser Thr Val Ala Asp Gly Leu Ile Thr Thr Leu His
                325                 330                 335

Tyr Pro Ala Pro Lys Arg Asn Lys Pro Thr Val Tyr Gly Val Ser Pro
            340                 345                 350

Asn Tyr

<210> SEQ ID NO 16
<211> LENGTH: 120
<212> TYPE: PRT
<213> ORGANISM: Artificial Sequence
<220> FEATURE:
<223> OTHER INFORMATION: His6-HA4

<400> SEQUENCE: 16

His His His His His His Ser Ser Gly Glu Asn Leu Tyr Phe Gln Gly
1               5                   10                  15

His Ala Ser Gly Ser Ser Val Ser Val Pro Thr Lys Leu Glu Val
            20                  25                  30

Val Ala Ala Thr Pro Thr Ser Leu Leu Ile Ser Trp Asp Ala Pro Met
            35                  40                  45

Ser Ser Ser Ser Val Tyr Tyr Tyr Arg Ile Thr Tyr Gly Glu Thr Gly
    50                  55                  60

Gly Asn Ser Pro Val Gln Glu Phe Thr Val Pro Tyr Ser Ser Ser Thr
65                  70                  75                  80

Ala Thr Ile Ser Gly Leu Ser Pro Gly Val Asp Tyr Thr Ile Thr Val
            85                  90                  95

Tyr Ala Trp Gly Glu Asp Ser Ala Gly Tyr Met Phe Met Tyr Ser Pro
            100                 105                 110
```

```
<210> SEQ ID NO 17
<211> LENGTH: 239
<212> TYPE: PRT
<213> ORGANISM: Artificial Sequence
<220> FEATURE:
<223> OTHER INFORMATION: HA4-AsLOV2 (TG44 insertion)

<400> SEQUENCE: 17

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser
                20                  25                  30

Ser Val Tyr Tyr Tyr Arg Ile Thr Tyr Gly Glu Thr Gly Leu Glu Arg
            35                  40                  45

Ile Glu Lys Asn Phe Val Ile Thr Asp Pro Arg Leu Pro Asp Asn Pro
50                  55                  60

Ile Ile Phe Ala Ser Asp Ser Phe Leu Gln Leu Thr Glu Tyr Ser Arg
65                  70                  75                  80

Glu Glu Ile Leu Gly Arg Asn Cys Arg Phe Leu Gln Gly Pro Glu Thr
                85                  90                  95

Asp Arg Ala Thr Val Arg Lys Ile Arg Asp Ala Ile Asp Asn Gln Thr
            100                 105                 110

Glu Val Thr Val Gln Leu Ile Asn Tyr Thr Lys Ser Gly Lys Lys Phe
        115                 120                 125

Trp Asn Leu Phe His Leu Gln Pro Met Arg Asp Gln Lys Gly Asp Val
130                 135                 140

Gln Tyr Phe Ile Gly Val Gln Leu Asp Gly Thr Glu His Val Arg Asp
145                 150                 155                 160

Ala Ala Glu Arg Glu Gly Val Met Leu Ile Lys Lys Thr Ala Glu Asn
                165                 170                 175

Ile Asp Glu Ala Ala Gly Gly Gly Asn Ser Pro Val Gln Glu Phe Thr
            180                 185                 190

Val Pro Tyr Ser Ser Ser Thr Ala Thr Ile Ser Gly Leu Ser Pro Gly
        195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 18
<211> LENGTH: 239
<212> TYPE: PRT
<213> ORGANISM: Artificial Sequence
<220> FEATURE:
<223> OTHER INFORMATION: HA4-AsLOV2 (SG65 insertion)

<400> SEQUENCE: 18

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser
                20                  25                  30

Ser Val Tyr Tyr Tyr Arg Ile Thr Tyr Gly Glu Thr Gly Gly Asn Ser
            35                  40                  45

Pro Val Gln Glu Phe Thr Val Pro Tyr Ser Ser Ser Thr Ala Thr Ile
```

```
       50                  55                  60
Ser Gly Leu Glu Arg Ile Glu Lys Asn Phe Val Ile Thr Asp Pro Arg
 65                  70                  75                  80

Leu Pro Asp Asn Pro Ile Ile Phe Ala Ser Asp Ser Phe Leu Gln Leu
                 85                  90                  95

Thr Glu Tyr Ser Arg Glu Glu Ile Leu Gly Arg Asn Cys Arg Phe Leu
            100                 105                 110

Gln Gly Pro Glu Thr Asp Arg Ala Thr Val Arg Lys Ile Arg Asp Ala
        115                 120                 125

Ile Asp Asn Gln Thr Glu Val Thr Val Gln Leu Ile Asn Tyr Thr Lys
    130                 135                 140

Ser Gly Lys Lys Phe Trp Asn Leu Phe His Leu Gln Pro Met Arg Asp
145                 150                 155                 160

Gln Lys Gly Asp Val Gln Tyr Phe Ile Gly Val Gln Leu Asp Gly Thr
                165                 170                 175

Glu His Val Arg Asp Ala Ala Glu Arg Glu Gly Val Met Leu Ile Lys
            180                 185                 190

Lys Thr Ala Glu Asn Ile Asp Glu Ala Ala Gly Gly Leu Ser Pro Gly
        195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 19
<211> LENGTH: 239
<212> TYPE: PRT
<213> ORGANISM: Artificial Sequence
<220> FEATURE:
<223> OTHER INFORMATION: HA4-AsLOV2 (DA26 insertion)

<400> SEQUENCE: 19

Gly Ser Ser Val Ser Val Pro Thr Lys Leu Glu Val Val Ala Ala
  1               5                  10                  15

Thr Pro Thr Ser Leu Leu Ile Ser Trp Asp Gly Leu Glu Arg Ile Glu
                 20                  25                  30

Lys Asn Phe Val Ile Thr Asp Pro Arg Leu Pro Asp Asn Pro Ile Ile
             35                  40                  45

Phe Ala Ser Asp Ser Phe Leu Gln Leu Thr Glu Tyr Ser Arg Glu Glu
         50                  55                  60

Ile Leu Gly Arg Asn Cys Arg Phe Leu Gln Gly Pro Glu Thr Asp Arg
 65                  70                  75                  80

Ala Thr Val Arg Lys Ile Arg Asp Ala Ile Asp Asn Gln Thr Glu Val
                 85                  90                  95

Thr Val Gln Leu Ile Asn Tyr Thr Lys Ser Gly Lys Lys Phe Trp Asn
            100                 105                 110

Leu Phe His Leu Gln Pro Met Arg Asp Gln Lys Gly Asp Val Gln Tyr
        115                 120                 125

Phe Ile Gly Val Gln Leu Asp Gly Thr Glu His Val Arg Asp Ala Ala
    130                 135                 140

Glu Arg Glu Gly Val Met Leu Ile Lys Lys Thr Ala Glu Asn Ile Asp
145                 150                 155                 160

Glu Ala Ala Gly Ala Pro Met Ser Ser Ser Val Tyr Tyr Tyr Arg
                165                 170                 175

Ile Thr Tyr Gly Glu Thr Gly Gly Asn Ser Pro Val Gln Glu Phe Thr
```

Val Pro Tyr Ser Ser Thr Ala Thr Ile Ser Gly Leu Ser Pro Gly
          180                 185                 190

Val Asp Tyr Thr Ile Thr Val Tyr Ala Trp Gly Glu Asp Ser Ala Gly
    195                 200                 205

Tyr Met Phe Met Tyr Ser Pro Ile Ser Ile Asn Tyr Arg Thr Cys
225                 230                 235

<210> SEQ ID NO 20
<211> LENGTH: 239
<212> TYPE: PRT
<213> ORGANISM: Artificial Sequence
<220> FEATURE:
<223> OTHER INFORMATION: HA4-AsLOV2 (ED82 insertion)

<400> SEQUENCE: 20

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Thr Ala Thr Ile
    50                  55                  60

Ser Gly Leu Ser Pro Gly Val Asp Tyr Thr Ile Thr Val Tyr Ala Trp
65                  70                  75                  80

Gly Glu Gly Leu Glu Arg Ile Glu Lys Asn Phe Val Ile Thr Asp Pro
                85                  90                  95

Arg Leu Pro Asp Asn Pro Ile Ile Phe Ala Ser Asp Ser Phe Leu Gln
            100                 105                 110

Leu Thr Glu Tyr Ser Arg Glu Glu Ile Leu Gly Arg Asn Cys Arg Phe
        115                 120                 125

Leu Gln Gly Pro Glu Thr Asp Arg Ala Thr Val Arg Lys Ile Arg Asp
    130                 135                 140

Ala Ile Asp Asn Gln Thr Glu Val Thr Val Gln Leu Ile Asn Tyr Thr
145                 150                 155                 160

Lys Ser Gly Lys Lys Phe Trp Asn Leu Phe His Leu Gln Pro Met Arg
                165                 170                 175

Asp Gln Lys Gly Asp Val Gln Tyr Phe Ile Gly Val Gln Leu Asp Gly
            180                 185                 190

Thr Glu His Val Arg Asp Ala Ala Glu Arg Glu Gly Val Met Leu Ile
        195                 200                 205

Lys Lys Thr Ala Glu Asn Ile Asp Glu Ala Ala Gly Asp Ser Ala Gly
    210                 215                 220

Tyr Met Phe Met Tyr Ser Pro Ile Ser Ile Asn Tyr Arg Thr Cys
225                 230                 235

<210> SEQ ID NO 21
<211> LENGTH: 239
<212> TYPE: PRT
<213> ORGANISM: Artificial Sequence
<220> FEATURE:
<223> OTHER INFORMATION: HA4-AsLOV2 (DS83 insertion)

<400> SEQUENCE: 21

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Thr Ala Thr Ile
50                  55                  60

Ser Gly Leu Ser Pro Gly Val Asp Tyr Thr Ile Thr Val Tyr Ala Trp
65                  70                  75                  80

Gly Glu Asp Gly Leu Glu Arg Ile Glu Lys Asn Phe Val Ile Thr Asp
                85                  90                  95

Pro Arg Leu Pro Asp Asn Pro Ile Ile Phe Ala Ser Asp Ser Phe Leu
                100                 105                 110

Gln Leu Thr Glu Tyr Ser Arg Glu Glu Ile Leu Gly Arg Asn Cys Arg
                115                 120                 125

Phe Leu Gln Gly Pro Glu Thr Asp Arg Ala Thr Val Arg Lys Ile Arg
130                 135                 140

Asp Ala Ile Asp Asn Gln Thr Glu Val Thr Val Gln Leu Ile Asn Tyr
145                 150                 155                 160

Thr Lys Ser Gly Lys Lys Phe Trp Asn Leu Phe His Leu Gln Pro Met
                165                 170                 175

Arg Asp Gln Lys Gly Asp Val Gln Tyr Phe Ile Gly Val Gln Leu Asp
                180                 185                 190

Gly Thr Glu His Val Arg Asp Ala Ala Glu Arg Glu Gly Val Met Leu
                195                 200                 205

Ile Lys Lys Thr Ala Glu Asn Ile Asp Glu Ala Ala Gly Ser Ala Gly
                210                 215                 220

Tyr Met Phe Met Tyr Ser Pro Ile Ser Ile Asn Tyr Arg Thr Cys
225                 230                 235

<210> SEQ ID NO 22
<211> LENGTH: 239
<212> TYPE: PRT
<213> ORGANISM: Artificial Sequence
<220> FEATURE:
<223> OTHER INFORMATION: HA4-AsLOV2 (GG45 insertion)

<400> SEQUENCE: 22

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Leu Glu
        35                  40                  45

Arg Ile Glu Lys Asn Phe Val Ile Thr Asp Pro Arg Leu Pro Asp Asn
50                  55                  60

Pro Ile Ile Phe Ala Ser Asp Ser Phe Leu Gln Leu Thr Glu Tyr Ser
65                  70                  75                  80

Arg Glu Glu Ile Leu Gly Arg Asn Cys Arg Phe Leu Gln Gly Pro Glu
                85                  90                  95

Thr Asp Arg Ala Thr Val Arg Lys Ile Arg Asp Ala Ile Asp Asn Gln
                100                 105                 110

Thr Glu Val Thr Val Gln Leu Ile Asn Tyr Thr Lys Ser Gly Lys Lys
                115                 120                 125

Phe Trp Asn Leu Phe His Leu Gln Pro Met Arg Asp Gln Lys Gly Asp
130                 135                 140

Val Gln Tyr Phe Ile Gly Val Gln Leu Asp Gly Thr Glu His Val Arg
145                 150                 155                 160

Asp Ala Ala Glu Arg Glu Gly Val Met Leu Ile Lys Lys Thr Ala Glu
                165                 170                 175

Asn Ile Asp Glu Ala Ala Gly Gly Asn Ser Pro Val Gln Glu Phe Thr
            180                 185                 190

Val Pro Tyr Ser Ser Ser Thr Ala Thr Ile Ser Gly Leu Ser Pro Gly
        195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 23
<211> LENGTH: 239
<212> TYPE: PRT
<213> ORGANISM: Artificial Sequence
<220> FEATURE:
<223> OTHER INFORMATION: HA4-AsLOV2 (PT18 insertion)

<400> SEQUENCE: 23

Gly Ser Ser Val Ser Val Pro Thr Lys Leu Glu Val Val Ala Ala
1               5                   10                  15

Thr Pro Gly Leu Glu Arg Ile Glu Lys Asn Phe Val Ile Thr Asp Pro
                20                  25                  30

Arg Leu Pro Asp Asn Pro Ile Ile Phe Ala Ser Asp Ser Phe Leu Gln
            35                  40                  45

Leu Thr Glu Tyr Ser Arg Glu Glu Ile Leu Gly Arg Asn Cys Arg Phe
    50                  55                  60

Leu Gln Gly Pro Glu Thr Asp Arg Ala Thr Val Arg Lys Ile Arg Asp
65                  70                  75                  80

Ala Ile Asp Asn Gln Thr Glu Val Thr Val Gln Leu Ile Asn Tyr Thr
                85                  90                  95

Lys Ser Gly Lys Lys Phe Trp Asn Leu Phe His Leu Gln Pro Met Arg
                100                 105                 110

Asp Gln Lys Gly Asp Val Gln Tyr Phe Ile Gly Val Gln Leu Asp Gly
            115                 120                 125

Thr Glu His Val Arg Asp Ala Ala Glu Arg Glu Gly Val Met Leu Ile
        130                 135                 140

Lys Lys Thr Ala Glu Asn Ile Asp Glu Ala Ala Gly Thr Ser Leu Leu
145                 150                 155                 160

Ile Ser Trp Asp Ala Pro Met Ser Ser Ser Val Tyr Tyr Tyr Arg
                165                 170                 175

Ile Thr Tyr Gly Glu Thr Gly Gly Asn Ser Pro Val Gln Glu Phe Thr
            180                 185                 190

Val Pro Tyr Ser Ser Ser Thr Ala Thr Ile Ser Gly Leu Ser Pro Gly
        195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 24
<211> LENGTH: 239
<212> TYPE: PRT
<213> ORGANISM: Artificial Sequence
<220> FEATURE:

<223> OTHER INFORMATION: HA4-AsLOV2 (SP68 insertion)

<400> SEQUENCE: 24

```
Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser
            20                  25                  30

Ser Val Tyr Tyr Tyr Arg Ile Thr Tyr Gly Glu Thr Gly Gly Asn Ser
            35                  40                  45

Pro Val Gln Glu Phe Thr Val Pro Tyr Ser Ser Ser Thr Ala Thr Ile
    50                  55                  60

Ser Gly Leu Ser Gly Leu Glu Arg Ile Glu Lys Asn Phe Val Ile Thr
65                  70                  75                  80

Asp Pro Arg Leu Pro Asp Asn Pro Ile Ile Phe Ala Ser Asp Ser Phe
                85                  90                  95

Leu Gln Leu Thr Glu Tyr Ser Arg Glu Glu Ile Leu Gly Arg Asn Cys
            100                 105                 110

Arg Phe Leu Gln Gly Pro Glu Thr Asp Arg Ala Thr Val Arg Lys Ile
            115                 120                 125

Arg Asp Ala Ile Asp Asn Gln Thr Glu Val Thr Val Gln Leu Ile Asn
130                 135                 140

Tyr Thr Lys Ser Gly Lys Lys Phe Trp Asn Leu Phe His Leu Gln Pro
145                 150                 155                 160

Met Arg Asp Gln Lys Gly Asp Val Gln Tyr Phe Ile Gly Val Gln Leu
                165                 170                 175

Asp Gly Thr Glu His Val Arg Asp Ala Ala Glu Arg Glu Gly Val Met
            180                 185                 190

Leu Ile Lys Lys Thr Ala Glu Asn Ile Asp Glu Ala Ala Gly Pro Gly
            195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235
```

<210> SEQ ID NO 25
<211> LENGTH: 239
<212> TYPE: PRT
<213> ORGANISM: Artificial Sequence
<220> FEATURE:
<223> OTHER INFORMATION: AsLOV2-HA4 (N-terminus)

<400> SEQUENCE: 25

```
Gly Leu Glu Arg Ile Glu Lys Asn Phe Val Ile Thr Asp Pro Arg Leu
1               5                   10                  15

Pro Asp Asn Pro Ile Ile Phe Ala Ser Asp Ser Phe Leu Gln Leu Thr
            20                  25                  30

Glu Tyr Ser Arg Glu Glu Ile Leu Gly Arg Asn Cys Arg Phe Leu Gln
            35                  40                  45

Gly Pro Glu Thr Asp Arg Ala Thr Val Arg Lys Ile Arg Asp Ala Ile
    50                  55                  60

Asp Asn Gln Thr Glu Val Thr Val Gln Leu Ile Asn Tyr Thr Lys Ser
65                  70                  75                  80

Gly Lys Lys Phe Trp Asn Leu Phe His Leu Gln Pro Met Arg Asp Gln
                85                  90                  95

Lys Gly Asp Val Gln Tyr Phe Ile Gly Val Gln Leu Asp Gly Thr Glu
            100                 105                 110
```

```
His Val Arg Asp Ala Ala Glu Arg Glu Gly Val Met Leu Ile Lys Lys
        115                 120                 125

Thr Ala Glu Asn Ile Asp Glu Ala Ala Gly Gly Ser Ser Val Ser Ser
130                 135                 140

Val Pro Thr Lys Leu Glu Val Val Ala Ala Thr Pro Thr Ser Leu Leu
145                 150                 155                 160

Ile Ser Trp Asp Ala Pro Met Ser Ser Ser Val Tyr Tyr Tyr Arg
                165                 170                 175

Ile Thr Tyr Gly Glu Thr Gly Gly Asn Ser Pro Val Gln Glu Phe Thr
                180                 185                 190

Val Pro Tyr Ser Ser Ser Thr Ala Thr Ile Ser Gly Leu Ser Pro Gly
                195                 200                 205

Val Asp Tyr Thr Ile Thr Val Tyr Ala Trp Gly Glu Asp Ser Ala Gly
210                 215                 220

Tyr Met Phe Met Tyr Ser Pro Ile Ser Ile Asn Tyr Arg Thr Cys
225                 230                 235
```

<210> SEQ ID NO 26
<211> LENGTH: 239
<212> TYPE: PRT
<213> ORGANISM: Artificial Sequence
<220> FEATURE:
<223> OTHER INFORMATION: AsLOV2-HA4 (C-terminus)

<400> SEQUENCE: 26

```
Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
                20                  25                  30

Ser Val Tyr Tyr Tyr Arg Ile Thr Tyr Gly Glu Thr Gly Gly Asn Ser
                35                  40                  45

Pro Val Gln Glu Phe Thr Val Pro Tyr Ser Ser Ser Thr Ala Thr Ile
            50                  55                  60

Ser Gly Leu Ser Pro Gly Val Asp Tyr Thr Ile Thr Val Tyr Ala Trp
65              70                  75                  80

Gly Glu Asp Ser Ala Gly Tyr Met Phe Met Tyr Ser Pro Ile Ser Ile
                85                  90                  95

Asn Tyr Arg Thr Cys Gly Leu Glu Arg Ile Glu Lys Asn Phe Val Ile
                100                 105                 110

Thr Asp Pro Arg Leu Pro Asp Asn Pro Ile Ile Phe Ala Ser Asp Ser
            115                 120                 125

Phe Leu Gln Leu Thr Glu Tyr Ser Arg Glu Glu Ile Leu Gly Arg Asn
130                 135                 140

Cys Arg Phe Leu Gln Gly Pro Glu Thr Asp Arg Ala Thr Val Arg Lys
145                 150                 155                 160

Ile Arg Asp Ala Ile Asp Asn Gln Thr Glu Val Thr Val Gln Leu Ile
                165                 170                 175

Asn Tyr Thr Lys Ser Gly Lys Lys Phe Trp Asn Leu Phe His Leu Gln
                180                 185                 190

Pro Met Arg Asp Gln Lys Gly Asp Val Gln Tyr Phe Ile Gly Val Gln
            195                 200                 205

Leu Asp Gly Thr Glu His Val Arg Asp Ala Ala Glu Arg Glu Gly Val
        210                 215                 220

Met Leu Ile Lys Lys Thr Ala Glu Asn Ile Asp Glu Ala Ala Gly
225                 230                 235
```

<210> SEQ ID NO 27
<211> LENGTH: 239
<212> TYPE: PRT
<213> ORGANISM: Artificial Sequence
<220> FEATURE:
<223> OTHER INFORMATION: HA4-AsLOV2 (SS59 insertion)

<400> SEQUENCE: 27

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Gly Leu Glu Arg Ile
    50                  55                  60

Glu Lys Asn Phe Val Ile Thr Asp Pro Arg Leu Pro Asp Asn Pro Ile
65                  70                  75                  80

Ile Phe Ala Ser Asp Ser Phe Leu Gln Leu Thr Glu Tyr Ser Arg Glu
                85                  90                  95

Glu Ile Leu Gly Arg Asn Cys Arg Phe Leu Gln Gly Pro Glu Thr Asp
            100                 105                 110

Arg Ala Thr Val Arg Lys Ile Arg Asp Ala Ile Asp Asn Gln Thr Glu
        115                 120                 125

Val Thr Val Gln Leu Ile Asn Tyr Thr Lys Ser Gly Lys Lys Phe Trp
    130                 135                 140

Asn Leu Phe His Leu Gln Pro Met Arg Asp Gln Lys Gly Asp Val Gln
145                 150                 155                 160

Tyr Phe Ile Gly Val Gln Leu Asp Gly Thr Glu His Val Arg Asp Ala
                165                 170                 175

Ala Glu Arg Glu Gly Val Met Leu Ile Lys Lys Thr Ala Glu Asn Ile
            180                 185                 190

Asp Glu Ala Ala Gly Ser Thr Ala Thr Ile Ser Gly Leu Ser Pro Gly
        195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 28
<211> LENGTH: 239
<212> TYPE: PRT
<213> ORGANISM: Artificial Sequence
<220> FEATURE:
<223> OTHER INFORMATION: HA4-AsLOV2 (MY90 insertion)

<400> SEQUENCE: 28

Gly Ser Ser Val Ser Ser Val Pro Thr Lys Leu Glu Val Val Ala Ala
1               5                   10                  15

Thr Pro Thr Ser Leu Leu Ile Ser Trp Asp Ala Pro Met Ser Ser Ser
            20                  25                  30

Ser Val Tyr Tyr Tyr Arg Ile Thr Tyr Gly Glu Thr Gly Gly Asn Ser
        35                  40                  45

Pro Val Gln Glu Phe Thr Val Pro Tyr Ser Ser Ser Thr Ala Thr Ile
    50                  55                  60

Ser Gly Leu Ser Pro Gly Val Asp Tyr Thr Ile Thr Val Tyr Ala Trp

```
65                  70                  75                  80
Gly Glu Asp Ser Ala Gly Tyr Met Phe Met Gly Leu Glu Arg Ile Glu
                85                  90                  95

Lys Asn Phe Val Ile Thr Asp Pro Arg Leu Pro Asp Asn Pro Ile Ile
            100                 105                 110

Phe Ala Ser Asp Ser Phe Leu Gln Leu Thr Glu Tyr Ser Arg Glu Glu
        115                 120                 125

Ile Leu Gly Arg Asn Cys Arg Phe Leu Gln Gly Pro Glu Thr Asp Arg
    130                 135                 140

Ala Thr Val Arg Lys Ile Arg Asp Ala Ile Asp Asn Gln Thr Glu Val
145                 150                 155                 160

Thr Val Gln Leu Ile Asn Tyr Thr Lys Ser Gly Lys Lys Phe Trp Asn
                165                 170                 175

Leu Phe His Leu Gln Pro Met Arg Asp Gln Lys Gly Asp Val Gln Tyr
            180                 185                 190

Phe Ile Gly Val Gln Leu Asp Gly Thr Glu His Val Arg Asp Ala Ala
        195                 200                 205

Glu Arg Glu Gly Val Met Leu Ile Lys Lys Thr Ala Glu Asn Ile Asp
    210                 215                 220

Glu Ala Ala Gly Tyr Ser Pro Ile Ser Ile Asn Tyr Arg Thr Cys
225                 230                 235

<210> SEQ ID NO 29
<211> LENGTH: 258
<212> TYPE: PRT
<213> ORGANISM: Artificial Sequence
<220> FEATURE:
<223> OTHER INFORMATION: His6-HA4-AsLOV2 (SS58 insertion)

<400> SEQUENCE: 29

His His His His His His Ser Ser Gly Glu Asn Leu Tyr Phe Gln Gly
1               5                   10                  15

His Ala Ser Gly Ser Ser Val Ser Val Pro Thr Lys Leu Glu Val
            20                  25                  30

Val Ala Ala Thr Pro Thr Ser Leu Leu Ile Ser Trp Asp Ala Pro Met
        35                  40                  45

Ser Ser Ser Ser Val Tyr Tyr Tyr Arg Ile Thr Tyr Gly Glu Thr Gly
    50                  55                  60

Gly Asn Ser Pro Val Gln Glu Phe Thr Val Pro Tyr Ser Gly Leu Glu
65                  70                  75                  80

Arg Ile Glu Lys Asn Phe Val Ile Thr Asp Pro Arg Leu Pro Asp Asn
                85                  90                  95

Pro Ile Ile Phe Ala Ser Asp Ser Phe Leu Gln Leu Thr Glu Tyr Ser
            100                 105                 110

Arg Glu Glu Ile Leu Gly Arg Asn Cys Arg Phe Leu Gln Gly Pro Glu
        115                 120                 125

Thr Asp Arg Ala Thr Val Arg Lys Ile Arg Asp Ala Ile Asp Asn Gln
    130                 135                 140

Thr Glu Val Thr Val Gln Leu Ile Asn Tyr Thr Lys Ser Gly Lys Lys
145                 150                 155                 160

Phe Trp Asn Leu Phe His Leu Gln Pro Met Arg Asp Gln Lys Gly Asp
                165                 170                 175

Val Gln Tyr Phe Ile Gly Val Gln Leu Asp Gly Thr Glu His Val Arg
            180                 185                 190

Asp Ala Ala Glu Arg Glu Gly Val Met Leu Ile Lys Lys Thr Ala Glu
```

-continued

```
                195                 200                 205
Asn Ile Asp Glu Ala Ala Gly Ser Ser Thr Ala Thr Ile Ser Gly Leu
    210                 215                 220

Ser Pro Gly Val Asp Tyr Thr Ile Thr Val Tyr Ala Trp Gly Glu Asp
225                 230                 235                 240

Ser Ala Gly Tyr Met Phe Met Tyr Ser Pro Ile Ser Ile Asn Tyr Arg
                245                 250                 255

Thr Cys

<210> SEQ ID NO 30
<211> LENGTH: 239
<212> TYPE: PRT
<213> ORGANISM: Artificial Sequence
<220> FEATURE:
<223> OTHER INFORMATION: HA4-AsLOV2 (YS57 insertion)

<400> SEQUENCE: 30

Gly Ser Ser Val Ser Val Pro Thr Lys Leu Glu Val Val Ala Ala
1               5                   10                  15

Thr Pro Thr Ser Leu Leu Ile Ser Trp Asp Ala Pro Met Ser Ser
                20                  25                  30

Ser Val Tyr Tyr Tyr Arg Ile Thr Tyr Gly Glu Thr Gly Gly Asn Ser
                35                  40                  45

Pro Val Gln Glu Phe Thr Val Pro Tyr Gly Leu Glu Arg Ile Glu Lys
50                  55                  60

Asn Phe Val Ile Thr Asp Pro Arg Leu Pro Asp Asn Pro Ile Ile Phe
65                  70                  75                  80

Ala Ser Asp Ser Phe Leu Gln Leu Thr Glu Tyr Ser Arg Glu Glu Ile
                85                  90                  95

Leu Gly Arg Asn Cys Arg Phe Leu Gln Gly Pro Glu Thr Asp Arg Ala
                100                 105                 110

Thr Val Arg Lys Ile Arg Asp Ala Ile Asp Asn Gln Thr Glu Val Thr
                115                 120                 125

Val Gln Leu Ile Asn Tyr Thr Lys Ser Gly Lys Lys Phe Trp Asn Leu
    130                 135                 140

Phe His Leu Gln Pro Met Arg Asp Gln Lys Gly Asp Val Gln Tyr Phe
145                 150                 155                 160

Ile Gly Val Gln Leu Asp Gly Thr Glu His Val Arg Asp Ala Ala Glu
                165                 170                 175

Arg Glu Gly Val Met Leu Ile Lys Lys Thr Ala Glu Asn Ile Asp Glu
                180                 185                 190

Ala Ala Gly Ser Ser Thr Ala Thr Ile Ser Gly Leu Ser Pro Gly
                195                 200                 205

Val Asp Tyr Thr Ile Thr Val Tyr Ala Trp Gly Glu Asp Ser Ala Gly
    210                 215                 220

Tyr Met Phe Met Tyr Ser Pro Ile Ser Ile Asn Tyr Arg Thr Cys
225                 230                 235

<210> SEQ ID NO 31
<211> LENGTH: 258
<212> TYPE: PRT
<213> ORGANISM: Artificial Sequence
<220> FEATURE:
<223> OTHER INFORMATION: His6-HA4-AsLOV2 (SS58 insertion, C450V mutant)

<400> SEQUENCE: 31

His His His His His His Ser Ser Gly Glu Asn Leu Tyr Phe Gln Gly
```

```
                1               5                    10                  15
        His Ala Ser Gly Ser Ser Val Ser Val Pro Thr Lys Leu Glu Val
                        20                  25                  30
        Val Ala Ala Thr Pro Thr Ser Leu Leu Ile Ser Trp Asp Ala Pro Met
                        35                  40                  45
        Ser Ser Ser Ser Val Tyr Tyr Tyr Arg Ile Thr Tyr Gly Glu Thr Gly
                50                      55                  60
        Gly Asn Ser Pro Val Gln Glu Phe Thr Val Pro Tyr Ser Gly Leu Glu
         65                     70                  75                  80
        Arg Ile Glu Lys Asn Phe Val Ile Thr Asp Pro Arg Leu Pro Asp Asn
                            85                  90                  95
        Pro Ile Ile Phe Ala Ser Asp Ser Phe Leu Gln Leu Thr Glu Tyr Ser
                        100                 105                 110
        Arg Glu Glu Ile Leu Gly Arg Asn Val Arg Phe Leu Gln Gly Pro Glu
                        115                 120                 125
        Thr Asp Arg Ala Thr Val Arg Lys Ile Arg Asp Ala Ile Asp Asn Gln
                130                 135                 140
        Thr Glu Val Thr Val Gln Leu Ile Asn Tyr Thr Lys Ser Gly Lys Lys
        145                 150                 155                 160
        Phe Trp Asn Leu Phe His Leu Gln Pro Met Arg Asp Gln Lys Gly Asp
                            165                 170                 175
        Val Gln Tyr Phe Ile Gly Val Gln Leu Asp Gly Thr Glu His Val Arg
                        180                 185                 190
        Asp Ala Ala Glu Arg Glu Gly Val Met Leu Ile Lys Lys Thr Ala Glu
                        195                 200                 205
        Asn Ile Asp Glu Ala Ala Gly Ser Ser Thr Ala Thr Ile Ser Gly Leu
                    210                 215                 220
        Ser Pro Gly Val Asp Tyr Thr Ile Thr Val Tyr Ala Trp Gly Glu Asp
        225                 230                 235                 240
        Ser Ala Gly Tyr Met Phe Met Tyr Ser Pro Ile Ser Ile Asn Tyr Arg
                        245                 250                 255
        Thr Cys

<210> SEQ ID NO 32
<211> LENGTH: 678
<212> TYPE: PRT
<213> ORGANISM: Artificial Sequence
<220> FEATURE:
<223> OTHER INFORMATION: SH2-PDC1

<400> SEQUENCE: 32

Met Gly Ser Leu Glu Lys His Ser Trp Tyr His Gly Pro Val Ser Arg
        1               5                   10                  15
        Asn Ala Ala Glu Tyr Leu Leu Ser Ser Gly Ile Asn Gly Ser Phe Leu
                        20                  25                  30
        Val Arg Glu Ser Glu Ser Ser Pro Gly Gln Arg Ser Ile Ser Leu Arg
                        35                  40                  45
        Tyr Glu Gly Arg Val Tyr His Tyr Arg Ile Asn Thr Ala Ser Asp Gly
                    50                  55                  60
        Lys Leu Tyr Val Ser Ser Glu Ser Arg Phe Asn Thr Leu Ala Glu Leu
        65                      70                  75                  80
        Val His His His Ser Thr Val Ala Asp Gly Leu Ile Thr Thr Leu His
                        85                  90                  95
        Tyr Pro Ala Pro Lys Arg Asn Lys Pro Thr Val Tyr Gly Val Ser Pro
                        100                 105                 110
```

-continued

```
Asn Tyr Ala Ser Ser Glu Ile Thr Leu Gly Lys Tyr Leu Phe Glu Arg
            115                 120                 125

Leu Lys Gln Val Asn Val Asn Thr Val Phe Gly Leu Pro Gly Asp Phe
    130                 135                 140

Asn Leu Ser Leu Leu Asp Lys Ile Tyr Glu Val Glu Gly Met Arg Trp
145                 150                 155                 160

Ala Gly Asn Ala Asn Glu Leu Asn Ala Ala Tyr Ala Ala Asp Gly Tyr
                165                 170                 175

Ala Arg Ile Lys Gly Met Ser Cys Ile Ile Thr Thr Phe Gly Val Gly
                180                 185                 190

Glu Leu Ser Ala Leu Asn Gly Ile Ala Gly Ser Tyr Ala Glu His Val
            195                 200                 205

Gly Val Leu His Val Val Gly Val Pro Ser Ile Ser Ala Gln Ala Lys
    210                 215                 220

Gln Leu Leu Leu His His Thr Leu Gly Asn Gly Asp Phe Thr Val Phe
225                 230                 235                 240

His Arg Met Ser Ala Asn Ile Ser Glu Thr Thr Ala Met Ile Thr Asp
                245                 250                 255

Ile Ala Thr Ala Pro Ala Glu Ile Asp Arg Cys Ile Arg Thr Thr Tyr
                260                 265                 270

Val Thr Gln Arg Pro Val Tyr Leu Gly Leu Pro Ala Asn Leu Val Asp
            275                 280                 285

Leu Asn Val Pro Ala Lys Leu Leu Gln Thr Pro Ile Asp Met Ser Leu
290                 295                 300

Lys Pro Asn Asp Ala Glu Ser Glu Lys Glu Val Ile Asp Thr Ile Leu
305                 310                 315                 320

Ala Leu Val Lys Asp Ala Lys Asn Pro Val Ile Leu Ala Asp Ala Cys
                325                 330                 335

Cys Ser Arg His Asp Val Lys Ala Glu Thr Lys Lys Leu Ile Asp Leu
                340                 345                 350

Thr Gln Phe Pro Ala Phe Val Thr Pro Met Gly Lys Gly Ser Ile Asp
            355                 360                 365

Glu Gln His Pro Arg Tyr Gly Gly Val Tyr Val Gly Thr Leu Ser Lys
    370                 375                 380

Pro Glu Val Lys Glu Ala Val Glu Ser Ala Asp Leu Ile Leu Ser Val
385                 390                 395                 400

Gly Ala Leu Leu Ser Asp Phe Asn Thr Gly Ser Phe Ser Tyr Ser Tyr
                405                 410                 415

Lys Thr Lys Asn Ile Val Glu Phe His Ser Asp His Met Lys Ile Arg
                420                 425                 430

Asn Ala Thr Phe Pro Gly Val Gln Met Lys Phe Val Leu Gln Lys Leu
            435                 440                 445

Leu Thr Thr Ile Ala Asp Ala Ala Lys Gly Tyr Lys Pro Val Ala Val
    450                 455                 460

Pro Ala Arg Thr Pro Ala Asn Ala Ala Val Pro Ala Ser Thr Pro Leu
465                 470                 475                 480

Lys Gln Glu Trp Met Trp Asn Gln Leu Gly Asn Phe Leu Gln Glu Gly
                485                 490                 495

Asp Val Val Ile Ala Glu Thr Gly Thr Ser Ala Phe Gly Ile Asn Gln
                500                 505                 510

Thr Thr Phe Pro Asn Asn Thr Tyr Gly Ile Ser Gln Val Leu Trp Gly
            515                 520                 525
```

Ser Ile Gly Phe Thr Thr Gly Ala Thr Leu Gly Ala Ala Phe Ala Ala
530                 535                 540

Glu Glu Ile Asp Pro Lys Lys Arg Val Ile Leu Phe Ile Gly Asp Gly
545                 550                 555                 560

Ser Leu Gln Leu Thr Val Gln Glu Ile Ser Thr Met Ile Arg Trp Gly
                565                 570                 575

Leu Lys Pro Tyr Leu Phe Val Leu Asn Asn Asp Gly Tyr Thr Ile Glu
                580                 585                 590

Lys Leu Ile His Gly Pro Lys Ala Gln Tyr Asn Glu Ile Gln Gly Trp
                595                 600                 605

Asp His Leu Ser Leu Leu Pro Thr Phe Gly Ala Lys Asp Tyr Glu Thr
                610                 615                 620

His Arg Val Ala Thr Thr Gly Glu Trp Asp Lys Leu Thr Gln Asp Lys
625                 630                 635                 640

Ser Phe Asn Asp Asn Ser Lys Ile Arg Met Ile Glu Ile Met Leu Pro
                645                 650                 655

Val Phe Asp Ala Pro Gln Asn Leu Val Glu Gln Ala Lys Leu Thr Ala
                660                 665                 670

Ala Thr Asn Ala Lys Gln
                675

<210> SEQ ID NO 33
<211> LENGTH: 351
<212> TYPE: PRT
<213> ORGANISM: Artificial Sequence
<220> FEATURE:
<223> OTHER INFORMATION: His6-SUMO-HA4-AsLOV2 (SS58 insertion, V416I,
      G528A, N538E mutant)

<400> SEQUENCE: 33

His His His His His His Gly Ser Gly Ser Gly Ser Asp Gln Glu Ala
1               5                   10                  15

Lys Pro Ser Thr Glu Asp Leu Gly Asp Lys Lys Glu Gly Glu Tyr Ile
                20                  25                  30

Lys Leu Lys Val Ile Gly Gln Asp Ser Ser Glu Ile His Phe Lys Val
                35                  40                  45

Lys Met Thr Thr His Leu Lys Lys Leu Lys Glu Ser Tyr Cys Gln Arg
50                  55                  60

Gln Gly Val Pro Met Asn Ser Leu Arg Phe Leu Phe Glu Gly Gln Arg
65                  70                  75                  80

Ile Ala Asp Asn His Thr Pro Lys Glu Leu Gly Met Glu Glu Glu Asp
                85                  90                  95

Val Ile Glu Val Tyr Gln Glu Gln Thr Gly Gly His Met Ala Ser Lys
                100                 105                 110

Gly Ser Ser Val Ser Ser Val Pro Thr Lys Leu Glu Val Val Ala Ala
                115                 120                 125

Thr Pro Thr Ser Leu Leu Ile Ser Trp Asp Ala Pro Met Ser Ser Ser
                130                 135                 140

Ser Val Tyr Tyr Tyr Arg Ile Thr Tyr Gly Glu Thr Gly Gly Asn Ser
145                 150                 155                 160

Pro Val Gln Glu Phe Thr Val Pro Tyr Ser Gly Leu Glu Arg Ile Glu
                165                 170                 175

Lys Asn Phe Ile Ile Thr Asp Pro Arg Leu Pro Asp Asn Pro Ile Ile
                180                 185                 190

Phe Ala Ser Asp Ser Phe Leu Gln Leu Thr Glu Tyr Ser Arg Glu Glu
                195                 200                 205

```
Ile Leu Gly Arg Asn Cys Arg Phe Leu Gln Gly Pro Glu Thr Asp Arg
    210                 215                 220

Ala Thr Val Arg Lys Ile Arg Asp Ala Ile Asp Asn Gln Thr Glu Val
225                 230                 235                 240

Thr Val Gln Leu Ile Asn Tyr Thr Lys Ser Gly Lys Lys Phe Trp Asn
                245                 250                 255

Leu Phe His Leu Gln Pro Met Arg Asp Gln Lys Gly Asp Val Gln Tyr
            260                 265                 270

Phe Ile Gly Val Gln Leu Asp Gly Thr Glu His Val Arg Asp Ala Ala
        275                 280                 285

Glu Arg Glu Ala Val Met Leu Ile Lys Lys Thr Ala Glu Glu Ile Asp
    290                 295                 300

Glu Ala Ala Gly Ser Ser Thr Ala Thr Ile Ser Gly Leu Ser Pro Gly
305                 310                 315                 320

Val Asp Tyr Thr Ile Thr Val Tyr Ala Trp Gly Glu Asp Ser Ala Gly
                325                 330                 335

Tyr Met Phe Met Tyr Ser Pro Ile Ser Ile Asn Tyr Arg Thr Cys
            340                 345                 350

<210> SEQ ID NO 34
<211> LENGTH: 258
<212> TYPE: PRT
<213> ORGANISM: Artificial Sequence
<220> FEATURE:
<223> OTHER INFORMATION: His6-HA4-AsLOV2 (SS58 insertion, V416I mutant)

<400> SEQUENCE: 34

His His His His His His Ser Ser Gly Glu Asn Leu Tyr Phe Gln Gly
1               5                   10                  15

His Ala Ser Gly Ser Ser Val Ser Val Pro Thr Lys Leu Glu Val
            20                  25                  30

Val Ala Ala Thr Pro Thr Ser Leu Leu Ile Ser Trp Asp Ala Pro Met
        35                  40                  45

Ser Ser Ser Ser Val Tyr Tyr Tyr Arg Ile Thr Tyr Gly Glu Thr Gly
50                  55                  60

Gly Asn Ser Pro Val Gln Glu Phe Thr Val Pro Tyr Ser Gly Leu Glu
65                  70                  75                  80

Arg Ile Glu Lys Asn Phe Ile Ile Thr Asp Pro Arg Leu Pro Asp Asn
                85                  90                  95

Pro Ile Ile Phe Ala Ser Asp Ser Phe Leu Gln Leu Thr Glu Tyr Ser
            100                 105                 110

Arg Glu Glu Ile Leu Gly Arg Asn Cys Arg Phe Leu Gln Gly Pro Glu
        115                 120                 125

Thr Asp Arg Ala Thr Val Arg Lys Ile Arg Asp Ala Ile Asp Asn Gln
    130                 135                 140

Thr Glu Val Thr Val Gln Leu Ile Asn Tyr Thr Lys Ser Gly Lys Lys
145                 150                 155                 160

Phe Trp Asn Leu Phe His Leu Gln Pro Met Arg Asp Gln Lys Gly Asp
                165                 170                 175

Val Gln Tyr Phe Ile Gly Val Gln Leu Asp Gly Thr Glu His Val Arg
            180                 185                 190

Asp Ala Ala Glu Arg Glu Gly Val Met Leu Ile Lys Lys Thr Ala Glu
        195                 200                 205

Asn Ile Asp Glu Ala Ala Gly Ser Ser Thr Ala Thr Ile Ser Gly Leu
    210                 215                 220
```

Ser Pro Gly Val Asp Tyr Thr Ile Thr Val Tyr Ala Trp Gly Glu Asp
225                 230                 235                 240

Ser Ala Gly Tyr Met Phe Met Tyr Ser Pro Ile Ser Ile Asn Tyr Arg
            245                 250                 255

Thr Cys

<210> SEQ ID NO 35
<211> LENGTH: 431
<212> TYPE: PRT
<213> ORGANISM: Artificial Sequence
<220> FEATURE:
<223> OTHER INFORMATION: HA4-irFP

<400> SEQUENCE: 35

Met Gly Ser Ser Val Ser Ser Val Pro Thr Lys Leu Glu Val Val Ala
1               5                   10                  15

Ala Thr Pro Thr Ser Leu Leu Ile Ser Trp Asp Ala Pro Met Ser Ser
            20                  25                  30

Ser Ser Val Tyr Tyr Tyr Arg Ile Thr Tyr Gly Glu Thr Gly Gly Asn
            35                  40                  45

Ser Pro Val Gln Glu Phe Thr Val Pro Tyr Ser Ser Ser Thr Ala Thr
    50                  55                  60

Ile Ser Gly Leu Ser Pro Gly Val Asp Tyr Thr Ile Thr Val Tyr Ala
65              70                  75                  80

Trp Gly Glu Asp Ser Ala Gly Tyr Met Phe Met Tyr Ser Pro Ile Ser
                85                  90                  95

Ile Asn Tyr Arg Thr Cys Gly Gly Gly Ala Glu Gly Ser Val Ala Arg
            100                 105                 110

Gln Pro Asp Leu Leu Thr Cys Asp Asp Glu Pro Ile His Ile Pro Gly
        115                 120                 125

Ala Ile Gln Pro His Gly Leu Leu Leu Ala Leu Ala Ala Asp Met Thr
    130                 135                 140

Ile Val Ala Gly Ser Asp Asn Leu Pro Glu Leu Thr Gly Leu Ala Ile
145                 150                 155                 160

Gly Ala Leu Ile Gly Arg Ser Ala Ala Asp Val Phe Asp Ser Glu Thr
                165                 170                 175

His Asn Arg Leu Thr Ile Ala Leu Ala Glu Pro Gly Ala Ala Val Gly
            180                 185                 190

Ala Pro Ile Thr Val Gly Phe Thr Met Arg Lys Asp Ala Gly Phe Ile
        195                 200                 205

Gly Ser Trp His Arg His Asp Gln Leu Ile Phe Leu Glu Leu Glu Pro
    210                 215                 220

Pro Gln Arg Asp Val Ala Glu Pro Gln Ala Phe Phe Arg Arg Thr Asn
225                 230                 235                 240

Ser Ala Ile Arg Arg Leu Gln Ala Ala Glu Thr Leu Glu Ser Ala Cys
                245                 250                 255

Ala Ala Ala Ala Gln Glu Val Arg Lys Ile Thr Gly Phe Asp Arg Val
            260                 265                 270

Met Ile Tyr Arg Phe Ala Ser Asp Phe Ser Gly Glu Val Ile Ala Glu
        275                 280                 285

Asp Arg Cys Ala Glu Val Glu Ser Lys Leu Gly Leu His Tyr Pro Ala
    290                 295                 300

Ser Thr Val Pro Ala Gln Ala Arg Arg Leu Tyr Thr Ile Asn Pro Val
305                 310                 315                 320

```
Arg Ile Ile Pro Asp Ile Asn Tyr Arg Pro Val Pro Val Thr Pro Asp
            325                 330                 335

Leu Asn Pro Val Thr Gly Arg Pro Ile Asp Leu Ser Phe Ala Ile Leu
            340                 345                 350

Arg Ser Val Ser Pro Val His Leu Glu Phe Met Arg Asn Ile Gly Met
            355                 360                 365

His Gly Thr Met Ser Ile Ser Ile Leu Arg Gly Glu Arg Leu Trp Gly
            370                 375                 380

Leu Ile Val Cys His His Arg Thr Pro Tyr Tyr Val Asp Leu Asp Gly
385                 390                 395                 400

Arg Gln Ala Cys Glu Leu Val Ala Gln Val Leu Ala Trp Gln Ile Gly
            405                 410                 415

Val Met Glu Glu Ala Ala Ala Thr Pro Thr Cys Asn Met Arg Asp
            420                 425                 430

<210> SEQ ID NO 36
<211> LENGTH: 569
<212> TYPE: PRT
<213> ORGANISM: Artificial Sequence
<220> FEATURE:
<223> OTHER INFORMATION: HA4-AsLOV2-irFP (SS58 insertion)

<400> SEQUENCE: 36

Met Gly Ser Ser Val Ser Ser Val Pro Thr Lys Leu Glu Val Val Ala
1               5                   10                  15

Ala Thr Pro Thr Ser Leu Leu Ile Ser Trp Asp Ala Pro Met Ser Ser
            20                  25                  30

Ser Ser Val Tyr Tyr Tyr Arg Ile Thr Tyr Gly Glu Thr Gly Gly Asn
            35                  40                  45

Ser Pro Val Gln Glu Phe Thr Val Pro Tyr Ser Gly Leu Glu Arg Ile
        50                  55                  60

Glu Lys Asn Phe Val Ile Thr Asp Pro Arg Leu Pro Asp Asn Pro Ile
65                  70                  75                  80

Ile Phe Ala Ser Asp Ser Phe Leu Gln Leu Thr Glu Tyr Ser Arg Glu
                85                  90                  95

Glu Ile Leu Gly Arg Asn Cys Arg Phe Leu Gln Gly Pro Glu Thr Asp
            100                 105                 110

Arg Ala Thr Val Arg Lys Ile Arg Asp Ala Ile Asp Asn Gln Thr Glu
        115                 120                 125

Val Thr Val Gln Leu Ile Asn Tyr Thr Lys Ser Gly Lys Lys Phe Trp
130                 135                 140

Asn Leu Phe His Leu Gln Pro Met Arg Asp Gln Lys Gly Asp Val Gln
145                 150                 155                 160

Tyr Phe Ile Gly Val Gln Leu Asp Gly Thr Glu His Val Arg Asp Ala
                165                 170                 175

Ala Glu Arg Glu Gly Val Met Leu Ile Lys Lys Thr Ala Glu Asn Ile
            180                 185                 190

Asp Glu Ala Ala Gly Ser Ser Thr Ala Thr Ile Ser Gly Leu Ser Pro
        195                 200                 205

Gly Val Asp Tyr Thr Ile Thr Val Tyr Ala Trp Gly Glu Asp Ser Ala
210                 215                 220

Gly Tyr Met Phe Met Tyr Ser Pro Ile Ser Ile Asn Tyr Arg Thr Cys
225                 230                 235                 240

Gly Gly Gly Ala Glu Gly Ser Val Ala Arg Gln Pro Asp Leu Leu Thr
            245                 250                 255
```

-continued

```
Cys Asp Asp Glu Pro Ile His Ile Pro Gly Ala Ile Gln Pro His Gly
            260                 265                 270

Leu Leu Leu Ala Leu Ala Ala Asp Met Thr Ile Val Ala Gly Ser Asp
        275                 280                 285

Asn Leu Pro Glu Leu Thr Gly Leu Ala Ile Gly Ala Leu Ile Gly Arg
    290                 295                 300

Ser Ala Ala Asp Val Phe Asp Ser Glu Thr His Asn Arg Leu Thr Ile
305                 310                 315                 320

Ala Leu Ala Glu Pro Gly Ala Val Gly Ala Pro Ile Thr Val Gly
                325                 330                 335

Phe Thr Met Arg Lys Asp Ala Gly Phe Ile Gly Ser Trp His Arg His
            340                 345                 350

Asp Gln Leu Ile Phe Leu Glu Leu Pro Pro Gln Arg Asp Val Ala
        355                 360                 365

Glu Pro Gln Ala Phe Phe Arg Arg Thr Asn Ser Ala Ile Arg Arg Leu
    370                 375                 380

Gln Ala Ala Glu Thr Leu Glu Ser Ala Cys Ala Ala Ala Gln Glu
385                 390                 395                 400

Val Arg Lys Ile Thr Gly Phe Asp Arg Val Met Ile Tyr Arg Phe Ala
                405                 410                 415

Ser Asp Phe Ser Gly Glu Val Ile Ala Glu Asp Arg Cys Ala Glu Val
            420                 425                 430

Glu Ser Lys Leu Gly Leu His Tyr Pro Ala Ser Thr Val Pro Ala Gln
        435                 440                 445

Ala Arg Arg Leu Tyr Thr Ile Asn Pro Val Arg Ile Ile Pro Asp Ile
    450                 455                 460

Asn Tyr Arg Pro Val Pro Val Thr Pro Asp Leu Asn Pro Val Thr Gly
465                 470                 475                 480

Arg Pro Ile Asp Leu Ser Phe Ala Ile Leu Arg Ser Val Ser Pro Val
                485                 490                 495

His Leu Glu Phe Met Arg Asn Ile Gly Met His Gly Thr Met Ser Ile
            500                 505                 510

Ser Ile Leu Arg Gly Glu Arg Leu Trp Gly Leu Ile Val Cys His His
        515                 520                 525

Arg Thr Pro Tyr Tyr Val Asp Leu Asp Gly Arg Gln Ala Cys Glu Leu
    530                 535                 540

Val Ala Gln Val Leu Ala Trp Gln Ile Gly Val Met Glu Glu Ala Ala
545                 550                 555                 560

Ala Thr Pro Thr Cys Asn Met Arg Asp
                565

<210> SEQ ID NO 37
<211> LENGTH: 368
<212> TYPE: PRT
<213> ORGANISM: Artificial Sequence
<220> FEATURE:
<223> OTHER INFORMATION: SH2-mCherry-CAAX

<400> SEQUENCE: 37

Met Ser Leu Glu Lys His Ser Trp Tyr His Gly Pro Val Ser Arg Asn
1               5                   10                  15

Ala Ala Glu Tyr Leu Leu Ser Ser Gly Ile Asn Gly Ser Phe Leu Val
            20                  25                  30

Arg Glu Ser Glu Ser Ser Pro Gly Gln Arg Ser Ile Ser Leu Arg Tyr
        35                  40                  45
```

```
Glu Gly Arg Val Tyr His Tyr Arg Ile Asn Thr Ala Ser Asp Gly Lys
            50                  55                  60

Leu Tyr Val Ser Ser Glu Ser Arg Phe Asn Thr Leu Ala Glu Leu Val
 65                  70                  75                  80

His His His Ser Thr Val Ala Asp Gly Leu Ile Thr Thr Leu His Tyr
                 85                  90                  95

Pro Ala Pro Lys Arg Asn Lys Pro Thr Val Tyr Gly Val Ser Pro Asn
                100                 105                 110

Tyr Val Ser Lys Gly Glu Glu Asp Asn Met Ala Ile Ile Lys Glu Phe
                115                 120                 125

Met Arg Phe Lys Val His Met Glu Gly Ser Val Asn Gly His Glu Phe
130                 135                 140

Glu Ile Glu Gly Glu Gly Glu Gly Arg Pro Tyr Glu Gly Thr Gln Thr
145                 150                 155                 160

Ala Lys Leu Lys Val Thr Lys Gly Gly Pro Leu Pro Phe Ala Trp Asp
                165                 170                 175

Ile Leu Ser Pro Gln Phe Met Tyr Gly Ser Lys Ala Tyr Val Lys His
                180                 185                 190

Pro Ala Asp Ile Pro Asp Tyr Leu Lys Leu Ser Phe Pro Glu Gly Phe
                195                 200                 205

Lys Trp Glu Arg Val Met Asn Phe Glu Asp Gly Gly Val Val Thr Val
210                 215                 220

Thr Gln Asp Ser Ser Leu Gln Asp Gly Glu Phe Ile Tyr Lys Val Lys
225                 230                 235                 240

Leu Arg Gly Thr Asn Phe Pro Ser Asp Gly Pro Val Met Gln Lys Lys
                245                 250                 255

Thr Met Gly Trp Glu Ala Ser Ser Glu Arg Met Tyr Pro Glu Asp Gly
                260                 265                 270

Ala Leu Lys Gly Glu Ile Lys Gln Arg Leu Lys Leu Lys Asp Gly Gly
                275                 280                 285

His Tyr Asp Ala Glu Val Lys Thr Thr Tyr Lys Ala Lys Lys Pro Val
290                 295                 300

Gln Leu Pro Gly Ala Tyr Asn Val Asn Ile Lys Leu Asp Ile Thr Ser
305                 310                 315                 320

His Asn Glu Asp Tyr Thr Ile Val Glu Gln Tyr Glu Arg Ala Glu Gly
                325                 330                 335

Arg His Ser Thr Gly Gly Met Asp Glu Leu Tyr Lys Gly Ser Gly Ser
                340                 345                 350

Gly Ser Lys Lys Lys Lys Lys Ser Lys Thr Lys Cys Val Ile Met
                355                 360                 365
```

<210> SEQ ID NO 38
<211> LENGTH: 43
<212> TYPE: PRT
<213> ORGANISM: Artificial Sequence
<220> FEATURE:
<223> OTHER INFORMATION: Residues 1-43 of LaM8

<400> SEQUENCE: 38

```
Gln Val Gln Leu Val Glu Ser Gly Gly Gly Leu Val Gln Ala Gly Gly
 1               5                  10                  15

Ser Leu Arg Leu Ser Cys Ala Val Ser Gly Arg Pro Phe Ser Glu Tyr
                20                  25                  30

Asn Leu Gly Trp Phe Arg Gln Ala Pro Gly Lys
                35                  40
```

```
<210> SEQ ID NO 39
<211> LENGTH: 43
<212> TYPE: PRT
<213> ORGANISM: Artificial Sequence
<220> FEATURE:
<223> OTHER INFORMATION: Residues 1-43 of LaM4

<400> SEQUENCE: 39

Gln Val Gln Leu Val Glu Ser Gly Gly Ser Leu Val Gln Pro Gly Gly
1               5                   10                  15

Ser Leu Arg Leu Ser Cys Ala Ala Ser Gly Arg Phe Ala Glu Ser Ser
            20                  25                  30

Ser Met Gly Trp Phe Arg Gln Ala Pro Gly Lys
        35                  40

<210> SEQ ID NO 40
<211> LENGTH: 44
<212> TYPE: PRT
<213> ORGANISM: Artificial Sequence
<220> FEATURE:
<223> OTHER INFORMATION: Residues 1-44 of LaG9

<400> SEQUENCE: 40

Ala Asp Val Gln Leu Val Glu Ser Gly Gly Gly Leu Val Gln Ala Gly
1               5                   10                  15

Gly Ser Leu Arg Leu Ser Cys Ala Ala Ser Gly Arg Thr Phe Ser Thr
            20                  25                  30

Ser Ala Met Gly Trp Phe Arg Gln Ala Pro Gly Lys
        35                  40

<210> SEQ ID NO 41
<211> LENGTH: 42
<212> TYPE: PRT
<213> ORGANISM: Artificial Sequence
<220> FEATURE:
<223> OTHER INFORMATION: Residues 44-85 of LaM8

<400> SEQUENCE: 41

Glu Arg Glu Phe Val Ala Arg Ile Arg Ser Ser Gly Thr Thr Val Tyr
1               5                   10                  15

Thr Asp Ser Val Lys Gly Arg Phe Ala Ser Arg Asp Asn Ala Lys
            20                  25                  30

Asn Met Gly Tyr Leu Gln Leu Asn Ser Leu
        35                  40

<210> SEQ ID NO 42
<211> LENGTH: 43
<212> TYPE: PRT
<213> ORGANISM: Artificial Sequence
<220> FEATURE:
<223> OTHER INFORMATION: Residues 44-86 of LaM4

<400> SEQUENCE: 42

Glu Arg Glu Phe Val Ala Ala Ile Ser Trp Ser Gly Gly Ala Thr Asn
1               5                   10                  15

Tyr Ala Asp Ser Ala Lys Gly Arg Phe Thr Leu Ser Arg Asp Asn Thr
            20                  25                  30

Lys Asn Thr Val Tyr Leu Gln Met Asn Ser Leu
        35                  40

<210> SEQ ID NO 43
<211> LENGTH: 43
```

```
<212> TYPE: PRT
<213> ORGANISM: Artificial Sequence
<220> FEATURE:
<223> OTHER INFORMATION: Residues 45-87 of LaG9

<400> SEQUENCE: 43

Glu Arg Glu Phe Val Ala Arg Ile Thr Trp Ser Ala Gly Tyr Thr Ala
1               5                   10                  15

Tyr Ser Asp Ser Val Lys Gly Arg Phe Thr Ile Ser Arg Asp Lys Ala
            20                  25                  30

Lys Asn Thr Val Tyr Leu Gln Met Asn Ser Leu
        35                  40

<210> SEQ ID NO 44
<211> LENGTH: 39
<212> TYPE: PRT
<213> ORGANISM: Artificial Sequence
<220> FEATURE:
<223> OTHER INFORMATION: Residues 86-124 of LaM8

<400> SEQUENCE: 44

Glu Phe Glu Asp Thr Ala Val Tyr Tyr Cys Ala Met Ser Arg Val Asp
1               5                   10                  15

Thr Asp Ser Pro Ala Phe Tyr Asp Tyr Trp Gly Gln Gly Thr Gln Val
            20                  25                  30

Thr Val Ser Thr Pro Arg Ser
        35

<210> SEQ ID NO 45
<211> LENGTH: 41
<212> TYPE: PRT
<213> ORGANISM: Artificial Sequence
<220> FEATURE:
<223> OTHER INFORMATION: Residues 87-127 of LaM4

<400> SEQUENCE: 45

Lys Pro Asp Asp Thr Ala Val Tyr Tyr Cys Ala Ala Asn Leu Gly Asn
1               5                   10                  15

Tyr Ile Ser Ser Asn Gln Arg Leu Tyr Gly Tyr Trp Gly Gln Gly Thr
            20                  25                  30

Gln Val Thr Val Ser Ser Pro Phe Thr
        35                  40

<210> SEQ ID NO 46
<211> LENGTH: 39
<212> TYPE: PRT
<213> ORGANISM: Artificial Sequence
<220> FEATURE:
<223> OTHER INFORMATION: Residues 88-126 of LaG9

<400> SEQUENCE: 46

Lys Pro Glu Asp Thr Ala Val Tyr Tyr Cys Ala Ser Arg Ser Ala Gly
1               5                   10                  15

Tyr Ser Ser Ser Leu Thr Arg Arg Glu Asp Tyr Ala Tyr Trp Gly Gln
            20                  25                  30

Gly Thr Gln Val Thr Val Ser
        35

<210> SEQ ID NO 47
<211> LENGTH: 138
<212> TYPE: PRT
<213> ORGANISM: Artificial Sequence
<220> FEATURE:
```

<223> OTHER INFORMATION: AsLOV2 V416I, G528A, N538E mutant

<400> SEQUENCE: 47

```
Gly Leu Glu Arg Ile Glu Lys Asn Phe Ile Ile Thr Asp Pro Arg Leu
1               5                   10                  15
Pro Asp Asn Pro Ile Ile Phe Ala Ser Asp Ser Phe Leu Gln Leu Thr
            20                  25                  30
Glu Tyr Ser Arg Glu Glu Ile Leu Gly Arg Asn Cys Arg Phe Leu Gln
        35                  40                  45
Gly Pro Glu Thr Asp Arg Ala Thr Val Arg Lys Ile Arg Asp Ala Ile
    50                  55                  60
Asp Asn Gln Thr Glu Val Thr Val Gln Leu Ile Asn Tyr Thr Lys Ser
65                  70                  75                  80
Gly Lys Lys Phe Trp Asn Leu Phe His Leu Gln Pro Met Arg Asp Gln
                85                  90                  95
Lys Gly Asp Val Gln Tyr Phe Ile Gly Val Gln Leu Asp Gly Thr Glu
            100                 105                 110
His Val Arg Asp Ala Ala Glu Arg Glu Ala Val Met Leu Ile Lys Lys
        115                 120                 125
Thr Ala Glu Glu Ile Asp Glu Ala Ala Gly
    130                 135
```

<210> SEQ ID NO 48
<211> LENGTH: 138
<212> TYPE: PRT
<213> ORGANISM: Artificial Sequence
<220> FEATURE:
<223> OTHER INFORMATION: AsLOV2 V416I mutant

<400> SEQUENCE: 48

```
Gly Leu Glu Arg Ile Glu Lys Asn Phe Ile Ile Thr Asp Pro Arg Leu
1               5                   10                  15
Pro Asp Asn Pro Ile Ile Phe Ala Ser Asp Ser Phe Leu Gln Leu Thr
            20                  25                  30
Glu Tyr Ser Arg Glu Glu Ile Leu Gly Arg Asn Cys Arg Phe Leu Gln
        35                  40                  45
Gly Pro Glu Thr Asp Arg Ala Thr Val Arg Lys Ile Arg Asp Ala Ile
    50                  55                  60
Asp Asn Gln Thr Glu Val Thr Val Gln Leu Ile Asn Tyr Thr Lys Ser
65                  70                  75                  80
Gly Lys Lys Phe Trp Asn Leu Phe His Leu Gln Pro Met Arg Asp Gln
                85                  90                  95
Lys Gly Asp Val Gln Tyr Phe Ile Gly Val Gln Leu Asp Gly Thr Glu
            100                 105                 110
His Val Arg Asp Ala Ala Glu Arg Glu Gly Val Met Leu Ile Lys Lys
        115                 120                 125
Thr Ala Glu Asn Ile Asp Glu Ala Ala Gly
    130                 135
```

<210> SEQ ID NO 49
<211> LENGTH: 6
<212> TYPE: PRT
<213> ORGANISM: Artificial Sequence
<220> FEATURE:
<223> OTHER INFORMATION: histidine tag

<400> SEQUENCE: 49

His His His His His His

```
<210> SEQ ID NO 50
<211> LENGTH: 6
<212> TYPE: PRT
<213> ORGANISM: Artificial Sequence
<220> FEATURE:
<223> OTHER INFORMATION: polyglycine linker

<400> SEQUENCE: 50

Gly Gly Gly Gly Gly Gly
1               5
```

LIGHT-RESPONSIVE FUSION PROTEINS FOR CONTROLLING BINDING TO TARGETS

RELATED APPLICATIONS

This application is a continuation-in-part of International Application No. PCT/US2018/063447, filed on Nov. 30, 2018, which claims the benefit of U.S. Provisional Application No. 62/593,750, filed on Dec. 1, 2017, and this application claims the benefit of U.S. Provisional Application No. 62/962,517, filed on Jan. 17, 2020.

GOVERNMENT SUPPORT

This invention was made with government support under Grant No. EB024247 and F32GM128304-01 awarded by the National Institutes of Health. The government has certain rights in the invention.

The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith: File name: 53911010003_Sequence_Listing.txt; created Mar. 21, 2023, 99,393 Bytes in size.

BACKGROUND

Developing stringent control over the activity of biological therapies could potentially unlock a new level of therapeutic potential for already-potent treatments. Unlike traditional therapeutic agents, such controlled therapies could integrate user-defined information to determine activity. For example, a user could define where and when therapeutic behaviors are executed, allowing biological therapies to overcome dosing limitations of their inert pharmaceutical counterparts while at the same time limiting off-target side effects. In theory, all drugs could be maximally dosed (and thereby maximally effective) if they could be selectively delivered only at the right location and at the right time.

Manufactured proteins are a ubiquitous part of the $21^{st}$ century economy. These engineered molecules play crucial roles in medicine, manufacturing, biotechnology, energy production, agriculture, and even cosmetics and beauty products. Indeed, beauty companies now produce protein ingredients by the ton and protein-based biopharmaceuticals make up nine of the 10 top-earning drugs. However, while proteins allow for manipulation of complex chemical and biological systems, an ability to control protein activity is lacking. This means that, for instance, once a given skin care product has been applied or a biopharmaceutical has been administered, it will be active everywhere rather than only where it is needed. In almost every context where manufactured proteins are used, this leads to a reduction in efficacy and, especially in health and cosmetic applications, a reduction in safety, thereby limiting their potential market.

SUMMARY

There is a need for a platform technology that enables caregivers and/or patients to control therapeutic activity of biological therapies. Developing technology that allows user-defined control over the activity of engineered proteins unlocks a new level of both therapeutic and commercial potential for already-potent products. Unlike traditional engineered proteins, such controlled molecules could integrate user-defined information to determine activity. For example, a user could define where and when therapeutic behaviors are executed, allowing light-switchable biopharmaceuticals to overcome dosing limitations of their inert pharmaceutical counterparts while at the same time limiting off-target side effects. In theory, all drugs could be maximally dosed (and thereby maximally effective) if they could be selectively delivered to the right location at the right time.

Beyond therapeutic applications, control over protein binding has further potential applications in biomanufacturing. For example, light-switchable binding scaffolds can improve industrial protein purification via single-step purification columns that reduce the time and money required to obtain a pure product.

Accordingly, provided herein are light-responsive fusion proteins and methods of identifying and using light-responsive fusion proteins, for example, to treat a subject in need thereof.

An embodiment is an isolated fusion protein comprising a light-responsive domain and a heterologous peptide component, wherein exposure of the fusion protein to light induces a conformational change in the fusion protein that alters an activity of the fusion protein and the activity is a binding activity selected from an in vitro binding activity and an in vivo extracellular binding activity.

Another embodiment is a method of altering an activity of a fusion protein comprising a light-responsive domain and a heterologous peptide component. The method comprises exposing the fusion protein to light that induces a conformational change in the fusion protein, thereby altering an activity of the fusion protein. The conformational change alters an activity of the fusion protein and the activity is a binding activity selected from an in vitro binding activity and an in vivo extracellular binding activity.

Another embodiment is a method for treating a subject in need thereof, comprising administering to the subject a therapeutically effective amount of a therapeutic fusion protein comprising a light-responsive domain and a therapeutic protein or peptide, and delivering a sufficient amount of light to at least a portion of the subject to induce the conformational change, thereby altering the therapeutic efficacy of the fusion protein exposed to the light and treating the subject. Exposure of the fusion protein to light induces a conformational change in the fusion protein that alters its therapeutic efficacy.

Another embodiment is a method of identifying a fusion protein comprising a light-responsive domain and a heterologous peptide component, wherein exposure of the fusion protein to light induces a conformational change that alters its ability to bind a target protein. The method comprises providing one or more phages displaying a fusion protein intended to bind a target protein. The fusion protein comprises a light-responsive domain and a heterologous peptide component. The immobilized target protein is exposed to the one or more phages in the presence of light under conditions sufficient to induce binding of the target protein and the fusion protein, and one or more phages is eluted in the absence of light, thereby eluting one or more phages displaying a fusion protein that binds the target protein upon exposure to light and dissociates from the target protein in the absence of light. Alternatively, immobilized target protein is exposed to the one or more phages in the absence of light under conditions sufficient to induce binding of the target protein and the fusion protein, and one or more phages is eluted in the presence of light, thereby eluting one or more phages displaying a fusion protein that binds the target protein in the absence of light and dissociates from the target protein upon exposure to light. A fusion protein comprising a light-responsive domain and a heterologous peptide component, wherein the fusion protein undergoes a light-dependent conformational change that alters its ability to bind the target protein, is thereby identified.

Another embodiment is a method of identifying a fusion protein comprising a light-responsive domain and a heterologous peptide component, wherein exposure of the fusion protein to light induces a conformational change that alters its ability to bind a target protein. The method comprises providing one or more cells expressing a fusion protein intended to bind a target protein. The fusion protein comprises a light-responsive domain and a heterologous peptide component. One or more cells is sorted using fluorescence-activated cell sorting (FACS). Immobilized target protein is exposed to the one or more cells in the presence of light under conditions sufficient to induce binding of the target protein and the fusion protein, and one or more cells is eluted in the absence of light, thereby eluting one or more cells expressing a fusion protein that binds the target protein upon exposure to light and dissociates from the target protein in the absence of light. Alternatively, immobilized target protein is exposed to the one or more cells in the absence of light under conditions sufficient to induce binding of the target protein and the fusion protein, and one or more cells is eluted in the presence of light, thereby eluting one or more cells expressing a fusion protein that binds the target protein in the absence of light and dissociates from the target protein upon exposure to light. A fusion protein comprising a light-responsive domain and a heterologous peptide component, wherein the fusion protein undergoes a photodependent conformational change that alters its ability to bind the target protein, is thereby identified.

Another embodiment is a method of purifying a target protein from a cell lysate. The method comprises providing a substrate comprising an immobilized fusion protein intended to bind a target protein, the fusion protein comprising a light-responsive domain and a heterologous peptide component. Exposure of the fusion protein to light induces a conformational change that alters its ability to bind the target protein. The method comprises exposing the substrate to the cell lysate in the presence of light under conditions sufficient to induce binding of the target protein and the fusion protein; and eluting the target protein in the absence of light, wherein the fusion protein binds the target protein upon exposure to light and dissociates from the target protein in the absence of light, thereby purifying the target protein. Alternatively, the method comprises exposing the substrate to the cell lysate in the absence of light under conditions sufficient to induce binding of the target protein and the fusion protein; and eluting the target protein in the presence of light, wherein the fusion protein binds the target protein in the absence of light and dissociates from the target protein upon exposure to light, thereby purifying the target protein.

Another embodiment is an isolated fusion protein comprising a light-responsive domain, a heterologous peptide component, and a cell-penetrating peptide component, wherein exposure of the fusion protein to light induces a conformational change in the fusion protein that alters an activity (e.g., a binding activity) of the fusion protein.

Another embodiment is a method of delivering a fusion protein to a cell, comprising contacting the cell extracellularly with an isolated fusion protein comprising a light-responsive domain, a heterologous peptide component, and a cell-penetrating peptide component, wherein exposure of the fusion protein to light induces a conformational change in the fusion protein that alters an activity (e.g., a binding activity) of the fusion protein, wherein the fusion protein is delivered intracellularly. In some embodiments, the heterologous peptide component also acts as a cell-penetrating peptide. For example, an antimicrobial peptide can serve as both the heterologous peptide component and cell penetrating peptide (e.g., an antimicrobial peptide can insert into a cell membrane and act as an antimicrobial agent, wherein delivery of the antimicrobial peptide is controlled with light).

Another embodiment is a chimeric antigen receptor (CAR), comprising an extracellular antigen-binding domain, a transmembrane domain and an intracellular signaling domain, wherein the extracellular antigen-binding domain comprises a light-responsive domain and a heterologous peptide component, wherein exposure of the CAR to light induces a conformational change in the extra-cellular antigen-binding domain that alters an activity (e.g., an in vivo extracellular binding activity) of the extra-cellular antigen-binding domain.

Another embodiment is a fusion protein comprising a light-responsive domain and a heterologous peptide component, wherein the heterologous peptide component is selected from the group consisting of a nanobody, a monobody, an antibody, a growth factor, and a designed ankyrin repeat protein (DARPin), wherein exposure of the fusion protein to light induces a conformational change in the fusion protein that alters an activity (e.g., a binding activity) of the fusion protein.

Another embodiment is a method of delivering a fusion protein to a cell, comprising contacting the cell with a fusion protein comprising a light-responsive domain and a heterologous peptide component, wherein the heterologous peptide component is selected from the group consisting of a nanobody, a monobody, an antibody, a growth factor, and a designed ankyrin repeat protein (DARPin), wherein the fusion protein is delivered intracellularly.

Another embodiment is an isolated fusion protein comprising a light oxygen voltage (LOV) domain and a heterologous peptide component selected from a nanobody, monobody, antibody, DARPin or anticalin, wherein exposure of the fusion protein to light induces a conformational change in the fusion protein that alters an activity (e.g., a binding activity) of the fusion protein.

Another embodiment is chromatography media comprising a fusion protein of described herein immobilized (e.g., covalently, non-covalently) to chromatography resin.

Another embodiment is a column (e.g., chromatography column) comprising chromatography media comprising a fusion protein described herein immobilized (e.g., covalently, non-covalently) to chromatography resin.

Another embodiment is a method of purifying a target protein from a cell lysate. The method comprises providing a substrate comprising an immobilized fusion protein intended to bind a target protein, the fusion protein comprising a LOV domain and a heterologous peptide component selected from a nanobody, monobody, antibody, DARPin or anticalin, wherein exposure of the fusion protein to light induces a conformational change that alters its ability to bind the target protein. The substrate is exposed to the cell lysate in the presence of light under conditions sufficient to induce binding of the target protein and the fusion protein, and the target protein is eluted in the absence of light, wherein the fusion protein binds the target protein upon exposure to light and dissociates from the target protein in the absence of light, thereby purifying the target protein; or the substrate is exposed to the cell lysate in the absence of light under conditions sufficient to induce binding of the target protein and the fusion protein, and the target protein is eluted in the presence of light, wherein the fusion protein binds the target protein in the absence of light and dissociates from the target protein upon exposure to light, thereby purifying the target protein.

Another embodiment is a fusion protein comprising a light responsive domain consisting of amino acids 408-543 of SEQ ID NO:1, or a variant thereof having from one to 10 mutations.

BRIEF DESCRIPTION OF THE DRAWINGS

The foregoing will be apparent from the following more particular description of example embodiments.

FIG. 7A shows mCherry is localized to the membrane via a CAAX tag. FIG. 7B shows that a fluorescent nanobody is expressed in the cytoplasm.

FIGS. 8A-8F show examples of light-responsive nanobodies against mCherry. FIGS. 8A-8B show light-induced binding of a light-responsive nanobody to membrane-localized mCherry. The light-responsive nanobody was constructed with AsLOV2 fused between amino acids A74 and K75, and was fused to iRFP. Images show nanobody localization before and after blue light (in FIGS. 8A and 8B, respectively), as well as quantification of cytoplasmic nanobody levels during binding and unbinding (FIG. 8C). FIGS. 8D-8F show light-induced dissociation of a similarly-constructed light-responsive nanobody with AsLOV2 inserted between amino acids G15 and G16, as well as quantification of cytoplasmic nanobody levels during binding and unbinding (FIG. 8F).

FIGS. 9A-9F show examples of light-responsive DARPins against eGFP. FIGS. 9A-9D shows that a cycle of application and removal of blue light induces light-responsive DARPin binding and unbinding from the cell membrane. Light exposure is indicated by a blue border to each image. FIG. 9E shows the membrane localization of the DARPin's target, GFP, obtained by imaging with GFP excitation/emission settings. FIG. 9F shows a graph of the kinetics of binding/unbinding obtained by measuring cytoplasmic light-responsive DARPin fluorescent intensity over time.

FIG. 10A shows binding of the light-responsive monobody to SH2 domain fused to mCherry and localized to the membrane via CAAX tag. FIG. 10B shows light-induced dissociation of the light-responsive monobody from the binding target on the membrane. Blue light exposure is indicated by a blue border around the image.

FIGS. 11A-11F show results of an in vitro binding assay on agarose beads. FIGS. 11A-11C show that a mCherry-specific nanobody with AsLOV2 introduced between amino acids A74 and K75 exhibits light-induced binding in vitro. Images show mCherry fluorescence in the absence (FIG. 11A) and presence (FIG. 11B) of light, with quantification shown in a graph in FIG. 11C. FIGS. 11D-11E show that light-induced dissociation was obtained for the mCherry nanobody with AsLOV2 introduced between G15 and G16, with quantification shown in a graph in FIG. 11F.

FIGS. 13A-13B show graphs of size exclusion chromatography results demonstrating light-induced binding of light-responsive nanobody (Opto-NB) to mCherry (target) in FIG. 13A and light-induced dissociation of light-responsive nanobody (Opto-NB) to mCherry (target) in FIG. 13B.

FIG. 16A illustrates light-induced protein binding and dark-induced elution of protein of interest. FIG. 16B illustrates dark-induced protein binding and light-induced elution of protein of interest.

FIGS. 17A-17B show microscopic photographs of light-induced binding of nanobody-SOScat fusion to membrane localized mCherry controlling kinase translocation reporter and FIGS. 17C-17D show microscopic photographs of a light-induced dissociation of nanobody-SOScat fusion from membrane-localized mCherry controlling kinase translocation reporter. FIG. 17A and FIG. 17C show cells kept in the dark, whereas FIG. 17B and FIG. 17D show cells illuminated with blue light.

FIGS. 20A-20F show microscopic photographs of the experimental set-up for screening the effectiveness of SynNotch activity in dark and light conditions. FIGS. 20A-20C represent a positive control where the cells containing both constructs (FIG. 20A) are incubated with mCherry-coated agarose beads (FIG. 20B) leading to activation of SynNotch receptor further promoting BFP expression (FIG. 20C). FIGS. 20D-20F represent a negative control where the same cells as in FIG. 20A (FIG. 20D) are not incubated with the mCherry beads (FIG. 20E), therefore lacking the activation of SynNotch and subsequent expression of BFP (FIG. 20F).

FIG. 21A: Light-triggered conformational change of the Jα helix (green) of AsLOV2. FIG. 21B: Crystal structure of Monobody HA4 (blue) bound to SH2 domain (gray). The monobody fold consists of two β-sheets, βSh1(black) and βSh2 (light blue), and seven structurally conserved loops (red), where AsLOV2 was inserted in the chimeras described herein. Loop L4, where AsLOV2 is inserted in OptoMB, is shown with an arrow. The diagram below shows the relative size and location of loops (red), including positions of AsLOV2 insertion (red lines) and insertion sites of identified light-responsive chimeras, MS29 and SS58 (in OptoMB). FIG. 21C: Schematic diagram of pull-down screens used to identify light-responsive chimeras. $Co^{2+}$ agarose beads (pink) were used to immobilize $His_6$ (SEQ ID NO: 49)-YFP-SH2 (yellow-gray), which were then incubated with HA4-AsLOV2 chimeras (blue-orange) in either dark or light. After washing and eluting with imidazole, the eluents were resolved on SDS-PAGE, where differences in protein band intensity between samples exposed to different light conditions reflect differences in chimera SH2 binding. FIG. 21D: Chimera pull-down screen results showing SDS-PAGE protein bands of two chimeras that bind better in the dark than in the light. These light-responsive chimeras have AsLOV2 inserted in either Loop L2 (MS29) or Loop L4 (SS58, SS59 and MS29). FIG. 21E: Energy-minimized structural model of the dark conformation of OptoMB with AsLOV2 (orange with the Jα helix in green) inserted in position SS58 of HA4 (blue and black), interacting with the SH2 domain (gray). FIG. 21F: Complete SDS-PAGE gel of the results shown in FIG. 21D, including chimeras with the AsLOV2 domain inserted in positions SS58, SS59 and MS29 (with residues S30 to S32 of loop L2 deleted) of HA4. FIGS. 21G-21I: A representative sample of SDS-PAGE gels of other chimeras with the AsLOV2 domain inserted in different positions that either do not bind or bind poorly to SH2 (TG44, NS47, SA84, SG65, SP68, YS57 and PT18); or bind well to SH2, but show no difference in binding between light conditions (SS30).

FIG. 22A: Schematic diagram of OptoMB and YFP-SH2 darkness-dependent interaction. In the dark, OptoMB binds to SH2 domain of YFP-SH2 fusion; upon blue light stimulation, the AsLOV2 domain disrupts the HA4 domain of OptoMB, reducing its affinity to SH2. FIG. 22B: Time course of fluorescence microscopy images of YFP-SH2 binding to agarose beads conjugated with $OptoMB_{V416L}$ (top panel) or HA4 as control (lower panel). Starting with beads incubated in the dark, time course began upon blue light stimulation (t=0), followed by a sequence of images taken every 120 s for a total of 480 seconds. FIG. 22C: Size exclusion chromatography profiles of OptoMB and YFP-SH2 interactions in light (blue line) and dark (black line). FIGS. 22D-22E: BLI measurements of binding (left) and unbinding (right) activities of YFP-SH2 to immobilized OptoMB in the dark (FIG. 22D) (using $OptoMB_{C450V}$) or in the light (FIG. 22E) (using the lit-stabilized $OptoMB_{V416L}$). The calculated rate and dissociation constants are shown below the BLI data.

FIGS. 23A-23C show light-controlled affinity chromatography (LCAC) to purify SH2-tagged proteins using cobalt-immobilized OptoMB. FIG. 23A: Schematic diagram of functionalization of LCAC agarose beads using $His_6$ (SEQ ID NO: 49)-$OptoMB_{V416L\_G528A\_N538E}$ fused to an N-terminus SUMO tag (S) (bound to $Co^{2+}$ beads) and LCAC procedure involving incubation of crude E. coli extract, and washing in the dark, followed by elution with blue light in batch or column (see also FIGS. 26A-26D). Finally, SDS-PAGE was used to resolve the fractions from each purification step. FIGS. 23B-23C: SDS PAGE gel of LCAC-purified YFP-SH2 (FIG. 23B), and SH2-PDC1 (FIG. 23C). Molecular weight markers (M), lysate (L), unbound flow through (FT), washing step in the dark (Dark Wash), two consecutives light elution aliquots (Light Elution 1 and 2), and the imidazole elution (I) were resolved in 12% SDS-PAGE.

FIG. 24A: Schematic diagram of the membrane-binding assay used, where irFP-tagged OptoMB (blue-orange-purple), binds to a fusion of SH2 (gray), mCherry (red), and CAAX (black linker), anchored to the plasma membrane (PM) of HEK 293T cells. In the dark, OptoMB-irFP binds to the membrane-bound SH2 enhancing irFP signal at the PM, reducing its cytosolic signal. In blue light, OptoMB releases SH2, causing a reduction in irFP signal at the membrane and an increase in the cytosol. FIG. 24B: HEK 293T cells expressing SH2-mCherry-CAAX and irFP-tagged HA4 monobody, as control, imaged in the dark or blue light. Left panel shows mCherry fluorescence of SH2 fusion anchored to the PM; central and right panels show HA4-irFP fluorescence in the dark and after 30 s of blue light stimulation, respectively, showing irFP-HA4 localized to the cytosol in either light condition. FIG. 24C: HEK 293T cells expressing SH2-mCherry-CAAX and OptoMB-iRFP imaged in the dark or blue light. Left panel shows mCherry fluorescence of the SH2 fusion anchored to the PM. Central and right panels show HA4-irFP fluorescence in the dark and after 30 s of blue light stimulation, respectively, showing OptoMB enriched at the PM in the dark and in the cytosol in the light. FIG. 24D: Cytosolic irFP-HA4 fluorescence changing over time due to periodic pulses of blue light (blue sections). The fluorescence is expressed in percentage from the original value of cells exposed to the dark. Curve and shaded regions indicate mean±SD for at least 10 cells respectively. White scale bar in the cell images is 10 μm.

FIG. 25A: Light-enabled spatial control of OptoMB binding interactions shown with two OptoMB-coated agarose beads incubated in a circulating solution of YFP-SH2. The blue circle in the left panel indicates the light masked area which was used to illuminated only one bead. The central and right panels show the YFP-SH2 fluorescence on the surface of the beads in the dark and light, respectively, displaying a visible reduction in fluorescence of only the illuminated bead. FIG. 25B: Quantification of spatially controlled binding experiments of YFP-SH2 to two OptoMB-coated agarose beads (experiments shown in FIG. 25A), showing YFP fluorescence intensity of both illumined (blue) and unilluminated (gray) beads over time. FIG. 25C: Experimental setup of size exclusion chromatography runs using a Superdex 200 16/300 column (GE®). For experiments in the dark (left), the whole column was covered with thick aluminum foil, and the chromatography refrigerator covered with a black blanket to avoid light contamination (not shown). For experiments in the light (right), the column was wrapped with blue LEDs. FIG. 25D: Size exclusion chromatography experiments show identical elution profiles of the HA4-YFP-SH2 complex in dark (black) or light (blue) conditions. FIG. 25E: BLI measurements of binding (left) and unbinding (right) of YFP-SH2 to immobilized monobody HA4, and several replicates for OptoMB, OptoMB$_{C450V}$, OptoMB$_{V416L}$ and OptoMB$_{V416L\_G528A\_N538E}$ in different light conditions (see Supplementary Table 2). FIG. 25F: Comparison of binding ($k_{on}$), unbinding ($k_{off}$), and dissociation ($K_d$) constants calculated from BLI measurements for different OptoMB variants, corresponding to dark (gray or black) or lit (blue) states, including replicates. The red asterisks highlight measurements of $k_{on}$ below the limit of detection of $0.001\ \mu M^{-1}\ s^{-1}$. To calculate $K_d$ values from measurements below this limit, $k_{on}=0.001\ \mu M^{-1}\ s^{-1}$ was used. OptoMB$_{Triple}$ refers to the OptoMB$_{V416L\_G528A\_N538E}$ variant.

FIG. 26A: Schematic diagram of LCAC procedure using a column packed with agarose beads bound to a coating of OptoMB by His$_6$ (SEQ ID NO: 49)-tag. After flowing through crude extract and washing in the dark, elution is carried out by applying blue light to the surface of the column. FIG. 26B: SDS-PAGE gel of YFP-SH2 purified with OptoMB immobilized column. FIG. 26C: SDS-PAGE gel of YFP-SH2 purified using a column packed with agarose beads coated with His$_6$ (SEQ ID NO: 49)-OptoMB$_{V416L\_G528A\_N538E}$ (with a SUMO tag). FIG. 26D: SDS-PAGE gel of SH2-PDC1 purified using a column packed with agarose beads coated with OptoMB$_{V416L\_G528A\_N538E}$ (with a SUMO tag).

FIG. 27A: Schematic diagram of OptoMB$_{V416L\_G528A\_N538E}$ with SUMO tag (S) covalently conjugated to CNBr beads through surface-exposed primary amines, and their use in LCAC as described before. FIGS. 27B-27C: SDS-PAGE gel of YFP-SH2 (FIG. 27B) or SH2-PDC1 (FIG. 27C) purified using the SUMO-tagged OptoMB$_{V416L\_G528A\_N538E}$ conjugated to CNBr beads, in batch. Molecular weight markers (M), lysate (L), Unbound flow through (FT), washing step in the dark (Dark Wash), two consecutives light elution aliquots (Light Elution 1 and 2) and heat-treated beads resolved in SDS-PAGE gel (12% polyacrylamide).

FIG. 28A: Schematic of approach. By insertion into a solvent-exposed turn or loop, the light-switchable AsLOV2 domain (blue) could modulate the conformation of a nanobody (gray), thus allosterically altering its ability to bind to a target protein (red). Cytosolic irFP-fused OptoNBs were assayed for translocation to membrane-bound mCherry in the presence or absence of blue light. FIG. 28B: Crystal structure of the LaG4 nanobody (blue) bound to EGFP (green), (PDB:3OGO), indicating loops targeted for LOV domain insertion (arrows). Two loops are highlighted containing Ala74 (green arrow) and Gly15 (purple arrow). FIG. 28C: Results for insertion at 1-2 sites in all 8 loops. HEK293 cells expressing membrane-tethered mCherry (mCherry-CAAX) and cytosolic OptoNB-irFP (OptoNB) are shown, prior to blue light illumination. FIG. 28D: Quantification of change in cytosolic intensity for at least 10 cells per OptoNB variant in FIG. 28C. An increase in cytosolic OptoNB fluorescence corresponds to light-induced dissociation from membrane-bound mCherry, and vice versa for light-induced decrease in cytosolic irFP. FIG. 28E: Images before (gray box) and after (blue box) light stimulation for two OptoNB variants, LaM8-AK74 and LaM8-GG15, in HEK293T cells also expressing mCherry-CAAX, showing light-dependent changes in OptoNB localization in both cases.

FIG. 29A: AsLOV2 crystal structure (PDB:2VOU) indicating amino acids removed (red) to generate the optimized short AsLOV2 (408-543) for nanobody insertions. FIG. 29B: Comparison of photoswitchable OptoNB binding in original AsLOV2 ('o') and short AsLOV2 ('s') for 9 insertion sites near the original two hits, GG15 and AK74. Data analyzed is steady-state change in cytosolic intensity for at least 5 cells per construct. FIGS. 29C-29D: Light-induced membrane/cytosol translocation in HEK293T cells for the LaM8-AK74 (in FIG. 29C) and LaM8-GG15 (in FIG. 29D) OptoNBs. The percent change in cytosolic intensity from the original, dark-equilibrated value is shown. Curves and shaded regions indicate mean±SD for at least 10 cells.

FIG. 30A: Sequence alignment for LaM8 (anti-mCherry), LaM4 (anti-mCherry), and LaG9 (anti-EGFP) nanobodies. Residues that are not conserved are shown in red and the three complementarity-determining regions (CDRs) are boxed. Blue arrows indicate AsLOV2 insertion sites. FIG. 30B: Light-induced translocation of LaM8, LaM4 and LaG9 OptoNBs with LOV insertion at AK74 or GG15. The change in cytosolic intensity from the original, dark-equilibrated value is shown. Curves and shaded regions indicate mean±SD for at least 5 cells. FIGS. 30C-30D: NIH3T3 cell lines harboring OpoNB-controlled Ras/Erk pathway activity using LaM8-AK74 (in FIG. 30C) and LaM8-GG15 (in FIG. 30D). Upper diagrams show lentiviral constructs expressed in each cell: membrane-localized mCherry-CAAX, OptoNB-SOScat, and a live-cell biosensor of Erk activity (ErkKTR-irFP). Lower diagrams indicate mCherry and ErkKTR expression and localization for representative cells. Curves show the cytosolic to nuclear ratio of ErkKTR intensity for a representative cell during cycles of darkness and illumination (blue bars).

FIG. 31A: Size exclusion chromatography (SEC) for light-dependent protein separation. The column was wrapped with 450 nm blue LEDs to allow for direct illumination of the protein during the SEC run, or in aluminum foil to keep it in darkness. FIGS. 31B-31C: SEC elution profile for LaM8-AK74 (in FIG. 31B) and LaM4 TK74 (in FIG. 31C). Free mCherry, free OptoNB, and dark- and light-incubated OptoNB/mCherry mixtures are shown in the indicated curves. Shorter retention times indicate larger size and increased complex formation. FIG. 31D: Schematic representing light-induced binding of mCherry to OptoNB-coated beads. His-tagged OptoNBs are immobilized on Ni-NTA agarose beads, while untagged mCherry is in the buffer solution surrounding the beads. A change in illumination conditions results in mCherry-OptoNB binding and a brighter bead surface in the mCherry channel. FIGS. 31E-31F: Top panels: confocal mCherry images of beads coated with a mixture of His-tagged eGFP with His-tagged LaM8-AK74 in a 200:1 ratio (in FIG. 31E) or LaM8-GG15 in a 1000:1 ratio (in FIG. 31F). Beads were placed in 1 µM mCherry solution (in FIG. 31E) or 2 µM mCherry solution (in FIG. 31F). A 450 nm LED was toggled on and off (blue shading indicates LED illumination). Bottom panels: quantification of bead surface intensity during cycles of darkness and blue light illumination. FIG. 31G: Representative biolayer interferometry (BLI) traces for quantifying nanobody-protein binding and dissociation kinetics. Four phases indicate His-tagged OptoNB loading onto the Ni-NTA coated tips, equilibration in buffer, binding to different concentrations of soluble mCherry, and mCherry dissociation into buffer. FIG. 31H: Raw data (solid lines) and best-fit traces simultaneously fit to simple mass-action kinetic binding model (dashed lines) for the Ni-NTA sensor—immobilized LaM8 nanobody binding to soluble mCherry at eight concentrations.

FIG. 32A: Position DG62-66 targeted for the LOV domain insertion into the α-actin nanobody and mapped onto the crystal structure of the anti-GFP minimizer nanobody (PDB: 3G9A). Residues D62 and G66 (blue spheres) are highlighted within Loop 5 (dark blue). CDRs, Loop 1 and Loop 6 are colored as previously described in FIG. 28B. FIG. 32B: Still frames showing dark and illuminated conditions for a cell expressing the actin OptoNB fused to TagRFP. FIG. 32C: Light-induced translocation of actin OptoNBs. The light-induced change in cytosolic intensity from the original, dark-equilibrated value is shown. Bars indicate means±SEM for at least 10 cells. FIG. 32D: Reversible actin OptoNB translocation to and from the cytoskeleton in a representative cell. Curve indicates the mean intensity in a cytosolic region in response to pulses of blue light (blue bars). Upper images show the cell at the indicated time points. FIG. 32E: Spatial illumination leads to local nanobody unbinding. Left panels: representative images of a representative cell that was left un-illuminated or illuminated for 10 min on its left or right half. Dashed lines indicate positions of line scans for quantifying local enrichment along actin filaments. Right panels: quantification of actin optoNB fluorescence along the line scans in dark, left, or right illumination.

DETAILED DESCRIPTION

A description of example embodiments follows.

A first embodiment is a fusion protein comprising a light-responsive domain and a heterologous peptide component, wherein exposure of the fusion protein to light induces a conformational change in the fusion protein that alters an activity of the fusion protein.

Figure 2:
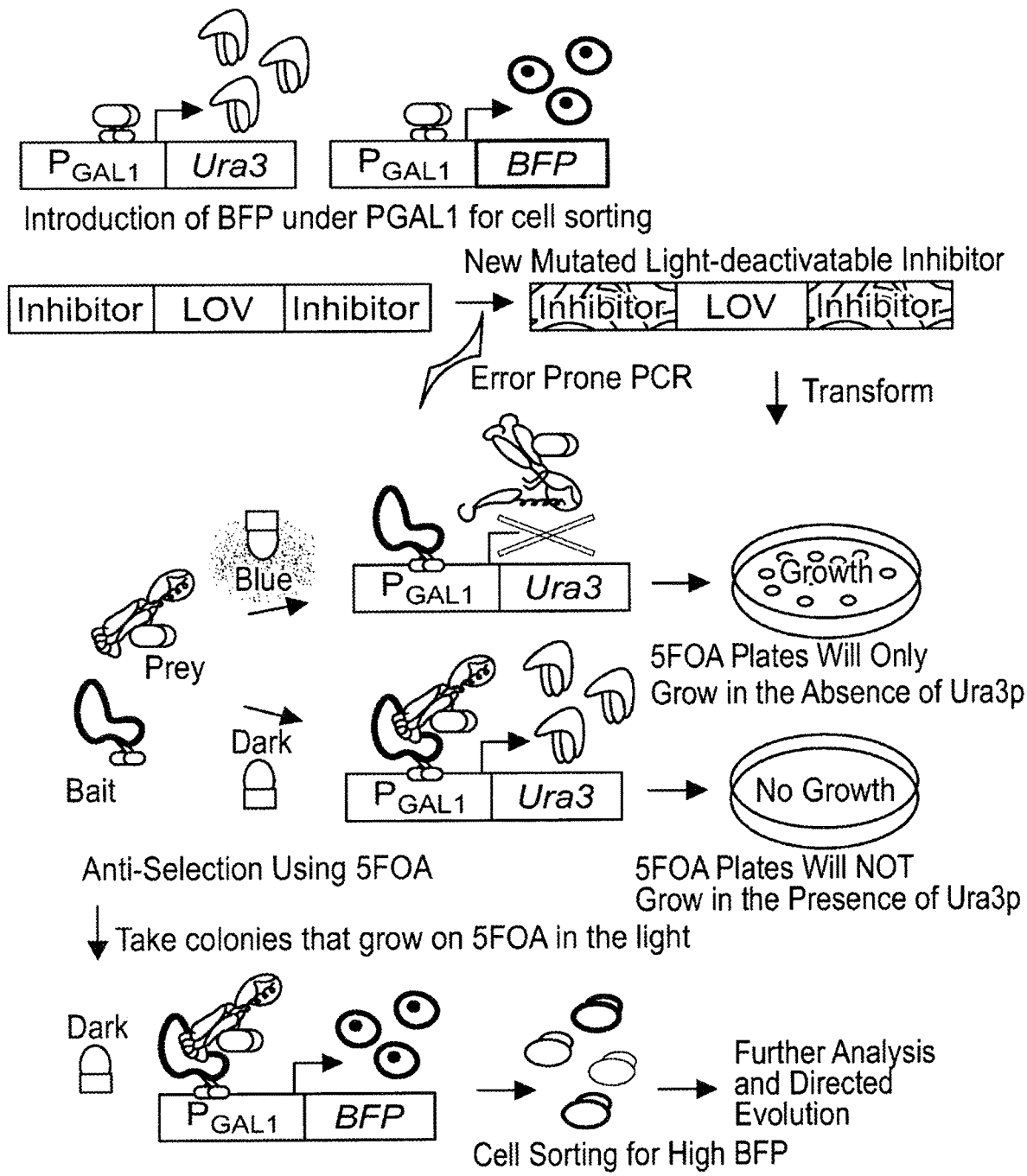
FIG. 2 is a depiction of directed evolution of light-switchable proteins for better kinetics/activity.

The term "fusion protein" refers to a synthetic, semi-synthetic or recombinant single protein molecule that comprises all or a portion of two or more different proteins and/or peptides. The fusion can be an N-terminal fusion (with respect to the heterologous peptide component), a C-terminal fusion (with respect to the heterologous peptide component) or an internal fusion (with respect to the light responsive domain and/or the heterologous peptide component). When the fusion protein is an internal fusion protein, the light responsive domain is typically inserted into the heterologous peptide component. See, for example, FIG. 2. Thus, in some embodiments, the fusion protein is an internal fusion protein, and the light responsive domain (e.g., LOV domain) is inserted into the heterologous peptide component.

Fusion proteins of the invention can be produced recombinantly or synthetically, using routine methods and reagents that are well known in the art. For example, a fusion protein of the invention can be produced recombinantly in a suitable host cell (e.g., bacteria, yeast, insect cells, mammalian cells) according to methods known in the art. See, e.g., *Current Protocols in Molecular Biology*, Second Edition, Ausubel et al. eds., John Wiley & Sons, 1992; and *Molecular Cloning: a Laboratory Manual*, 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

The fusion proteins described herein can include other amino acid sequences in addition to the amino acid sequences of the light-responsive domain and the heterologous peptide component. In some aspects, a fusion protein includes a linker amino acid sequence (e.g., positioned between the light-responsive domain and the heterologous peptide component). A variety of linker amino acid sequences are known in the art and can be used in the fusion proteins described herein. In some embodiments, a linker sequence includes one or more amino acid residues selected from Gly, Ser, Ala, Val, Leu, Ile, Thr, His, Asp, Glu, Asn, Gln, Lys and Arg. In some embodiments, a linker sequence includes a polyglycine sequence (e.g., a 6× glycine sequence, SEQ ID NO: 50).

In some aspects, the fusion protein is isolated. As used herein, "isolated" means substantially pure. For example, an isolated fusion protein makes up at least about 50%, about 60%, about 70%, about 80%, about 90%, about 95%, about 97%, about 98%, about 99% or about 99.5% by weight of a mixture containing substances (e.g., chemicals, proteins, peptides, other biological matter) other than the fusion protein.

"Light-responsive domain," as used herein, refers to a peptide or protein that, upon exposure to at least one particular wavelength of light (more typically, a range of wavelengths of light), undergoes a conformational change which mediates, in turn, a conformational change in the fusion protein. Conformational changes include unfolding, tilting, rotating and multimerizing (e.g., dimerizing, trimerizing), or a combination of any of the foregoing (e.g., unfolding and multimerizing). Accordingly, in some aspects, the conformational change is an allosteric change, such as the allosteric change undergone by AsLOV2 upon exposure to blue light. In some aspects, the conformational change induces multimerization (e.g., dimerization, trimerization) of the fusion protein.

Typically, the light-responsive domain is an optogenetic activator from the plants, fungi, or bacteria. Non-limiting examples of light responsive domains include light oxygen voltage (LOV) domains (e.g., EL222, YtvA, aureochrome-1, AsLOV2), blue light-using flavin adenine dinucleotide (FAD) (BLUF) domains (e.g., PixD, AppA, BLrP1, PAC, BlsA), cryptochrome domains (e.g., Cry2), fluorescent protein domains (e.g., Dendra, Dronpa, Kohinoor) and phytochromes (e.g., PhyB, CPh1, BphP, Phy1, PixJ, Ac-NEO1). In some aspects, the light-responsive domain is a light oxygen voltage (LOV) domain, e.g., AsLOV2, the LOV2 domain from *Avena sativa* Phototropin 1.

A light responsive domain, such as "light oxygen voltage 2 domain" or "LOV2 domain", can be naturally occurring or non-naturally occurring (e.g., engineered). For example, the LOV domain can be isolated (e.g., from a natural source), recombinant or synthetic. Examples of LOV domains that are suitable for use in the fusion proteins and methods described herein are known in the art and include variants of naturally occurring LOV domains (e.g., variants having at least about 70%, about 75%, about 80%, about 85%, about 90, about 95%, about 96%, about 97%, about 98% or about 99% identity to a naturally occurring LOV domain), such as AsLOV2, the LOV2 domain from *Avena sativa* Phototropin 1. In some embodiments, a LOV domain is a polypeptide having the amino acid sequence of AsLOV2, the LOV2 domain from *Avena sativa* Phototropin 1, assigned UniProt Accession No. 049003 (SEQ ID NO:1), or a variant thereof having at least about 70% (e.g., about 75%, about 80%, about 85%, about 90%, about 95%, about 96%, about 97%, about 98% or about 99%) identity to the amino acid sequence of SEQ ID NO:1. The AsLOV2 domain is typically considered to be amino acid residues 404-546 of SEQ ID NO:1, but, in some cases, further includes amino acid residue 547 of SEQ ID NO:1 and, therefore, can, in some cases, be amino acid residues 404-547 of SEQ ID NO:1.

As used herein, the term "sequence identity" means that two nucleotide or amino acid sequences, when optimally aligned, such as by the programs GAP or BESTFIT using default gap weights, share at least 50% sequence identity, e.g., at least 70% sequence identity, or at least 75% sequence identity, or at least 80% sequence identity, or at least 85% sequence identity, or at least 90% sequence identity, or at least 95% sequence identity, or at least 98% sequence identity, or at least about 99% sequence identity or more. For sequence comparison, typically one sequence acts as a reference sequence (e.g., parent sequence) to which test sequences are compared. Unless otherwise indicated, the sequence identity comparison can be examined throughout the entire length of a sequence (e.g., reference sequence, test sequence), or within a desired fragment of a given sequence (e.g., reference sequence, test sequence). In some embodiments, sequence identity of a test sequence and an indicated reference sequence is determined over the entire length of the test sequence. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., J. Mol. Biol. 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used.

It has been found that mutated (e.g., truncated) variants of light-responsive domains, in particular, mutated variants of AsLOV2 are also useful in the fusion proteins described herein. For example, truncated variants of AsLOV2, e.g., C-terminal truncation variants such as those containing amino acids 408-543 of SEQ ID NO:1, lack a nuclear export sequence, and have been found to be useful in the fusion proteins described herein. In addition, variants (e.g., truncated variants) of AsLOV2 containing a V416L/I substitution have been found to extend the lifetime of the photoactivated state. Variants (e.g., truncated variants) of AsLOV2 containing G528A and N538E substitutions are thought to stabilize the dark-state conformation of the domain. The triple mutant V416L/I-G528A-N538E has also been used successfully in the fusion proteins described herein.

Accordingly, in some embodiments, a LOV domain is a polypeptide comprising or consisting of the amino acid sequence of AsLOV2, the LOV2 domain from *Avena sativa* Phototropin 1, assigned UniProt Accession No. O49003 (SEQ ID NO:1), or a fragment and/or mutant thereof, or a variant of any of the foregoing having at least about 70% (e.g., about 75%, about 80%, about 85%, about 90%, about 95%, about 96%, about 97%, about 98% or about 99%) identity to the amino acid sequence of SEQ ID NO:1, or the fragment or mutant thereof. For example, in some embodiments, the LOV domain is a polypeptide comprising or consisting of the amino acid sequence of amino acids 404-547 (e.g., 404-546, 408-543) of SEQ ID NO:1, or a variant thereof having at least about 70% (e.g., about 75%, about 80%, about 85%, about 90%, about 95%, about 96%, about 97%, about 98% or about 99%) identity to the amino acid sequence of amino acids 404-547 (e.g., 404-546, 408-543) of SEQ ID NO:1. In some embodiments, the LOV domain is a polypeptide comprising or consisting of the amino acid sequence of amino acids 404-547 (e.g., 404-546, 408-543) of SEQ ID NO:1, or a variant thereof having at least about 70% (e.g., about 75%, about 80%, about 85%, about 90%, about 95%, about 96%, about 97%, about 98% or about 99%) identity to the amino acid sequence of amino acids 404-547 (e.g., 404-546, 408-543) of SEQ ID NO:1, which contains substitutions (e.g., conservative substitutions) at one or more (e.g., three) of the following amino acids of SEQ ID NO:1: V416, G528 and N538, e.g., contains one or more (e.g., three) of the following substitutions: V416L/I, G528A and N538E. In some embodiments, the LOV domain is a polypeptide comprising or consisting of the amino acid sequence of SEQ ID NO:9, or a variant thereof having at least about 70% (e.g., about 75%, about 80%, about 85%, about 90%, about 95%, about 96%, about 97%, about 98% or about 99%) identity to the amino acid sequence of SEQ ID NO:9, e.g., and contains substitutions (e.g., conservative substitutions) at one or more (e.g., three) of the following amino acids of SEQ ID NO:1: V416, G528 and N538, such as one or more (e.g., three) of the following substitutions: V416L/I, G528A and N538E. In some embodiments, the LOV domain is a polypeptide comprising or consisting of the amino acid sequence of SEQ ID NO:47, or a variant thereof having at least about 70% (e.g., about 75%, about 80%, about 85%, about 90%, about 95%, about 96%, about 97%, about 98% or about 99%) identity to the amino acid sequence of SEQ ID NO:47. In some embodiments, the LOV domain is a polypeptide comprising or consisting of the amino acid sequence of SEQ ID NO:48, or a variant thereof having at least about 70% (e.g., about 75%, about 80%, about 85%, about 90%, about 95%, about 96%, about 97%, about 98% or about 99%) identity to the amino acid sequence of SEQ ID NO:48. In some embodiments, the LOV domain is a light responsive domain described in the seventeenth or nineteenth embodiment, or any aspect or combination of aspects thereof.

"Heterologous peptide component," as used herein, refers to a protein or peptide component that is different from the protein or peptide of the light-responsive domain (whether or not derived from the same organism as the peptide or protein of the light-responsive domain). Typically, however, the heterologous peptide component is not derived from the same organism as the peptide or protein of the light-responsive domain. Examples of heterologous peptide components include nanobodies, monobodies, antibodies, growth factors, designed ankyrin repeat proteins (DARPins) (e.g., E40, pE59), antimicrobial peptides (e.g., LL-37, IDR-1018, IDR-1019, pexiganan, Bac2A, W3), enzymes and therapeutic proteins or peptides. Another example of a heterologous peptide component is an anticalin. In some embodiments, a heterologous peptide component selected from a nanobody, monobody, antibody, DARPin or anticalin (e.g., a nanobody, monobody or antibody).

Figures 21A, 21B:
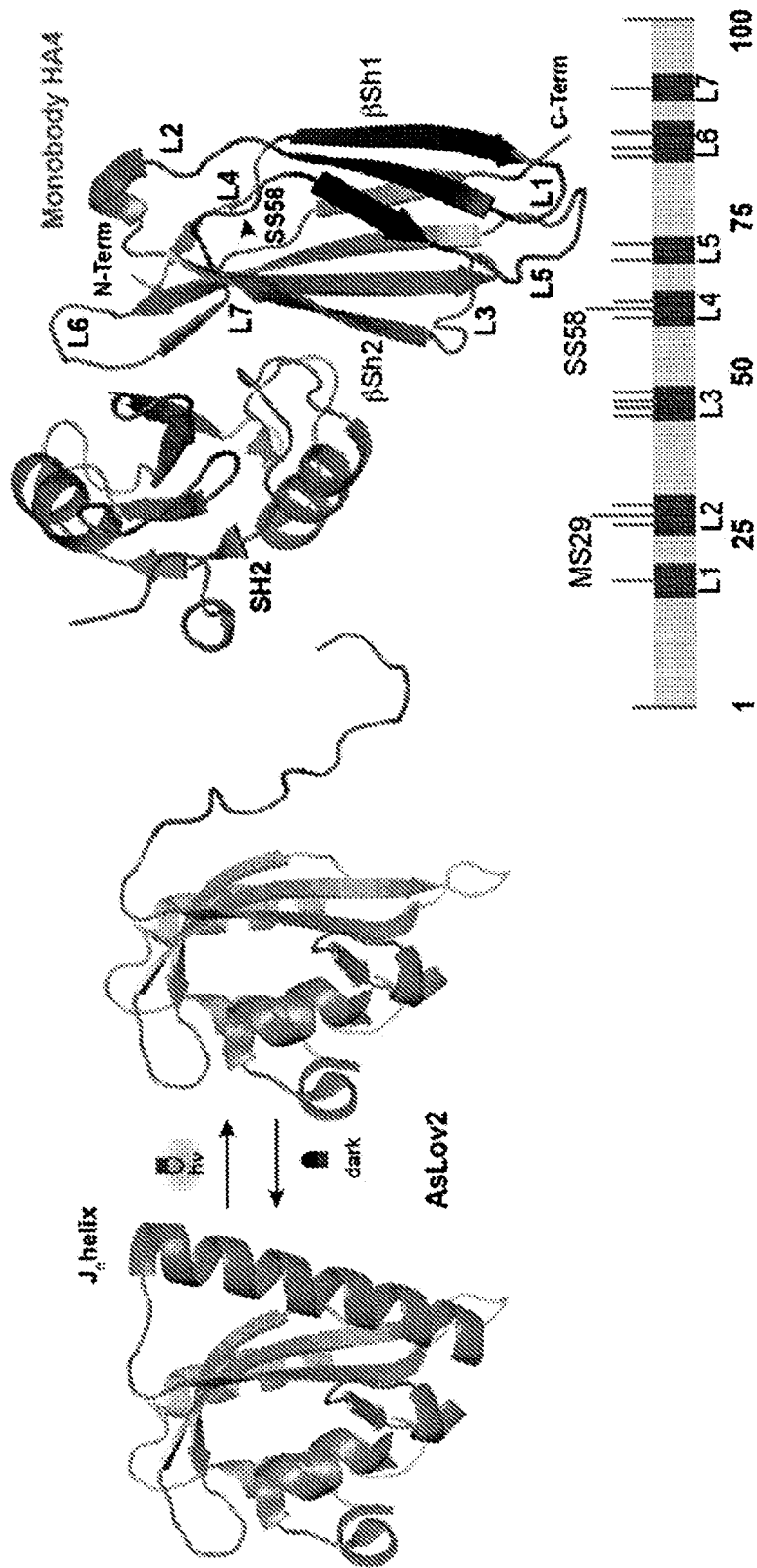
FIGS. 21A-21I show the design and screens of AsLOV2-Monobody chimeras and final OptoMB.

In some embodiments, a heterologous peptide component has one or more loops (e.g., solvent-exposed loops). "Loops," as used herein, refer to irregular structures in proteins that connect two or more secondary structures, such as α-helices and/or β-sheets. Typically, loops are located on a protein's surface, and are solvent-exposed. Loops represent convenient sites for insertion of a light responsive domain. Accordingly, in some embodiments wherein a heterologous peptide component has one or more loops (e.g., solvent-exposed loops), the light responsive domain (e.g., LOV domain) is inserted into a loop of the heterologous peptide component. For example, monobodies often have a first β-sheet connected to a second β-sheet by one or more loops. Thus, in some embodiments wherein a heterologous peptide component is a monobody having a first β-sheet connected to a second β-sheet by one or more loops, the light responsive domain (e.g., LOV domain) is inserted into a loop of the monobody that connects the first β-sheet to the second β-sheet. In some embodiments wherein the heterologous peptide component is a HA4 monobody, a light responsive domain (e.g., LOV domain) is inserted into loop 2 or loop 4 (e.g., loop 4) of the HA4 monobody. Identification of loops with a protein is within the abilities of a person of ordinary skill in the art. The loop numbers associated with the HA4 monobody are depicted in FIG. 21B.

A "therapeutic protein or peptide" is a heterologous peptide component useful as a therapeutic agent. Some therapeutic proteins or peptides can bind a cell surface target, such as a cell surface protein or receptor. In some embodiments, the therapeutic protein or peptide is a cytokine (e.g., an interferon), peptide hormone (e.g., insulin), growth factor, (e.g., an epidermal growth factor, a fibroblast growth factor, and platelet-derived growth factor). Examples of growth factors which bind and activate a receptor tyrosine kinase include epidermal growth factor and fibroblast growth factor-7 (also known as keratinocyte growth factor). Other nonlimiting examples of therapeutic proteins and peptides include insulin, monoclonal antibodies (e.g., ipilimumab, infliximab, adalimumab), circulating receptor fusion proteins (e.g., etanercept), thrombolytic proteins (e.g., tissue plasminogen activator), and natural product toxins (e.g., conotoxin).

In some embodiments, the heterologous peptide component (e.g., the therapeutic protein or peptide) is a nanobody (e.g., which binds and inhibits a cell surface receptor, such as a receptor tyrosine kinase). Typically, nanobodies are small binding proteins formed from the single variable domain of camelid antibodies. An example of a nanobody which binds and inhibits a receptor tyrosine kinase is the 7D12 anti-EGFR nanobody (Creative Biolabs, New York).

In some embodiments, the heterologous peptide component (e.g., the therapeutic protein or peptide) is a monobody. Monobodies, examples of which are known in the art, are synthetic binding proteins that are constructed using a fibronectin type III domain (FN3) as a molecular scaffold. Monobodies are an alternative to antibodies and nanobodies for creating a target-binding protein. Typically, a monobody fold includes two anti-parallel β-sheets. The first β-sheet is connected to the second β-sheet by one or more loops. Without wishing to be bound by any particular theory, it is believed that by inserting a light-responsive domain into a loop of a monobody that connects the first and second β-sheets, a light-triggered conformational change will disrupt, at least partially, the interaction(s) between the β-sheets and/or a potential binding partner. An example of a monobody is the HA4 monobody, which is depicted in FIG. 21B. As shown in FIG. 21B, HA4 contains two β-sheets and seven loops. Loops 2, 4 and 5 connect the two β-sheets to one another, whereas loops 1, 3, 6 and 7 lie within a single β-sheet.

In some embodiments, the heterologous peptide component is an antibody.

In some embodiments, the heterologous peptide component is a DARPin.

In some embodiments, the heterologous peptide component is an anticalin. An anticalin is an artificial protein able to bind to antigens, proteins or small molecules. Anticalins are derived from human lipocalins.

"Activity," as used herein with respect to proteins (e.g., fusion proteins), encompasses, for example, metabolic activity, enzymatic activity, binding activity and therapeutic (e.g., a biopharmaceutical) activity. In some aspects, the activity is a binding activity, for example, the ability to bind to a target protein in an in vitro binding activity assay or an in vivo extracellular or intracellular binding activity assay. Binding activity is altered, in the fusion proteins described herein, upon exposure of the fusion protein to light that induces a conformational change in the fusion protein and alters its interaction with the target protein. Typically, binding activity of the fusion proteins described herein is mediated by the heterologous peptide component of the fusion protein, which is made available for binding, or obstructed from binding, depending on the conformational state of the fusion protein.

"Binding activity" is observed when a fusion protein described herein binds to a target molecule, such as a protein, nucleic acid (e.g., deoxyribonucleic acid (DNA), ribonucleic acid (RNA)), carbohydrate, lipid, organic small molecule, etc. A fusion protein "binds to" a target molecule if the dissociation constant ($K_d$) of the interaction between the two species is less than about 10 µM less than about 1 µM or less than about 100 nM. Decreased binding (indicated by a larger $K_d$ value) corresponds to decreased binding activity. Increased binding (indicated by a smaller $K_d$ value) corresponds to increased binding activity. In some aspects, exposure of the fusion protein to light increases its binding activity. In some aspects, exposure of the fusion protein to light decreases its binding activity. In some aspects, the conformational change induced by exposing a fusion protein described herein to light results in an increase or decrease of activity (e.g., binding activity) of at least two-fold, at least five-fold, at least ten-fold, and more preferably at least fifty-fold. In some aspects, the fusion protein will not exhibit any measurable degree of activity in at least one conformational state.

Binding activity can be measured, e.g., by measuring a signal produced by the fusion protein. In some embodiments, the signal is an optical signal, such as luminescence, fluorescence or absorbance. Therefore, the signal produced by the fusion protein can be measured using optical methods, for example, luminescence, absorbance or fluorescence spectroscopy. Alternatively, low angle static light scattering and particle size analysis can be used to detect complex formation using, for example, a Zetasizer (available from Malvent Instruments, Ltd.). Other methods suitable for measuring the signal produced by a fusion protein include electronic absorption spectroscopy, nuclear magnetic resonance spectroscopy, X-ray crystallography, mass spectrometry, infrared and Raman spectroscopy and cyclic voltammetry.

In vitro binding activity is binding activity occurring outside of the cellular environment, for example, in test tubes, multi-well plates and/or Petri dishes containing no live cells. In vitro binding activity includes both intermolecular and intramolecular binding activity.

In vivo extracellular binding activity refers to binding activity occurring in the extracellular environment of live cells. Extracellular binding activity includes binding activity occurring between a fusion protein described herein and a cell surface target, such as a cell surface protein or receptor, as well as intramolecular binding activity of a fusion protein that occurs in the extracellular environment of live cells. For example, a nanobody (e.g., which binds and inhibits a cell surface receptor, such as a receptor tyrosine kinase) exhibits in vivo extracellular binding activity. Growth factors (e.g., an epidermal growth factor, a fibroblast growth factor, a growth factor which binds a receptor tyrosine kinase and activates or inhibits the receptor tyrosine kinase) also exhibit in vivo extracellular binding activity. See also FIG. 3, which depicts a light-activated protein therapeutic linked to a light-deactivated inhibitor. Binding activity between the light-activated protein therapeutic and the light-deactivated inhibitor occurring in the extracellular environment of live cells is also in vivo extracellular binding activity.

In vivo intracellular binding activity refers to binding activity occurring in the intracellular environment of live cells. Intracellular binding activity includes binding activity occurring between a fusion protein described herein and an intracellular target, as well as intramolecular binding activity of a fusion protein that occurs in the intracellular environment of live cells. Intracellular binding activity can be assessed using a variety of assays known in the art, including, for example, fluorescence microscopy.

Because the light-responsive domain and, hence, the fusion protein, is light responsive, exposure to light induces a conformational change that alters an activity of the fusion protein. In some aspects, the conformational change of the fusion protein (typically, the light-responsive domain of the fusion protein) will be induced by visible light (e.g., from about 400-nm to 700-nm light). In particular aspects, the conformational change will be induced by blue light (e.g., from about 380-nm to about 500-nm light, in particular, about 450-nm light), red light (e.g., from about 620-nm to about 750-nm light) or far-red light (e.g., from about 710-nm to about 850-nm light). In other aspects, the conformational change will be induced by infrared light (e.g., from greater than 700-nm to about 1-mm light). LOV domains, BLUF domains, cryptochromes and fluorescent proteins, for example, are typically responsive to blue light, and phytochromes, for example, are typically responsive to red light and far-red light. The C-terminal Jα helix of AsLOV2, in particular, undocks and unfolds upon excitation with blue light (e.g., $\lambda_{max}$=450 nm), resulting in a substantial increase in the distance between the N- and C-termini of AsLOV2, which are typically within less than 10 Å of one another in the absence of light.

In some aspects, the fusion protein is a therapeutic fusion protein.

In addition to being useful as a therapeutic, the fusion proteins described herein can be useful tools for research or industrial protein purification. For example, a fusion protein wherein the heterologous peptide component is a DNA polymerase could be useful as a light-responsive DNA polymerase in a polymerase chain reaction. The fusion proteins described herein could also facilitate protein purification by enabling light-responsive columns (e.g., columns containing a resin with an immobilized light-responsive substrate). For example, light, instead of harsh reagents otherwise used, can be used to elute a protein of interest. Such purification methods generally are less toxic and have a higher specificity than current approaches. Such purification methods also avoid the need for using harsh elution conditions, such as low pH, which can damage the protein of interest, reducing yields. Furthermore, such purification methods can be done in a "label-free" setup (where the fusion protein directly binds to a protein of interest) or with fusion proteins that are specific for a short peptide tag attached to the protein of interest.

Figure 3:
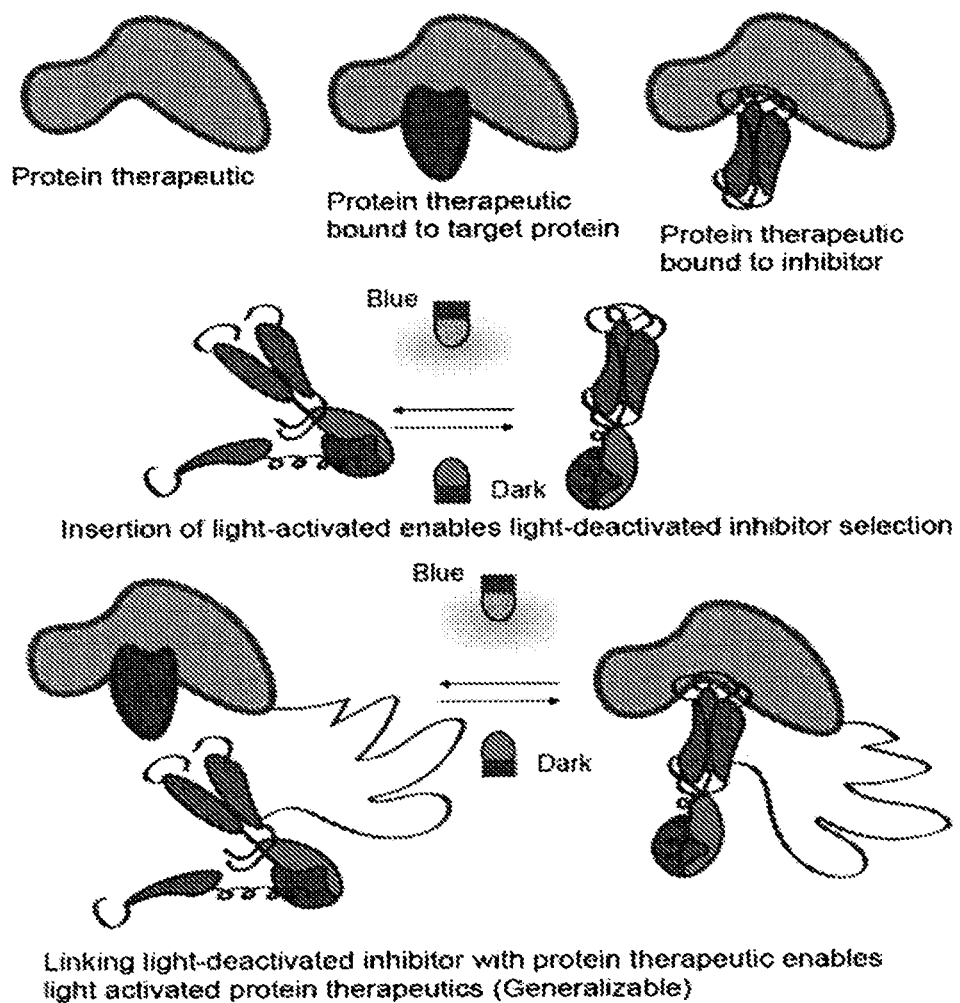
FIG. 3 is a depiction of a generalizable platform for light-activated therapeutics.

In some aspects, the fusion protein (e.g., a therapeutic fusion protein) comprises a light-responsive domain, a first heterologous peptide component (e.g., a therapeutic protein or peptide) and a second heterologous peptide component different from the first heterologous peptide component (e.g., an inhibitor, such as a nanobody, of the first heterologous peptide component), wherein exposure of the fusion protein to light induces a conformational change in the fusion protein that alters an activity of the fusion protein (e.g., a binding activity selected from an in vitro binding activity, an in vivo extracellular binding activity and an intracellular binding activity). FIG. 3 depicts a generalizable platform for light-activated therapeutics in accordance with this aspect of the invention. It will be appreciated that exposure of the fusion protein depicted in FIG. 3 to light induces a conformational change in the fusion protein that alters the therapeutic activity of the protein therapeutic depicted in FIG. 3. Exposure of the fusion protein depicted in FIG. 3 to light also alters the binding activity between the protein therapeutic and its target protein and the protein and its inhibitor, both of which are in vivo extracellular binding activities, if they occur in the extracellular environment of live cells.

In some aspects, the fusion protein comprises a cell-penetrating peptide component, allowing for intracellular delivery of the fusion protein. Fusion proteins comprising a cell-penetrating peptide component can be used to contact the outside of a cell, penetrate the cell, and then bind an intracellular target determined by the first heterologous peptide component (e.g., a nanobody, a monobody, or an antibody).

A "cell-penetrating peptide" is a short peptide that facilitates cellular intake/uptake of a molecular component with which it is associated. The cell-penetrating peptide can be associated with the fusion proteins described herein either through chemical linkage via covalent bonds or through non-covalent interactions. The function of the cell-penetrating peptide is to deliver the fusion protein into cells (e.g., through endocytosis). Examples of suitable cell penetrating peptides for the fusion proteins described herein is the Twin-arginine translocation (Tat) pathway signal sequence (InterPro Accession: IPR006311) and polyarginine sequences.

Alternatively, the fusion proteins described herein can be resurfaced to improve cell-penetrating ability, for example, as described in Chapman and McNaughton, *Cell Chem Biol.* 2016 May 19; 23(5):543-553, the relevant contents of which are incorporated herein by reference.

Also provided herein is a composition (e.g., a pharmaceutical composition, a cosmetic composition, a nutraceutical composition) comprising a pharmaceutically acceptable carrier and a fusion protein described herein. In some embodiments, the composition is a topical composition (e.g., topical pharmaceutical composition) comprising a fusion protein that comprises an antimicrobial peptide and light-responsive domain.

Compositions described herein may be administered orally, parenterally (including subcutaneously, intramuscularly, intravenously and intradermally), topically, rectally, nasally, buccally or vaginally. In some embodiments, provided compositions are administrable intravenously, intraarterially, and/or intraperitoneally. In some embodiments, the pharmaceutical composition is administrable locally (e.g., via buccal, nasal, rectal or vaginal route). In some embodiments, the pharmaceutical composition is administrable systemically (e.g., by ingestion).

The compositions of the present invention may be administered in an appropriate pharmaceutically acceptable carrier having an absorption coefficient similar to water, such as an aqueous gel. Alternatively, a transdermal patch can be used as a carrier. The pharmaceutical agents of the present invention can be administered in a gel, ointment, lotion, suspension, solution or patch, which incorporate any of the foregoing.

For other topical applications, the compositions can be formulated in a suitable ointment containing the active component suspended or dissolved in one or more carriers.

Carriers for topical administration of a pharmaceutical agent described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water.

A second embodiment is a method of altering an activity of a fusion protein comprising a light-responsive domain (e.g., a LOV domain, such as AsLOV2, the LOV2 domain from *Avena sativa* Phototropin 1) and a heterologous peptide component. The method comprises exposing the fusion protein to light that induces a conformational change in the fusion protein, thereby altering an activity of the fusion protein. The conformational change alters an activity of the fusion protein and, in some aspects, the activity is a binding activity selected from an in vitro binding activity and an in vivo extracellular binding activity.

A third embodiment is a method for treating a subject in need thereof, comprising administering to the subject a therapeutically effective amount of a therapeutic fusion protein comprising a light-responsive domain and a therapeutic protein or peptide, and delivering a sufficient amount of light (e.g., intensity, duration) to at least a portion of the subject to induce the conformational change, thereby altering the therapeutic efficacy of the fusion protein exposed to the light and treating the subject. Exposure of the fusion protein to light induces a conformational change in the fusion protein that alters its therapeutic efficacy.

A "subject" refers to a patient who has, or is at risk for developing, a disease or mental condition treatable by a therapeutic protein or peptide. A skilled medical professional (e.g., physician) can readily determine whether a subject has, or is at risk for developing such a condition. In an embodiment, the subject is a mammal (e.g., human, non-human primate, cow, sheep, goat, horse, dog, cat, rabbit, guinea pig, rat, mouse or other bovine, ovine, equine, canine, feline or rodent organism). In a particular embodiment, the subject is a human.

"Therapeutic efficacy," as used herein with respect to a fusion protein, means that, when administered to a subject in a therapeutically effective amount, the fusion protein is capable of achieving a desired therapeutic or prophylactic effect (e.g., a therapeutic effect) under the conditions of administration. The effectiveness of a therapy can be determined by suitable methods known to those of skill in the art.

As used herein, a "therapeutically effective amount" is an amount that is sufficient to achieve the desired therapeutic or prophylactic (e.g., therapeutic) effect under the conditions of administration. The effectiveness of a therapy can be determined by suitable methods known to those of skill in the art.

In some aspects, exposure of the fusion protein to light increases its therapeutic efficacy and, hence, delivering a sufficient amount of light increases the therapeutic efficacy of the fusion protein exposed to the light. In some aspects, exposure of the fusion protein to light decreases its therapeutic efficacy and, hence, delivering a sufficient amount of light decreases the therapeutic efficacy of the fusion protein exposed to the light.

A fourth embodiment is a method of identifying a fusion protein comprising a light-responsive domain (e.g., a LOV2, such as an AsLOV2, domain) and a heterologous peptide component (e.g., a therapeutic protein or peptide), wherein exposure of the fusion protein to light induces a conformational change that alters its ability to bind a target protein. The method comprises providing one or more phages displaying a fusion protein intended to bind a target protein. The fusion protein comprises a light-responsive domain and a heterologous peptide component. The immobilized target protein is exposed to the one or more phages in the presence of light under conditions sufficient to induce binding of the target protein and the fusion protein, and one or more phages is eluted in the absence of light, thereby eluting one or more phages displaying a fusion protein that binds the target protein upon exposure to light and dissociates from the target protein in the absence of light. Alternatively, immobilized target protein is exposed to the one or more phages in the absence of light under conditions sufficient to induce binding of the target protein and the fusion protein, and one or more phages is eluted in the presence of light, thereby eluting one or more phages displaying a fusion protein that binds the target protein in the absence of light and dissociates from the target protein upon exposure to light. A fusion protein comprising a light-responsive domain and a heterologous peptide component, wherein the fusion protein undergoes a photodependent conformational change that alters its ability to bind the target protein, is thereby identified.

In some aspects, the fourth embodiment further comprises determining the nucleic acid sequence of the coding sequence of the fusion protein or the amino acid sequence of the fusion protein displayed on the one or more eluted phages.

In some aspects, the fourth embodiment further comprises generating the one or more phages using random transposon-mediated insertion of the coding sequence of the light-responsive domain into the coding sequence of the heterologous peptide component.

In some aspects, the fourth embodiment further comprises providing a library of phages, each phage displaying a fusion protein intended to bind a target protein and comprising a light-responsive domain and a heterologous peptide component, and exposing immobilized target protein to the library of phages.

A fifth embodiment is a method of identifying a fusion protein comprising a light-responsive domain (e.g., a LOV2, such as an AsLOV2, domain) and a heterologous peptide component (e.g., a therapeutic protein or peptide), wherein exposure of the fusion protein to light induces a conformational change that alters its ability to bind a target protein. The method comprises providing one or more cells expressing a fusion protein intended to bind a target protein. The fusion protein comprises a light-responsive domain and a heterologous peptide component. One or more cells is sorted using fluorescence-activated cell sorting (FACS). Immobilized target protein is exposed to the one or more cells in the presence of light under conditions sufficient to induce binding of the target protein and the fusion protein, and one or more cells is eluted in the absence of light, thereby eluting one or more cells expressing a fusion protein that binds the target protein upon exposure to light and dissociates from the target protein in the absence of light. Alternatively, immobilized target protein is exposed to the one or more cells in the absence of light under conditions sufficient to induce binding of the target protein and the fusion protein, and one or more cells is eluted in the presence of light, thereby eluting one or more cells expressing a fusion protein that binds the target protein in the absence of light and dissociates from the target protein upon exposure to light. A fusion protein comprising a light-responsive domain and a heterologous peptide component, wherein the fusion protein undergoes a photodependent conformational change that alters its ability to bind the target protein, is thereby identified.

In some aspects, the fifth embodiment further comprises determining the nucleic acid sequence of the coding sequence of the fusion protein or the amino acid sequence of the fusion protein expressed by the one or more cells.

In some aspects, the fifth embodiment further comprises generating the one or more cells by transforming plasmids generated using random transposon-mediated insertion of the coding sequence of the light-responsive domain into the coding sequence of the biopharmaceutical into the one or more cells.

In some aspects, the fifth embodiment further comprises providing a library of cells, each cell expressing a fusion protein intended to bind a target protein and comprising a light-responsive domain and a heterologous peptide component, and exposing immobilized target protein to the library of cells.

A sixth embodiment is a method of purifying a target protein from a cell lysate. The method comprises providing a substrate comprising an immobilized fusion protein intended to bind a target protein, the fusion protein comprising a light-responsive domain and a heterologous peptide component. Exposure of the fusion protein to light induces a conformational change that alters its ability to bind the target protein. The method comprises exposing the substrate to the cell lysate in the presence of light under conditions sufficient to induce binding of the target protein and the fusion protein; and eluting the target protein in the absence of light, wherein the fusion protein binds the target protein upon exposure to light and dissociates from the target protein in the absence of light, thereby purifying the target protein. Alternatively, the method comprises exposing the substrate to the cell lysate in the absence of light under conditions sufficient to induce binding of the target protein and the fusion protein; and eluting the target protein in the presence of light, wherein the fusion protein binds the target protein in the absence of light and dissociates from the target protein upon exposure to light, thereby purifying the target protein.

In some aspects of the sixth embodiment, the light-responsive domain is a light oxygen voltage (LOV) domain, such as AsLOV2, the LOV2 domain from *Avena sativa* Phototropin 1.

In some aspects of the sixth embodiment, the target protein comprises a purification tag, wherein the immobilized fusion protein binds the purification tag on the target protein under conditions sufficient to induce binding. In some aspects of the sixth embodiment, the target protein does not possess a purification tag (i.e., tag-less purification).

In some aspects of the sixth embodiment, the substrate is a resin. In some embodiments, the resin is inside of a purification column.

In some aspects of the methods described herein, light (e.g., visible light, such as blue light, red light and/or far-red light, infrared light) is delivered using two photon excitation.

A seventh embodiment is an isolated fusion protein comprising a light-responsive domain, a heterologous peptide component, and a cell-penetrating peptide component, wherein exposure of the fusion protein to light induces a conformational change in the fusion protein that alters an activity (e.g., a binding activity) of the fusion protein. The cell-penetrating peptide allows for intracellular delivery of the fusion protein. Fusion proteins comprising a cell-penetrating peptide component can be used to contact the outside of a cell, penetrate the cell, and then bind a target determined by the first heterologous peptide component (e.g., a nanobody, a monobody, or an antibody).

An eighth embodiment is a method of delivering a fusion protein to a cell, comprising contacting the cell extracellularly with an isolated fusion protein comprising a light-responsive domain, a heterologous peptide component, and a cell-penetrating peptide component, wherein exposure of the fusion protein to light induces a conformational change in the fusion protein that alters an activity (e.g., a binding activity) of the fusion protein, wherein the fusion protein is delivered intracellularly.

A ninth embodiment is a chimeric antigen receptor (CAR), comprising an extracellular antigen-binding domain, a transmembrane domain and an intracellular signaling domain, wherein the extracellular antigen-binding domain comprises a light-responsive domain and a heterologous peptide component, wherein exposure of the CAR to light induces a conformational change in the extra-cellular antigen-binding domain that alters an activity (e.g., an in vivo extracellular binding activity) of the extra-cellular antigen-binding domain.

In some aspects, the present disclosure provides isolated lymphocytes expressing the CAR described herein. In some aspects, the lymphocyte is a T lymphocyte.

The term "Chimeric Antigen Receptor" or, alternatively, "CAR," refers to a recombinant polypeptide construct comprising at least an extracellular antigen binding domain, a transmembrane domain and an intracellular signaling domain comprising a functional signaling domain.

An "intracellular signaling domain," as the term is used herein, refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

A tenth embodiment is a fusion protein comprising a light-responsive domain and a heterologous peptide component, wherein the heterologous peptide component is selected from the group consisting of a nanobody, a monobody, an antibody, a growth factor, and a designed ankyrin repeat protein (DARPin), wherein exposure of the fusion protein to light induces a conformational change in the fusion protein that alters an activity (e.g., a binding activity) of the fusion protein.

An eleventh embodiment is a method of delivering a fusion protein to a cell, comprising contacting the cell with a fusion protein comprising a light-responsive domain and a heterologous peptide component, wherein the heterologous peptide component is selected from the group consisting of a nanobody, a monobody, an antibody, a growth factor, and a designed ankyrin repeat protein (DARPin), wherein the fusion protein is delivered intracellularly. In some aspects, the fusion protein is delivered by externally contacting the cell with a nucleic acid encoding the fusion protein. In a further aspect, the nucleic acid encoding the fusion protein is in a viral expression vector. Once introduced into a cell, the nucleic acid can be expressed transiently, or subsequent to stable integration into the cell's genome.

The term "expression vector" or "vector", used interchangeably herein, refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

A twelfth embodiment is an isolated fusion protein comprising a light oxygen voltage (LOV) domain and a heterologous peptide component selected from a nanobody, monobody, antibody, DARPin or anticalin, wherein exposure of the fusion protein to light induces a conformational change in the fusion protein that alters an activity (e.g., a binding activity) of the fusion protein.

A thirteenth embodiment is chromatography media comprising a fusion protein described herein immobilized (e.g., covalently, non-covalently) to chromatography resin. Chromatography resin suitable for use in the chromatography media described herein is commercially available, and includes agarose and sepharose beads, such as those described in the Exemplification. Fusion proteins can be covalently immobilized on chromatography resin, for example, by treating cyanogen bromide-activated sepharose beads with fusion protein, thereby making covalent bonds between the resin and the primary amino groups in the protein, and/or cross-linking. Fusion proteins can be non-covalently immobilized on chromatography resin, for example, using a traditional affinity pair. Thus, a fusion protein described herein can be designed so as to further comprise an affinity or other purification tag, such as a His$_6$ (SEQ ID NO: 49) tag. Under appropriate conditions, the His$_6$ (SEQ ID NO: 49) tag can be used to immobilize the His$_6$ (SEQ ID NO: 49)-containing fusion protein to a metal (e.g., $Co^{2+}$, $Ni^{2+}$, $Cu^{2+}$, $Zn^{2+}$)-modified resin. Other affinity pairs that can be used to immobilize fusion proteins on resin include antigen-antibody pairs (such as the hemagglutinin (HA)-anti-HA pair and protein A, protein G or protein L-antibody pair).

A fourteenth embodiment is a column (e.g., chromatography column) comprising (e.g., packed with) chromatography media described herein. In some aspects of this embodiment, the column further comprises one or more light-emitting diodes (LEDs), e.g., to enable light illumination of the column for use in one or more of the methods described herein. In some aspects of this embodiment, the column is transparent.

A fifteenth embodiment is a method of purifying a target protein from a cell lysate. The method comprises providing a substrate comprising an immobilized fusion protein intended to bind a target protein, the fusion protein comprising a LOV domain and a heterologous peptide component selected from a nanobody, monobody, antibody, DARPin or anticalin, wherein exposure of the fusion protein to light induces a conformational change that alters its ability to bind the target protein. The substrate is exposed to the cell lysate in the presence of light under conditions sufficient to induce binding of the target protein and the fusion protein, and the target protein is eluted in the absence of light, wherein the fusion protein binds the target protein upon exposure to light and dissociates from the target protein in the absence of light, thereby purifying the target protein; or the substrate is exposed to the cell lysate in the absence of light under conditions sufficient to induce binding of the target protein and the fusion protein, and the target protein is eluted in the presence of light, wherein the fusion protein binds the target protein in the absence of light and dissociates from the target protein upon exposure to light, thereby purifying the target protein.

In some aspects of the fifteenth embodiment, the substrate comprises chromatography resin, such as any of the chromatography resin described herein. In some aspects of the fifteenth embodiment, the chromatography resin is in (e.g., packed in) a column (e.g., purification column).

It will be understood that any of the fusion proteins and/or chromatography media and/or columns described herein can be used in a method of purifying a target protein from a cell lysate (e.g., a method according to the sixth and/or fifteenth embodiment).

A sixteenth embodiment is a fusion protein comprising a light responsive domain consisting of amino acids 404-547 (e.g., 404-546, 408-543) of SEQ ID NO:1, or a variant thereof having from one to 30 mutations (e.g., insertions, substitutions, deletions), for example, from one to 25, from one to 20, from one to 15, from one to ten, from one to five, 10, 9, 8, 7, 6, 5, 4, 3, 2 or 1 mutation(s). In some aspects of the sixteenth embodiment, the one or more mutations comprises a substitution (e.g., a conservative substitution) at one or more (e.g., three) of the following amino acids of SEQ ID NO:1: V416, G528 and N538. In some aspects of the sixteenth embodiment, the one or more substitutions comprise one or more (e.g., three) of the following substitutions: V416L/I, G528A and N538E. In some aspects of the sixteenth embodiment, the one or more mutations comprise an insertion, e.g., of an amino acid (e.g., glycine) at the N-terminus of amino acids 404-547 (e.g., 404-546, 408-543) of SEQ ID NO:1 and the C-terminus of amino acids 404-547 (e.g., 404-546, 408-543) of SEQ ID NO:1. In some aspects of the sixteenth embodiment, the light responsive domain consists of SEQ ID NO:9, or a variant thereof having from one to 30 substitutions, for example, from one to 25, from one to 20, from one to 15, from one to ten, from one to five, 10, 9, 8, 7, 6, 5, 4, 3, 2 or 1 substitution(s) (e.g., conservative substitutions), e.g., at one or more (e.g., three) of the following amino acids: V416, G528 and N538, such as one or more (e.g., three) of the following substitutions: V416L/I, G528A and N538E. In some aspects of the sixteenth embodiment, the light responsive domain consists of SEQ ID NO:9. In some aspects of the sixteenth embodiment, the light responsive domain consists of SEQ ID NO: 47. In some aspects of the sixteenth embodiment, the light responsive domain consists of SEQ ID NO: 48.

A seventeenth embodiment is a light responsive domain consisting of amino acids 404-547 (e.g., 404-546, 408-543) of SEQ ID NO:1, or a variant thereof having from one to 30 mutations (e.g., insertions, substitutions, deletions), for example, from one to 25, from one to 20, from one to 15, from one to ten, from one to five, 10, 9, 8, 7, 6, 5, 4, 3, 2 or 1 mutation(s). In some aspects of the seventeenth embodiment, the one or more mutations comprises a substitution (e.g., a conservative substitution) at one or more (e.g., three) of the following amino acids of SEQ ID NO:1: V416, G528 and N538. In some aspects of the seventeenth embodiment, the one or more substitutions comprise one or more (e.g., three) of the following substitutions: V416L/I, G528A and N538E. In some aspects of the seventeenth embodiment, the one or more mutations comprise an insertion, e.g., of an amino acid (e.g., glycine) at the N-terminus of amino acids 404-547 (e.g., 404-546, 408-543) of SEQ ID NO:1 and the C-terminus of amino acids 404-547 (e.g., 404-546, 408-543) of SEQ ID NO:1. In some aspects of the seventeenth embodiment, the light responsive domain consists of SEQ ID NO:9, or a variant thereof having from one to 30 substitutions, for example, from one to 25, from one to 20, from one to 15, from one to ten, from one to five, 10, 9, 8, 7, 6, 5, 4, 3, 2 or 1 substitution(s) (e.g., conservative substitutions), e.g., at one or more (e.g., three) of the following amino acids of SEQ ID NO:1: V416, G528 and N538, such as one or more (e.g., three) of the following substitutions: V416L/I, G528A and N538E. In some aspects of the seventeenth embodiment, the light responsive domain consists of SEQ ID NO:9. In some aspects of the seventeenth embodiment, the light responsive domain consists of SEQ ID NO: 47. In some aspects of the seventeenth embodiment, the light responsive domain consists of SEQ ID NO: 48.

An eighteenth embodiment is a fusion protein comprising a light responsive domain consisting of amino acids 404-547 (e.g., 404-546, 408-543) of SEQ ID NO:1, or a variant thereof having at least about 70% (e.g., about 75%, about 80%, about 85%, about 90%, about 95%, about 96%, about 97%, about 98% or about 99%) identity to the amino acid sequence of amino acids 408-543 of SEQ ID NO:1, e.g., determined over the entire length of the variant sequence. In some aspects of the eighteenth embodiment, the variant sequence contains substitutions (e.g., conservative substitutions) at one or more of the following amino acids of SEQ ID NO:1: V416, G528 and N538. In some aspects of the eighteenth embodiment, the variant sequence contains one or more (e.g., three) of the following substitutions: V416L/I, G528A and N538E. In some aspects of the eighteenth embodiment, the light responsive domain consists of SEQ ID NO:9, or a variant thereof having at least about 70% (e.g., about 75%, about 80%, about 85%, about 90%, about 95%, about 96%, about 97%, about 98% or about 99%) identity to the amino acid sequence of SEQ ID NO:9, determined over the entire length of the variant sequence, e.g., and contains substitutions (e.g., conservative substitutions) at one or more (e.g., three) of the following amino acids of SEQ ID NO:1: V416, G528 and N538, such as one or more (e.g., three) of the following substitutions: V416L/I, G528A and N538E. In some aspects of the eighteenth embodiment, the light responsive domain consists of the amino acid sequence of SEQ ID NO:9. In some aspects of the eighteenth embodiment, the light responsive domain consists of the amino acid sequence of SEQ ID NO:47. In some aspects of the eighteenth embodiment, the light responsive domain consists of the amino acid sequence of SEQ ID NO:48.

A nineteenth embodiment is a light responsive domain consisting of amino acids 404-547 (e.g., 404-546, 408-543) of SEQ ID NO:1, or a variant thereof having at least about 70% (e.g., about 75%, about 80%, about 85%, about 90%, about 95%, about 96%, about 97%, about 98% or about 99%) identity to the amino acid sequence of amino acids 408-543 of SEQ ID NO:1, e.g., determined over the entire length of the variant sequence. In some aspects of the nineteenth embodiment, the variant sequence contains substitutions (e.g., conservative substitutions) at one or more of the following amino acids of SEQ ID NO:1: 416, 528 and 538. In some aspects of the nineteenth embodiment, the variant sequence contains one or more (e.g., three) of the following substitutions: V416L/I, G528A and N538E. In some aspects of the nineteenth embodiment, the light responsive domain consists of SEQ ID NO:9, or a variant thereof having at least about 70% (e.g., about 75%, about 80%, about 85%, about 90%, about 95%, about 96%, about 97%, about 98% or about 99%) identity to the amino acid sequence of SEQ ID NO:9, determined over the entire length of the variant sequence, e.g., and contains substitutions (e.g., conservative substitutions) at one or more (e.g., three) of the following amino acids of SEQ ID NO:1: 416, 528 and 538, such as one or more (e.g., three) of the following substitutions: V416L/I, G528A and N538E. In some aspects of the nineteenth embodiment, the light responsive domain consists of the amino acid sequence of SEQ ID NO:9. In some aspects of the nineteenth embodiment, the light responsive domain consists of the amino acid sequence of SEQ ID NO:47. In some aspects of the nineteenth embodiment, the light responsive domain consists of the amino acid sequence of SEQ ID NO:48.

In some embodiments, an amino acid substitution is a conservative substitution. As used herein with respect to amino acid substitutions, a "conservative substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) A→G, S; (b) R→K, H; (c) N→Q, H; (d) D→E, N; (e) C→S, A; (f) Q→N; (g) E→D, Q; (h) G→A; (i) H→N, Q; (j) I→L, V; (k) L→I, V; (l) K→R, H; (m) M→L, I, Y; (n) F→Y, M, L; (o) P→A; (p) S→T; (q) T→S; (r) W→Y, F; (s) Y→W, F; and (t) V→I, L. Further conservative amino acid substitutions are known to a person skilled in the art.

EMBODIMENTS

1. An isolated fusion protein comprising a light-responsive domain and a heterologous peptide component, wherein exposure of the fusion protein to light induces a conformational change in the fusion protein that alters an activity of the fusion protein, wherein the activity is a binding activity selected from an in vitro binding activity and an in vivo extracellular binding activity.
2. The fusion protein of embodiment 1, wherein the light-responsive domain is a light oxygen voltage (LOV) domain.
3. The fusion protein of embodiment 2, wherein the LOV domain is the LOV2 domain from *Avena sativa* Phototropin 1.
4. The fusion protein of embodiment 1, 2 or 3, wherein the peptide component is interferon.
5. The fusion protein of embodiment 1, 2 or 3, wherein the peptide component is ipilimumab.
6. The fusion protein of embodiment 1, 2 or 3, wherein the peptide component is conotoxin.
7 The fusion protein of embodiment 1, 2 or 3, wherein the peptide component is a nanobody, monobody or an antibody.
8. The fusion protein of embodiment 1, 2 or 3, wherein the peptide component is a growth factor.
9. The fusion protein of embodiment 1, 2 or 3, wherein the peptide component is a designed ankyrin repeat protein (DARPin).
10. The fusion protein of embodiment 1, 2 or 3, wherein the peptide component is an antimicrobial peptide.
11. The fusion protein of embodiment 1, 2 or 3, wherein the peptide component is an enzyme.
12. The fusion protein of embodiment 1, 2 or 3, wherein the peptide component is a therapeutic protein or peptide.
13. The fusion protein of any one of embodiments 1-12, wherein the conformational change is an allosteric change.
14. The fusion protein of any one of embodiments 1-12, wherein the conformational change induces multimerization of the fusion protein.
15. The fusion protein of any one of embodiments 1-14, wherein exposure of the fusion protein to light increases its binding activity.
16. The fusion protein of any one of embodiments 1-14, wherein exposure of the fusion protein to light decreases its binding activity.
17. The fusion protein of embodiment 15 or 16, wherein the light is visible light.
18. The fusion protein of embodiment 17, wherein the light is blue light.
19. The fusion protein of embodiment 15 or 16, wherein the light is infrared light.
20. An isolated fusion protein comprising a light-responsive domain, a heterologous peptide component, and a cell-penetrating peptide component, wherein exposure of the fusion protein to light induces a conformational change in the fusion protein that alters an activity of the fusion protein, wherein the activity is a binding activity.
21. A composition comprising a pharmaceutically acceptable carrier and a fusion protein of any one of the preceding embodiments.
22. A method of delivering a fusion protein to a cell, comprising contacting the cell extracellularly with the isolated fusion protein of embodiment 20, wherein the fusion protein is delivered intracellularly.
23. A method of altering an activity of a fusion protein comprising a light-responsive domain and a heterologous peptide component, the method comprising:
    exposing the fusion protein to light that induces a conformational change in the fusion protein, wherein the conformational change alters an activity of the fusion protein, wherein the activity is a binding activity selected from an in vitro binding activity and an in vivo extracellular binding activity,
    thereby altering an activity of the fusion protein.
24. The method of claim 23, wherein the photoactivatable domain is a light oxygen voltage (LOV) domain.
25. The method of embodiment 24, wherein the LOV domain is the LOV2 domain from *Avena sativa* Phototropin 1.
26. A method for treating a subject in need thereof, comprising:
    administering to the subject a therapeutically effective amount of a therapeutic fusion protein of any one of embodiments 1-20, wherein exposure of the fusion protein to light induces a conformational change in the fusion protein that alters its therapeutic efficacy; and
    delivering a sufficient amount of light to at least a portion of the subject to induce the conformational change, thereby altering the therapeutic efficacy of the fusion protein exposed to the light, thereby treating the subject in need thereof
27. The method of embodiment 26, wherein exposure of the fusion protein to light increases its therapeutic efficacy and, hence, delivering a sufficient amount of light increases the therapeutic efficacy of the fusion protein exposed to the light.
28. The method of embodiment 26, wherein exposure of the fusion protein to light decreases its therapeutic efficacy and, hence, delivering a sufficient amount of light decreases the therapeutic efficacy of the fusion protein exposed to the light.
29. The method of embodiment 26 or 27, wherein light is delivered using two photon excitation.
30. The method of any one of embodiments 26-29, wherein the light is visible light.
31. The method of embodiment 30, wherein the light is blue light.
32. The method of any one of embodiments 26-29, wherein the light is infrared light.
33. A method of identifying a fusion protein comprising a light-responsive domain and a heterologous peptide component, wherein exposure of the fusion protein to light induces a conformational change that alters its ability to bind a target protein, the method comprising:
providing one or more phages displaying a fusion protein intended to bind a target protein, the fusion protein comprising a light-responsive domain and a heterologous peptide component; and
exposing immobilized target protein to the one or more phages in the presence of light under conditions sufficient to induce binding of the target protein and the fusion protein; and
eluting one or more phages in the absence of light, thereby eluting one or more phages displaying a fusion protein that binds the target protein upon exposure to light and dissociates from the target protein in the absence of light; or
exposing immobilized target protein to the one or more phages in the absence of light under conditions sufficient to induce binding of the target protein and the fusion protein; and
eluting one or more phages in the presence of light, thereby eluting one or more phages displaying a fusion protein that binds the target protein in the absence of light and dissociates from the target protein upon exposure to light,
thereby identifying a fusion protein comprising a light-responsive domain and a heterologous peptide component, wherein the fusion protein undergoes a photodependent conformational change that alters its ability to bind the target protein.
34. The method of embodiment 33, wherein the light-responsive domain is a light oxygen voltage (LOV) domain.
35. The method of embodiment 34, wherein the LOV domain is the LOV2 domain from *Avena sativa* Phototropin 1.
36. The method of embodiment 33, 34 or 35, wherein the peptide component is a therapeutic protein or peptide.
37. The method of any one of embodiments 33-36, further comprising determining the nucleic acid sequence of the coding sequence of the fusion protein or the amino acid sequence of the fusion protein displayed on the one or more eluted phages.
38. The method of any one of embodiments 33-37, further comprising generating the one or more phages using random transposon-mediated insertion of the coding sequence of the light-responsive domain into the coding sequence of the heterologous peptide component.
39. The method of any one of embodiments 33-38, comprising providing a library of phages, each phage displaying a fusion protein intended to bind a target protein and comprising a light-responsive domain and a heterologous peptide component, and exposing immobilized target protein to the library of phages.
40. A method of identifying a fusion protein comprising a light-responsive domain and a heterologous peptide component, wherein exposure of the fusion protein to light induces a conformational change that alters its ability to bind a target protein, the method comprising:
providing one or more cells expressing a fusion protein intended to bind a target protein, the fusion protein comprising a light-responsive domain and a heterologous peptide component;
sorting the one or more cells using fluorescence-activated cell sorting (FACS); and
exposing immobilized target protein to the one or more cells in the presence of light under conditions sufficient to induce binding of the target protein and the fusion protein; and
eluting one or more cells in the absence of light, thereby eluting one or more cells expressing a fusion protein that binds the target protein upon exposure to light and dissociates from the target protein in the absence of light; or
exposing immobilized target protein to the one or more cells in the absence of light under conditions sufficient to induce binding of the target protein and the fusion protein; and
eluting one or more cells in the presence of light, thereby eluting one or more cells expressing a fusion protein that binds the target protein in the absence of light and dissociates from the target protein upon exposure to light,
thereby identifying a fusion protein comprising a light-responsive domain and a heterologous peptide component, wherein the fusion protein undergoes a photodependent conformational change that alters its ability to bind the target protein.
41. The method of embodiment 40, wherein the light-responsive domain is a light oxygen voltage (LOV) domain.
42. The method of embodiment 41, wherein the LOV2 domain is the LOV2 domain from *Avena sativa* Phototropin 1.
43. The method of embodiment 40, 41 or 42, wherein the peptide component is a therapeutic protein or peptide.
44. The method of any one of embodiments 40-43, further comprising determining the nucleic acid sequence of the coding sequence of the fusion protein or the amino acid sequence of the fusion protein expressed by the one or more cells.
45. The method of any one of embodiments 40-44, further comprising generating the one or more cells by transforming plasmids generated using random transposon-mediated insertion of the coding sequence of the light-responsive domain into the coding sequence of the biopharmaceutical into the one or more cells.
46. The method of any one of embodiments 40-45, comprising providing a library of cells, each cell expressing a fusion protein intended to bind a target protein and comprising a light-responsive domain and a heterologous peptide component, and exposing immobilized target protein to the library of cells.

47. A method of purifying a target protein from a cell lysate, the method comprising:
providing a substrate comprising an immobilized fusion protein intended to bind a target protein, the fusion protein comprising a light-responsive domain and a heterologous peptide component, wherein exposure of the fusion protein to light induces a conformational change that alters its ability to bind the target protein; and
exposing the substrate to the cell lysate in the presence of light under conditions sufficient to induce binding of the target protein and the fusion protein; and
eluting the target protein in the absence of light, wherein the fusion protein binds the target protein upon exposure to light and dissociates from the target protein in the absence of light, thereby purifying the target protein; or
exposing the substrate to the cell lysate in the absence of light under conditions sufficient to induce binding of the target protein and the fusion protein; and
eluting the target protein in the presence of light, wherein the fusion protein binds the target protein in the absence of light and dissociates from the target protein upon exposure to light, thereby purifying the target protein.

48. The method of embodiment 47, wherein the light-responsive domain is a light oxygen voltage (LOV) domain.

49. The method of embodiment 48, wherein the LOV domain is the LOV2 domain from *Avena sativa* Phototropin 1.

50. The method of any one of embodiments 47-49, wherein the target protein comprises a purification tag and wherein the immobilized fusion protein binds the purification tag on the target protein under conditions sufficient to induce binding.

51. The method of any one of embodiments 47-50, wherein the substrate comprises the immobilized fusion protein conjugated to a resin.

52. The method of embodiment 51, wherein the resin is in a purification column.

53. A chimeric receptor (CR), comprising an extracellular antigen-binding domain, a transmembrane domain and an intracellular signaling domain, wherein the extracellular binding domain comprises a light-responsive domain and a heterologous peptide component, wherein exposure of the CR to light induces a conformational change in the extracellular binding domain that alters an activity of the extracellular binding domain, wherein the activity is an in vivo extracellular binding activity.

54. An isolated cell expressing the CR of embodiment 53.

55. The isolated cell of embodiment 54, wherein the cell is a lymphocyte.

56. The isolated lymphocyte of embodiment 55, where the lymphocyte is a T lymphocyte.

57. A fusion protein comprising a light-responsive domain and a heterologous peptide component, wherein the heterologous peptide component is selected from the group consisting of a nanobody, a monobody, an antibody, a designed ankyrin repeat protein (DARPin), a cytokine, a growth factor, a peptide hormone, an antimicrobial peptide, and a peptide toxin, wherein exposure of the fusion protein to light induces a conformational change in the fusion protein that alters an activity of the fusion protein, wherein the activity is a binding activity.

58. A method of delivering a fusion protein to a cell, comprising contacting the cell with the fusion protein of embodiment 57, wherein the fusion protein is delivered intracellularly.

59. A method of delivering a fusion protein to a cell, comprising externally contacting the cell with a nucleic acid encoding the fusion protein of embodiment 57.

60. The method of embodiment 59, wherein the nucleic acid encoding the fusion protein is in a viral expression vector.

61. An isolated fusion protein comprising a light oxygen voltage (LOV) domain and a heterologous peptide component selected from a nanobody, monobody, antibody, designed ankyrin repeat protein (DARPin) or anticalin, wherein exposure of the fusion protein to light induces a conformational change in the fusion protein that alters an activity of the fusion protein, wherein the activity is a binding activity.

62. The fusion protein of embodiment 61, wherein the LOV domain is the LOV2 domain from *Avena sativa* phototropin 1 (AsLOV2), or a variant or fragment thereof.

63. The fusion protein of embodiment 61 or 62, wherein the LOV domain comprises the sequence of SEQ ID NO:9 or a sequence having at least 75% identity to the sequence of SEQ ID NO:9.

64. The fusion protein of embodiment 63, wherein the LOV domain consists of the sequence of SEQ ID NO:9 or a sequence having at least 75% identity to the sequence of SEQ ID NO:9.

65. The fusion protein of any one of embodiments 61-64, wherein the heterologous peptide component is a nanobody, monobody or antibody.

66. The fusion protein of any one of embodiments 61-64, wherein the heterologous peptide component is a DARPin.

67. The fusion protein of any one of embodiments 61-66, wherein the fusion protein is an internal fusion protein, and the LOV domain is inserted into the heterologous peptide component.

68. The fusion protein of embodiment 7, wherein the heterologous peptide component has one or more loops, and the LOV domain is inserted into a loop of the heterologous peptide component.

69. The fusion protein of any one of embodiments 61-65, 67 and 68, wherein the heterologous peptide component is a monobody having a first β-sheet connected to a second β-sheet by one or more loops.

70. The fusion protein of embodiment 69, wherein the LOV domain is inserted into a loop of the monobody that connects the first β-sheet to the second β-sheet.

71. The fusion protein of any one of claims 61-65 and 67-69, wherein the heterologous peptide component is a HA4 monobody.

72. The fusion protein of embodiment 71, wherein the LOV domain is inserted into loop 2 or loop 4 of the HA4 monobody.

73. The fusion protein of embodiment 72, wherein the LOV domain is inserted into loop 4 of the HA4 monobody.

74. Chromatography media comprising a fusion protein of any of the foregoing embodiments immobilized on chromatography resin.

75. A column comprising chromatography media of embodiment 74.

76. A method of purifying a target protein from a cell lysate, the method comprising:
providing a substrate comprising an immobilized fusion protein intended to bind a target protein, the fusion protein comprising a LOV domain and a heterologous peptide component selected from a nanobody, monobody, antibody, designed ankyrin repeat protein (DARPin) or anticalin, wherein exposure of the fusion protein to light induces a conformational change that alters its ability to bind the target protein; and exposing the substrate to the cell lysate in the presence of light under conditions sufficient to induce binding of the target protein and the fusion protein;

and eluting the target protein in the absence of light, wherein the fusion protein binds the target protein upon exposure to light and dissociates from the target protein in the absence of light, thereby purifying the target protein; or exposing the substrate to the cell lysate in the absence of light under conditions sufficient to induce binding of the target protein and the fusion protein;

and eluting the target protein in the presence of light, wherein the fusion protein binds the target protein in the absence of light and dissociates from the target protein upon exposure to light, thereby purifying the target protein.

77. The method of embodiment 76, wherein the substrate comprises chromatography resin.
78. The method of embodiment 77, wherein the chromatography resin is in a purification column.
79. The method of any one of embodiments 76-78, wherein the fusion protein is covalently attached to the substrate.
80. The method of embodiments 76-78, wherein the fusion protein is non-covalently attached to the substrate.
81. A fusion protein comprising a light responsive domain consisting of amino acids 408-543 of SEQ ID NO:1, or a variant thereof having from one to 10 mutations.
82. The fusion protein of claim 81, wherein the light responsive domain consists of the amino acid sequence of SEQ ID NO:9, or a variant thereof having from one to eight substitutions.
83. The fusion protein of claim 81 or 82, wherein the light responsive domain consists of the amino acid sequence of SEQ ID NO:47.

EXEMPLIFICATION

Yeast 2 Hybrid (Y2H) Screening of Light-Switchable Protein Binding

Unless otherwise specified, liquid yeast cultures were grown in 24-well plates, at 30° C. and shaken at 200 rpm, in either YPD or SC-dropout media with 2% glucose.

When cells were grown under light, blue LED panels (HQRP New Square 12" Grow Light Blue LED 14W) were placed 40 cm from cell cultures. To control light duty cycles, the LED panels were regulated with a Nearpow Multifunctional Infinite Loop Programmable Plug-in Digital Timer Switch (from Amazon).

Figure 1:
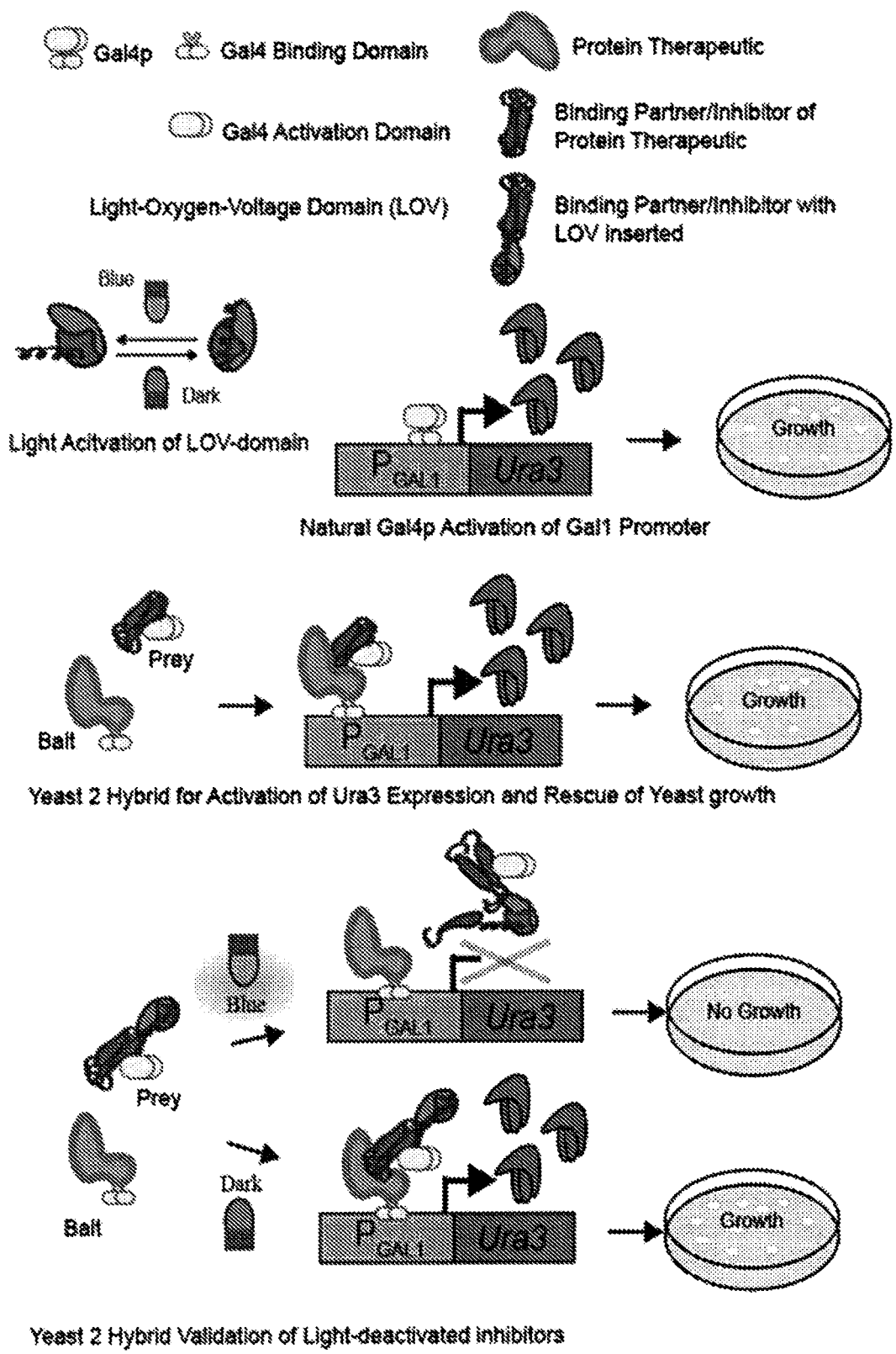
FIG. 1 is a depiction of a yeast 2 hybrid screening of light-switchable protein binding.

Y2H_Report_Ura3: Gal1 promoter driving Ura3 gene was placed into an integration vector that will restore trp1 auxotrophy (pNH60x series);

Y2H_Bait_X: Adh1 promoter driving Gal4 binding domain attached to eGFP, mcherry, or any protein therapeutic was placed into an integration vector that will restore His3 auxotrophy (pNH60x series);

Y2H_Prey_X: Adh1 promoter driving the Sv40 nuclear localization sequence connected to the Gal4 activation domain connected to the nanobody or inhibitor against the bait (see FIG. 1) was placed into a CEN/ARS plasmid that will restore Leu2 auxotrophy (pRS41x series);

Y2H_Prey_X was opened at optimally determined amino acid sites in conserved or high likelihood regions by backbone PCR;

Light-oxygen-voltage domain was added to the Y2H_Prey_X plasmid through Gibson isothermal assembly. This makes Y2H_Prey_LightSense_X plasmids;

CEN.PK2-1C (MATa his3 Δ1 leu2-3_112 trp1-289 ura3-53) strains with GAL4 and GAL80 knocked out were transformed with Y2H_Report_Ura, Y2H_Bait_X and Y2H_Prey_LightSense_X plasmids and selected on plates that lacked histidine, leucine, and tryptophan.

Colonies were picked and grown in SC-Leucine-Ura media overnight under light. Samples were then diluted into 24-well plates to an $OD_{600}$ of 0.1. Samples were then placed in light or tinfoiled. Measurements were taken at 0 hours (H), 9H . . . 43H.

The exponential phase of the data was identified as the most linear portion of the plot of $Log_e(OD)$ versus time, and then fit to $Log_e(OD)=Log_e(OD_0)+\mu^*t$, where $OD_0$ and $\mu$ are constants, using least squares linear regression. The $\mu$ constant from these calculations is taken as the mean specific growth rate.

Directed Evolution for Better Kinetics/Activity

Y2H_Prey_LightSense_X identified with some light-deactivation activity were mutagenized to improve the final inhibitors. Y2H_Prey_LightSense_X was amplified through backbone PCR at the Gal4 activation domain and the terminator. The inhibitor-LOV gene was amplified using GenemorphII random mutagenesis kit from Agilent technologies. These pieces were combined into a Gibson assembly mix to make Y2H_Prey_LightSense_X_mutants.

Y2H_Report_Ura3_BFP: Gal1 promoter driving Ura3 gene and Gal1 promoter driving blue fluorescent protein (BFP) gene was placed into an integration vector that will restore trp 1 auxotrophy (pNH60x series).

CEN.PK2-1C (MATa his3 Δ1 leu2-3_112 trp1-289 ura3-53) strains with GAL4 and GAL80 knocked out were transformed with Y2H_Report_Ura3_BFP, Y2H_Bait_X, and Y2H_Prey_LightSense_X_mutants plasmids and selected on plates that lacked histidine, leucine, and tryptophan.

The new yeast were plated onto SC-Leucine+5FOA plates while exposed to light. One the colonies that grow have low leakiness (do not bind in the light to the protein therapeutic). 5FOA will kill yeast cells if they have Ura3 protein in them.

Colonies that grew on previous test were then grown in the dark and sorted using cell sorting based on flow cytometry. This process was repeated and good mutants were identified, sequenced, and tested using other methods.

Library Generation

Figure 4A:
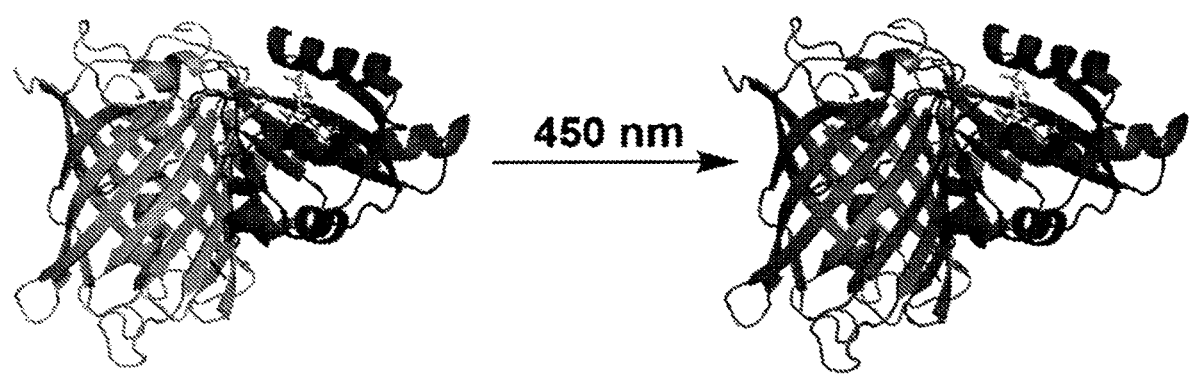
FIG. 4A is a model of photoswitchable mCherry (red/grey) fluorescence through AsLov2 (blue) structural change.
Figure 4B:
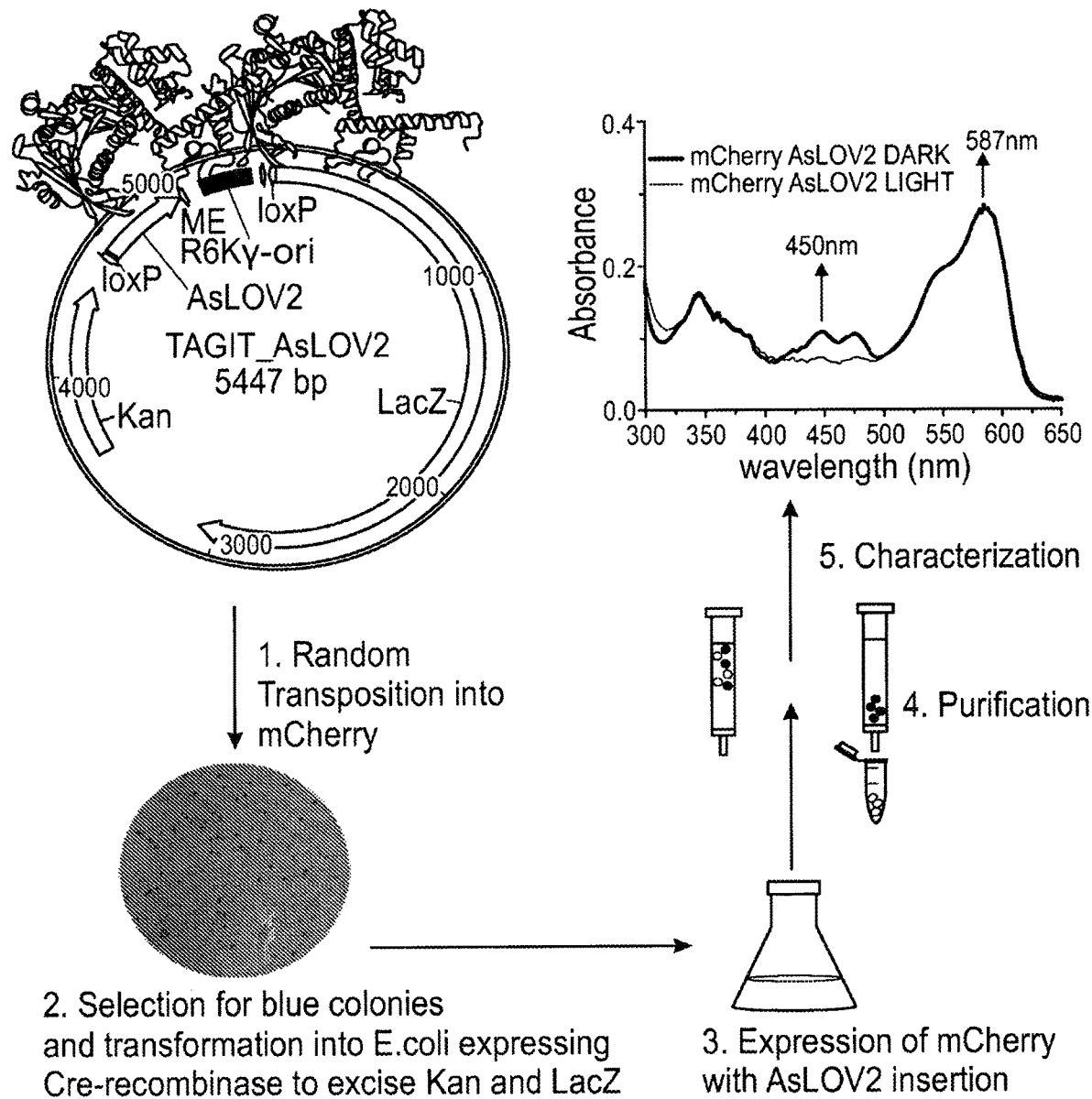
FIG. 4B is a depiction of the workflow for preliminary studies used to validate library generation using transposon assisted gene insertion technology (TAGIT).
Figure 5A:
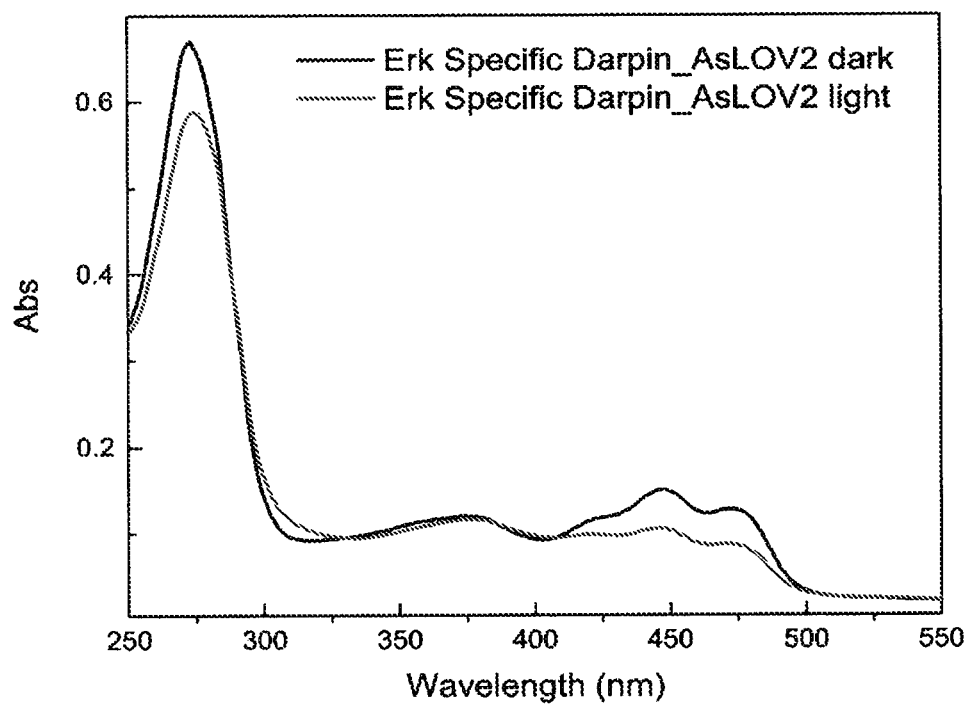
FIG. 5A is a graph showing that an AsLOV2 domain inserted into the ERK2-specific DARPin E40 retains its ability to undergo blue light-induced conformational shifts.
Figure 5B:
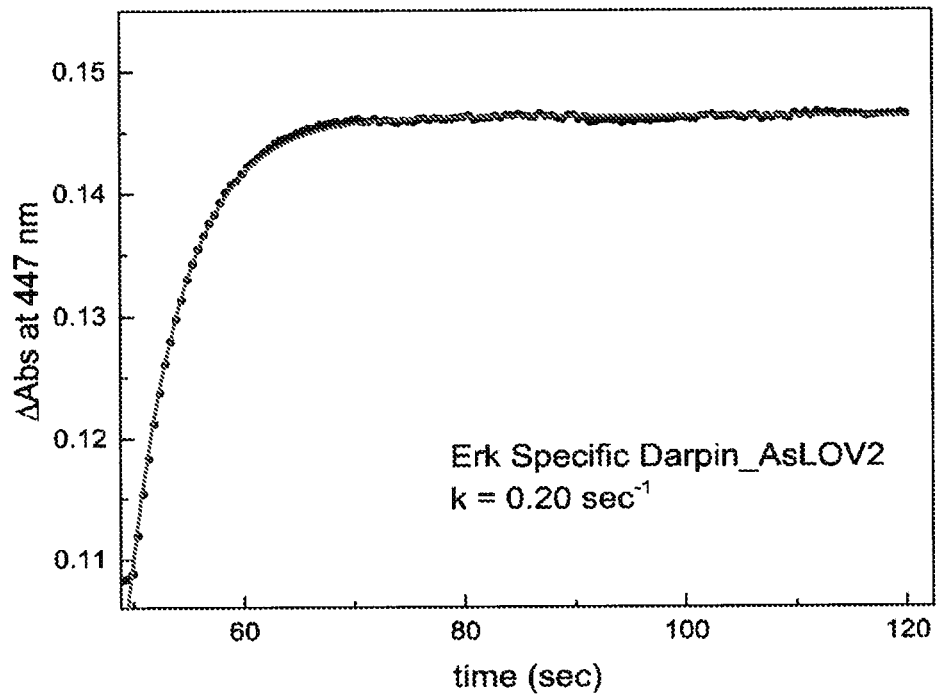
FIG. 5B is a graph showing that insertion of the AsLOV2 domain from FIG. 5A into DARPin E40 does not dramatically impact the dark recovery time of the AsLOV2 domain.
Figure 6A:
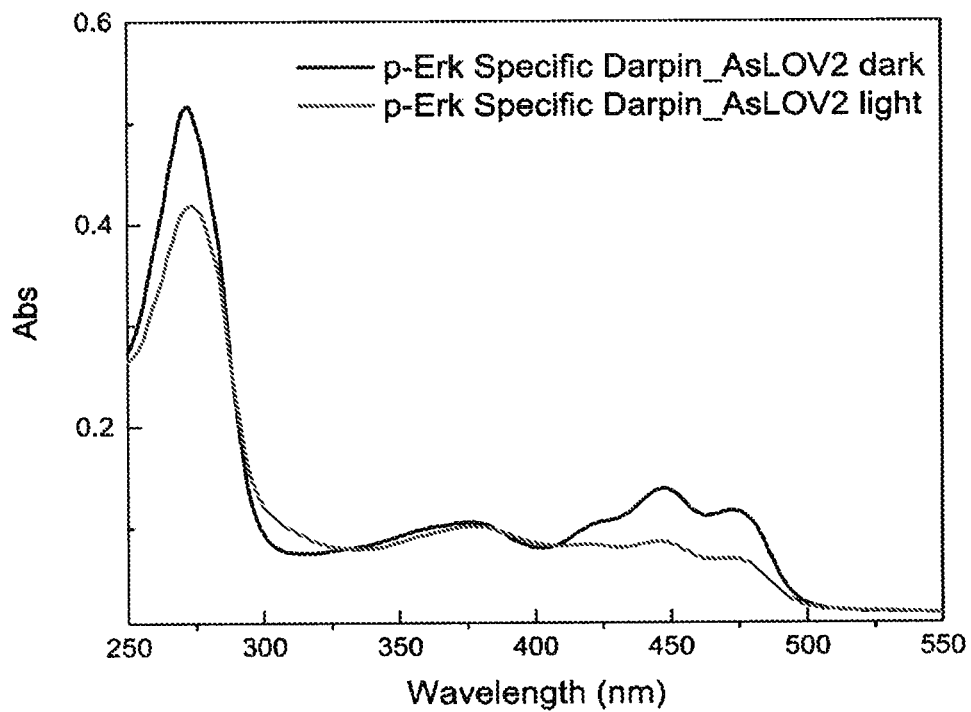
FIG. 6A is a graph showing that an AsLOV2 domain inserted into the ppErk2-specific DARPin pE59 retains its ability to undergo blue light-induced conformational shifts.
Figure 6B:
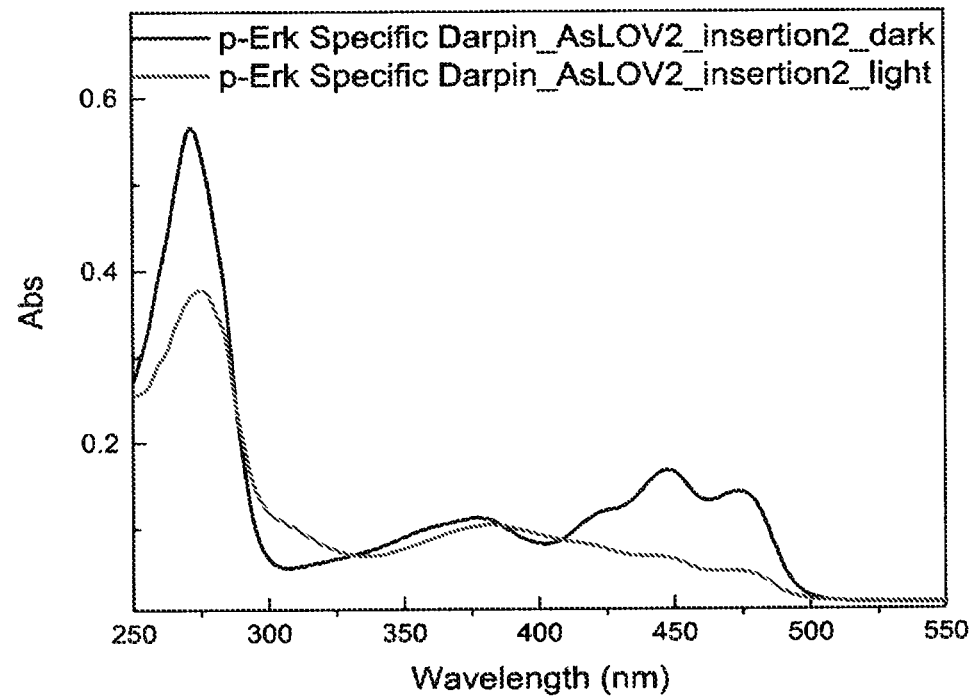
FIG. 6B is a graph showing that an AsLOV2 domain inserted into DARPin pE59 retains its ability to undergo blue light-induced conformational shifts. The AsLOV2-containing pE59 DARPin construct of FIG. 6A is different from the AsLOV2-containing pE59 DARPin construct of FIG. 6B.

The TAGIT plasmid was generated using TAGIT-GFP plasmid as a template (generously provided by Dr. James Gregory) and inserting AsLOV2 in place of GFP using Gibson method. As a first proof-of-principle test, whether the TAGIT system could be used to generate a library of light-switchable fusion proteins (the TAGIT workflow is shown in FIG. 4B) was validated. To simplify subsequent validation, a library of AsLOV2 insertions into the mCherry red fluorescent protein was generated, with the intention of screening for blue light switchable changes in mCherry fluorescence.

Tn5 transposition reaction was performed in vitro using commercially available EZ-Tn5 Transposase (Epicentre) to randomly insert a TAGIT transposon containing AsLOV2 into a bacterial expression vector driving arabinose-inducible mCherry expression. Transposition was achieved successfully, leading to colonies that were kanamycin resistant, conferred by successful insertion of the TAGIT transposon. Moreover, in-frame insertions were identified by the translation of mCherry-LacZ fusion proteins, resulting in blue colonies in a blue/white selection assay. The DNA from the generated library was then transformed into Strataclone Solopack *E. coli* cells expressing Cre recombinase. Cre recognizes LoxP sites included in the TAGIT transposon to successfully excise the LacZ and KanR genes, leaving a library of mCherry sequences with a randomly inserted, in-frame AsLOV2 domain. Individual successful insertions were validated by sequencing. Finally, it was verified that AsLOV2 can be properly folded along with the protein of interest by expressing, purifying, and characterizing multiple AsLOV2-mCherry fusion proteins. Using UV-visible spectroscopy, it was confirmed that the AsLOV2 can indeed bind its chromophore and undergo a natural photocycle, and that mCherry can still fluoresce (FIG. 4B). These proof-of-principle experiments demonstrated that the TAGIT transposon system can be used to generate rich construct libraries and generate functional, photoswitchable fusion proteins.

This approach was further modified for high-throughput library construction of diverse targets. An in vitro Tn5 transposase reaction (Epicentre EZ-Tn5 Transposase) was used to randomly insert the AsLOV2-domain at all nucleotide positions within all three coding sequences. The AsLOV2 plasmid includes a LacZ gene lacking a START codon that will only be expressed if fusion is in-frame. By transforming the resulting fusion plasmids into Lac⁻ Ara⁺ BW2581 *E. coli* and growing cultures in lactose, only constructs with in-frame fusion between AsLOV2 and the protein of interest were selected. Finally, the DNA of entire library was purified and transformed into Cre recombinase-expressing bacteria (StrataClone Solopack) to excise the LacZ gene, leading to in-frame expression of AsLOV2 at all amino acid positions. This approach was used to generate libraries where the target proteins included various nanobodies, DARPins, and biotherapeutics of interest. Additionally, this approach was used to generate the libraries for yeast-two-hybrid screening, phage display, and pull-down assays, where the appropriate plasmid with the target gene was used in the transposition reaction to then smoothly transition into the desired screening platform. For example, for phage display screening, pJSC plasmid was used along with the TAGIT plasmid in the transposition reaction.

Phage Display for Screening

This idea is very like the yeast 2 hybrid approach. The phase display method was used by putting a protein of interest (e.g., a nanobody) into the phage display plasmid. The binding partner of the protein of interest was then immobilized on a column and the selection done by eluting in the light and in the dark. The method was altered using "A twin-arginine translocation (Tat)-mediated phage display system" (Paschke et al 2004), which is needed to express an active LOV domain.

Day 1: This is to Grow Up the Phagemid Library and then Infect it with Helper Phage Overnight, Resulting in Phage which Display the VHH Library on their Surface as Fusions to pIII.

1. Inoculate 100 ml SOC+Amp in 500 mL Erlenmeyer flask with 200 μL-1 mL of thawed library stock (ideally want a starting $OD_{600}$=0.1-0.2). Amp is for plasmid selection. Glucose in SOC suppresses expression of VHH to prevent growth bias in library.
2. Grow culture at 37° C. with shaking until $OD_{600}$ is 0.5-0.7.
3. Add VCMS13 helper phage (around 1 mL of a 10^13 pfu/mL stock is typically used).
4. Incubate inoculated culture 30 minutes (min) at 37° C. without shaking.
5. Incubate 1H 30 min at 37° C. with shaking.
6. Split culture into 2×50 mL conical tubes and spin down 10 min at 8000 rpm at 4° C.
7. Resuspend pellets in 100 mL total 2YT/0.1% glucose/100 ug/mL Amp/70 μg/mL Kan in 500 mL Erlenmeyer flask. Amp if for plasmid selection, kan is for helper phage selection.
8. Grow overnight at 30° C. with shaking.

**start 100 mL overnight culture of ER2738 in 2YT/Tet and grow at 37° C. with shaking in preparation for panning. This strain is available from NEB and has a tet-inducible pili through which the phage infects the cell. Alternatively, you can use TG1s for this step.

Day 2: This is where the Panning of the Phage Library Generated Overnight Against the Immobilized Antigen is Performed.

1. Split phage culture into 2×50 mL conical tubes and spin down 10 min at 8000 rpm 4° C.
2. Pour supernatant to two clear centrifuge bottles and add 10 mL 20% PEG/2.5M NaCl, (⅕$^{th}$ volume) to each. Incubate 2 h at 4° C. on ice. Using clear bottles will make it easier to see the phage pellet after centrifuging.
3. Spin down 20 min at 8000 rpm at 4° C. Mark orientation so the location of the pellet is known.
4. Pour off supernatant. Resuspend phage pellet (will appear white and fluffy, may be streaked down side of the tube) in 4 mL PBS. Split this between 4 epi tubes (1 mL in each), and add 200 μL of the above PEG solution (⅕$^{th}$ volume) to each. Incubate 1H at 4° C. on ice.
5. Spin down 10 min at 13,000 rpm at 4° C., and remove supernatant. Spin again for another minute and remove any residual liquid.
6. Resuspend the four phage pellets in 1 mL PBS total volume.
7. Spin resuspended material 5 min at 4° C. at 13,000 rpm. You want to keep the supernatant this time, as this is now your phage library stock. Transfer supernatant to a fresh tube, and calculate concentration by measuring the A296 and A320 (you can do this using the protein measurement tool on the nanodrop).

$$\text{Phage concentration:} \#pfu/mL = \frac{6000 \times 10^{\wedge}14 \times (A296 - A320)}{7200 \text{ bp}}$$

Panning Round 2

1. Add 2 μL of pre-cleared phage to each of the protein-biotin-strep tubes+1 mL 1% BSA/PBS and incubate for 15 min at room temperature (RT) with inversion.
2. Aspirate supernatant, wash beads 15×1 mL with PBS/0.1% Tween (PBST).
3. For final wash, add 500 μL PBST and incubate at 37° C. for 1H with inversion
4. Add 500 μl saturated ER2738 bacteria to each tube, incubate 15 min at 37° C. with inversion.
   a. On the previous day, 100 mL overnight culture of ER2738 in 2YT/Tet will have been started and grown at 37° C. with shaking.
5. Remove cells and store as "Elution 1."
6. Add 500 μl 0.2M glycine, pH 2.2 and incubate 10 min at RT with inversion.
   a. 1.5 g glycine for 100 mL, use HCl to adjust pH to 2.2.

7. Remove glycine and add to 754, 1M Tris pH 9.1 to neutralize, save as "E2."
   a. 12.12 g for 100 ml, use HCl to adjust pH to 9.1.
8. Pool elutions E1 and E2, and incubate for 15 min at 37° C.
9. Remove 100 µl pooled elutions to titer library for individual colonies, plate the remainder on "big" 2YT/2% glucose/Tet/Amp plates.
10. Grow all overnight at 37° C. and determine titers.
    a. Titer by making 10-fold serial dilutions in PBS, and plating 100 µL of each on "small" 2YT/2% glucose/Tet/Amp plates.

Day 3
1. Scrape down plates with 2 mL SOC+Amp per plate, pool together and add 50% sterile glycerol to 15% final concentration. Aliquot into cryotubes and store at −80° C. as "second round panning" library.
2. Pick individual colonies off of titer plates into 96 well plates, using 200 µl SOC+Amp+Tet per well. Cover with airpore sheet (Qiagen) to allow for oxygen exchange. Grow overnight at 37° C. with agitation. This will be the "Master Plate" for bug soup.

Protein Expression and Purification
Wild-Type AsLOV2 Expression and Purification The codon optimized gene encoding C-terminal LOV2 domain of *Avena sativa* phototropin 1 (AsLOV2) containing residues 404-546 in pet15b vector (generously provided by Professor Peter Tonge) was sub-cloned into pBAD vector containing residues 404-546 or residues 408-543 using in-fusion method. The resulting plasmid was transformed into Top10 *E. coli* cells for protein expression and a single colony was used to inoculate a 5 mL culture of LB media supplemented with Ampicillin (Amp) at 100 µg/mL. After incubating the culture at 37° C. and 250 rpm overnight, it was used to inoculate 250 mL of 2×YT/Amp media in a 1 L flask. The 1 L flask was shaken at 37° C. and 250 rpm until the $OD_{600}$ reached approximately 0.8. The temperature was decreased to 20° C. followed by addition of 0.5% arabinose to induce protein expression overnight (approximately 16 h) in the dark. Cells were harvested by centrifugation at 4° C. and 5000 rpm and stored at −80° C.

The cell pellet resulting from a 250 mL culture was thawed and resuspended in 40 mL of buffer A (20 mM Tris, 150 mM NaCl pH 8.0) supplemented with protease inhibitor cocktail tablet (cOmplete, Roche). The cells were then lysed using a sonicator with about 8 cycles of 15 seconds on and 1 minute off. Cell debris was removed by centrifugation (40,000 rpm for 90 min). The supernatant was incubated with FMN (0.25 mg/mL) for approximately 30 min on ice and in the dark to ensure a homogeneous population of protein bound chromophore followed by loading it onto a column with Ni-NTA resin previously equilibrated with buffer A. The column was washed with buffer A containing increasing concentrations of imidazole (0 mM, 10 mM and 20 mM) until AsLOV2 eluted at 250 mM imidazole. The protein was dialyzed overnight against buffer A and its purity was assessed by SDS-PAGE.

DARPins and DARPin-AsLOV2 Fusions

Protocol for expression and purification of wild-type AsLOV2 was used as described above.

Nanobodies and Nanobody-AsLOV2 Fusions

The DNA for the desired nanobody was synthesized through IDT and subcloned into pGEX6P1, pET22b, and pBAD vector using in-fusion method. The resulting plasmid was transformed into BL21(DE3) *E. coli* cells or Shuffle T7Express *E. coli* cells for protein expression and a single colony was used to inoculate a 5 mL culture of LB media supplemented with Ampicillin (Amp) or Carbenicillin (Carb) at 100 µg/mL. After incubating the culture at 37° C. and 250 rpm overnight, it was used to inoculate 250 mL of 2×YT/Amp media in a 1 L flask. The 1 L flask was shaken at 37° C. and 250 rpm until the $OD_{600}$ reached approximately 0.8. The temperature was decreased to 20° C. followed by addition of 0.8 mM IPTG or 0.2% Arabinose to induce protein expression overnight (approximately 16 h) in the dark. Cells were harvested by centrifugation at 4° C. and 5000 rpm and stored at −80° C.

The purification was conducted as described for wild-type AsLOV2.

UV-Vis Spectroscopy

Absorption spectra of all protein samples were obtained using a UV-visible spectrometer. The concentration of the protein samples was kept at approximately 50 µM (20 mM Tris, 150 mM NaCl pH 8.0). Dark-adapted spectra were obtained first and then in order to acquire a light state spectra, samples were illuminated with blue LED for 1 minute. Scanning kinetics were used to record the recovery of the dark state from the light state for the light-sensitive proteins. Single exponential decay equation was used to fit the absorbance at 447 nm over time to acquire the rate of the recovery.

Mammalian Cell Assay Screen for Assessing Protein Binding in Intracellular Environment for a Light-Responsive Fusion Protein (Comprising Heterologous Peptide Components, Including Nanobodies/Darpins/Monobodies and other tight binders such as affibodies, antibodies etc.)

The goal of this screening platform was to express candidate light-responsive fusion proteins fused to a fluorescent protein in the cytoplasm of a mammalian cell, along with the binding target expressed on the cell membrane. Then, light can be used to switch binding on and off, leading to a change in the fusion protein's localization from cytosol to membrane. This assay comprises a screening platform for individual fusion protein variants. This approach was used to screen nanobody, monobody, and DARPin heterologous peptide components against targets of interest.

Figure 7A:
FIGS. 7A-7B are microscopic fluorescence images showing a mammalian cell assay set up to image ligand binding.
Figure 7B:
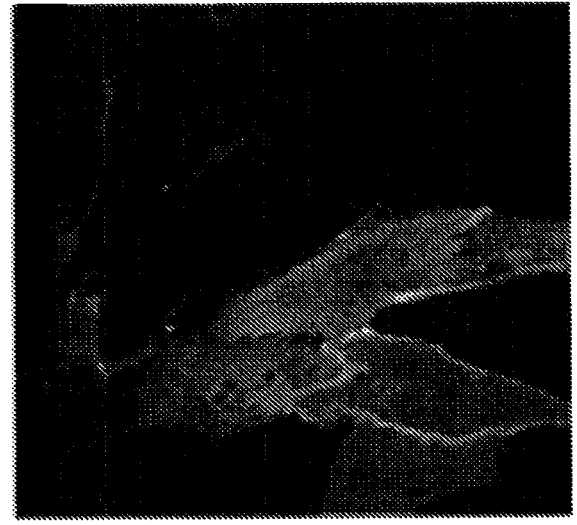

Necessary DNA was cloned into PHR vectors using standard Gibson assembly-based cloning. Constructs containing either the light-responsive-nanobody fusion, light-responsive-DARPin fusion, or light-responsive-monobody fusion (fused to fluorescent protein such as iRFP for visualization purposes) or target were introduced into NIH3T3 cells using lentiviral transduction. The target (i.e. mCherry) was localized to the membrane using a CAAX tag, with the binding partner (ie. nanobody, DARPin, monobody) expressed in the cytoplasm (FIGS. 7A-7B). In this example, the nanobody is membrane-localized due to its interaction with mCherry, which can then be screened for light sensitivity. The interaction between the light-responsive fusion protein and target was imaged over time, either in the absence or presence of blue light. The mammalian cells were kept at 37° C. with 5% $CO_2$ for the duration of all imaging experiments. Imaging was done using Nikon Eclipse Ti microscope with a Prior linear motorized stage, a Yokogawa CSU-X1 spinning disk, an Agilent laser line module containing 405, 488, 561 and 650 nm lasers, an iXon DU897 EMCCD camera, and a 60× oil immersion objective lens. Also, a 450 nm LED light source was used for photo excitation with blue light, which was delivered through a Polygon400 digital micro-mirror device (DMD; Mightex Systems).

Figure 10A:
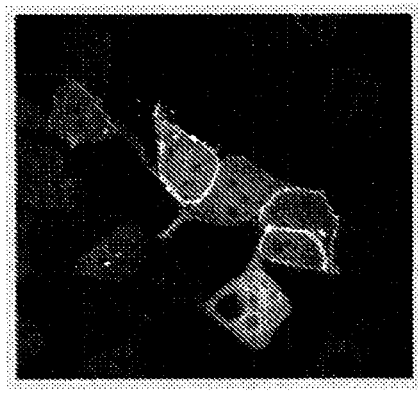
FIGS. 10A-10B show an example of a light-responsive monobody against SH2 domain.
Figure 10B:
Figure 11C:
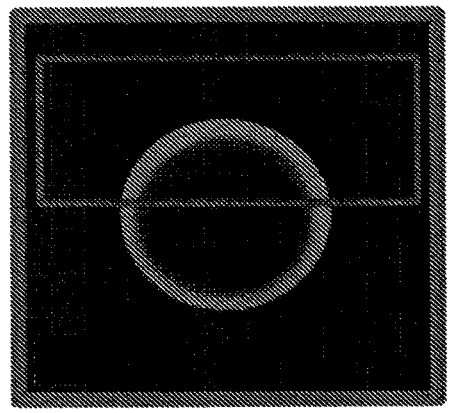
Figure 11F:
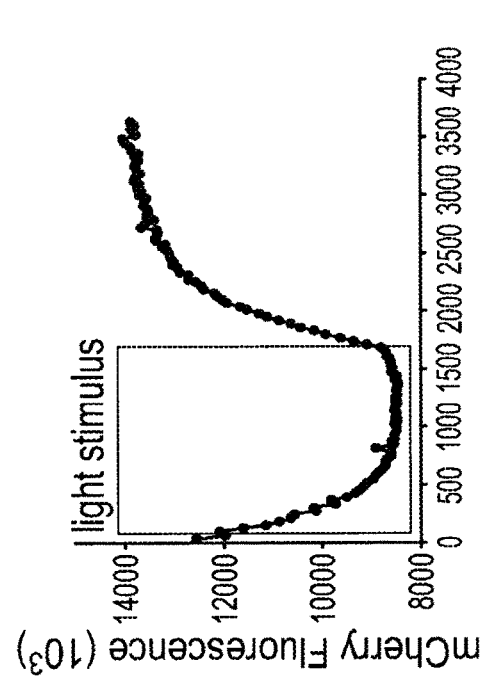
Figure 11B:
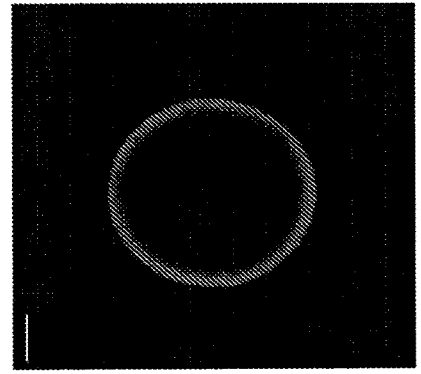
Figure 11E:
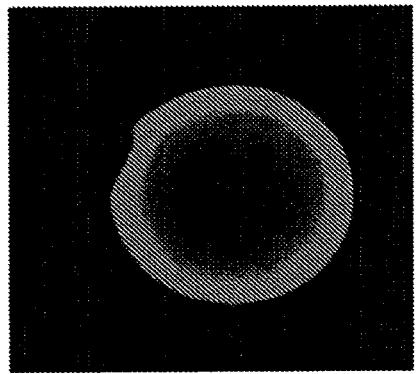

With this assay, light-induced binding as well as light-induced dissociation from specific nanobody-LOV domain fusion proteins was observed (FIGS. 8A-8F). Notably, the site at which a LOV domain is inserted was sufficient to switch between light-induced binding and light-induced dissociation. Similar results have also been obtained from the other classes of protein binders: DARPins (FIGS. 9A-9F) and monobodies (FIGS. 10A and 10B).

Bacterial Production and Purification of Opto-Binders for In Vitro Protein Binding Assays In addition to expression within mammalian cells, protein binders can be used in vitro as extracellular therapeutics or in the context of protein biochemistry (for protein purification, crystallography, etc). For the expression of light-responsive-nanobody fusion proteins, constructs were cloned into pBAD plasmid with N-terminal His tag. Shuffle T7 Express cells (NEB) were transformed by the plasmid containing the light-responsive-nanobody fusion. The rest of the expression and purification follow the previously described protocol herein.

In Vitro Binding of Light-Responsive Fusion Proteins from Targets in Purified Protein Solutions To demonstrate the light dependent binding in vitro, a binding assay with purified light-responsive fusion proteins was set up, which was validated using the light-responsive-nanobody fusion protein hits from FIG. 7 and FIG. 8. A purified light-responsive-nanobody was fused to Ni-NTA agarose beads via its His-tag, and the purified target with no tag was added to the solution with the beads. The results of binding and dissociation are shown in FIGS. 11A-11F.

The binding and dissociation of the target was monitored by imaging the fluorescent target (e.g., mCherry) binding on and off the bead. A microscopy imaging system with 20× objective lens was used to image the beads. Blue light was delivered through DMDs either illuminating the entire bead or with a spatial pattern (e.g., by illuminating half of the agarose bead in FIG. 11B), which demonstrated good spatial control of binding/unbinding only in the illuminated region.

Light-Switchable Changes in Elution Rate Using Size Exclusion Chromatography

Figure 12:
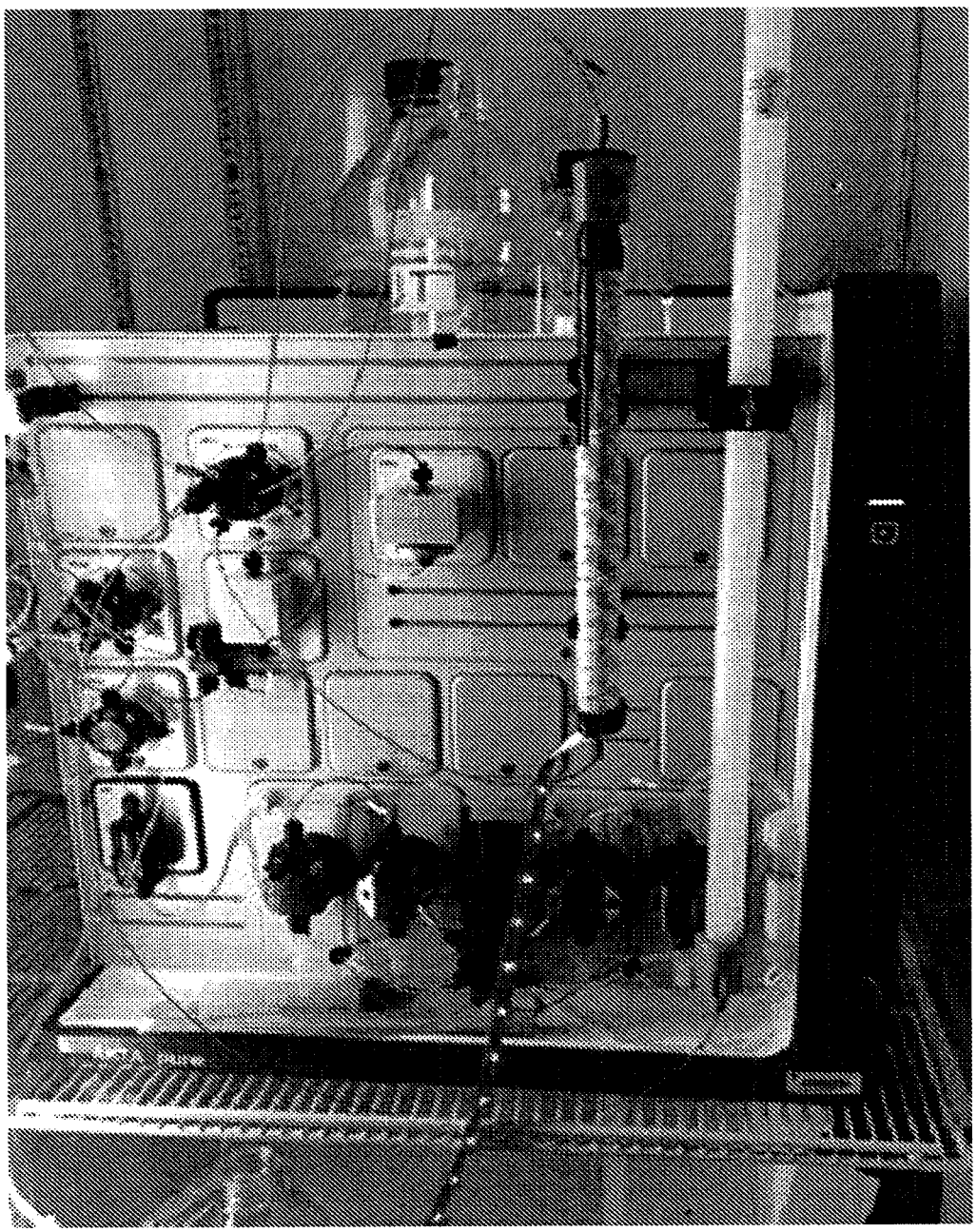
FIG. 12 shows a set-up for size exclusion chromatography (SEC) with the column modified by wrapping with blue LEDs.

To further characterize light-controlled binding size exclusion chromatography (SEC) was performed using purified protein samples. The premise behind SEC is that when dissolved molecules of various sizes flow through the column, the larger molecules elute faster while smaller molecules enter a larger fraction of the column's pores and take longer to elute (Nagy and Vekey, 2008). Thus, over a run the molecules are sorted by size. The chromatography column was modified with blue light LEDs for light delivery (FIG. 12). The ligand and target complex was incubated for approximately 30 minutes either in the light or dark and then run on the column either in the light or dark. The results show either light-induced binding or dissociation based on the light-responsive fusion protein (FIGS. 13A and 13B). The column also represents a proof-of-principle basic prototype of a light-controlled purification column: a column with a resin inside that can be modified with the correct light input for separating proteins based on their light sensitivity.

This purification column allows the rate of elution of a protein of interest to be controlled with light.

Quantification of Light-Induced Change in Binding Affinities Using OCTET

Techniques have also been developed to quantify the binding affinity in the lit and dark states for a light-controlled fusion protein. Crucially, point mutations are available that lock LOV domains in their lit and dark states. By using these mutant LOV domains in the appropriate fusion constructs, binding experiments need not be performed in the presence of specific light conditions. However, we can also measure the light state binding and dissociation using the OCTET biomolecular interaction assay (ForteBio) by inserting a light plate into the instrument during the measurement.

Figure 14:
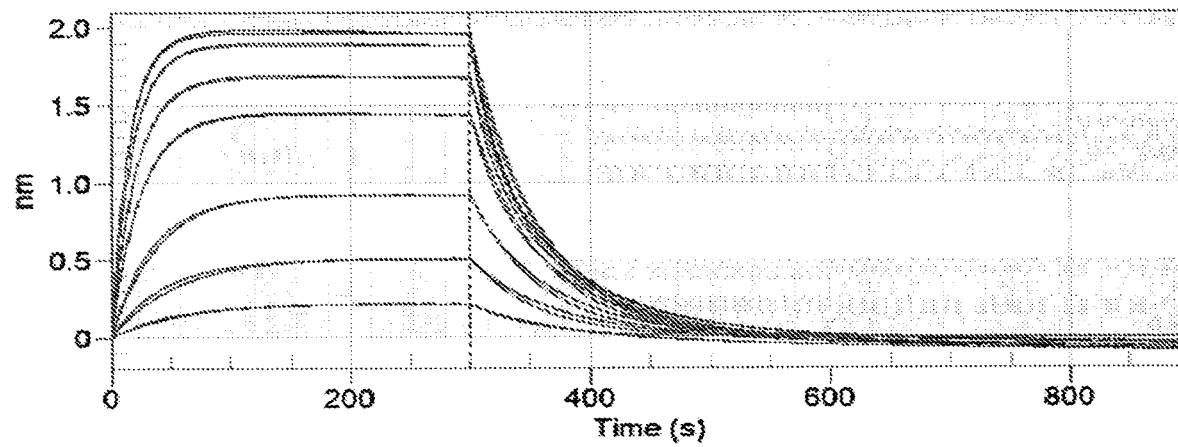
FIG. 14 shows representative kinetic traces from OCTET measurements for a nanobody against mCherry. First trace represents binding of mCherry to the nanobody (kon) and second trace represents dissociation of mCherry from the nanobody (koff).

Light-induced change in affinity was quantified using the OCTET biomolecular interaction assay (ForteBio). His-tag was kept on all ligand samples and the tag was cleaved off of the target. In order to adequately measure the affinities of the ligands towards their target in the dark as well as under blue light conditions, point mutations were inserted into the photoactive protein which lead to the protein being locked in the dark or in the light position simulating the actual light inputs. Ni-NTA Biosensors were used to bind the ligand and the measurements were conducted based on the standard protocols provided by ForteBio (FIG. 14). Association rate constants as well as dissociation rate constants were measured and used to calculate the affinity constants listed in Table 1.

TABLE 1

Kinetic parameters for mCherry specific nanobodies. LaM8 denotes the type of a nanobody; GG15 and AK74 denote the insertion of the AsLOV2 domain in the nanobody. Mutants that lack the protein in the dark (C450V) or the light state (I539E) were used to allow for measurements using this instrumental setting.

| Sample | kon (1/Ms) | koff (1/s) | Kd |
| --- | --- | --- | --- |
| LaM8 | $7.52 \times 10^4$ | 0.02 | 322 nM |
| LaM8 GG15 C450V | $5.13 \times 10^5$ | 0.02 | 378 nM |
| LaM8 GG15 I539E | $4.97 \times 10^5$ | 0.06 | 1.24 uM |
| LaM8 AK74 C450V | $2.39 \times 10^5$ | 0.41 | 17.2 uM |
| LaM8 AK74 I539E | $3.86 \times 10^5$ | 0.12 | 3.15 uM |

Figure 15:
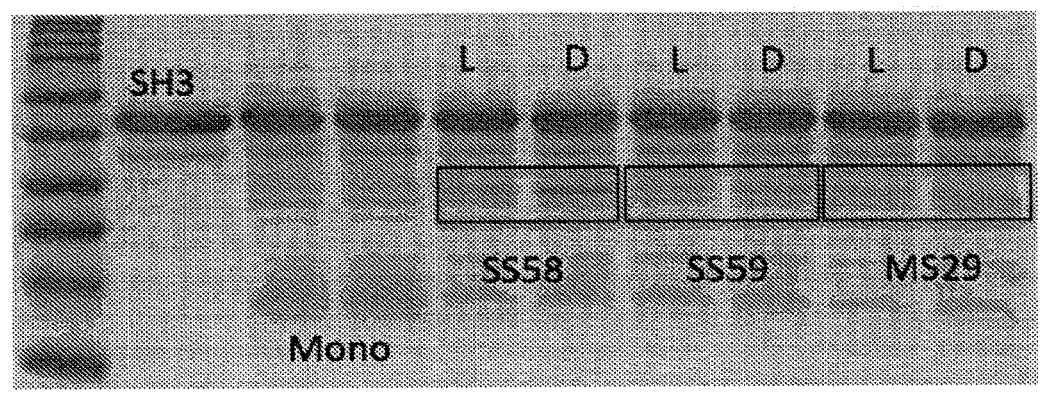
FIG. 15 shows a gel showing results of screening monobody-LOV fusion proteins for light-dependent binding to the c-Abl SH3 domain. An insertion of AsLOV2 at position 58 (SS58) shows increased monobody-LOV binding in the dark (presence of dark band) compared to light.

Light-Dependent Binding Partner Screening Method for Light-Assisted Protein Purification In addition to the cell-based screens described herein, screens were developed based on directly measuring light-dependent binding between a light-responsive fusion protein and substrate in vitro. This screening platform was applied to monobody-LOV domain fusions, where monobodies are another protein binding domain where the activity can be switched on and off. Results for a screen of light-responsive-monobody fusions is shown in FIG. 15

A binding target was expressed as a 6×His (SEQ ID NO: 49)-YFP-protein fusion (6×His (SEQ ID NO: 49): Histidine tag; YFP: yellow fluorescent protein; binding targets include, e.g., SUMO tag and SH2 tag). The fusion protein was expressed and grown in 500 mL of autoinduction media+kanamycin for 16 hours. Monobody and Monobody-LOV fusions/chimeras were grown in 250 mL of autoinduction media+kanamycin for 16 hours. For each test, 1 monobody control and 3 Monobody-LOV fusions/chimeras were tested.

Cells were harvested at 7,000 rpm for 25 minutes at 4° C. and supernatant was discarded. Pellets were resuspended in 8 mL (for the 6×His (SEQ ID NO: 49)-YFP-binder) or 3 mL (for the monobodies or monobody chimeras) of wash buffer (100 mM Tris, pH 8.0, 150 mM NaCl, 1% Glycerol, 5 mM Imidazole) with additional 1 mM PMSF and 0.5 mg/mL lysozyme. Resuspended cells were broken apart using the CryoMill with liquid nitrogen. Broken cells were melted an addition 4 mL of wash buffer+1×PMSF were added to the 6×His (SEQ ID NO: 49)-YFP-binder while 2 mL of wash buffer+1×PMSF were added to the monobodies or monobody chimeras. Lysates were then spun down at 14,000 rpm for 30 minutes at 4° C. The 6×His (SEQ ID NO: 49)-YFP-binder supernatant was then run through a Co-NTA column and washed with washed buffer. The beads (now with 6×His (SEQ ID NO: 49)-YFP-binder immobilized) were then resuspended in wash buffer to a total volume of 13.5 mL. This mixture was then divided into 9 15 mL conical tubes. 4 of these tubes were labeled for experimentation under blue light. 4 of these tubes were labeled for experimentation in the dark (red light was used for visualization). The remaining tube was left as a control.

Monobody and Monobody-LOV fusion/chimera supernatants were then split in half with half added to the tubes designated for light experimentations and the other half added to tubes designated for dark experimentations. Tubes were then placed into 4° C. under 20 rpm for 45 minutes for binding under respective light conditions. Tubes were then allowed to settle at 4° C. under respective light conditions for 30 minutes. Supernatants were removed while attempting to retain as much resin as possible. 10 mL of wash buffer was added to each tube and rotated at 20 rpm for 45 minutes. This was again allowed to settle at 4° C. under respective light conditions for 30 minutes and supernatant was again discarded. Washing was repeated 3 times. All light conditions were held constant with careful experimentation to minimize light exposure for the dark samples. After the last dumping of the supernatant, proteins were eluted with elution buffer (100 mM Tris, pH 8.0, 150 mM NaCl, 1% Glycerol, 500 mM Imidazole).

Wash buffer=100 mM Tris, pH 8.0, 150 mM NaCl, 1% Glycerol, 5 mM Imidazole

Elution buffer=100 mM Tris, pH 8.0, 150 mM NaCl, 1% Glycerol, 500 mM Imidazole

Light-Assisted Protein Purification with or without Common Purification Tags

One biotechnological application of the endogenous-protein light-responsive fusion proteins described herein is in the purification of proteins of interest. Optogenetic control can be used over nanobodies, monobodies and DARPins (or other protein binding domains) to bind to their specific target within a crude mixture of proteins. Then, after appropriate washing to remove unbound proteins, the target protein of interest can be eluted by changing illumination conditions (either exposing the purification system to light or darkness). This is particularly useful because it obviates the need for toxic or caustic elution steps (which are often performed under conditions that can alter the activity of the target, or require substantial use of expensive or toxic reagents). It also enhances the options for tag-less purification, e.g., of therapeutic antibodies which typically cannot be used in humans if fused to standard purification tags. An optogenetic Protein A or anti-antibody binder can be used for highly specific light-based binding and elution of any antibody in a protein purification method.

Light-assisted protein purification can be used in, for example, three distinct modalities:

Light-responsive fusion proteins against a specific protein target for tag-less purification;

Light-responsive fusion proteins against commonly used purification tags to purify tagged proteins with light, eliminating toxic, poorly-selective and/or expensive wash steps; and Light-responsive fusion proteins derived from commonly-used purification proteins based on affinity against targets with widespread therapeutic or industrial value (e.g., Protein A, Protein L, and Protein G, which target the constant domains of antibodies).

Figure 16A:
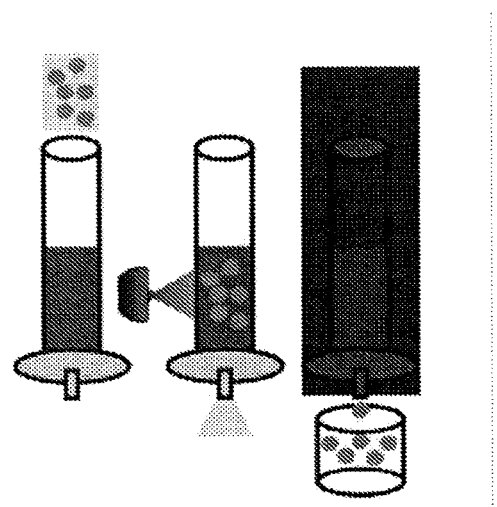
FIGS. 16A-16B illustrate light-assisted protein purification.
Figure 16B:
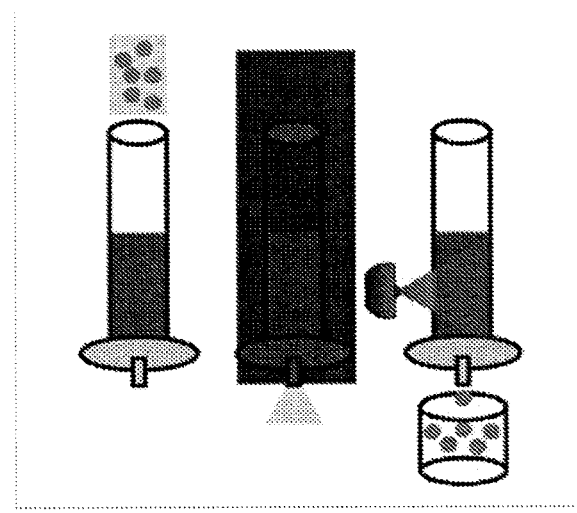

As an example of this approach, a light-based elution assay is described (FIGS. 16A and 16B). First, the light-responsive fusion proteins (e.g., light-responsive nanobody fusion, light-responsive DARPin fusion, light-responsive monobody fusion, light-responsive antibody fusion, etc.) is immobilized on the resin (creating an opto-resin) and placed in a purification column that is modified with blue LEDs. The target protein (protein to be purified) is expressed and lysed with the conditions best suited for the specific target. The lysate is cleared by ultracentrifugation at 30,000 rpm for 1 hour at 4° C. The supernatant is equilibrated with the opto-resin at 4° C. under 20 rpm for 45 minutes for binding under respective light conditions. Tubes are then allowed to settle at 4° C. under respective light conditions for 30 minutes. The column is washed with multiple column volumes of lysis buffer under the binding light conditions and then eluted either in the dark or in the light, depending on the specific activity of the fusion protein. This method can be optimized with the buffer conditions and equilibration times based on the target protein being purified.

Engineering Light Control Over Cell Signaling Pathways, Including Light-Induced Binding and Light-Induced Dissociation, Using Light-Responsive Fusion Proteins Light-responsive fusion proteins can be genetically expressed in cells and made to hetero-dimerize to their target protein in either the presence or absence of light. This makes them capable of recapitulating all the functions of existing light-gated heterodimerization systems, including the Phy/PIF, iLID-SSPB, and Cry2-CIB systems that have become staples of modern cell biology.

Figure 17A:
FIGS. 17A-17D show light control over Erk signaling.
Figure 17B:
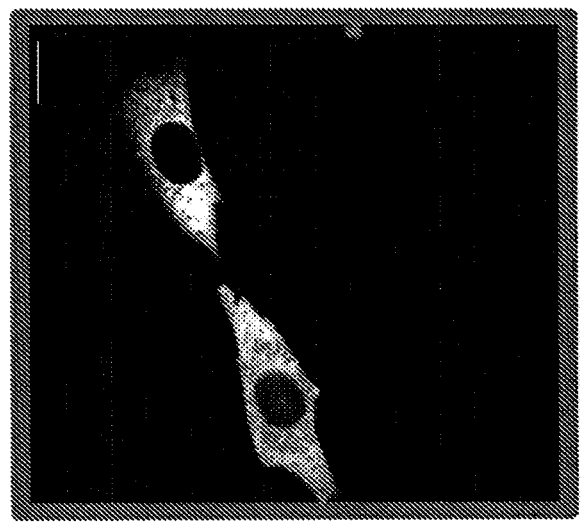
Figure 17C:
Figure 17D:
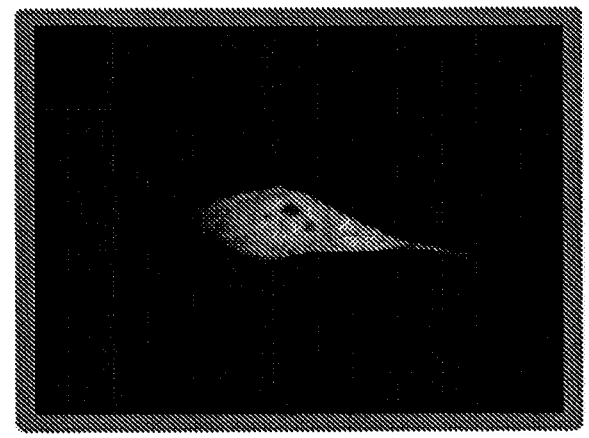

To demonstrate this capability, a currently used optogenetic tool, the OptoSOS system, was modified to be controlled by the association between a light-responsive fusion protein (i.e., opto-binder) of the present disclosure and its target. The following DNA constructs were generated, representing a nanobody/target directed OptoSOS system (construct a) and the Erk-specific Kinase Translocation Reporter (KTR) fused to iRFP (construct b):

A membrane bound target+cytosolic opto-binder:
pHR SFFVp (opto-binder)-irFP-SOScat-P2A-(target)-CAAX A biosensor of SOS-induced Erk kinase activity:
pHR SFFVp KTR-iRFP Both constructs were introduced into NIH3T3 cells using lentiviral transduction. Note that expression of construct a is less than that of construct b, so irFP imaging can be used to assess KTR localization, which exits the nucleus when the biological pathway (Erk signaling) is activated (through SOScat being localized to the membrane and activating Ras). FIGS. 17A and 17B, show light-induced activation of Erk (FIG. 17A: before light; FIG. 17B: after light) using a fusion between SOScat and the LaM8-AK74 light-responsive nanobody fusion. FIGS. 17C and 17D, show light-induced inactivation of Erk using an OptoSOS-fused LaM8-GG15 light-responsive-nanobody fusion, which dissociates upon photo-stimulation.

In addition to recapitulating known OptoSOS results using prior systems without light-responsive fusion proteins (Toettcher et al, Cell 2013), this embodiment described demonstrates that the response can be inverted by using a light-dissociable fusion protein. Because Erk activity directly controls cell proliferation in a number of systems, this also offers a two-hybrid screening platform for testing light-responsive fusion protein variants for light-switchable activity, using cell proliferation as a functional readout.

Light-Switchable Inhibition of Endogenous Cellular Proteins Using Light-Responsive Fusion Proteins In the example above, a method to use light-responsive fusion proteins as an alternative for engineered heterodimerization was described, such as controlling the membrane localization of the Erk-activating SOScat construct. The same binders can be used for binding to, and modulating the activity of, naturally-occurring proteins in the host cell. In doing so, light-responsive fusion proteins fundamentally expand the toolbox of light-controlled protein binding reactions.

Figures 18A, 18B, 18C:
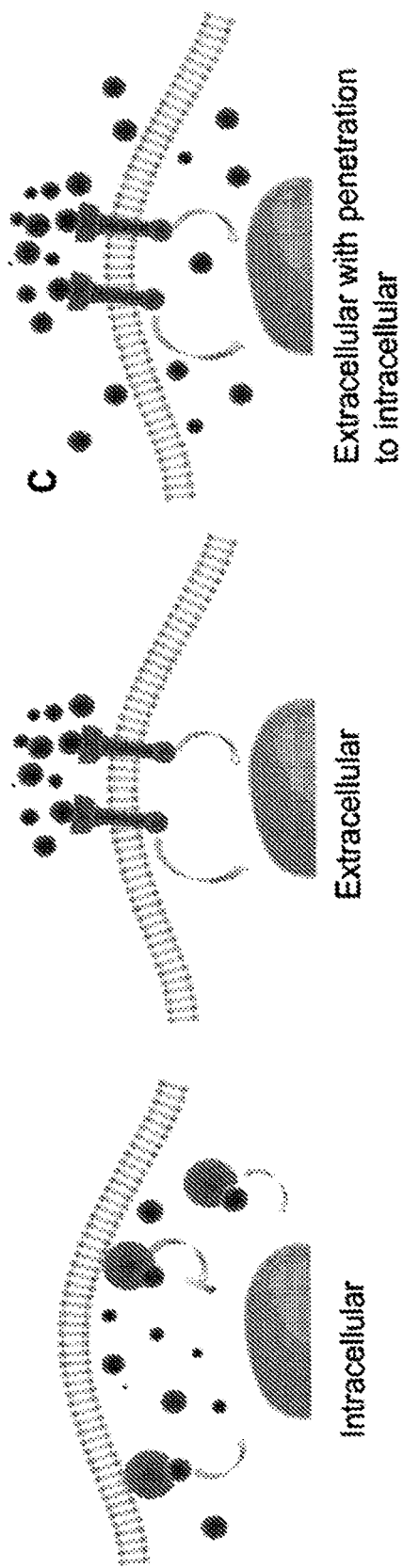
FIGS. 18A-18C illustrate three ways of influencing cellular responses with light-responsive fusion proteins (also referred to herein as "opto-binders"): within the intracellular environment, if the light-responsive fusion protein is genetically expressed in the host cell (FIG. 18A); from the extracellular environment, if the light-responsive fusion protein is added to the extracellular medium and acts on a cell surface expressed receptor (FIG. 18B); or within the intracellular environment but without genetic encoding, if the light-responsive fusion protein is fused to a cell-penetrating peptide, enters the cell and interacts with its intracellular target (FIG. 18C). In addition, or alternatively, the heterologous peptide component and/or light-responsive domain in the fusion protein can also be modified to render the fusion protein more cell permeable (e.g., obviating the need for a cell-penetrating peptide).

Because many of the protein domains used in light-responsive fusion proteins (such as, e.g., nanobodies or monobodies) bind to naturally-occurring, endogenous proteins, they can also be used to bind to these endogenous proteins after being made photoswitchable. Thus, embodiments of the invention can be used for light-controlled binding to endogenous proteins in various modes (FIG. 18), including inside the cell using a genetically-encoded light-responsive fusion protein (FIG. 18A) or outside of the cell (FIG. 18B, 18C) using a light-responsive fusion protein that is added to cells' external environment, and which then binds to a naturally-occurring target protein on the cell surface in a light-switchable manner (FIG. 18B). Further, embodiments can utilize a light-responsive fusion protein that is fused to a cell-penetrating peptide (FIG. 18C), and which can be added outside of cells, penetrate them, and bind to their target.

Binding is often able to modulate a target protein's activity. This is achieved by blocking access to a particular patch of the protein's surface to out-compete binding by natural proteins (steric control), or by inducing a conformational change in the target protein that alters its natural function (allosteric control). The ability to target endogenous proteins and regulate their activity in a light-controllable way introduces an extraordinary benefit to metabolic engineering.

Figure 19:
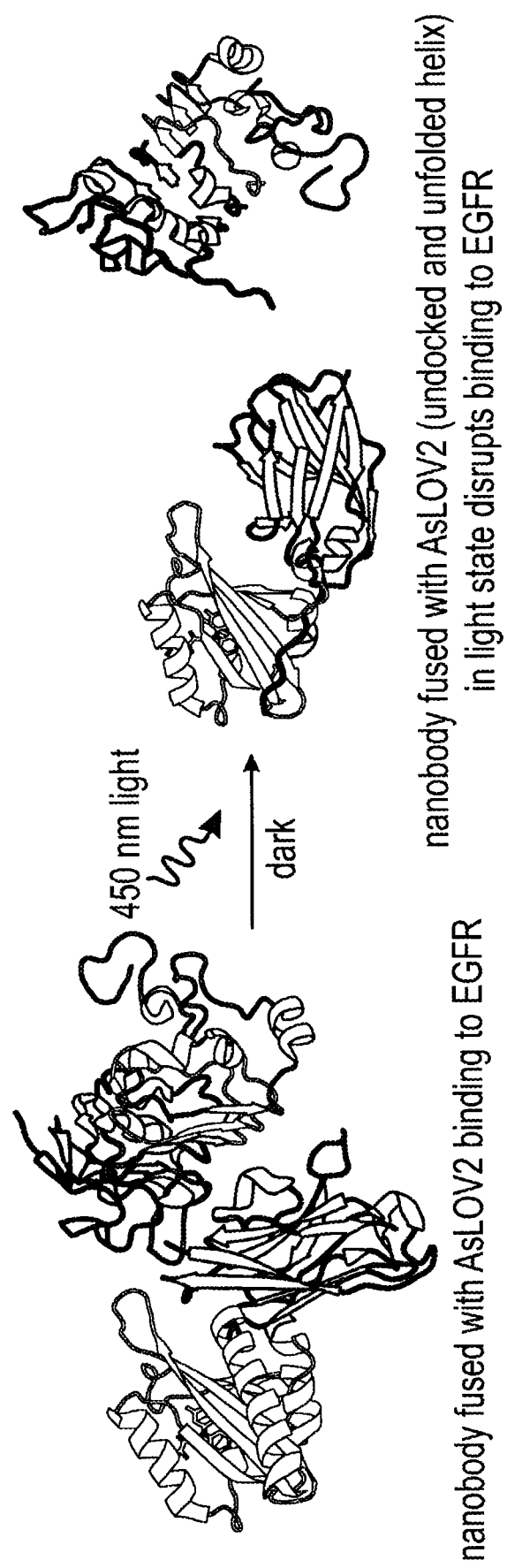
FIG. 19 illustrates EGFR-specific light-responsive nanobodies useful for light-switchable EGFR inhibition. Image to the left of the arrow shows binding in the dark between a light-responsive nanobody and its EGFR target domain (domain III), leading to inhibition of EGF binding and EGFR signaling activity. Image to the right of the arrow shows light-induced conformational change in the light-responsive nanobody induces dissociation from EGFR, restoring the function of this growth factor pathway.

Extracellular light-controlled protein inhibition is schematized in FIG. 19 using the example of a light-responsive-nanobody that binds to domain III of the EGF receptor, thereby inhibiting its activity.

Thus, light-responsive fusion proteins offer extracellular and intracellular methods for inhibiting natural protein function in a light-switchable manner. Additional applications include, e.g., local light stimulation to prevent EGFR inhibition by anti-cancer nanobodies at sites of side-effects (using light-dissociated fusion proteins), or, conversely, local light stimulation to enhance anti-cancer activity at the site of a tumor (using light-induced fusion proteins).

Mammalian Cell Assay Screen for Assessing Protein Binding in Extracellular Environment for Light-Responsive Fusion Proteins with Future Applications in T-Cell Therapy Chimeric antigen receptor expressing T cells (CAR-T cells) are frequently used to treat cancers that express specific antigens to which the chimeric antigen receptor (CAR) can be targeted. Notably, CARs are often designed as a fusion between an extracellular single-chain antibody (scFv) and intracellular signaling domains; the scFv can be swapped out for other binding domains that target particular cellular antigens. In an embodiment, CARs are modified with a light-responsive fusion protein as its extracellular targeting domain, leading to light-controllable CAR-T activation in vivo. Such light-based control can be used to limit CAR-T activation at undesired sites (e.g., sites of high auto-immune reaction or sites distant from a primary tumor) or enhance CAR-T activation at known tumor sites or sites of co-stimulation (e.g., by local injection of other immunomodulatory compounds).

A reduced, idealized model was generated to enable cell surface expression of a light-responsive fusion protein whose activity can be transduced to an intracellular response (thereby mimicking the response of a CAR-T cell). As a basis for this approach, the SynNotch technology developed in the laboratory of Wendell Lim (Morsut et al. *Cell,* 2016; Roybal et al. *Cell,* 2016) was utilized. Cells expressing the following were engineered:

a transmembrane protein that is cleaved into a functional transcription factor upon binding, and where binding is achieved by a light-regulated opto-binder: pHR SFFVp Opto-binder-Notch transmembrane-VP16-Gal4; and a Gal4-responsive gene cassette that expresses the BFP blue fluorescent protein in response to the SynNotch receptor's activation, as well as iRFP to mark expressing cells: pHR SFFVp UAS-BFP (term.) PGKp iRFP, where "term." is a transcription terminator sequence.

The light-responsive-nanobody target (e.g., mCherry) was supplied as a purified protein fused to agarose beads in order to activate binding to the Opto-binder-Notch construct, thereby inducing cleavage and expressing BFP in responsive cells (FIG. 20). In further embodiments, BFP expression can be enhanced under specific illumination conditions for individual light-responsive fusion proteins.

Light-Responsive Monobodies for Dynamic Control of Customizable Protein Binding

The following experiments are also described in Carrasco-Lopez, C., et al., "Light-responsive monobodies for dynamic control of customizable protein binding," *bioRxiv* (2019), 2020.03.08.831909. The entire contents of Carrasco-Lopez, C., et al. and its supplementary materials are incorporated herein by reference.

Abstract. Customizable, high affinity protein-protein interactions, such as those mediated by antibodies and antibody-like molecules, are invaluable to basic and applied research and have become pillars for modern therapeutics. The ability to reversibly control the binding activity of these proteins to their targets on demand would significantly expand their applications in biotechnology, medicine, and research. Here is presented, as proof-of-principle, a light-controlled monobody (OptoMB) that works in vitro and in vivo, whose affinity for its SH2-domain target exhibits a 300-fold shift in binding affinity upon illumination. The αSH2-OptoMB can be used to purify SH2-tagged proteins directly from crude *E. coli* extract, achieving 99.8% purity and over 40% yield in a single purification step. This OptoMB belongs to a new class of light-sensitive protein binders referred to herein as OptoBinders (OptoBNDRs) which, by virtue of their ability to be designed to bind a protein of interest, have the potential to find new powerful applications as light-switchable binders of untagged proteins with high affinity and selectivity, and with the temporal and spatial precision afforded by light.

Introduction. The high binding affinity and selectivity of antibodies and antibody-like proteins, such as monobodies, nanobodies, affibodies, anticalins and DARPins, have made them central tools of modern medicine, biotechnology, and basic and applied research[1-7]. Because of their ability to be raised, selected, or designed to bind practically any protein of interest[6,8,9], these protein binders have found multiple applications in diagnostics[3,10,11], therapeutics[4,12,13] and biologics manufacturing[14-16]. As such, they have revolutionized the way disease is treated[13,17-19], proteins are purified[20-23], and biological phenomena are studied[9,24-27]. The enormous impact that high affinity protein binders have had in medicine, biotechnology, and research stems from their usually irreversible binding to very specific targets. However, their repertoire of applications could still be greatly expanded if they were engineered with optogenetic control over their binding affinities, such that they could bind their targets instantly and reversibly depending on light conditions, while maintaining their characteristically high affinity and selectivity.

Protein binders can be developed from a variety of scaffolds, including based on immunoglobulin domains[28,29] or other small single-domain proteins[2,17]. Monobodies belong to a class of high affinity protein binders that have non-immunoglobulin scaffolds[30,31]. They are derived from the 10$^{th}$ domain of human fibronectin, engineered to structurally and functionally resemble nanobodies[28,30,31]. As antibody mimetics with human origins, their use as biologic drugs is expected to substantially reduce unwanted immune responses[17,32]. Their high affinity, specificity and straightforward expression in multiple cell types also make them a versatile tool for research[6,31]. The small size and relative stability of monobodies (less than 100 amino acids), as well as their lack of disulfide bridges, robust activity inside[33] and outside of cells[34], and their ability to be selected to bind countless different proteins with high affinity and selectivity, make them ideal candidates to develop light-switchable protein binders by fusing them to light-responsive proteins.

A protein domain used for optogenetic tool development is the second light, oxygen, and voltage (LOV) domain from the oat, *Avena sativa*, photosensor Phototrophin 1, called the AsLOV2 domain[35]. This domain elicits its light response through a large conformational change (FIG. 21A) triggered by the formation of a covalent bond between a photoexcited flavin chromophore, FMN, and a conserved cysteine[36,37]. The C-terminal helix, Jα, of AsLOV2 is packed against its core domain in the dark. Upon blue light stimulation (optimally, 447 nm) the covalent bond between FMN and the conserved cysteine causes the Jα helix to undock, become disordered and move away from the core domain[38,39,40]. Back in the dark, the covalent bond with FMN decays, allowing the Jα helix to fold back into its tightly packed dark state conformation[39,40].

Insertion of AsLOV2 into solvent-exposed loops of kinases, phosphatases and guanine exchange factors make their enzymatic activities and downstream signaling events light-dependent[41]. A light-switchable Cas9 nuclease has also been developed using the AsLOV2 homolog from *Rhodobacter sphaeroides*, RsLOV, in which the light-triggered conformational change of RsLOV dissociates a sterically occluded RsLOV-Cas9 chimera homodimer to release Cas9 nuclease activity[42]. This approach was also demonstrated in smaller proteins by fusing AsLOV2 to the small natural CRISPR inhibitor AcrIIA4, resulting in a light-responsive anti-CRISPR system to control genome editing with light[43].

Here it is shown that by fusing a monobody to the AsLOV2 domain, a light-dependent monobody, or OptoMonobody (OptoMB), whose binding affinity to the monobody's cognate protein target is controllable with light can be obtained. Taking a structure-based protein engineering approach, the AsLOV2 domain was inserted into structurally conserved, solvent exposed, loops of a monobody that binds the SH2 domain of Abl kinase. One of these chimeras preferentially bound to the SH2 domain in the dark, both in vitro and in mammalian cells. The approximately 300-fold change in binding affinity between lit and dark states was used to implement light-based protein purification[44] using an OptoMB resin in what is referred to herein as "light-controlled affinity chromatography" (LCAC). This work, and an accompanying study reporting light-dependent nanobodies or OptoNanobodies (OptoNBs)[45], represent the first demonstrations of protein binders with high affinity and selectivity, engineered with light-control of their binding activity. The new class of light-responsive protein binders, or OptoBinders (OptoBNDRs), which in principle can be engineered, screened, or selected to bind any protein of interest, have great potential to be used in numerous new applications in biotechnology, synthetic biology, and basic research.

Results: Design and selection of OptoMonobodies. To demonstrate the feasibility of developing a light-sensitive monobody, the HA4 monobody, which binds with high affinity ($K_d$~7 nM) to the SH2 domain of the human Abl kinase, in vitro and in vivo[46], was chosen. This is an interesting and valuable target, as many proteins containing SH2 domains in general, and Abl kinase in particular, are involved in human health and disease[47-49]. In addition, the availability of the crystal structure of HA4 bound to SH2 domain[46] is a valuable resource for rational protein engineering approaches. The strategy to develop a light-sensitive HA4 was to design various chimeras of this monobody with the light-oxygen-voltage-(LOV) sensing domain of Phototropin1 from *Avena sativa*, AsLOV2, and test their ability to bind and release the SH2 domain depending on light conditions.

To build chimeras, a truncated version of AsLOV2, which induces light-dependent conformational changes in engineered nanobody chimeras more efficiently than its full-length counterpart[45], was used. The strategy was to insert the shortened AsLOV2 domain in all seven structurally-conserved, solvent-exposed loops of HA4 (FIG. 21B). Given the large conformational change of AsLOV2 triggered by light (FIG. 21A), the hypothesis was that the native conformation of the monobody domain in some chimeras would be preserved in the dark, allowing it to bind to SH2, but disrupted in the light, causing it to release its target. Guided by the crystal structure of HA4 bound to SH2 (PDB ID: 3k2m)[46], potential sites within the seven solvent-exposed loops in HA4 where AsLOV2 could be inserted were explored. As many positions as possible were selected in each loop, avoiding those in which it was believed that the dark state conformation of AsLOV2 would disrupt the core β-sheets of the monobody or interfere with the monobody-SH2 binding interaction. Positions where the light-triggered conformational change of the AsLOV2 Jα helix might be impeded by clashes with the monobody core were also excluded. After this structural analysis, 17 AsLOV2 insertion sites across all solvent exposed loops of HA4, as well as N- or C-terminal fusions (FIG. 21B and Supplementary Table 1), were selected.

SUPPLEMENTARY TABLE 1

Positions within HA4 in which the AsLOV2 domain was inserted.

| Insertion Name | Insertion Description |
| --- | --- |
| SS30 | Inserted within S30 and S31 |
| NS47 | Inserted within N47 and S48 |
| SA84 | Inserted within S84 and A85 |
| TG44 | Inserted within T44 and G45 |
| SS58 | Inserted within S58 and S59 |
| SG65 | Inserted within S65 and G66 |
| DA26 | Inserted within D26 and A27 |
| MS29 | Inserted within M29 and S30 |
| MS29-3 | Inserted within M29 and S33 residues 30-32 were removed |
| ED82 | Inserted within E82 and D83 |
| DS83 | Inserted within D83 and S84 |
| GG45 | Inserted within G45 and G46 |
| GN45 | Inserted within G45 and N48 residues 46-47 were removed |

SUPPLEMENTARY TABLE 1-continued

Positions within HA4 in which
the AsLOV2 domain was inserted.

| Insertion Name | Insertion Description |
| --- | --- |
| TN44 | Inserted within T44 and N48 residues 45-47 were removed |
| PT18 | Inserted within P18 and T19 |
| SP68 | Inserted within S68 and P69 |
| SP68-1 | Inserted within S68 and P69 residue 67 was removed |
| N-terminus | Inserted at N-terminus |
| C-terminus | Inserted at C-terminus |
| SS59 | Inserted within S59 and S60 |
| PT18 | Inserted within P18 and T19 residue 17 was removed |
| MY90 | Inserted within M90 and Y91 |
| YS57 | Inserted within Y57 and S58 |

Figure 21C:
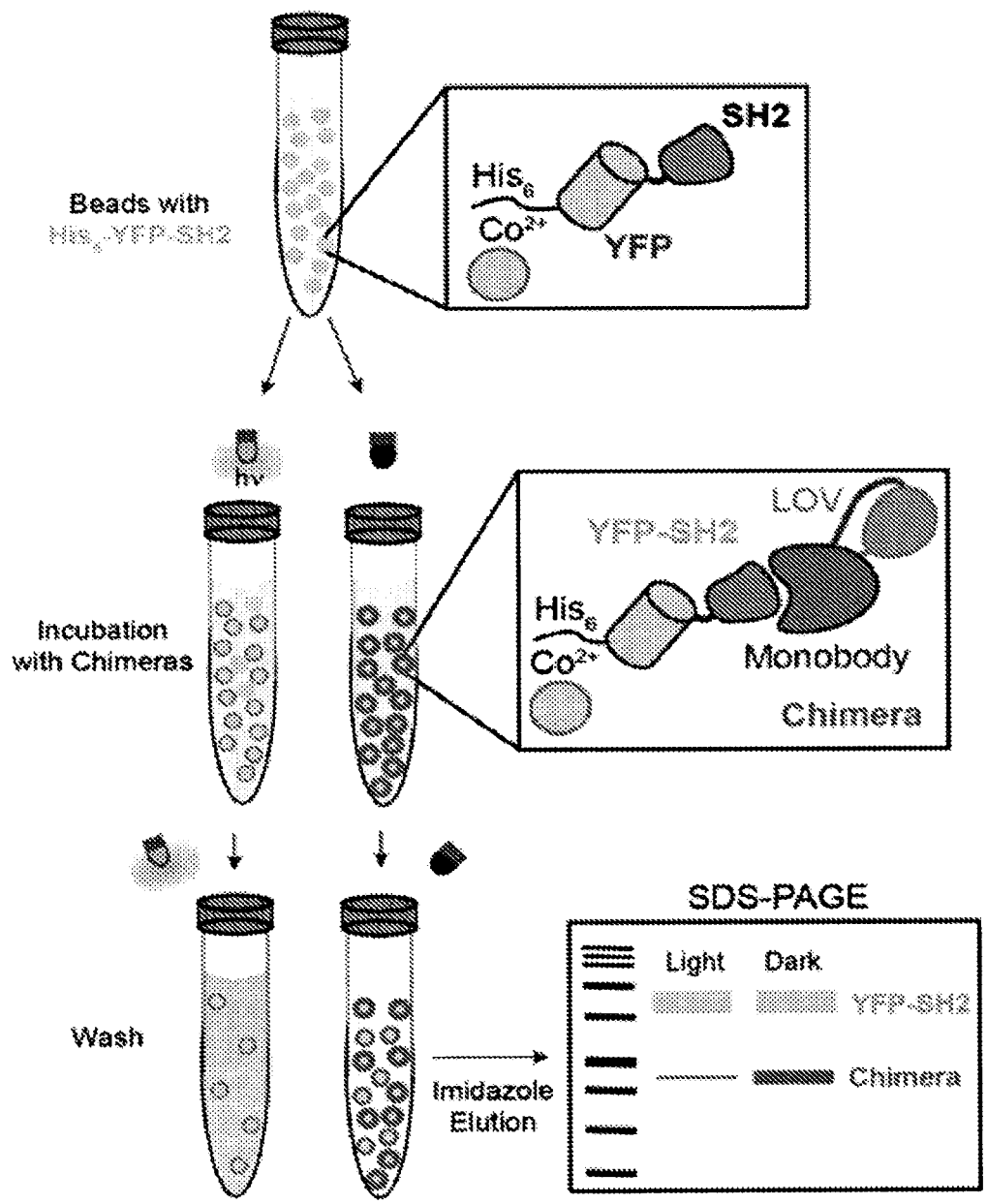
Figure 21D:
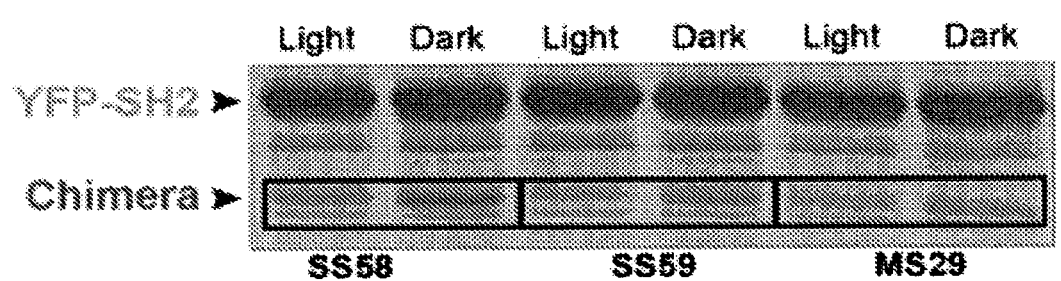

To find chimeras that can bind the SH2 domain in the dark but not in the light, the constructs were screened using an in vitro pull-down assay (FIG. 21C). First, an N-terminally His-tagged fusion of yellow fluorescent protein (YFP) and SH2 domain (His$_6$ (SEQ ID NO: 49)-YFP-SH2) were produced in E. coli, and immobilized onto cobalt-charged agarose beads. Then, the beads were incubated with crude extracts of E. coli expressing each of the different AsLOV2-HA4 chimeras, in either blue light or darkness. After washing the beads under the same light conditions (see Methods), the products were eluted with imidazole and resolved with denaturing polyacrylamide gel electrophoresis (SDS-PAGE) to analyze the binding of each chimera in different light conditions (FIGS. 21C-21D). It was anticipated that chimeras that bind to SH2 preferentially in the dark would show a more intense band on SDS-PAGE for samples that were incubated and washed in the dark, relative to the samples treated in the light (FIGS. 21C-21I).

It was found that AsLOV2 insertions in two different HA4 loops produced chimeras with the expected behavior in the pull-down assays. One promising chimera had AsLOV2 inserted between residues Met29 and Ser30 (a site referred to as MS29, following a naming system for sites used in this study), located in loop L2 of HA4 (FIGS. 21B and 21D-I). An effect involving this loop was only observed when AsLOV2 was inserted at position MS29 and loop L2 was shortened by removing the three surrounding amino acids (Ser30, Ser31 and Ser32, see SEQ ID NO:3). Another chimera with positive results had AsLOV2 inserted between Ser58 and Ser59 (site SS58) located in loop L4 of HA4 (FIGS. 21B, 21D). Insertions at other positions within loop L4 ($^{57}$YSSS$^{60}$) showed smaller degrees of variation in band intensity between beads treated in the light versus in the dark (FIGS. 21D-21I). This suggests that loop L4 is a "hot spot" for favorable orientations between AsLOV2 and the monobody to produce light-responsive chimeras that switch between a conformation that allows target binding (in the dark) and one that promotes target dissociation (in the light). Compared to AsLOV2 insertions at other positions in loop L4, the insertion at SS58 showed the largest qualitative difference between the chimera bound to beads in different light conditions (FIGS. 21D-21I), with a band that was approximately 2.1 times more intense in dark compared to light. Therefore, this chimera was chosen for further study, and named αSH2 OptoMonobody (henceforth, OptoMB).

Figure 21E:
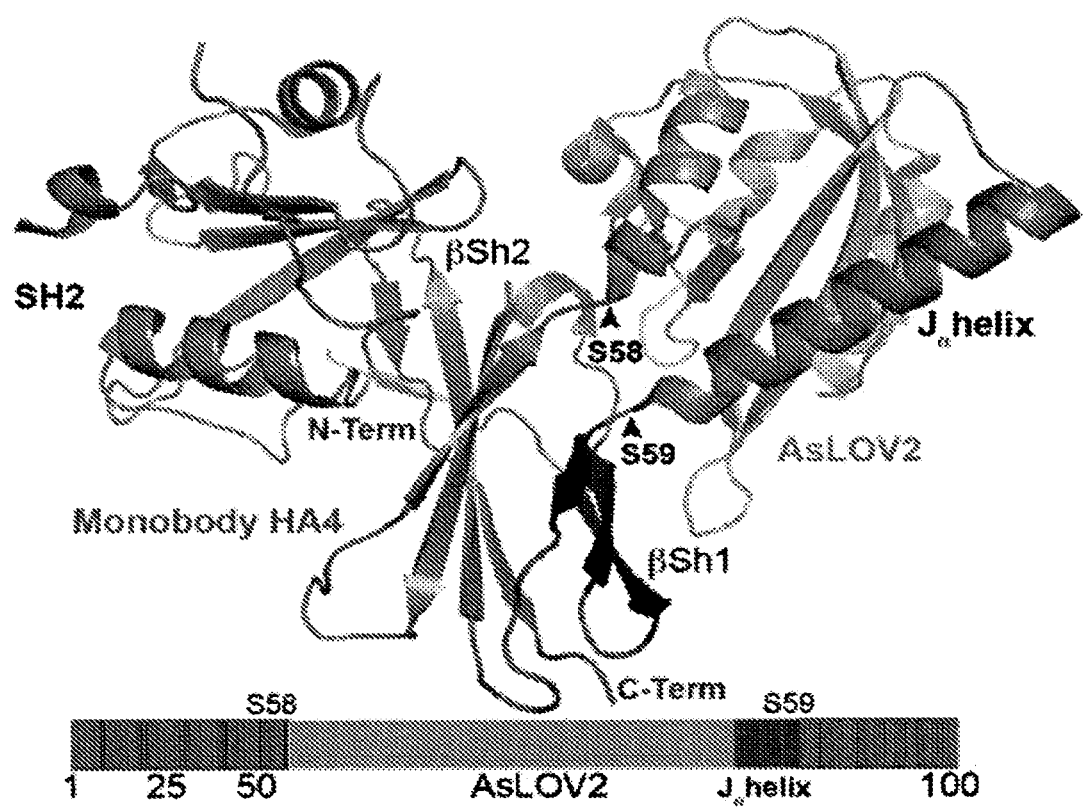
Figure 21F:
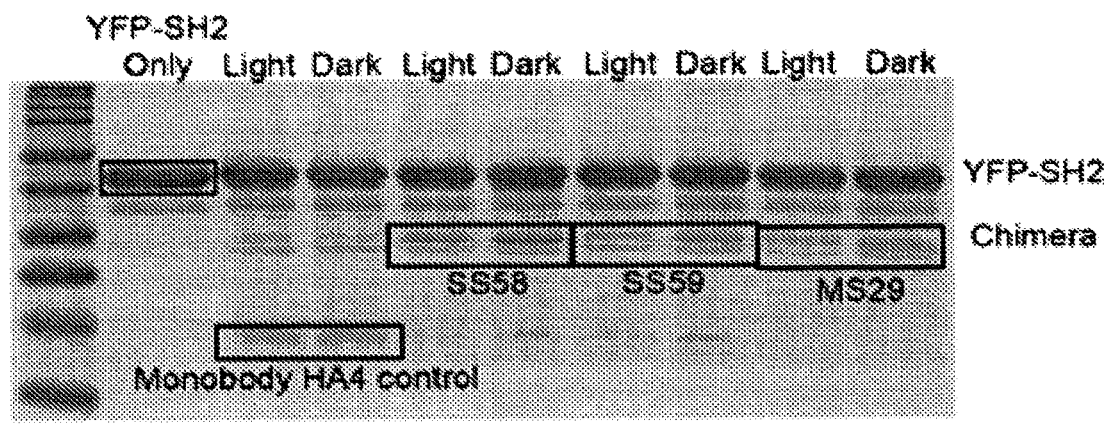
Figure 21G:
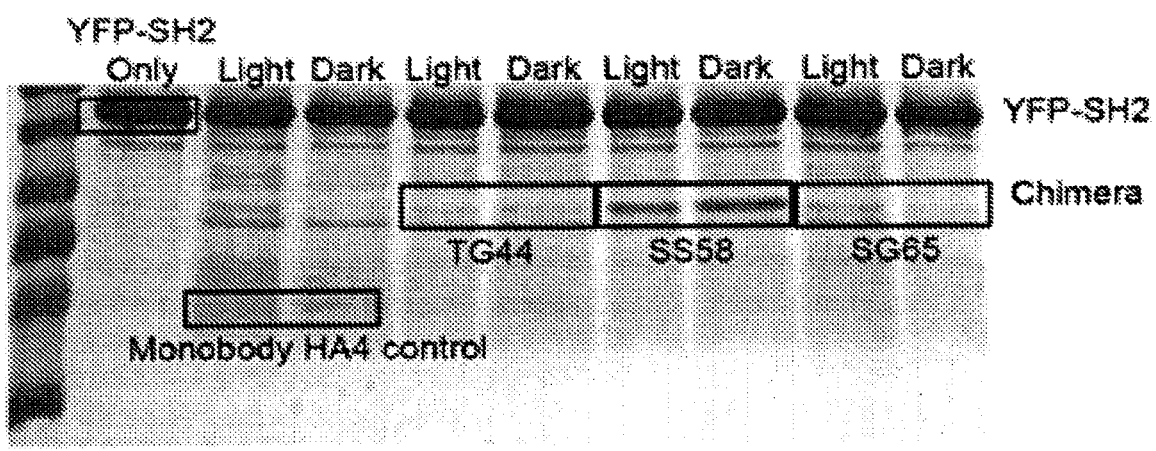
Figure 21H:
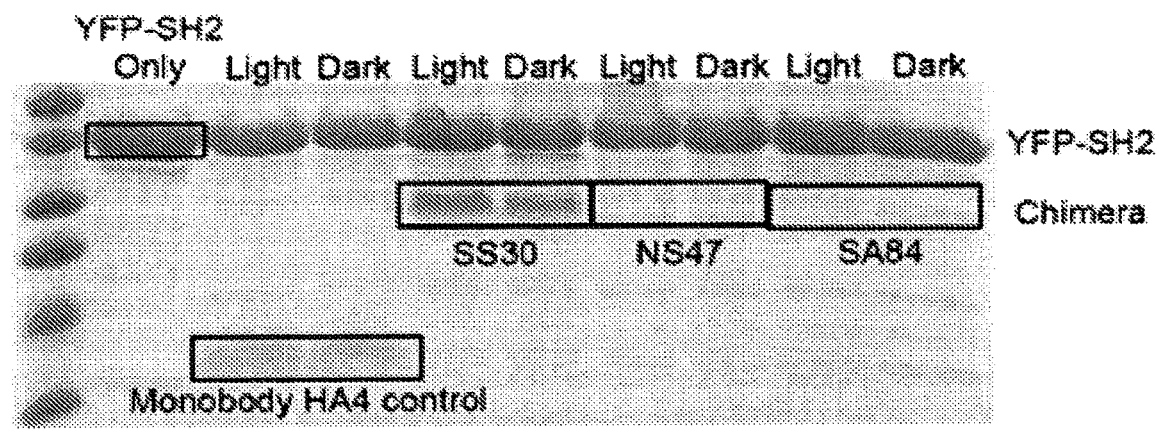
Figure 21I:
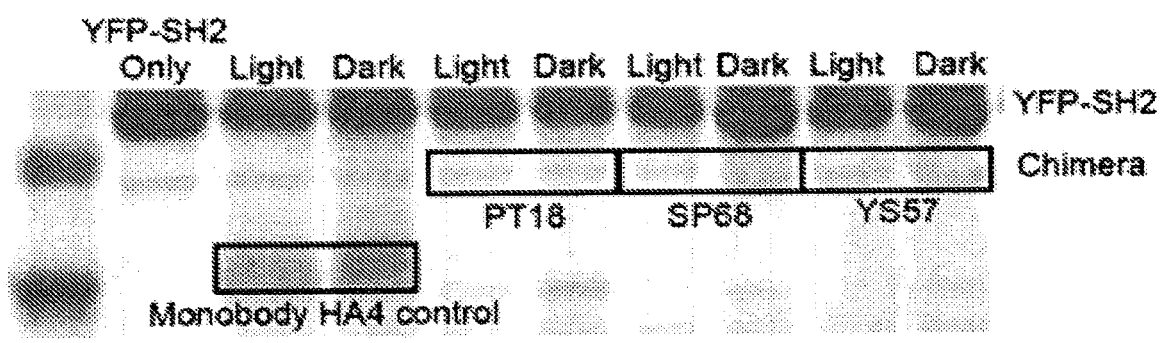

Rotation of the energy-minimized structural model of OptoMB is shown in FIG. 21E. The light-responsive chimera of AsLOV2 (orange), containing the Jα helix that undergoes structural rearrangement upon light stimulation (green), is inserted at position SS58 (in loop L4) of HA4 monobody (blue), bound to SH2 domain (gray). Loop L4, in the monobody, connects βSh2 (blue) with βSh1 (black) forming the core of the monobody fold. The structural model of this OptoMB (FIG. 21E) revealed that the orientation of AsLOV2 in this chimera (modeled in the dark state) is compatible with SH2 binding and suggests a possible mechanism by which a light-triggered conformational change of the Jα helix may disrupt the HA4 monobody to disfavor SH2 binding (see Discussion).

Figure 22A:
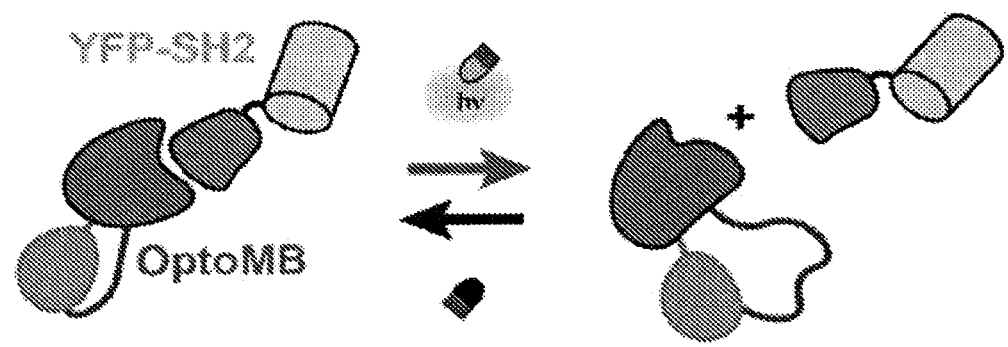
FIGS. 22A-22E show in vitro characterization of OptoMB.
Figure 22B:
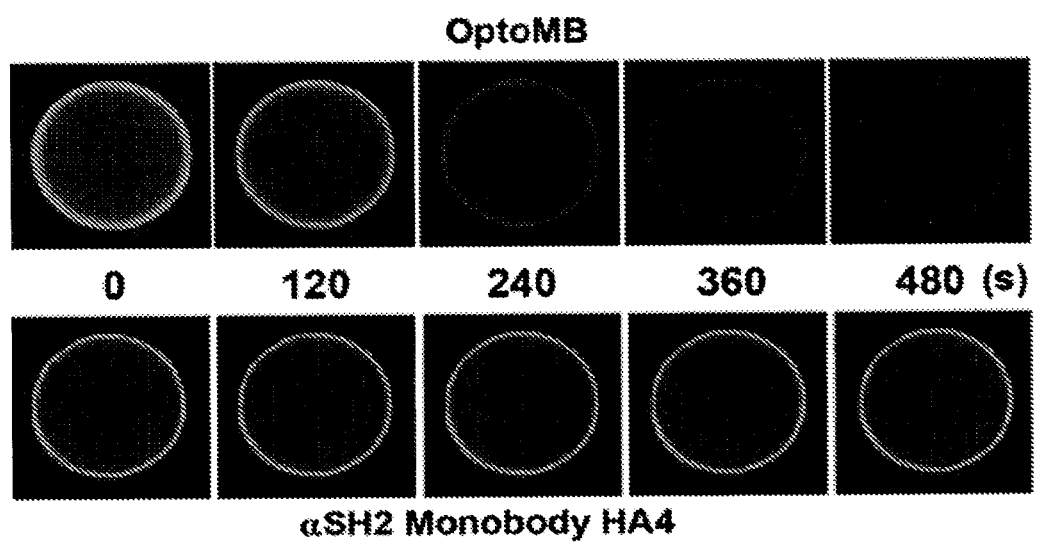
Figure 25A:
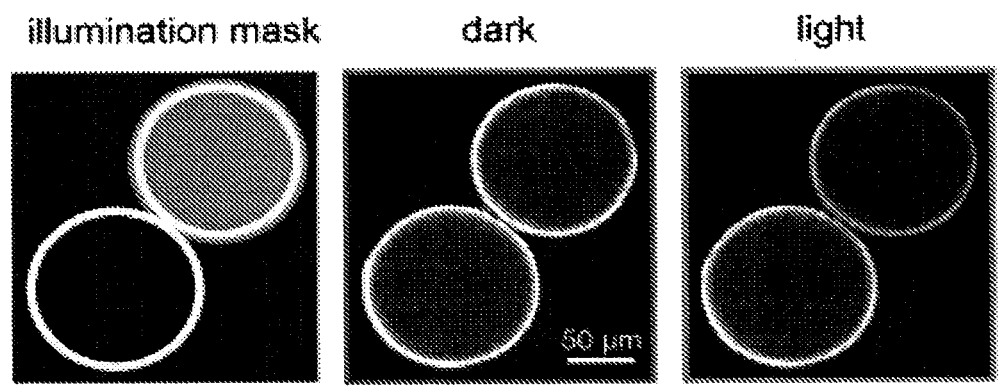
FIGS. 25A-25F show in vitro characterization of OptoMB.
Figure 25B:
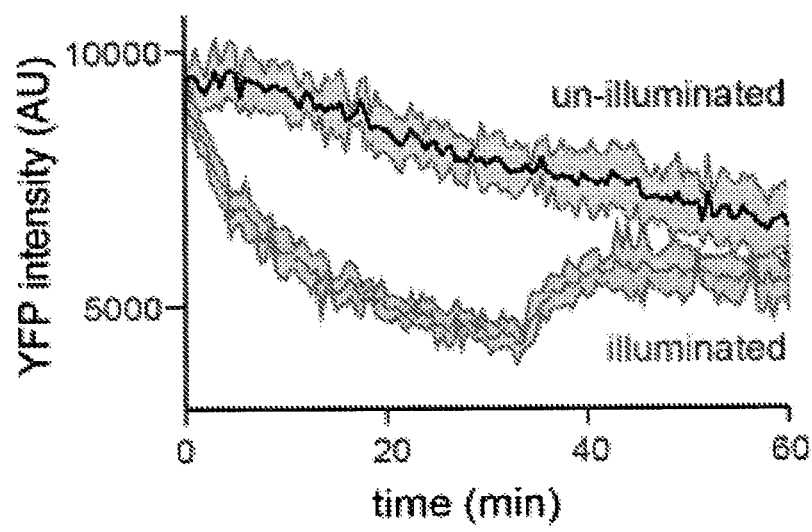

In vitro characterization of OptoMB. The in vitro light-dependent interaction of the OptoMB and SH2 domain (FIG. 22A) can be visualized by fluorescence microscopy using immobilized OptoMB. His-tagged OptoMBs harboring a mutation in AsLOV2 (V416L) that extends the lifetime of the photoactivated state[50] (OptoMB$_{V416L}$) were immobilized onto Ni-charged agarose beads. Immobilized parental HA4 monobodies were used in parallel as a control. The monobody-coated beads were then incubated with a fusion of yellow fluorescent protein and SH2 (YFP-SH2) in the dark until they reached equilibrium, and imaged over time using confocal microscopy in the presence or absence of blue light (450 nm). For OptoMB-coated beads, light exposure induced a rapid decrease in YFP signal on the surface of the bead within one imaging frame (2 minutes), consistent with light-triggered dissociation of the SH2 domain (FIG. 22B, upper panel). In contrast, no fluorescence change was observed under identical conditions for the control HA4-coated beads (FIG. 22B, lower panel). Localized illumination could also be used to restrict SH2 unbinding to a single bead in a crowded field (FIG. 25A). In this case, YFP fluorescence was rapidly and reversibly controlled for the illuminated bead but not a nearby un-illuminated bead (FIG. 25B). These results demonstrate that OptoMBs provide temporal, spatial, and reversible control over protein binding.

Figure 22C:
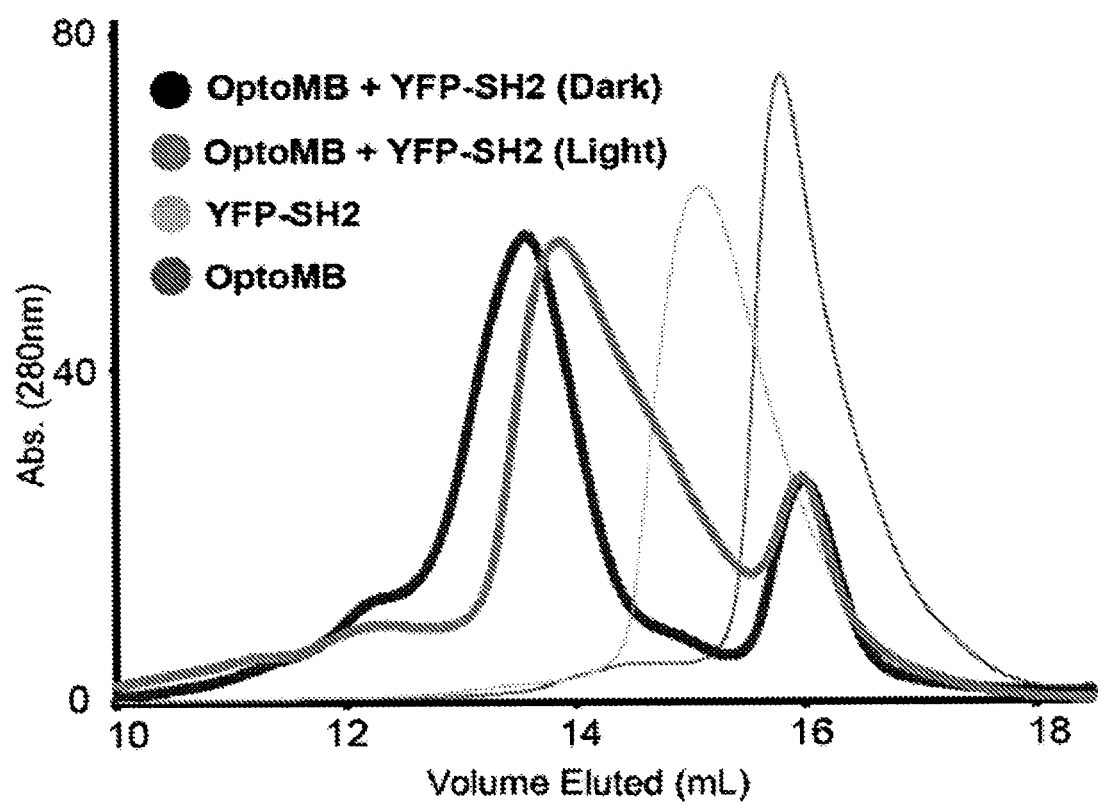
Figure 22D:
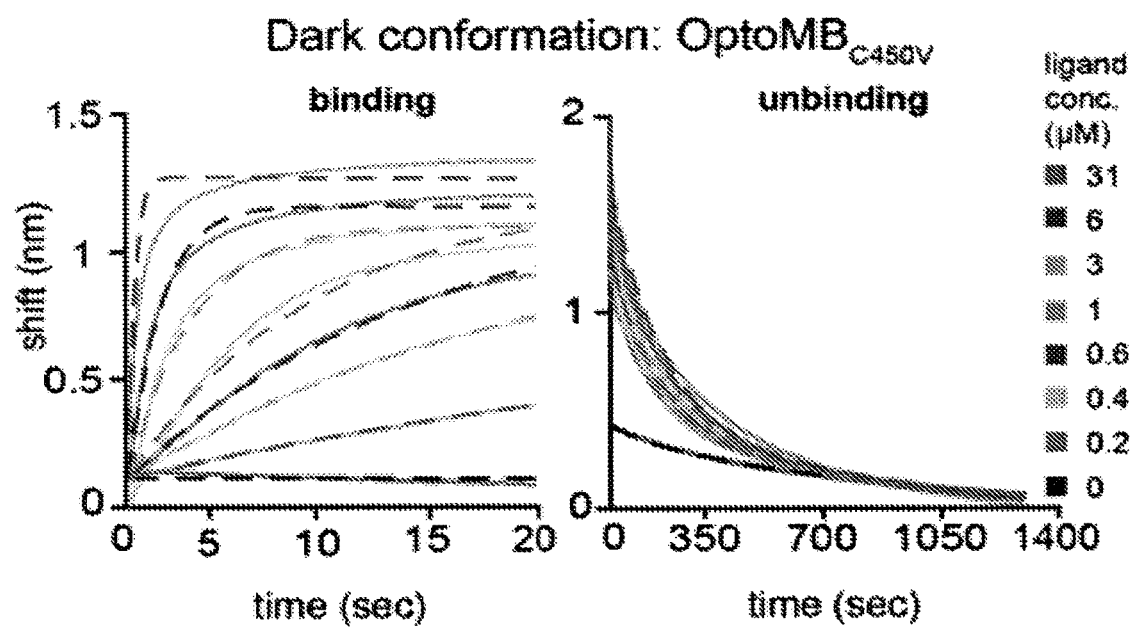
Figure 22E:
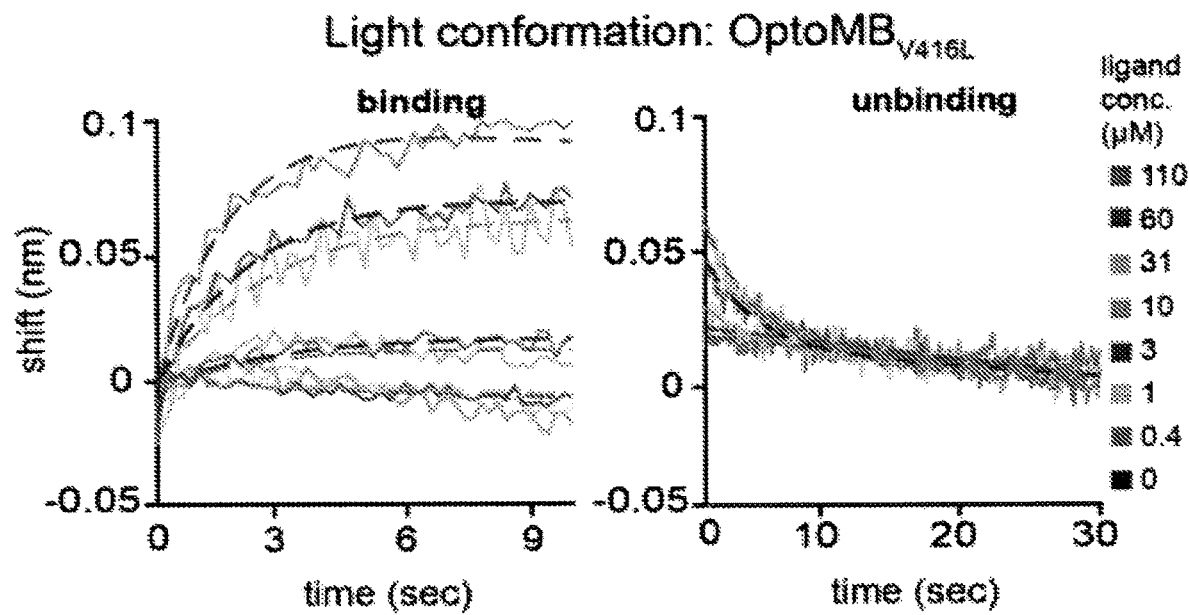
Figure 25C:
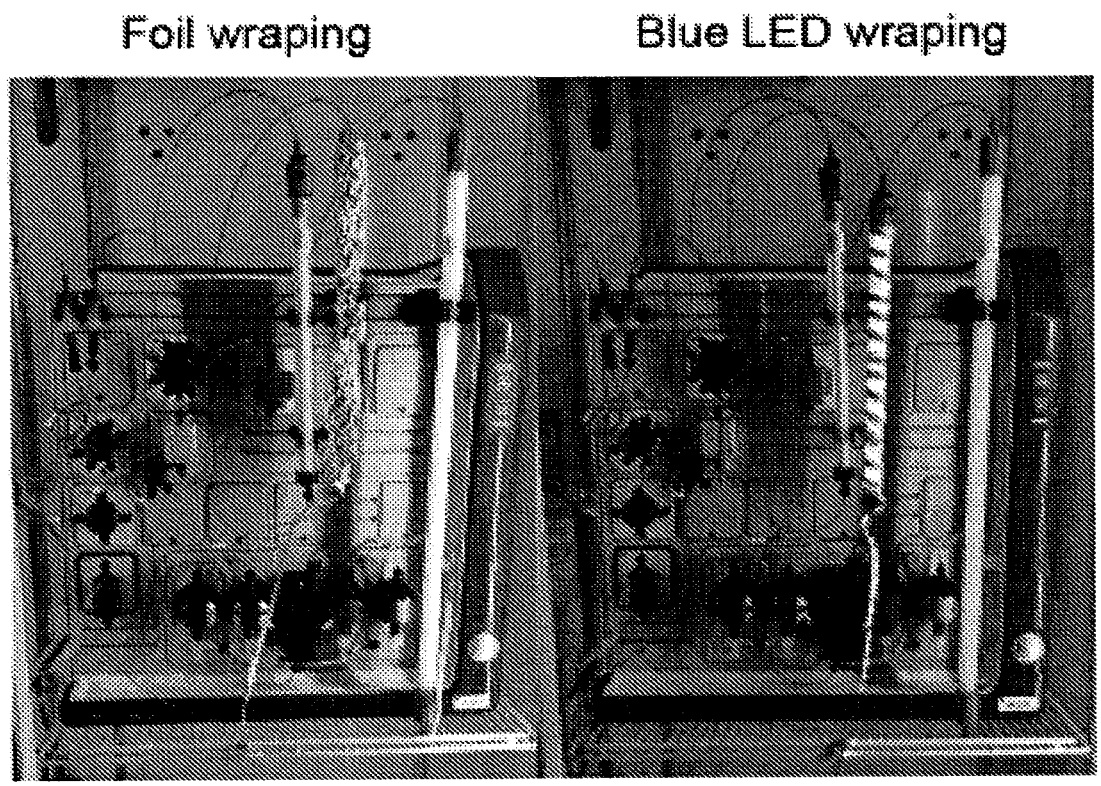
Figure 25D:
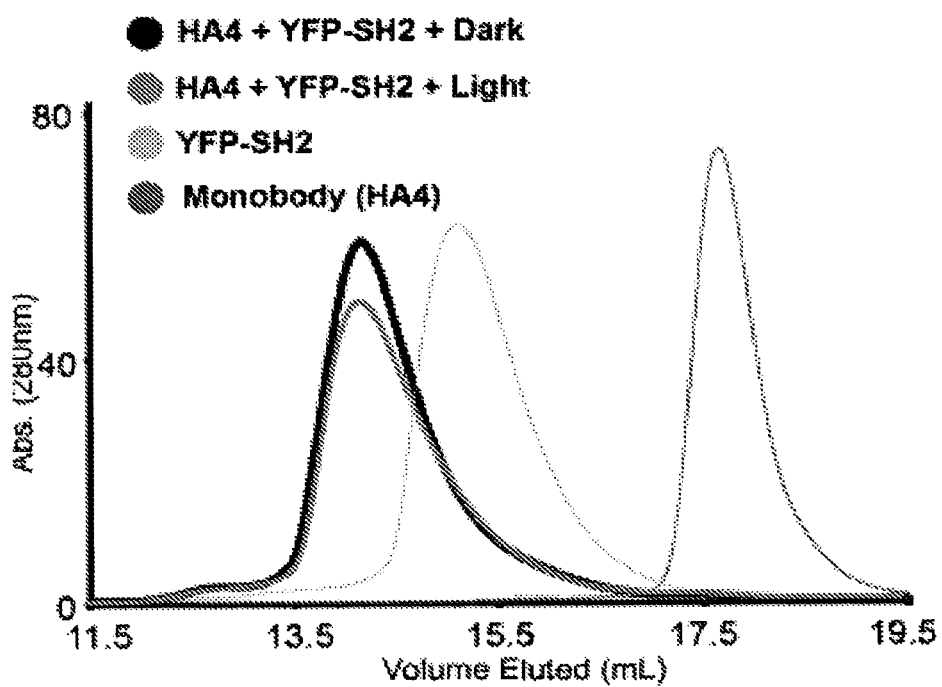
Figure 25E:
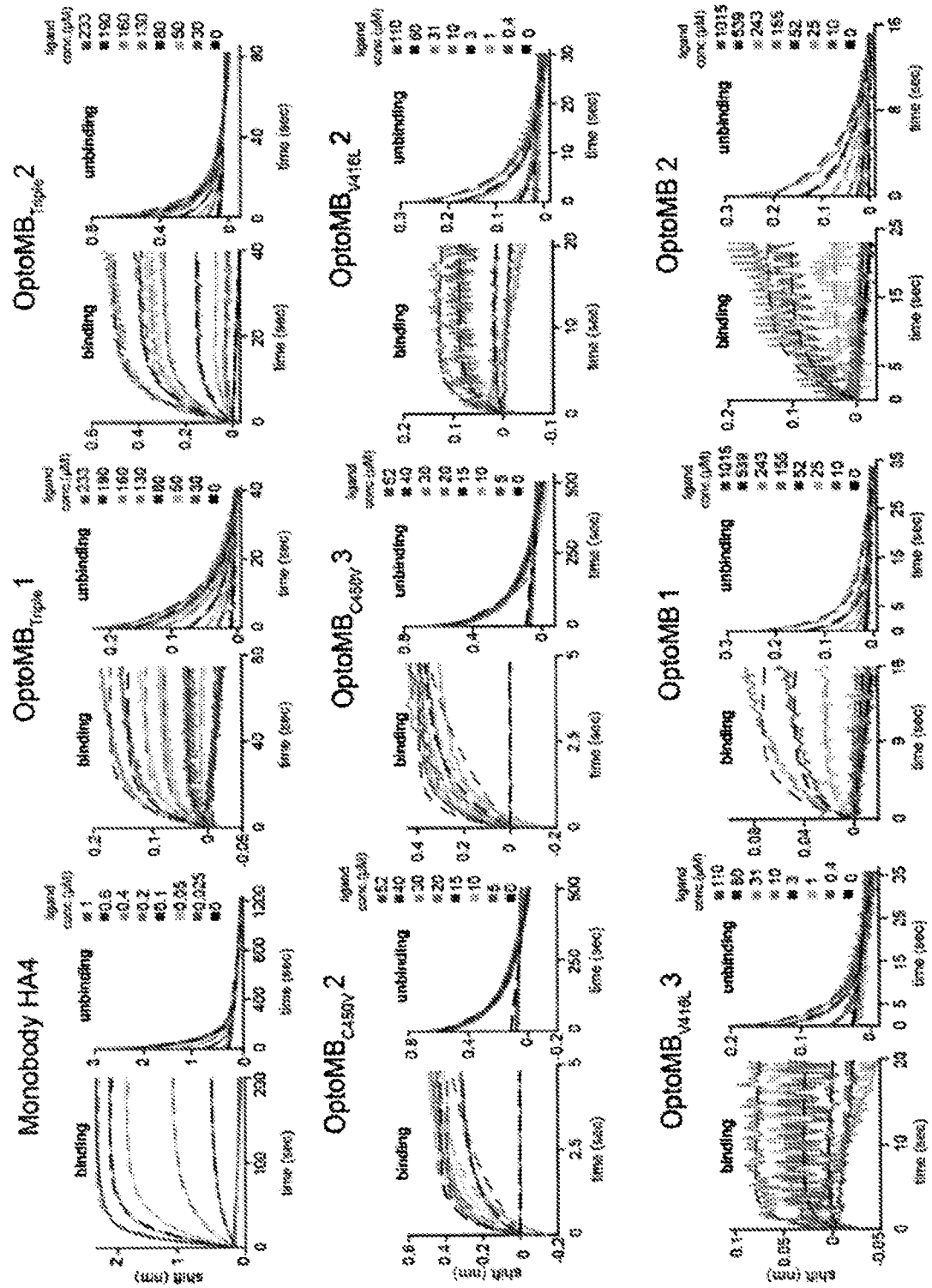
Figure 25F:
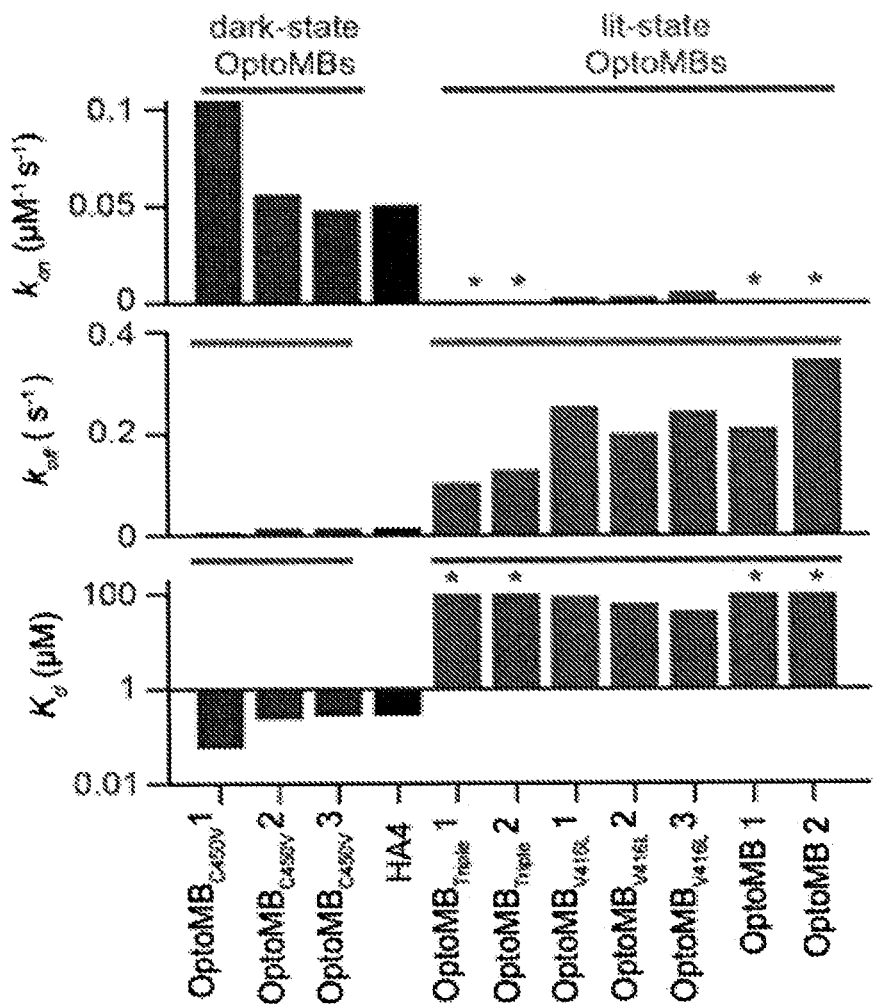
Figure 26A:
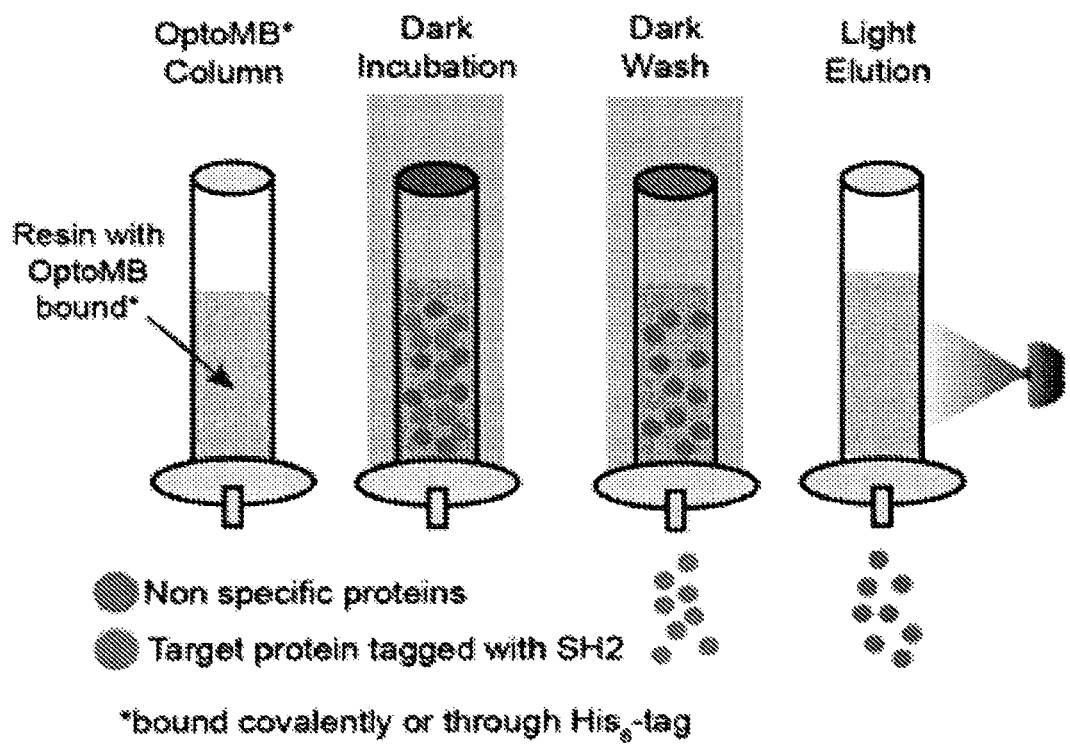
FIGS. 26A-26D show light-controlled affinity chromatography (LCAC) to purify SH2-tagged proteins using OptoMB immobilized on $Co^{2+}$ agarose beads.
Figure 26B:
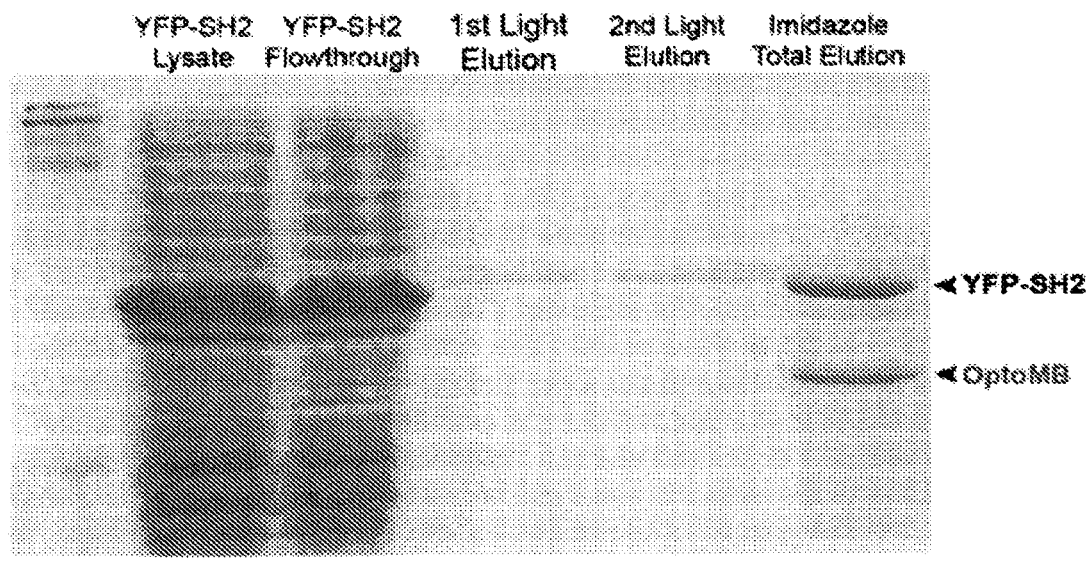
Figure 26C:
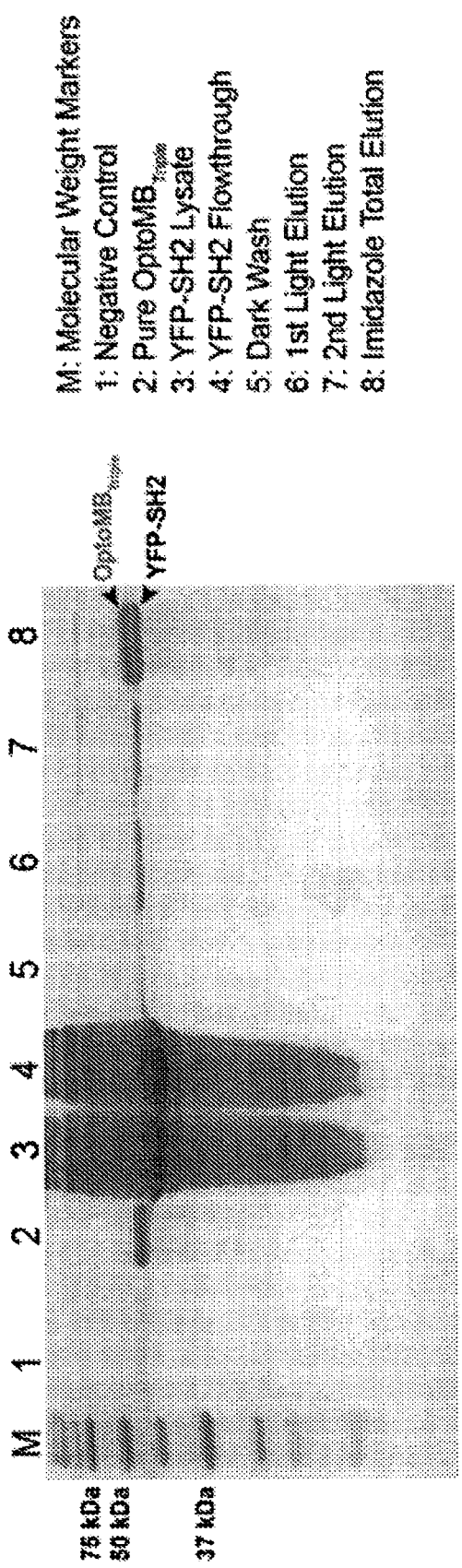
Figure 26D:
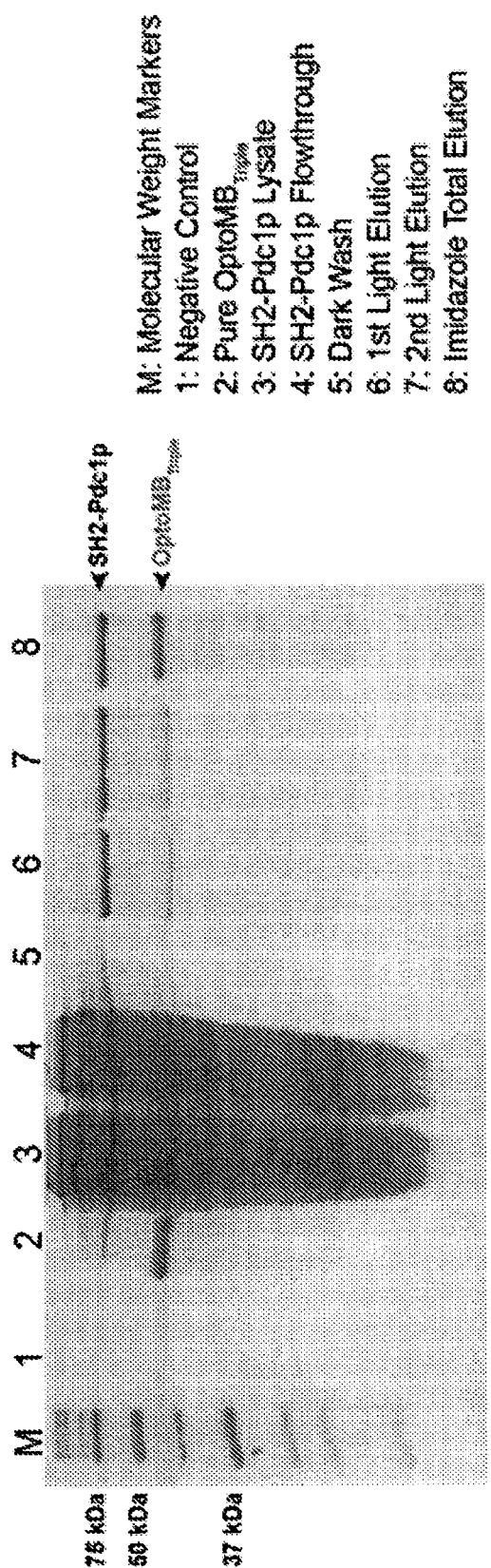

The light dependency of OptoMB interactions with YFP-SH2 can also be analyzed in solution by size exclusion chromatography (SEC). Mixtures of purified YFP-SH2 and OptoMB (or HA4 monobody, as control), in which OptoMB was added in excess (see Methods), were prepared. Each sample was then loaded to a gel filtration column under continuous darkness or blue light (FIG. 25C). It was found that for both the dark-incubated OptoMB sample (FIG. 22C) and the HA4 monobody in either light condition (FIG. 25D), the YFP-SH2 eluted primarily as a monobody-bound complex. In contrast, the illuminated OptoMB sample showed a higher retention time for the YFP-SH2-OptoMB complex and a larger proportion of the YFP-SH2 eluting as a monomer on its own (FIG. 22C). Taken together, the bead-imaging and SEC data are both consistent with a blue light-triggered reduction in the OptoMB-SH2 binding affinity, both in solution and on protein-coated surfaces.

To quantify the changes in OptoMB-SH2 binding, the kinetic rate constants and binding affinity were determined in different light conditions. In these assays, advantage was taken of three classes of mutations in AsLOV2 to vary properties of the OptoMB binding switch. Bio-layer interferometry (BLI) uses visible light for measuring changes in binding, so a light-insensitive OptoMB was first prepared by introducing the well-characterized C450V mutation in AsLOV2 that renders it light-insensitive[36,51] (OptoMB$_{C450V}$). Conversely, it was ensured that illumination could drive efficient conversion to the lit state by generating additional OptoMB variants with mutations that extend the lifetime of the lit state after illumination from approximately 80 to 821 or up to 4300 sec in vitro (AsLOV2 V416I[49] or V416L[52], respectively). Finally, the AsLOV2

G528A and N538E mutations (to make the triple mutant OptoMB$_{V416I\_G528A\_N538E}$), which have been reported to stabilize the dark state conformation and potentially decrease leakiness in the absence of illumination[53,54] were added. The resulting binding and dissociation data were fit to a mass-action kinetic binding model (FIG. 22D-22E and FIG. 25E-25F), allowing estimates of the rate constants of binding ($k_{on}$) and unbinding ($k_{off}$) as well as the overall dissociation constant ($K_d$) of the OptoMB-SH2 interaction in different light conditions to be obtained (Table 2; Supplementary Table 2).

TABLE 2

Rate and dissociation constants from BLI experiments.

| Variant | State measured | $k_{on}$ ($\mu M^{-1} s^{-1}$) | $k_{off} (s^{-1})$ | $K_d$ ($\mu M$) |
|---|---|---|---|---|
| Monobody HA4 | — | 0.0631 | 0.0145 | 0.23 |
| OptoMB | Light conformation | <0.001 | 0.21 ± 0.09 | >100 |
| #OptoMB$_{C450V}$ | Dark conformation | 0.071 ± 0.033 | 0.01 ± 0.004 | 0.19 ± 0.11 |
| #OptoMB$_{V416L}$ | Light conformation | 0.004 ± 0.001 | 0.23 ± 0.02 | 63 ± 23 |

Average of three individual measurements.

It was found that the binding affinity of OptoMB to SH2 changed dramatically when switching from dark to light conditions. The average dissociation constant of the OptoMB-SH2 interaction in the dark (OptoMB$_{C450V}$) was $K_d$=0.19±0.11 µM, which is comparable to the measurements for the HA4 monobody. However, in the light (OptoMB$_{V416L}$), the average dissociation constant drastically increased to $K_d$=63±23 µM. This amounts to an approximately 330 fold-change in binding affinity between light conditions, which explains the light-dependent behaviors observed in the bead-imaging experiments. The change in $K_d$ of the lit state arises equally from a decrease in the binding rate constant ($k_{on}$) and an increase in the unbinding rate constant ($k_{off}$). These data are consistent with a light-induced change in the conformation of the OptoMB that disrupts the binding interface, substantially decreasing the likelihood of a productive association between the lit-state OptoMB and its target SH2, and equally increasing the likelihood of dissociation of the bound complex.

Light-Controlled Affinity Chromatography (LCAC) with Immobilized OptoMB. It was reasoned that the substantial change in OptoMB binding affinity could open the door to purifying a protein of interest simply by shifting illumination conditions (FIG. 23A), a procedure referred to herein as "light-controlled affinity chromatography" (LCAC). Two variants of His-tagged OptoMBs harboring either the wild-type AsLOV2 or the triple-mutant (OptoMB$_{V416I\_G528A\_N538E}$) described above were immobilized onto Co-charged agarose beads to make an αSH2-OptoMB affinity resin. OptoMB-coated beads were then incubated with crude lysate from *E. coli* overexpressing YFP-SH2. After washing thoroughly in the dark (see Methods), products were eluted with blue light either in batch (FIG. 23B) or in a column (FIGS. 26A-26D). After elution, beads were washed with imidazole to recover any remaining protein bound to the beads in order to estimate the capacity and yields of the resin. With these initial LCAC purification trials, 95-98% purity was achieved in a single step, with yields ranging from 18-30% and binding capacities from 112-145 nmol (4.5-6 mg) of SH2-tagged YFP per mL of OptoMB resin, depending on the OptoMB variant used (Supplementary Table 3).

SUPPLEMENTARY TABLE 2

Rate and dissociation constants from BLI experiments.

| Variant | State measured | Illumination | $k_{on}$ ($\mu M^{-1} s^{-1}$) | $k_{off} (s^{-1})$ | $K_d$ ($\mu M$) |
|---|---|---|---|---|---|
| Monobody HA4 | — | ambient | 0.051 | 0.0145 | 0.28 |
| OptoMB 1 | Lit conformation | ambient* | <0.001 | 0.34 | >100 |
| OptoMB 2 | Lit conformation | 450 nm light | <0.001 | 0.21 | >100 |
| OptoMB$_{C450V}$ 1 | Dark conformation | ambient** | 0.11 | 0.006 | 0.06 |
| OptoMB$_{C450V}$ 2 | Dark conformation | ambient** | 0.056 | 0.013 | 0.23 |
| OptoMB$_{C450V}$ 3 | Dark conformation | 450 nm light | 0.048 | 0.013 | 0.27 |
| OptoMB$_{V416L}$ 1 | Lit conformation | ambient* | 0.0029 | 0.25 | 87 |
| OptoMB$_{V416L}$ 2 | Lit conformation | 450 nm light | 0.0033 | 0.20 | 60 |
| OptoMB$_{V416L}$ 3 | Lit conformation | 450 nm light | 0.0058 | 0.24 | 42 |
| #OptoMB$_{V416I\_G528A\_N538E}$ 1 | Lit conformation | ambient* | <0.001 | 0.10 | >100 |
| #OptoMB$_{V416I\_G528A\_N538E}$ 2 | Lit conformation | ambient* | <0.001 | 0.13 | >100 |

*Due to the sensitivity of these constructs, ambient light in the laboratory as well as internal light from the digital panels of the Octet (BLI instrument) was sufficient to trigger the lit conformation.
**This is a light-insensitive mutant, and neither ambient nor LED light affected its basal dark conformation.
SUMO tagged

SUPPLEMENTARY TABLE 3

Purification parameters of LCAC batch experiments

| Purified protein | OptoMB version | Resin type | Purity# (%) | Resin Capacity# (mg/mL) | Yield# (% of recovery from the resin) |
|---|---|---|---|---|---|
| YFP-SH2 | Wt AsLOV2 | Talon* | 98.25 (±2.26) | 5.85 (±0.67) | 17.8 (±2.18) |
| YFP-SH2 | #OptoM$_{V416I\_G528A\_N538E}$ | Talon* | 95.32 (±0.46) | 4.5 (±0.33) | 29.79 (±3.28) |

SUPPLEMENTARY TABLE 3-continued

Purification parameters of LCAC batch experiments

| Purified protein | OptoMB version | Resin type | Purity[#] (%) | Resin Capacity[#] (mg/mL) | Yield[#] (% of recovery from the resin) |
|---|---|---|---|---|---|
| SH2-PDC1 | [#]OptoM$_{V416I\_G528A\_N538E}$ | Talon* | 95.53 (±1.05) | 5.24 (±0.52) | 39.01 (±2.61) |
| YFP-SH2 | [#]OptoM$_{V416I\_G528A\_N538E}$ | CNBr** | 99.78 (±0.22) | 2.55 (±0.22) | 40.29 (±3.02) |
| SH2-PDC1 | [#]OptoM$_{V416I\_G528A\_N538E}$ | CNBr** | 96.69 (±1.24) | 1.55 (±0.18) | 42.28 (±4.34) |

Figure 23A:
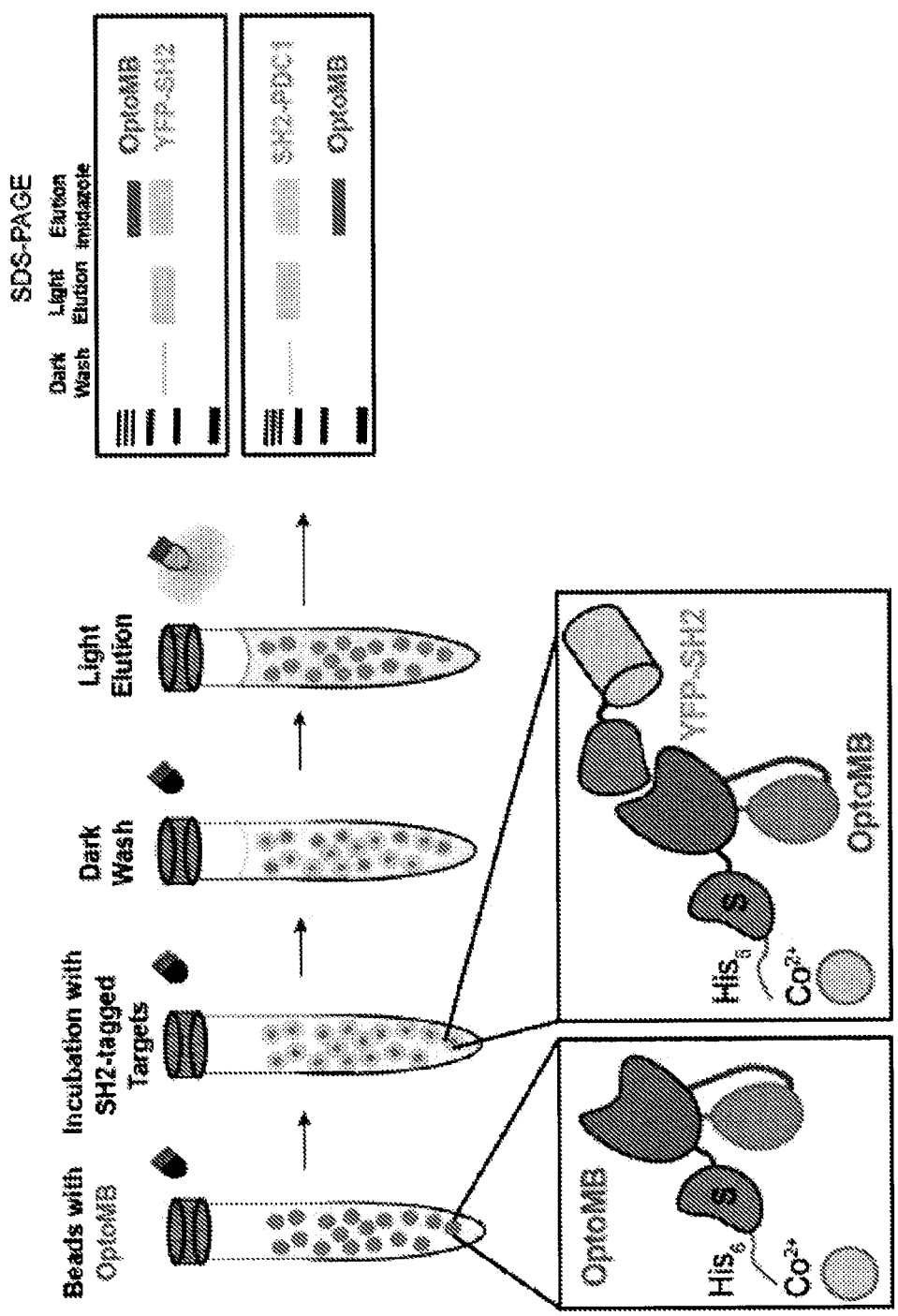
Figure 27A:
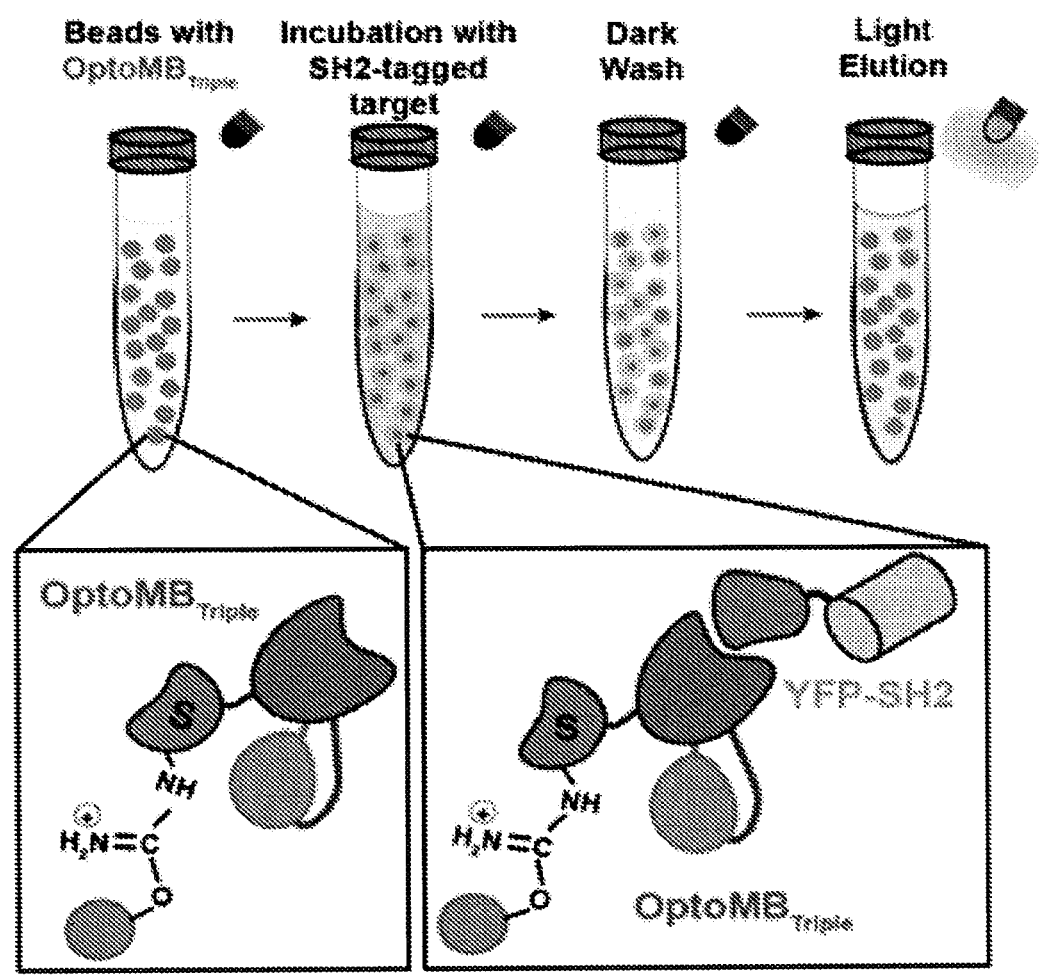
FIGS. 27A-27C show light-controlled affinity chromatography to purify SH2-tagged proteins using cyanogen bromide (CNBr)-conjugated OptoMB.
Figure 27B:
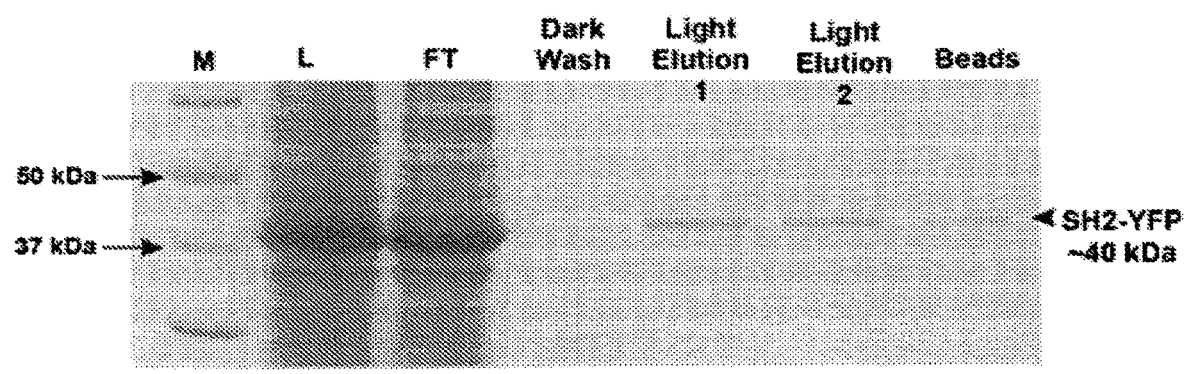
Figure 27C:
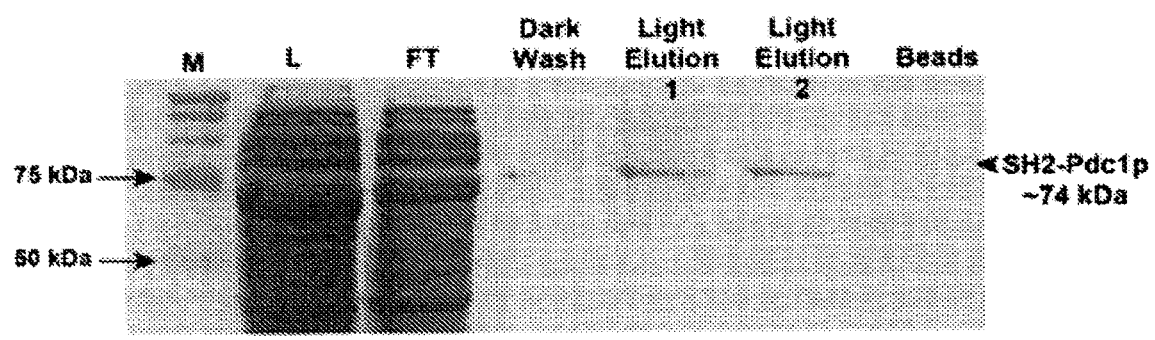

*OptoMB was His-tag bound
**OptoMB was covalently conjugated
[#]Calculations are explained in Methods
[#]SUMO tagged To test whether LCAC could be applied to larger and more complex proteins, it was also used to purify the main pyruvate decarboxylase from *Saccharomyces cerevisiae*, Pdc1p. This enzyme catalyzes the decarboxylation of pyruvate to acetaldehyde for ethanol fermentation, and is composed of a homotetramer of 61 kDa monomers[55], significantly larger than YFP. The SH2 domain was fused to the N-terminus of Pdc1p (SH2-PDC1), and LCAC performed to purify it from crude *E. coli* lysate, as described above, using a resin coated with OptoMB$_{V416I\_G528A\_N538E}$. This procedure enabled purification of Pdc1p to 96% purity with a 39% yield (FIG. 23C and Supplementary Table 3). It is noteworthy that this purification works considerably well, despite the potential binding avidity of Pdc1p tetramers that would be predicted to increase the protein's apparent affinity in both the light and dark. These results demonstrate that LCAC can be applied to purify relatively large proteins with quaternary structures of up to at least 300 kDa (including the fused SH2 domain), achieving a high degree of purity and an acceptable yield. The results with YFP-SH2 and SH2-PDC1 further demonstrate that OptoMB-assisted purification is compatible with both N- and C-terminal SH2 tags. While metal-affinity beads are effective at immobilizing OptoMB for LCAC (FIGS. 23A-23C and FIGS. 26A-26D), they may be incompatible with some protein purification methods. Thus, to determine whether an alternative resin could be used for LCAC, OptoMB$_{V416I\_G528A\_N538E}$ was immobilized onto cyanogen bromide-activated sepharose beads (CNBr-beads), which immobilizes proteins by making covalent bonds with its primary amines (see Methods). Following the same purification protocol as above, it was found that CNBr-beads are also effective at purifying both YFP and Pdc1p (FIGS. 27A-27C). A single step of CNBr-based purification achieved yields above 40% and purity of 96.7-99.8%, surpassing any other LCAC method tested (Supplementary Table 3). These gains are likely related to the reduced non-specific binding of *E. coli* proteins to CNBr-sepharose and covalent OptoMB attachment, which allowed for more extensive washing at higher salt concentrations. It was observed that the total loading capacity was not as high as that of OptoMB-coated Co-agarose (Supplementary Table 3), probably because random crosslinking to the CNBr-beads inactivated a significant fraction of the OptoMB by occluding its binding surface to SH2. Although much could still be done to further improve LCAC by optimizing the resin, method, or amino acid sequence of the OptoMB, these experiments demonstrate the feasibility of a practical in vitro application of light-responsive monobodies for protein purification. This approach would make it possible to use buffer conditions that are optimal for protein stability throughout the purification process without needing to elute with a buffer exchange, which may damage the protein of interest (such as the low pH commonly used in antibody-based purification), or require lengthy and expensive subsequent dialysis. It also opens the possibility of using protein-specific OptoMBs to purify proteins that are difficult to fuse to affinity tags.

Figure 24A:
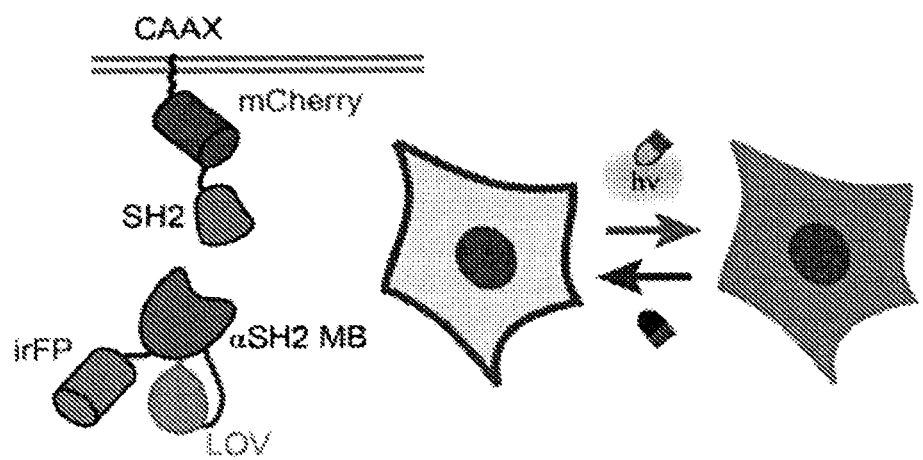
FIGS. 24A-24D show in vivo characterization of OptoMB using mammalian cells.

Light-dependent OptoMB binding in vivo. It has been shown that OptoMB-SH2 binding can be controlled with light in vitro; as a final test of this system, it was assessed whether similar control can be achieved in live mammalian cells where monobodies have been reported to work[33]. HEK293T cells were transduced with lentiviral vectors encoding a membrane-localized, fluorescent SH2 target protein (SH2-mCherry-CAAX) and cytosolic fluorescent OptoMB (OptoMB-irFP), reasoning that a light-dependent change in SH2-OptoMB binding would cause the OptoMB to redistribute between the cytosol and plasma membrane (PM) (FIG. 24A), as has been observed for conventional optogenetic protein-protein interactions in previous studies[56-58]. As a control, irFP-labeled HA4 monobody was expressed instead of OptoMB, which would be expected to bind to the membrane-localized SH2-mCherry-CAAX regardless of illumination conditions.

Figure 24B:
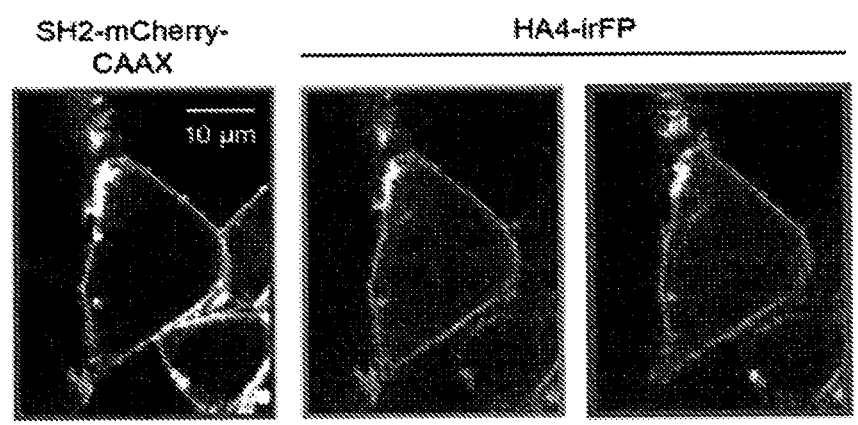
Figure 24C:
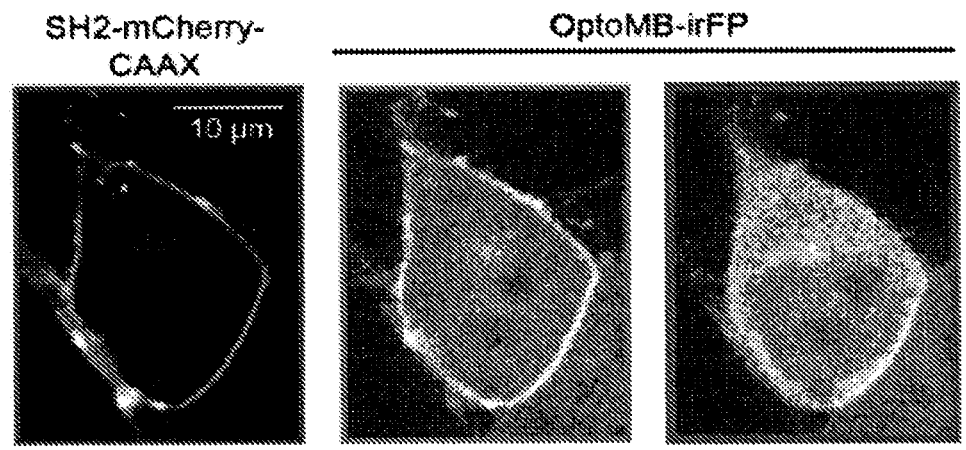

Fluorescence imaging confirmed the PM localization of SH2-mCherry-CAAX (FIGS. 24B-24C, left panels), as well as constitutively PM-bound HA4-irFP (FIG. 24B). In contrast, a light-dependent shift in OptoMB localization was observed (FIG. 24C), with PM enrichment in the dark and rapid redistribution to the cytosol upon light stimulation. Applying cycles of light and darkness further revealed that light-controlled binding is fully reversible intracellularly (FIG. 24C). The extent of OptoMB cytosol-to-membrane redistribution was also compared to the well-established iLID-SSPB optogenetic heterodimerization tool. This analysis showed that the OptoMB displays a change in cytosolic intensity between light conditions that is equal in magnitude (both close to 60%) to that of iLID-SSPB, but with opposite sign. These experiments demonstrate functional photoswitching of OptoMB binding in cells to a level comparable to existing optogenetic tools, opening the door to their application in this context. These experiments demonstrate functional photoswitching of OptoMB binding inside cells, opening the door to its in vivo application.

Discussion. It is shown that by taking a rational protein engineering approach it is possible to develop a light-switchable monobody (OptoMB). By fusing the light-responsive AsLOV2 domain to a structurally conserved loop of the HA4 monobody that binds the SH2 domain of human Abl kinase, an OptoMB was developed that shows an approximately 330-fold drop in binding affinity when changing conditions from darkness to blue light. In comparison, the well-established iLID optogenetic switch displays an approximately 58-fold change in binding affinity between light conditions[40]. Furthermore, the light responsiveness of OptoMB is reversible and effective at controlling binding to proteins fused to SH2 (at either its N- or C-terminus), both in vitro and in cells. OptoMBs, along with light-switchable nanobodies (OptoNBs)[30], belong to a new class of light-dependent protein binders called OptoBinders (OptoBNDRs), which offer promising new in vivo and in vitro applications.

A close inspection of the structural model of OptoMB and binding measurements suggested a possible mechanism for the light-dependent binding affinity of OptoMB. The monobody protein fold consists of two antiparallel β-sheets (βSh1 and βSh2) that interact with each other to form the protein core (FIG. 1b). In the original chimera screens, AsLOV2 was inserted in all intervening loops within (L1, L3, L6 and L7) and between (L2, L4 and L5) these β-sheets, which are accessible in the side-binding mode of monobodies. The only chimeras that showed a change in binding affinity in different light conditions were those with AsLOV2 inserted in loops L2 and L4, with L4 being the only loop with positive results at multiple insertion sites. Both of these loops connect βSh1 and βSh2 with each other, suggesting that chimeras involving either loop may act by a similar mechanism, where the light-triggered conformational change of the Jα helix pulls the βSh1 and βSh2 apart from each other. Chimeras with AsLOV2 inserted in loop L5, located at the opposite side of the βSh1-βSh2 interaction relative to L2 and L4, show equally faint SDS-PAGE bands in either light condition, suggesting limited expression in *E. coli*, or weak binding to SH2 independently of light. The consequence of pulling on βSh1 and βSh2 from loops L2 or L4 is probably at least a partial disruption of the interactions and angle between them. This in turn would likely change the curvature of βSh2, which defines the shape of the paratope-like surface of H4A and its specific binding interactions with SH2[46]. Interestingly, because the conserved fold of monobodies always includes βSh1 and βSh2 interactions[31], this light-triggered disruption of the binding surface may be transferable to other monobodies (e.g., with a side-binding mode). It also suggests that mutating residues involved in βSh1-βSh2 interactions may provide some opportunities to tune the photoswitchable behavior of the OptoMB, by stabilizing either the dark- or lit-state conformations.

Figure 24D:
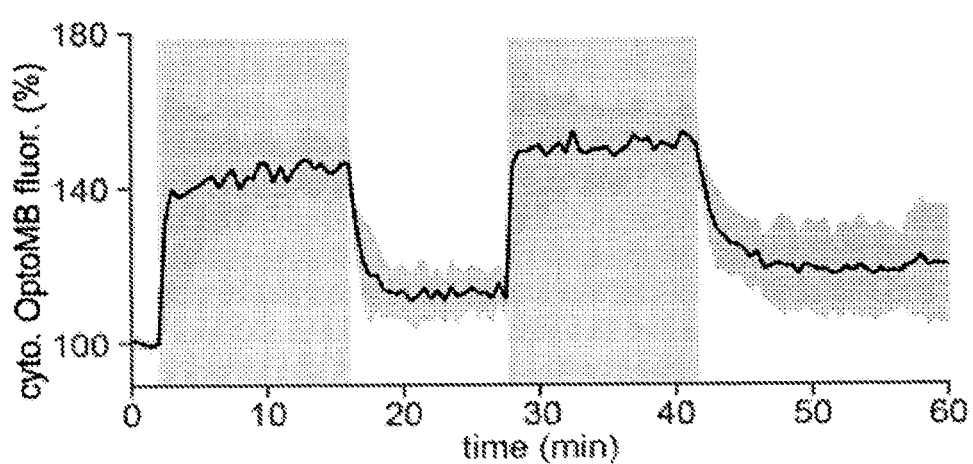

This model of light-induced disruption of the monobody's target-binding site is also consistent with measurements of binding kinetics. It was originally reasoned that light stimulation might strain the OptoMB-SH2 interaction causing it to dissociate without necessarily inducing dramatic changes in binding site accessibility, thus predicting mostly a light-induced increase in the OptoMB-SH2 off-rate ($k_{off}$). However, our BLI measurements revealed that both $k_{on}$ and $k_{off}$ are equally affected in the light (approximately 20-fold change in opposite directions, Table 1, Supplementary Table 2). This suggests a significant disruption of the binding surface of the OptoMB in the light, which not only accelerates the dissociation of the bound chimera, but also slows down its binding to the target to begin with. Such disruption would be expected from pulling on the β-sheet interactions that make the core of the monobody fold. However, despite what is likely to be a substantial conformational change in the OptoMB, it was found that productive binding is reversible in vitro (FIG. 25B) and in mammalian cells (FIG. 24D). Overall, these data are consistent with a large change in the overall orientation or conformation of the βSh1-βSh2 sheets, substantially disrupting binding but without driving irreversible protein misfolding. It is possible that the small size of the monobody domain, the short range of interactions between βSh1 and βSh2, and the lack of disulfide bonds in the monobody fold facilitate this high efficiency of interconversion between binding states.

Previous studies have measured the free energy available from the dark-to-light conformational change of AsLOV2 using NMR spectroscopy[59] and developed analytical models to study equilibrium constants of the dark- and lit-states of AsLOV2[53]. These studies predict that 3.8 kcal/mol of energy is transmitted from the absorption of one photon to structural rearrangements in AsLOV2. If all of this energy was transmitted to a change in OptoMB binding, it would result in an approximately 600-fold difference in binding affinity between the dark and lit states. BLI experiments measured a change in $K_d$ values of 150- to 300-fold, which is within the same order of magnitude of this maximum theoretical prediction, indicating that the light-induced conformational change of AsLOV2 is efficiently transmitted to disrupt the SH2 binding surface of the monobody domain. It is noted that the AsLOV2 domain might be altered to tune the efficiency of the light-induced conformational change, for instance by further stabilizing the lit or dark state conformations or by altering its photoswitching kinetics (FIGS. 23B-23C and Supplementary Table 2). In principle, these changes could increase the overall energy beyond the 3.8 kcal/mol measured for the wild-type AsLOV2 domain.

The performance of the light-dependent OptoMB/SH2 binding pair is comparable to that of other optical dimerization systems previously used to control transcription, protein-protein interactions, or protein localization[60-62]. However, these previous systems have been developed by fusing proteins of interest to specific light-dependent interaction partners (such as PhyB/PIF3 or Cry2/CIB) evolved in photosensitive organisms. While the demonstrations in this study relied on fusing SH2 to different proteins, the true potential of this technology is not so much to replace the light-responsive tags used in previous optogenetic systems with SH2 and OptoMB, but in the possibility of engineering other monobodies against different targets of interest to make their specific interaction light-dependent. The relative simplicity of the monobody fold and the likely structural mechanism that confers light-dependent binding makes it reasonable to expect that other monobodies could be engineered to be light-dependent; starting from inserting AsLOV2 in loop L4 and then optimizing the precise position of the insertion site and the linkers. Monobodies could in principle be designed and selected to bind any protein of interest[6,31] or to different epitopes on a single target[31]. The approach may thus be useful to design reversible interactions to a protein of interest without the need for a binding tag, which for some proteins may be impractical, not possible, or interfere with their natural activity.

Methods: Plasmid construction of chimeras for bacterial expression. One-step isothermal assembly reactions (Gibson assembly) were performed using previously described methods[61]. The monobody HA4 and the SH2 domain (codon optimized for *E. coli* expression) were ordered as gBlocks from Integrated DNA Technologies (IDT) containing homology arms. The following vectors from the pCri system[63] were used: pCri-7b for constructs without a 6×-histidine tag (SEQ ID NO: 49); pCri-8b for constructs with a 6x-histidine tag (SEQ ID NO: 49, N-terminus), and pCri-11b for constructs with both SUMO and 6x-histidine tags (SEQ ID NO: 49, N-terminus). As the pCri vectors contain YFP, the synthetized SH2 domain was inserted into pCri-7b and 8b (previously linearized with XhoI) by Gibson assembly to construct EZ-L664 and EZ-L703 (see Supplementary table 4). Monobody HA4 was inserted into pCri-7b; the vector was digested (opened) with NheI and XhoI and Gibson-assembled to build the template (EZ-L663) used for the AsLOV2 insertions. A stop codon was added before the in-frame (C-terminus) 6x-histidine tag (SEQ ID NO: 49) of pCri-7b. The AsLOV2 domain (residues 408-543) was either amplified by PCR from previous constructs[45] (wt AsLOV2), or synthesized as IDT gBlocks (AsLOV2 mutants). To insert AsLOV2 into the monobody, the backbone from the initial construct containing HA4 (EZ-L663) was PCR amplified, using Takara Hifi PCR premix, starting from the insertion positions (Supplementary Table 1) that were selected (and adding homology arms to AsLOV2). Next, chimeras were finally assembled mixing each of the amplified products of the backbone PCR from EZ-L663 with the AsLOV2 domain obtained from either PCR amplification (wt AsLOV2) or synthesized by gBlocks (AsLOV2 mutants). SUMO tags were added by inserting (with Gibson assembly) the PCR product of the full-length chimeras (with homology arms) into the pCri-11b plasmid, previously opened with NheI and XhoI. PDC1 was amplified from *S. cerevisiae* (S288C) genomic DNA using PCR, also with homology arms, and the construct (EZ-L886) was built via Gibson assembly (3 fragments) with digested pCri-7b (NheI and XhoI) and the PCR product of SH2 amplified from EZ-L664 (with homology arms). All constructs (Supplementary Table 4) were sequenced by Genewiz and all protein sequences are available in the sequence listing. Chemically competent DH5a was used to clone all vectors. After verifying the plasmid sequence, vectors were used to transform chemically competent BL21 (DE3) or Rosetta strains for protein expression.

SUPPLEMENTARY TABLE 4

Constructs used in this study.

| Plasmid | Tag | Protein | Marker | Vector type |
|---|---|---|---|---|
| EZ-L663 | None | HA4 | Kanamycin | pCri-7b |
| EZ-L664 | His$_6$ (SEQ ID NO: 49) | YFP-SH2 | Kanamycin | pCri-8b |
| EZ-L703 | None | YFP-SH2 | Kanamycin | pCri-7b |
| EZ-L704 | His$_6$ | HA4 | Kanamycin | pCri-8b |
| EZ-L706 | None | HA4-AsLOV2 (SS58 (SEQ ID NO: 49) insertion) | Kanamycin | pCri-7b |
| EZ-L736 | None | HA4-AsLOV2 (MS29 insertion, residues 30-32 were removed) | Kanamycin | pCri-7b |
| EZ-L747 | None | HA4-AsLOV2 (SS59 insertion) | Kanamycin | pCri-7b |
| EZ-L765 | His$_6$ (SEQ ID NO: 49) | HA4-AsLOV2 (SS58 insertion) | Kanamycin | pCri-8b |

SUPPLEMENTARY TABLE 4-continued

Constructs used in this study.

| Plasmid | Tag | Protein | Marker | Vector type |
|---|---|---|---|---|
| EZ-L830 | His$_6$- (SEQ ID NO: 49)-SUMO | HA4-AsLOV2 (SS58 insertion, V416L mutant) | Kanamycin | pCri-11b |
| EZ-L884 | His$_6$ (SEQ ID NO: 49) | HA4-AsLOV2 (SS58 insertion, C450V mutant) | Kanamycin | pCri-8b |
| EZ-L886 | None | SH2-PDC1 | Kanamycin | pCri-7b |
| EZ-L889 | His$_6$- (SEQ ID NO: 49)-SUMO | HA4-AsLOV2 (SS58 insertion, V416I, G528A, N538E mutant) | Kanamycin | pCri-11b |
| EZ-L892 | His$_6$ (SEQ ID NO: 49) | HA4-AsLOV2 (SS58 insertion, V416I mutant) | Kanamycin | pCri-8b |
| AG-pHR1 | None | HA4-iRFP | Ampicillin | pHR |
| AG-pHR2 | None | HA4-AsLOV2-iRFP (SS58 insertion) | Ampicillin | pHR |
| AG-pHR3 | CAAX | SH2-mCherry-CAAX | Ampicillin | pHR |

Construction of the structural model of OptoMB. To build the structural model of the HA4-AsLOV2 chimera (OptoMB) interacting with the SH2 domain (FIG. 21E), a shortened version[45] (residues 408-543) of the AsLOV2 domain (PDB ID: 2V1A)[64] was manually inserted to residues S58 and S59 of the monobody HA4, using the program Coot[65]. The crystal structure of HA4 in complex with the SH2 domain (PDB ID: 3k2m)[46] was used as template. After a manual adjustment, an energy minimization of the HA4-AsLOV2 chimera was carried out with the website version of YASARA'_s energy minimization servers[66].

Plasmid Construction for mammalian cells. Constructs for mammalian cell experiments were cloned using backbone PCR and inFusion (Clontech). Monobody HA4 or OptoMB variants were PCR amplified and Gibson-assembled from bacterial plasmids (described above) into a pHR vector with a C-terminal irFP fusion (Addgene No. 111510). The SH2 domain was amplified from EZ-L664 using PCR, and Gibson-assembled into a pHR vector containing a C-terminal mCherry-CAAX fusion tag (Addgene #50839). Stellar *E. coli* cells (TaKaRa) were transformed with these plasmids for amplification and DNA storage. All plasmids were sequenced by Genewiz to verify quality.

Lentivirus Production and Transduction. HEK 293T cells were plated on a 12-well plate, reaching 40% confluency the next day. The cells were then co-transfected with the corresponding pHR plasmid and lentiviral packaging plasmids (pMD and CMV) using Fugene HD (Promega). Cells were incubated for approximately 48 hours, and virus was collected and filtered through a 0.45-mm filter. In addition, 2 μL of polybrene and 40 μL of HEPES were added to the 2-mL viral solution. For infection, HEK 293T cells were plated on a 6-well plate, and allowed to adhere and reach 40% confluency. At that time, the cells were infected with 200-500 μL of viral solution. For iLID-SSPB translocation experiments, NIH3T3 cells were puromycin-selected after lentiviral transduction with an iLID-SSPB expression plasmid (pHR BFP-SSPB-SOScat-2A-PuroR-2A-iLID-CAAX)

and a clonal cell line was established to limit cell-to-cell variability in expression. All imaging was done at least 48 hours post infection. Cells were cultured in DMEM media with 10% FBS, penicillin (100 U/mL), and streptomycin (0.1 mg/mL).

Screening for light-responsive monobodies. A 6×-histidine tagged fusion of YFP and SH2 ($His_6$ (SEQ ID NO: 49)-YFP-SH2) was grown in 500 mL of autoinduction[67] media+Kanamycin (Kan)(50 µg/mL) for 16 hours at 30° C. Monobody HA4 and monobody-AsLOV2 chimeras were grown in 250 mL of autoinduction media+Kan for 16 hours at 30° C. For each test, monobody HA4 (used as control) and 3 different monobody-AsLOV2 chimeras were tested simultaneously. Cells were then harvested by centrifugation at 7500×g for 20 minutes at 4° C. in a Lynx 4000 centrifuge (Sorvall™), and supernatant was discarded. Cell pellets were resuspended in Binding buffer (Tris 100 mM pH 8.0, NaCl 150 mM, Glycerol 1% and 5 mM imidazole) supplemented with 1 mM of PMSF, adding 8 mL to the cells containing $His_6$ (SEQ ID NO: 49)-YFP-SH2 and 3 mL for the monobody HA4 and each of the chimeras. The resuspended cells were flash-frozen forming droplets directly into liquid nitrogen (LN2) and placed in small (LN2-cold) grinding vials to be disrupted using a CryoMill system (Spex sample Prep®) with a cycle of 2 minutes grinding and 3 minutes cooling (14 times). The broken cell powder was thawed in 50 mL Falcon tubes at room temperature with the addition of 4 mL of Lysis buffer (Binding buffer supplemented with 1 mM PMSF and 2 mg/mL of DNAse) for $His_6$ (SEQ ID NO: 49)-YFP-SH2 and 2 mL of Lysis buffer for monobody HA4 and each of the chimeras. Once thawed, the bacterial lysates were centrifuged at 25,000×g in a Lynx 4000 centrifuge (Sorvall™) for 30 minutes at 4° C. and the supernatant (clarified lysate) was transferred to 15 mL conical tubes. To enhance AsLOV2 activity, flavin mononucleotide (FMN) was added to a final concentration of 0.25 mg/ml, to each of the chimera-containing lysate and then incubated for 15 minutes at 4° C. by vertical rotation in a tube Revolver/Rotator at 50 rpm (Thermo Scientific™). The $His_6$ (SEQ ID NO: 49)-YFP-SH2 supernatant was then mixed with 4.5 mL of a 50% suspension of Co-charged agarose resin (Talon®), previously equilibrated in Binding buffer, and incubated at 4° C., rocking for 45 min. The suspension was sedimented by gravity and the supernatant discarded. The beads were then thoroughly washed with Binding buffer with approximately 50 times the resin or column volume. The beads (now with $His_6$ (SEQ ID NO: 49)-YFP-SH2 bound) were then finally resuspended in Binding buffer to a total volume of 13.5 mL. The bead suspension was equally divided into 9 conical tubes of 15 mL (having each 1.5 mL of the bead suspension). Four of these tubes were used for experiments under blue light with LED panels (450 nm and intensity of 45 µmol/m²/s) while the other four were used for experiments in the dark (wrapped in aluminum foil). Experiments were performed in a dark room and red light was used occasionally for visualization purposes. The remaining tube was left as a control for $His_6$ (SEQ ID NO: 49)-YFP-SH2 binding. Samples of 2.5 mL of bacterial clarified lysates containing either the monobody HA4 supernatant or each one of the chimeras were added to separate tubes of resin. The mixtures were then incubated for 45 minutes (at 4° C. and constant vertical rotation of 20 rpm) under blue light or dark conditions. Tubes were then allowed to settle at 4° C. under the same light conditions in which they were incubated, for 15-20 minutes. After carefully discarding the supernatants, the beads were washed 5 to 6 times; each time with 10 mL of Binding buffer and rotating at 20 rpm for 15 minutes. After each wash, the mixtures were allowed to settle at 4° C. for 15-20 minutes under the same light conditions as they were incubated under, and the supernatants were again discarded. This step was repeated until beads were washed with approximately 40-50 resin-volumes. During the course of the experiments, light conditions within the room were carefully held constant and red light was for visualization purposes used only when needed, specially to minimize any blue light exposure of the dark samples when opening the wrapped tubes to exchange buffer (washing, incubation and elution). After the last wash, proteins were eluted with 2.5 mL of Elution buffer (Tris 100 mM pH 8.0, 150 mM NaCl, 1% Glycerol, 500 mM Imidazole) and then equal volumes of elution samples (dark and light) for each chimera (and control) were loaded onto 12% polyacrylamide gels and resolved with SDS-PAGE. To calculate the difference in binding between light and dark conditions for each chimera, densitometry calculations were performed, and the integrated intensities of the bands corresponding to the chimeras were used, applying the FIJI implementation of ImageJ.

Purification of Monobody HA4, OptoMB (and all its Variants), and YFP-SH2. HA4, monobody-AsLOV2 chimeras (OptoMB and variants), and YFP-SH2 constructs were purified using N-terminal 6×-histidine (SEQ ID NO: 49) tag fusions and metal affinity chromatography. Chimeras were protected from excessive ambient light exposure to prevent potential protein destabilization and improve yields. This included covering the shakers with black blankets during expression, wrapping culture flasks and tubes (containing crude or purified proteins) with thick aluminum foil and performing the chromatography in the dark or with red light (when needed). OptoMB (and all its variants) were expressed at 18° C. for three days in 1 L or 2 L of Autoinduction media[67] (plus Kan 50 µg/mL). HA4 and YFP-SH2 were expressed in 1 L or 2 L of Autoinduction media (plus Kan 50 µg/mL) for 16 h at 30° C. Cells were then harvested by centrifugation at 7500×g for 20 minutes at 4° C. in a Lynx 6000 centrifuge (Sorvall™) and supernatant was discarded. Each cell pellet was resuspended in between 8 to 12 mL of Binding buffer and frozen droplets were prepared as described above and immediately transferred to a large (LN2-cold) grinding tube. Cryogenic grinding was performed as described above. Broken cells (frozen powder) were thawed in 50 mL Falcon tubes at room temperature with the addition of Lysis buffer up to 5% of the initial cell culture volume. After clarifying the bacterial lysates by centrifugation as described above, these were loaded onto columns of 2 to 5 mL (50% suspension) of Co-charged resin (Talon®) previously equilibrated with Binding buffer (Tris 100 mM pH 8.0, NaCl 150 mM, Glycerol 1% and 5 mM Imidazole). Columns were washed with 40-50 column volumes of Binding buffer and proteins eluted with Elution buffer (Binding buffer supplemented with 250 mM of imidazole). Proteins were then run through size exclusion chromatography (SEC) using a Hiprep™ HR 16/60 Sephacryl™ 200 with Buffer A (Tris 50 mM pH 8.0 and NaCl 150 mM), in an FPLC (AKTA pure from GE® Healthcare). The aliquots enriched with the target proteins were concentrated by centrifugation (in cycles of 10 min) at maximum speed in a Sorvall Legend XTR Benchtop centrifuge (Thermo Scientific™) using 15 mL Centricons® (Millipore) with a cutoff selected according to the molecular size of each protein, until concentrations between 3 to 8 mg/mL were reached.

Size-exclusion chromatography to characterize OptoMB-5112 interaction in solution. Purified monobody HA4 (75 µL from a 202 sample) or OptoMB (wt AsLOV2) (300 µL from a 40.7 µM sample) dissolved in Buffer A, were mixed with YFP-SH2 (200 µL from a 58.8 µM sample in Buffer A) in approximately 1.2:1 molar ratio of binder to target. Each mixture was incubated for 10 minutes in either dark or blue light (450 nm) before loading the full volume (275 or 500 µl) onto a Superdex™ 200 16/300 column (GE® Healthcare), which was then run at 1 mL/min with Buffer A at 4° C. (using an AKTA pure from GE® Healthcare). To test different light conditions, the column was either illuminated with wrapped blue LED strips (450 nm) or covered with aluminum foil for the total duration of the filtration (Supplementary FIG. 2c). For experiments in the dark, light sources in the room were also minimized, and the chromatography cabinet was covered with a black blanket. The SEC was monitored by UV absorbance at 280 nm.

Intracellular imaging of HEK293T cells. For live cell imaging, 0.17-mm, glass-bottomed, black-walled, 96-well plates (In Vitro Scientific) were used. Glass was first treated with 10 µg/mL of fibronectin in PBS for 20 minutes. HEK293T cells expressing both SH2-mCherry-CAAX and either the monobody HA4 or OptoMB were then plated and allowed to adhere onto the plate before imaging. Mineral oil (50 µL) was added on top of each well with cells prior to imaging, to limit media evaporation. The mammalian cells were kept at 37° C. with 5% $CO_2$ for the duration of the imaging experiments. The irFP and mCherry fluorescence were imaged using a Nikon Eclipse Ti microscope with a Prior linear motorized stage, a Yokogawa CSU-X1 spinning disk, an Agilent laser line module containing 405, 488, 561 and 650 nm lasers, an iXon DU897 EMCCD camera, and a 40× oil immersion objective lens. An LED light source was used for photoexcitation with blue light (450 nm), which was delivered through a Polygon400 digital micro-mirror device (DMD; Mightex Systems). For all LED illumination experiments, the LED power was adjusted to a final value of ~1 mW/cm² at the sample plane, as measured by a MQ-510 Quantum light meter with separate sensor (Apogee Instruments) using an equivalent blue LED light source placed above the sample.

Imaging of coated Agarose Beads. Approximately 200 µL of Ni-NTA agarose slurry (50% suspension) (Qiagen) equilibrated in Buffer A were mixed with 500 µL of 100 µM of either monobody HA4 or OptoMB (AsLOV2 V416L variant) in an Eppendorf tube (covered with aluminum foil), and incubated by vertical rotation (at 20 rpm for 20 minutes) at room temperature to allow binding through the 6×-histidine (SEQ ID NO: 49) tag until saturation. The excess protein was then washed twice with 1 mL of Buffer A, centrifuging the beads at low speed for 1 minute (1000 rpm in a benchtop centrifuge) each time; finally discarding the excess of supernatant after the second wash. Then, 50 µL of a purified YFP-SH2 solution at 2 µM (with the 6×-histidine (SEQ ID NO: 49) tag cleaved off) was added onto 0.17-mm, glass-bottomed, black-walled, 96-well plate (In Vitro Scientific) followed by 2 µL of the washed resin with the beads labeled with OptoMonobody (or monobody HA4 as control). The mixture was equilibrated for at least 1 hour at room temperature and up to overnight at 4° C. prior to imaging, performed at room temperature. The same microscope setup as described for the cells imaging was used, except for the objective (20× in this case), to follow YFP fluorescence over time on the surface of the bead. For the spatial control of the OptoMB-SH2 interaction on beads the same setup was used. Two beads in an area of around 200×250 µm were imaged at the same time applying a light (450 nm) mask, which uses a square ROI with dimension of 120×120 µm to cover and illuminate only one bead. The YFP fluorescence was recorded over time (for a total of 1 h) for both, the illuminated and the unilluminated bead. Quantification was performed by measuring the change in YFP fluorescence intensity over time in a defined region on the surface of the bead (using ImageJ[68]) and subtracting the background.

Calculation of binding kinetics by Bio-layer interferometry. Measurements of the binding ($k_{on}$) and unbinding ($k_{off}$) rate constants, as well as the dissociation (or affinity) constant ($K_d$) for HA4 monobody and OptoMB (including variants V416L and V416I-G528A-N538E) were performed on Octet RED96e instruments (ForteBio). Ni-NTA sensors (ForteBio) were first equilibrated using Buffer A for 10 minutes prior the measurement. A volume of 200 µL of Buffer A or protein solutions (previously dialyzed with Buffer A when needed) was added to clear, 96-well plates. During the experimental run, the Ni-NTA sensors were first immersed in Buffer A to record the baseline. Protein binders were then loaded by switching to wells with solutions of 6×-histidine (SEQ ID NO: 49) tagged HA4 monobody or OptoMB variants (with concentrations between 100 µg/mL and up to 1 mg/mL) until values of approximately 4 nm were reached (avoiding saturation of the sensors). The sensors were then transferred back into Buffer A to remove unbound protein. To measure the binding rate constant ($k_{on}$) the sensors with bound monobody HA4 or OptoMB variants were subsequently shifted to wells containing various concentrations of YFP-SH2 (at concentrations indicated in FIGS. 22D-22E and FIGS. 25E-25F). To measure the unbinding rate constant ($k_{off}$), the sensors were then moved to wells containing Buffer A to trigger dissociation of YFP-SH2. To measure binding kinetics of the light state, the lid of the Octet remained open during the measurement and a blue LED panel was held above the 96-well plate, maintaining constant blue illumination for the duration of the experiment. For the OptoMB variant with the AsLOV2 mutations V416I-G528A-N538E, lit states were sufficiently long-lived to remain fully activated in response to pre-illumination with a blue light panel and the continuous illumination of the Octet sensors. The raw binding and unbinding data were simultaneously fit to models of the binding and unbinding reactions:

$$y_{bind}^{i}(t)=[a_{on}^{i}(1-e^{-(k_{on}[SH2]_i+k_{off})t})+b_{on}^{i}]e^{-k_{leak}t}$$

$$y_{unbind}^{i}(t)=[a_{off}^{i}e^{-k_{off}t}+b_{off}^{i}]e^{-k_{leak}t}$$

This model incorporates the following dependent and independent variables:
$y_{bind}^{i}(t)$ refers to the $i^{th}$ binding curve
$y_{unbind}^{i}(t)$ the $i^{th}$ unbinding curve
$[SH2]_i$ refers to the concentration of YFP-SH2 used for the $i^{th}$ binding curve
t is the time elapsed since the start of the binding/unbinding phase.
It also includes the following parameters:
$k_{on}$ is the on-rate (enforced to be identical across all binding and unbinding curves)
$k_{off}$ is the off-rate (enforced to be identical across all binding and unbinding curves)
$k_{leak}$ represents the slow unbinding of His-tagged OptoMB from the probe, leading to a gradual decay of signal throughout the entire experiment.
$a_{on}^{i}$ is the total change in signal due to SH2 binding for the $i^{th}$ curve
$b_{on}^{i}$ is the signal baseline during the binding phase for the $i^{th}$ curve $a_{off}^i$ is the total change in signal due to SH2 unbinding for the $i^{th}$ curve $b_{off}^i$ is the signal baseline during the unbinding phase for the $i^{th}$ curve The model thus contains 4*n+3 parameters, where n is the number of distinct SH2 concentrations tested. Fits were performed using nonlinear gradient descent using the MATLAB fmincon function. Code is available as described in Ref 45.

Light-controlled affinity chromatography (LCAC) of SH2-tagged proteins using cobalt-immobilized OptoMB. To prepare OptoMB resin and columns, the purified variant OptoMB$_{V416L\_G528A\_N538E}$ (having a SUMO tag in the N-term to boost expression, Supplementary Table 4) was incubated with Co-charged resin (Talon®) (50% suspension) previously equilibrated in Buffer A, in order to produce 2.5 mL of resin with approximately 8 mg of OptoMB bound per mL. The Resin was rotated in 50 mL conical tubes (covered with aluminum foil) at room temperature for 20 minutes and then poured in 20 mL BioRad glass Econo-Columns and washed with Buffer A (50 column volumes). The use of imidazole in the Buffer A was avoided because it interferes with the photocycle of the AsLOV2 domain, enhancing the rate of recovery of the dark state thus reducing the lifetime of the lit state[69], which would reduce the efficiency of light elution. Production of the OptoMB resin (and columns) and the LCAC procedure were carried out at room temperature within a carefully controlled dark room to avoid blue light contamination, using red light from LED panels occasionally for visualization purposes. Approximately 10 to 12 mL of clarified bacterial lysates (obtained as described before from 1 L cultures) containing YFP-SH2 or SH2-PDC1 (without his-tags) were incubated with 2.5 mL of OptoMB resin in Buffer A, which was enough to saturate the OptoMB resin with binding targets. The mixture was then vertically rotated gently for 45 minutes in 15 ml conical tubes. The OptoMB resin was then poured into 10 mL BioRad glass Econo-Columns or left to settle to discard the supernatant by pipetting (experiments in batch). Approximately 80 column volumes of Buffer A were used to wash the OptoMB resin. When purifying in batch, 40 mL of Buffer A were added to the resin at a time in 50 mL conical tubes; after rotating for 5 minutes, the resin was left to settle to remove the supernatant by pipetting. This cycle was repeated until reaching 80 resin volumes. After washing, the resin was poured back into a 15-mL, conical tube. When purifying in batch, for each light-elution step we added 2-times the resin volume of Buffer A and incubated with gentle rocking in front of a blue light (450 nm) LED panel (approximately 20 cm away) for 10 to 15 minutes; then letting the resin settle while illuminated and recovering the light-eluted aliquot by pipetting. When purifying in columns, 2 column bed volumes of Buffer A were poured at a time while the column was exposed to blue light from three LED panels in a triangular conformation (surrounding the column), and collected by gravity. For both batch and column purifications, the elution steps were repeated until no more protein eluted from the resin (usually 4 to 5 times). In both methods, batch or column, after light-elution 4 times the resin volume of Buffer A containing 250 mM of imidazole was added to elute the proteins still bound to the resin after light-elution, needed to calculate yields and resin capacity. Samples from the different purification steps were resolved with SDS-PAGE, using 12% SDS-polyacrylamide gels.

Light-controlled affinity chromatography (LCAC) of SH2-tagged proteins using covalently coupled OptoMB. A total of 1-1.5 g (dry weight) of CNBr-activated Sepharose™ 4B (GE® Healthcare) was resuspended in Conjugation buffer (NaCHO$_3$ 0.1 M pH 8.3 and 500 mM NaCl) according to the manufacturer's specifications. The excess of Conjugation buffer was discarded and the hydrated resin mixed with purified OptoMB$_{V416L\_G528A\_N538E}$ (containing an N-terminal SUMO tag to boost expression, Supplementary Table 4), previously dialyzed against Conjugation buffer by centrifugation (using 15 mL Centricons® as describe above). For each preparation, 5 mL (50% suspension) of resin was conjugated with OptoMB at approximately 8 mg of OptoMB per mL of resin. The manufacturer's protocol was followed with minor modifications, keeping all protein immobilization steps (conjugation, blockage and acid/base washing cycles) in the dark by covering the tubes with thick aluminum foil. The acid/base washing cycles were reduced to one cycle, as the three washes recommended by the manufacturer results in loss of the FMN, the AsLOV2 co-factor (as evidenced by the loss of the protein's yellow coloration immediately after the second wash). Once OptoMB was conjugated, the resin was washed and equilibrated with Buffer AS (Buffer A with salt concentration increased to 300 mM NaCl). The OptoMB-conjugated resins were used immediately or stored at 4° C. (protected from light with foil), where they are stable for up to at least a week (yielding same results as fresh resin). To purify YFP-SH2 or SH2-PDC1, approximately 10 to 15 mL of the clarified bacterial lysates obtained from 1 L cultures (as described above) were incubated in batch with 5 mL (50% suspension) of the OptoMB-conjugated sepharose resin, which was enough to saturate the OptoMB resin with binding targets. The same protocol for LCAC purification with OptoMB-immobilized in Co-charged (Talon®) in batch described above was followed with CNBr-OptoMB resin, except Buffer AS was used instead of Buffer A. To calculate the yields and resin capacity, after the final light-elution step, 200 µl of the 50% resin suspension were resuspended in 100 µl of SDS-PAGE sample-loading buffer and incubated at 100° C. for 10 minutes in a heat block, before loading onto the gel. Samples from all purification steps were resolved on a 12% SDS-polyacrylamide gels.

Calculations of Protein Purity, Yield and Resin capacity. Protein purity was estimated using densitometric analysis in the FIJI implementation of ImageJ[68]. The software analyzes individual bands from a scanned gel, returning the integrated intensity of each band. For each aliquot of purified protein (eluted with light), the band representing the SH2-tagged protein was selected, and its integrated intensity was used to calculate the fraction of the purified target versus the overall total of protein present in that fraction.

The overall yield (y) represents the total amount (mg) of purified protein that eluted with light (TPE) as a percentage of the total amount (mg) of protein that was initially bound to the resin (TPB). TPE was calculated by multiplying the concentration (mg/mL) of all the light-eluted fractions ([TPE]) by their total volume (mL) (TPEvol). The concentrations of the fractions eluted with light were calculated using Absorbance at 280 nm with a spectrometer (Biospectrometer, Eppendorf). TPB was equal to TPE plus the total residual SH2-tagged protein remaining on the column after light-elution (TPR). To calculate the TPR, we recovered all residual protein using imidazole elution (of Co-Agarose-OptoMB) or heat treatment (of CNBr-OptoMB) of the beads after light-elution. Concentrations of recovered residual protein were calculated by running each sample on a 12% polyacrylamide gel alongside standards of the same SH2-tagged protein of known concentrations. Band intensities were then computed by densitometry analysis in FIJI as above. The amount of target protein still bound to the column was thus equal to the concentration retrieved in this final elution [TRP] multiplied by its total elution volume TRPvol. Finally, the resin capacity $C_R$ was calculated as TPB divided by the total volume of the resin used $V_R$.

$$y = TPE \times \frac{100}{TPB}$$

$$TPE = [TPE] \times TPEvol$$

$$TPB = \{[TRP] \times TRPvol\} + TPE$$

$$C_R = \frac{TPB}{V_R}$$

Where
y is the yield of purified protein obtained with the resin
TPE is the total amount of protein eluted with light
[TPE] is the concentration of all the fractions that eluted with light
TPEvol is the total volume of the light-elution fraction
TPB is the total amount of protein initially bound to the resin
[TRP] is the concentration of the total residual protein fraction that was still bound to the resin after the elution with light
TRPvol is the total volume of the fraction containing the total residual protein that was still bound to the resin after the elution with light, and was recovered by imidazole or heat treatment of the beads.
$C_R$ is the protein binding capacity of the resin
$V_R$ is the volume of resin used in the experiment

REFERENCES

1. Skerra, A. Alternative binding proteins: Anticalins—Harnessing the structural plasticity of the lipocalin ligand pocket to engineer novel binding activities. *FEBS J.* 275, 2677-2683 (2008).
2. Škrlec, K., Štrukelj, B. & Berlec, A. Non-immunoglobulin scaffolds: A focus on their targets. *Trends in Biotechnology* 33, 408-418 (2015).
3. Yu, X., Yang, Y.-P., Dikici, E., Deo, S. K. & Daunert, S. Beyond Antibodies as Binding Partners: The Role of Antibody Mimetics in Bioanalysis. *Annu. Rev. Anal. Chem.* 10, 293-320 (2017).
4. Frejd, F. Y. & Kim, K. T. Affibody molecules as engineered protein drugs. *Exp. Mol. Med.* 49, e306-8 (2017).
5. Plückthun, A. Designed Ankyrin Repeat Proteins (DARPins): Binding Proteins for Research, Diagnostics, and Therapy. *Annu. Rev. Pharmacol. Toxicol.* 55, 489-511 (2015).
6. Sha, F., Salzman, G., Gupta, A. & Koide, S. Monobodies and other synthetic binding proteins for expanding protein science. *Protein Science* 26, 910-924 (2017).
7 Ingram, J. R., Schmidt, F. I. & Ploegh, H. L. Exploiting Nanobodies' Singular Traits. *Annu. Rev. Immunol.* 36, (2018).
8. Sormanni, P., Aprile, F. A. & Vendruscolo, M. Third generation antibody discovery methods: In silico rational design. *Chemical Society Reviews* 47, 9137-9157 (2018).
9. Helma, J., Cardoso, M. C., Muyldermans, S. & Leonhardt, H. Nanobodies and recombinant binders in cell biology. *J. Cell Biol.* 209, 633-644 (2015).
10. Sullivan, M. A., Wentworth, T., Kobie, J. J. & Sanz, I. Anti-idiotypic monobodies for immune response profiling. *Methods* 58, 62-68 (2012).
11. Hu, Y., Liu, C. & Muyldermans, S. Nanobody-based delivery systems for diagnosis and targeted tumor therapy. *Front. Immunol.* 8, (2017).
12. Bannas, P., Hambach, J. & Koch-Nolte, F. Nanobodies and nanobody-based human heavy chain antibodies as antitumor therapeutics. *Front. Immunol.* 8, 1-13 (2017).
13. Vazquez-Lombardi, R. et al. Challenges and opportunities for non-antibody scaffold drugs. *Drug Discov. Today* 20, 1271-1283 (2015).
14. Bielser, J. M., Wolf, M., Souquet, J., Broly, H. & Morbidelli, M. Perfusion mammalian cell culture for recombinant protein manufacturing—A critical review. *Biotechnology Advances* 36, 1328-1340 (2018).
15. Tripathi, N. K. Production and Purification of Recombinant Proteins from *Escherichia coli*. *ChemBioEng Rev.* 3, 116-133 (2016).
16. Gronemeyer, P., Ditz, R. & Strube, J. Trends in Upstream and Downstream Process Development for Antibody Manufacturing. *Bioengineering* 1, 188-212 (2014).
17. Richards, D. A. Exploring alternative antibody scaffolds: Antibody fragments and antibody mimics for targeted drug delivery. *Drug Discov. Today Technol.* 30, 35-46 (2018).
18. Nishikido, T. & Ray, K. K. Non-antibody Approaches to Proprotein Convertase Subtilisin Kexin 9 Inhibition: siRNA, Antisense Oligonucleotides, Adnectins, Vaccination, and New Attempts at Small-Molecule Inhibitors Based on New Discoveries. *Front. Cardiovasc. Med.* 5, (2019).
19. Activity, A. et al. crossm Discovery and Characterization of a Novel CD4-Binding Adnectin with Potent. 1-19 (2017).
20. Rodrigo, G., Gruvegård, M. & Van Alstine, J. Antibody Fragments and Their Purification by Protein L Affinity Chromatography. *Antibodies* 4, 259-277 (2015).
21. Jin, J. et al. Accelerating the clinical development of protein-based vaccines for malaria by efficient purification using a four amino acid C-terminal 'C-tag'. *Int. I Parasitol.* 47, 435-446 (2017).
22. Pabst, T. M. et al. Camelid VHH affinity ligands enable separation of closely related biopharmaceuticals. *Biotechnol. J.* 12, 1-10 (2017).
23. Götzke, H. et al. A rationally designed and highly versatile epitope tag for nanobody-based purification, detection and manipulation of proteins. *bioRxiv* 640771 (2019). doi:10.1101/640771
24. Zhao, W., Pferdehirt, L. & Segatori, L. Quantitatively Predictable Control of Cellular Protein Levels through Proteasomal Degradation. *ACS Synth. Biol.* 7, 540-552 (2018).
25. Ponnambalam, S. et al. Affimer proteins are versatile and renewable affinity reagents. *Elife* 6, 1-35 (2017).
26. Zorba, A. et al. Allosteric modulation of a human protein kinase with monobodies. *Proc. Natl. Acad. Sci. U.S.A* 116, 13937-13942 (2019).
27. Spencer-Smith, R. et al. Inhibition of RAS function through targeting an allosteric regulatory site. *Nat. Chem. Biol.* 13, 62-68 (2017).
28. Hamers-Casterman, C. et al. Naturally occurring antibodies devoid of light chains. *Nature* 363, 446-448 (1993).
29. Holliger, P. & Hudson, P. J. Engineered antibody fragments and the rise of single domains. *Nat. Biotechnol.* 23, 1126-1136 (2005).
30. Koide, A., Bailey, C. W., Huang, X. & Koide, S. The fibronectin type III domain as a scaffold for novel binding proteins. *J. Mol. Biol.* 284, 1141-1151 (1998).

31. Koide, A., Wojcik, J., Gilbreth, R. N., Hoey, R. J. & Koide, S. Teaching an old scaffold new tricks: Monobodies constructed using alternative surfaces of the FN3 scaffold. *J. Mol. Biol.* 415, 393-405 (2012).
32. Tolcher, A. W. et al. Phase I and pharmacokinetic study of CT-322 (BMS-844203), a targeted adnectin inhibitor of VEGFR-2 based on a domain of human fibronectin. *Clin. Cancer Res.* 17, 363-371 (2011).
33. Gupta, A. et al. Facile target validation in an animal model with intracellularly expressed monobodies. *Nat. Chem. Biol.* 14, 895-900 (2018).
34. Schmit, N. E., Neopane, K. & Hantschel, O. Targeted Protein Degradation through Cytosolic Delivery of Monobody Binders Using Bacterial Toxins. *ACS Chem. Biol.* 14, 916-924 (2019).
35. Harper, S. M., Neil, L. C. & Gardner, K. H. Structural Basis of a Phototropin i111111. 301, 1541-1545 (2003).
36. Zayner, J. P., Antoniou, C. & Sosnick, T. R. The amino-terminal helix modulates light-activated conformational changes in AsLOV2. *J. Mol. Biol.* 419, 61-74 (2012).
37. Peter, E., Dick, B. & Baeurle, S. A. Mechanism of signal transduction of the LOV2-Ja photosensor from *Avena sativa*. *Nat. Commun.* 1, 122-127 (2010).
38. Crosson, S. & Moffat, K. Structure of a flavin-binding plant photoreceptor domain: Insights into light-mediated signal transduction. *Proc. Natl. Acad. Sci. U.S.A* 98, 2995-3000 (2001).
39. Konold, P. E. et al. Unfolding of the C-Terminal Jα Helix in the LOV2 Photoreceptor Domain Observed by Time-Resolved Vibrational Spectroscopy. *J. Phys. Chem. Lett.* 7, 3472-3476 (2016).
40. Harper, S. M., Christie, J. M. & Gardner, K. H. Disruption of the LOV-Jα helix interaction activates phototropin kinase activity. *Biochemistry* 43, 16184-16192 (2004).
41. Dagliyan, O. et al. Engineering extrinsic disorder to control protein activity in living cells. *Science* (80–.). 354, 1441-1444 (2016).
42. Richter, F. et al. Engineering of temperature- and light-switchable Cas9 variants. *Nucleic Acids Res.* 44, 10003-10014 (2016).
43. Bubeck, F. et al. Engineered anti-CRISPR proteins for optogenetic control of CRISPR-Cas9. *Nat. Methods* 15, 924-927 (2018).
44. Hörner, M. et al. Light-controlled affinity purification of protein complexes exemplified by the resting ZAP70 interactome. *Front. Immunol.* 10, 1-12 (2019).
45. Gil, A. A. et al. Optogenetic control of protein binding using light-switchable nanobodies. 9881, (2019).
46. Wojcik, J. et al. A potent and highly specific FN3 monobody inhibitor of the Abl SH2 domain. *Nat. Struct. Mol. Biol.* 17, 519-527 (2010).
47. Filippakopoulos, P., Müller, S. & Knapp, S. SH2 domains: modulators of nonreceptor tyrosine kinase activity. *Current Opinion in Structural Biology* 19, 643-649 (2009).
48. Marengere, L. E. M. & Pawson, T. Structure and function of SH2 domains. *J. Cell Sci.* 1994, 97-104 (2013).
49. Morlacchi, P., Robertson, F. M., Klostergaard, J. & McMurray, J. S. Targeting SH2 domains in breast cancer. *Future Med. Chem.* 6, 1909-1926 (2014).
50. Kawano, F., Aono, Y., Suzuki, H. & Sato, M. Fluorescence imaging-based high-throughput screening of fast- and slow-cycling LOV proteins. *PLoS One* 8, (2013).
51. Gil, A. A. et al. Femtosecond to Millisecond Dynamics of Light Induced Allostery in the *Avena sativa* LOV Domain. *J. Phys. Chem. B* 121, 1010-1019 (2017).
52. Zoltowski, B. D., Vaccaro, B. & Crane, B. R. Mechanism-based tuning of a LOV domain photoreceptor. *Nat. Chem. Biol.* 5, 827-834 (2009).
53. Strickland, D. et al. Rationally improving LOV domain-based photoswitches. *Nat. Methods* 7, 623-626 (2010).
54. Song, S. H. et al. Modulating LOV domain photodynamics with a residue alteration outside the chromophore binding site. *Biochemistry* 50, 2411-2423 (2011).
55. Lu, G., Dobritzsch, D., Baumann, S., Schneider, G. & König, S. The structural basis of substrate activation in yeast pyruvate decarboxylase. A crystallographic and kinetic study. *Eur. J. Biochem.* 267, 861-868 (2000).
56. Levskaya, A., Weiner, O. D., Lim, W. A. & Voigt, C. A. Spatiotemporal control of cell signalling using a light-switchable protein interaction. *Nature* 461, 997-1001 (2009).
57. Kennedy, M. J. et al. Rapid blue-light-mediated induction of protein interactions in living cells. *Nat. Methods* 7, 973-975 (2010).
58. Yazawa, M., Sadaghiani, A. M., Hsueh, B. & Dolmetsch, R. E. Induction of protein-protein interactions in live cells using light. *Nat. Biotechnol.* 27, 941-945 (2009).
59. Yao, X., Rosen, M. K. & Gardner, K. H. Estimation of the available free energy in a LOV2-Jα photoswitch. *Nat. Chem. Biol.* 4, 491-497 (2008).
60. Salinas, F., Rojas, V., Delgado, V., Agosin, E. & Larrondo, L. F. Optogenetic switches for light-controlled gene expression in yeast. *Appl. Microbiol. Biotechnol.* (2017). doi:10.1007/s00253-017-8178-8
61. Zhao, E. M. et al. Optogenetic regulation of engineered cellular metabolism for microbial chemical production. *Nature* 555, 683-687 (2018).
62. Yumerefendi, H. et al. Control of Protein Activity and Cell Fate Specification via Light-Mediated Nuclear Translocation. *PLoS One* 10, e0128443 (2015).
63. Goulas, T. et al. The pCri system: A vector collection for recombinant protein expression and purification. *PLoS One* 9, (2014).
64. Halavaty, A. S. & Moffat, K. N- and C-terminal flanking regions modulate light-induced signal transduction in the LOV2 domain of the blue light sensor phototropin 1 from *Avena sativa*. *Biochemistry* 46, 14001-14009 (2007).
65. Emsley, P., Lohkamp, B., Scott, W. G. & Cowtan, K. Features and development of Coot. *Acta Crystallogr. Sect. D Biol. Crystallogr.* 66, 486-501 (2010).
66. Krieger, E. et al. Improving physical realism, stereochemistry, and side-chain accuracy in homology modeling: Four approaches that performed well in CASP8. *Proteins Struct. Funct. Bioinforma.* 77, 114-122 (2009).
67. Studier, F. W. Protein production by auto-induction in high density shaking cultures. *Protein Expr. Purif.* 41, 207-34 (2005).
68. Schindelin, J. et al. Fiji: An open-source platform for biological-image analysis. *Nat. Methods* 9, 676-682 (2012).
69. Alexandre, M. T. A., Arents, J. C., Van Grondelle, R., Hellingwerf, K. J. & Kennis, J. T. M. A base-catalyzed mechanism for dark state recovery in the *Avena sativa* phototropin-1 LOV2 domain. *Biochemistry* 46, 3129-3137 (2007).

Optogenetic Control of Protein Binding Using Light-Switchable Nanobodies

The following experiments are also described in Gil, A. A., et al., "Optogenetic control of protein binding using light-switchable nanobodies," bioRxiv (2019), 739201. The entire contents of Gil, A. A., et al. and its supplementary materials are incorporated herein by reference.

Abstract. A growing number of optogenetic tools have been developed to control binding between two engineered protein domains. In contrast, relatively few tools confer light-switchable binding to a generic target protein of interest. Such a capability would offer substantial advantages, enabling photoswitchable binding to endogenous target proteins in vivo or light-based protein purification in vitro. Here is reported the development of opto-nanobodies (OptoNBs), a versatile class of chimeric photoswitchable proteins whose binding to proteins of interest can be enhanced or inhibited upon blue light illumination. It was found that OptoNBs are suitable for a range of applications: modulating intracellular protein localization and signaling pathway activity and controlling target protein binding to surfaces and in protein separation columns. This work represents a first step towards programmable photoswitchable regulation of untagged, endogenous target proteins.

Highlights
1. Opto-Nanobodies (OptoNBs) enable light-regulated binding to a wide range of protein targets.
2. Identification of an optimized LOV domain and two loop insertion sites for light-regulated binding.
3. OptoNBs function in vivo: when expressed in cells and fused to signaling domains, OptoNBs enable light-activated and light-inhibited Ras/Erk signaling.
4. OptoNBs function in vitro: Target proteins can be reversibly bound to OptoNB-coated beads and separated through size-exclusion chromatography.

Introduction. Nearly 20 years after the initial development of light-regulated transcription in yeast[1] and light-gated ion channels in neuroscience[2], optogenetics has been extended to almost every corner of cell biology. Optogenetic proteins are now available to control the fundamental currencies of protein heterodimerization[3-5], homo-dimerization[6,7], gene expression[1,8,9], degradation[10], nuclear-cytosolic translocation[11-14], and even liquid-liquid protein phase separation[15,16]. These techniques have enabled a new generation of precise perturbation studies to interrogate how the timing, spatial location, and identity of active proteins alter cellular and developmental processes.

Yet despite this growing suite of optogenetic tools, some applications have remained elusive. Light-gated protein-protein interactions are typically induced between a light-sensitive protein and a target peptide that is derived from the original plant or cyanobacterial host (e.g., dimerization between PhyB/PIF6 or Cry2/CIB)[3,5,6], or an engineered, synthetic protein-protein interaction (e.g., binding of an engineered AsLOV2 variant to a PDZ or SSPB peptide or between Dronpa monomers)[4,7,17]. In contrast, achieving light-switchable binding to an arbitrary target protein of interest has remained elusive. The ability to reversibly bind and release a protein of interest in response to light would hold considerable promise for reversibly regulating endogenous signaling activity in vivo, developing biologics that can be precisely targeted in space and time, and enabling protein purification without affinity tags.

Presented here are opto-nanobodies (OptoNBs): a class of engineered proteins capable of reversible, light-controlled binding against multiple protein targets. Nanobodies, small binding proteins formed from the single variable domain of camelid antibodies, provide a versatile scaffold for obtaining binding to a broad range of target epitopes and are functional in both intracellular and extracellular environments[18]. The approach for obtaining photoswitchable nanobodies involved inserting a photoswitchable light-oxygen-voltage (LOV) domain into solvent-exposed loops on proteins of interest[19]. Loop insertion sites and LOV domain variants were identified that triggered a light-inducible change in binding in three nanobodies against two model target proteins, EGFP and mCherry. It was further demonstrated that nanobody binding can be applied in vivo and in vitro, in applications ranging from control over mammalian Ras/Erk signaling to photoswitchable binding on agarose beads and in size exclusion columns. The OptoNB platform opens the door to developing light-switchable binders against a broad range of protein targets and may thus represent a first step toward a new class of photoswitchable biologics.

Figure 28A:
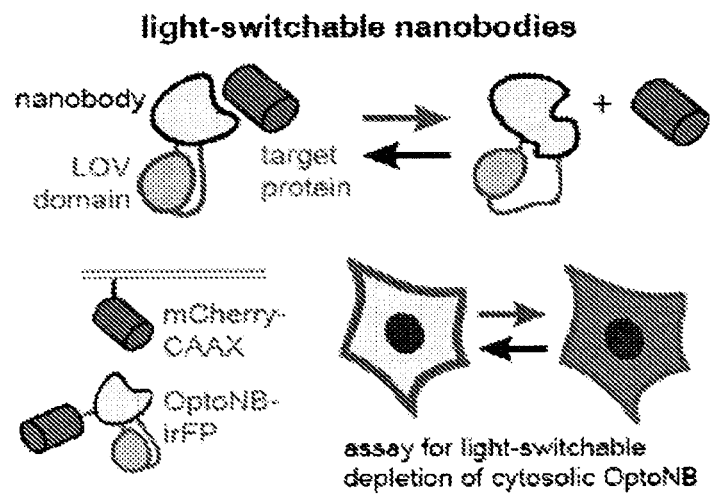
FIGS. 28A-28E show an initial screen for light-controllable nanobodies (OptoNBs).
Figure 28B:
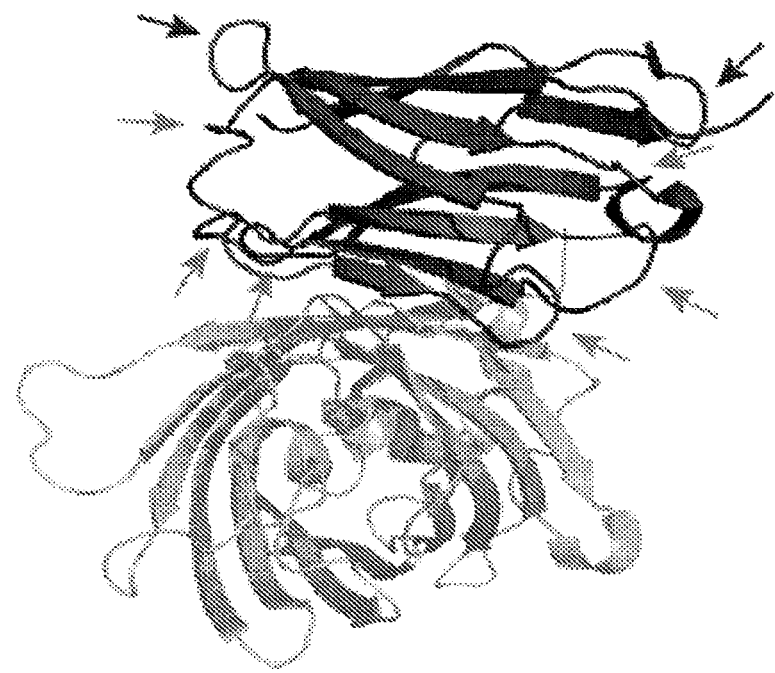

Results: Initial optoNBs exhibit weak light-switchable binding as well as nuclear export. The strategy to engineer light-controlled nanobodies is based on ligand- or light-gated 'hairpins': small domains that can be inserted in-frame into a solvent-exposed loop, whose conformation changes upon illumination or addition of a small molecule[19,20]. It was reasoned that by inserting a light-oxygen-voltage sensing domain from *Avena sativa* Phototropin 1 (AsLOV2) into the solvent-exposed loop of a nanobody, it may be possible to allosterically alter the conformation of its binding surface, disrupting recognition of a target protein (FIG. 28A). As a starting point, the focus was on regulating binding between a model target protein, mCherry, and the LaM8 anti-mCherry nanobody[21]. A broad approach to identify potential AsLOV2 insertion sites was taken, testing all eight conserved, solvent-exposed loops in the nanobody structure excluding the hypervariable complementarity determining regions (CDRs) (FIG. 28B, arrows).

Figure 28C:
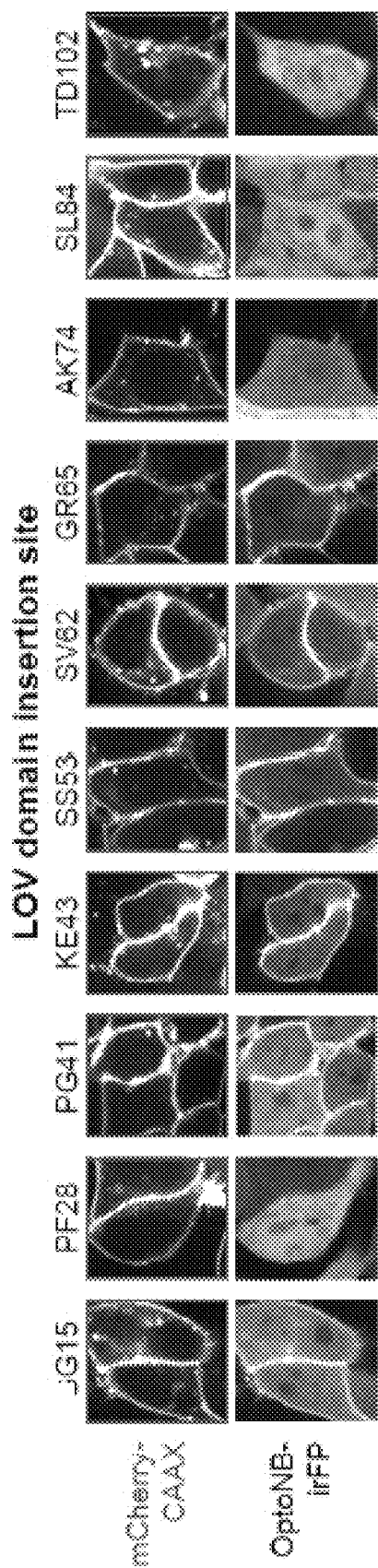

A cell-based assay for evaluating whether candidate opto-nanobodies exhibited light-switchable binding was first established. Prior work has shown that monitoring cytosol-to-membrane translocation is a fast and sensitive method to characterize light-switchable binding (FIG. 28A), revealing changes in protein localization for a diverse set of heterodimerization pairs and affinities[3,5,17]. A set of HEK293 cell lines expressing a membrane-tagged mCherry target protein (mCherry-CAAX) and one of 10 candidate OptoNBs that were each fused on their C-terminus to an infrared fluorescent protein (OptoNB-irFP) were first generated (FIG. 28A, lower panel, and FIG. 28C). Each cell line was then imaged to determine the OptoNB's subcellular localization in the presence or absence of 450 nm blue light.

Figure 28D:
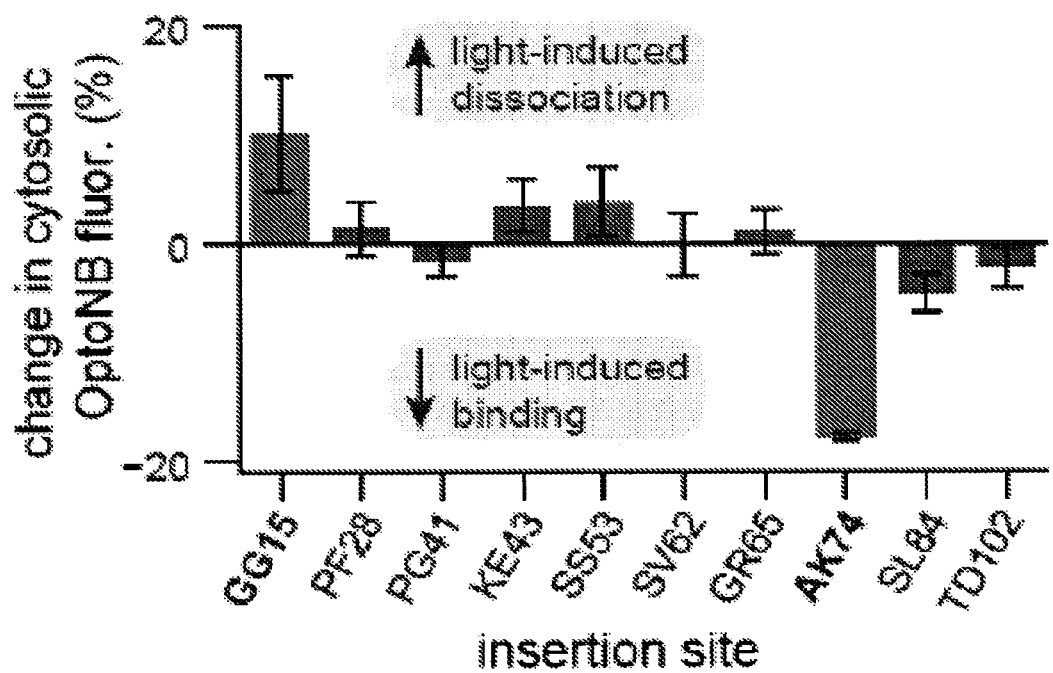
Figure 28E:
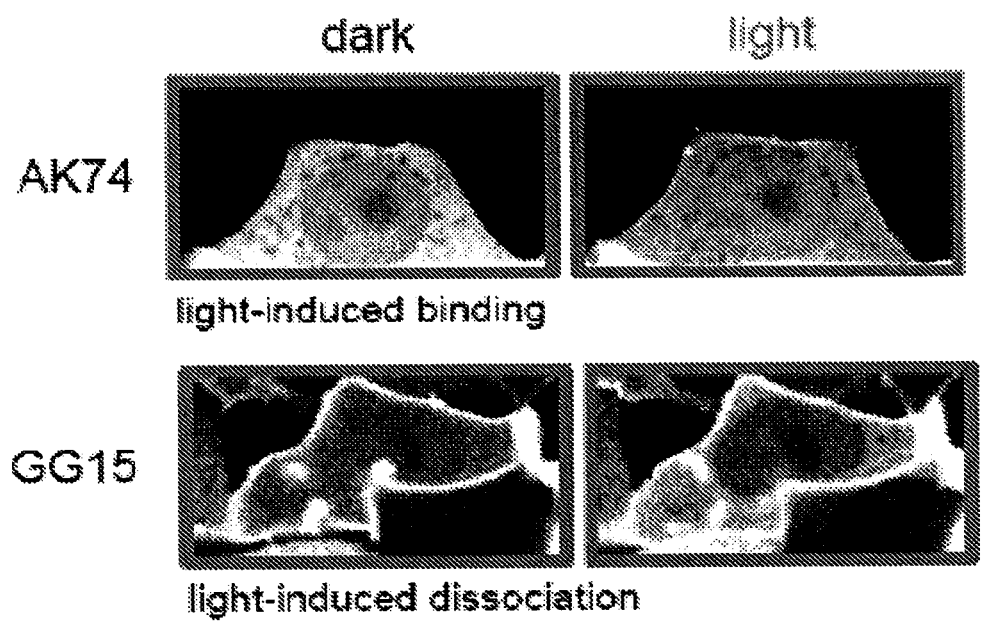

The initial screen yielded diverse results for different nanobody-LOV fusions. Colocalization between the nanobody and membrane-bound mCherry for LOV domains inserted into four out of five non-CDR loops (Loops 1, 3, 5 and 6) was observed, suggesting that nanobodies were broadly tolerant of LOV domain insertion without severe structural perturbation. Moreover, redistribution between cytosol and membrane for two OptoNB fusions was observed, those targeting the "GG15" and "AK74" insertion sites on Loops 1 and 6 of the nanobody (FIG. 28B, green and purple arrows). (Insertion sites are named herein based on the nanobody's flanking amino acids and the position number of insertion, so AK74 corresponds to the sequence . . . -Ala-AsLOV2-Lys- . . . with AsLOV2 inserted after Ala74.) It was found that light stimulation of these two sites triggered opposite effects on nanobody-mCherry binding: light-induced dissociation in the case of GG15 and binding in the case of AK74 (FIGS. 28D-28E). This set of chimeras with opposite response to light was surprising, as prior studies that took advantage of LOV insertion reported only light-induced disruption of protein function, which was explained by the increased flexibility of the light-stimulated state disrupting the fusion protein's active state[19,22]. In contrast, data on the AK74 chimera suggested that the AsLOV2 dark state can also disrupt function, which was restored upon blue light illumination. A second round of cell lines was constructed to test additional insertion sites in Loops 1 and 6, where hits were obtained (positions 15-17 and 72-77). Similar light-induced changes at one additional site within each loop (GS16 and DN72) were observed, demonstrating that multiple sites within a single loop can be used to achieve photoswitchable binding control.

These results demonstrate that LOV-nanobody chimeric proteins are indeed capable of photoswitchable binding. They also reveal two distinct classes of optoNBs, those for which binding occurs in the light and others for which it occurs in the dark. The ability to induce binding by switching to dark conditions is rare, as most previously-developed optogenetic tools exhibit light-induced binding; yet the few existing light-suppressible optogenetic tools available[23,24] have already proven useful for probing T cell signaling[25], controlling metabolic flux[26,27], and studying the consequences of protein phase separation[15]. Photoswitchable domain insertion thus holds promise for engineering light-based control of protein-protein interactions.

Figure 29A:
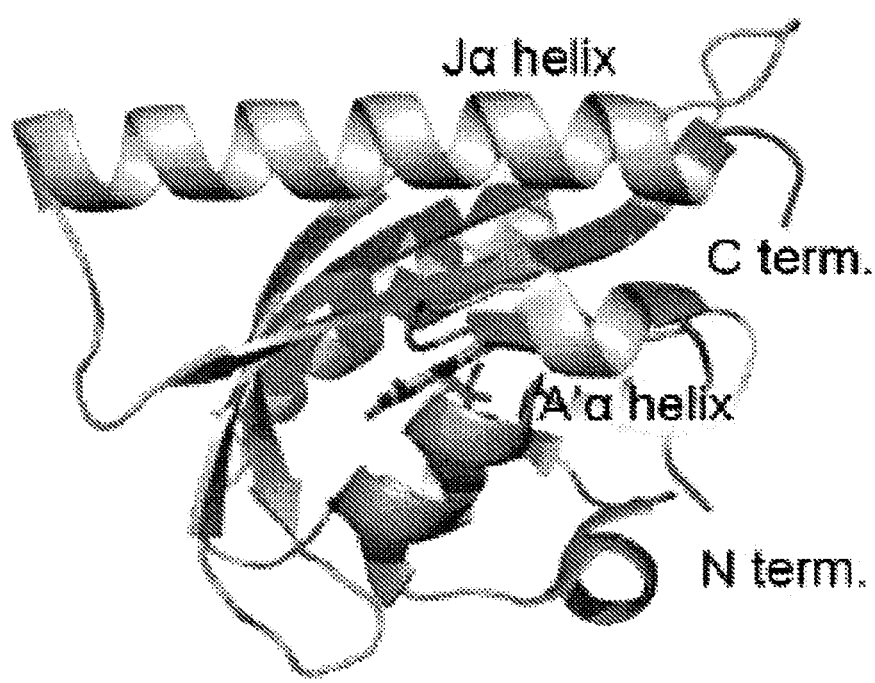
FIGS. 29A-29D show an optimized short LOV domain for OptoNB engineering.

An optimized LOV domain improves OptoNB function. The initial screen also revealed that, for some optoNBs (GG15, NA73, and MG77), light unexpectedly triggered nuclear export. Nuclear export was observed even in cells that did not express membrane mCherry; furthermore, it was quickly reversed in the dark for the GG15 and MG77 variants but was irreversible for the NA73 variant. Two improvements to the initial OptoNBs were sought: (1) eliminating undesired nuclear-cytosolic translocation of the nanobody and (2) achieving a larger change in binding between dark and illuminated conditions It was hypothesized that the light-induced nuclear/cytosolic translocation might arise due to light-triggered exposure of a nuclear export sequence (NES), as has been engineered in prior AsLOV2-based optogenetic tools[12,14]. Indeed, amino acid sequence analysis revealed a canonical NES (LxxxLxxLxL, where x is any amino acid and L is a hydrophobic amino acid that is often leucine) spanning the junction between the C-terminal Jα helix and nanobody for the GG15 and MG77 insertion sites. (A canonical NES for the NA73 variant was not observed, suggesting a different mechanism underlies its irreversible nuclear export.) It was sought to truncate residues from the nanobody's C-terminus to eliminate undesired NES activity. It was also reasoned that truncating amino acids from the nanobody-AsLOV2 junction may have an additional benefit, enabling tighter conformational coupling between the LOV domain and nanobody. A close examination of the crystal structure of AsLOV2 (PDB: 2V0U) suggested that removing linker residues at both the N and C termini of the AsLOV2 domain could more tightly couple it to the nanobody (FIG. 29A).

Figure 29B:
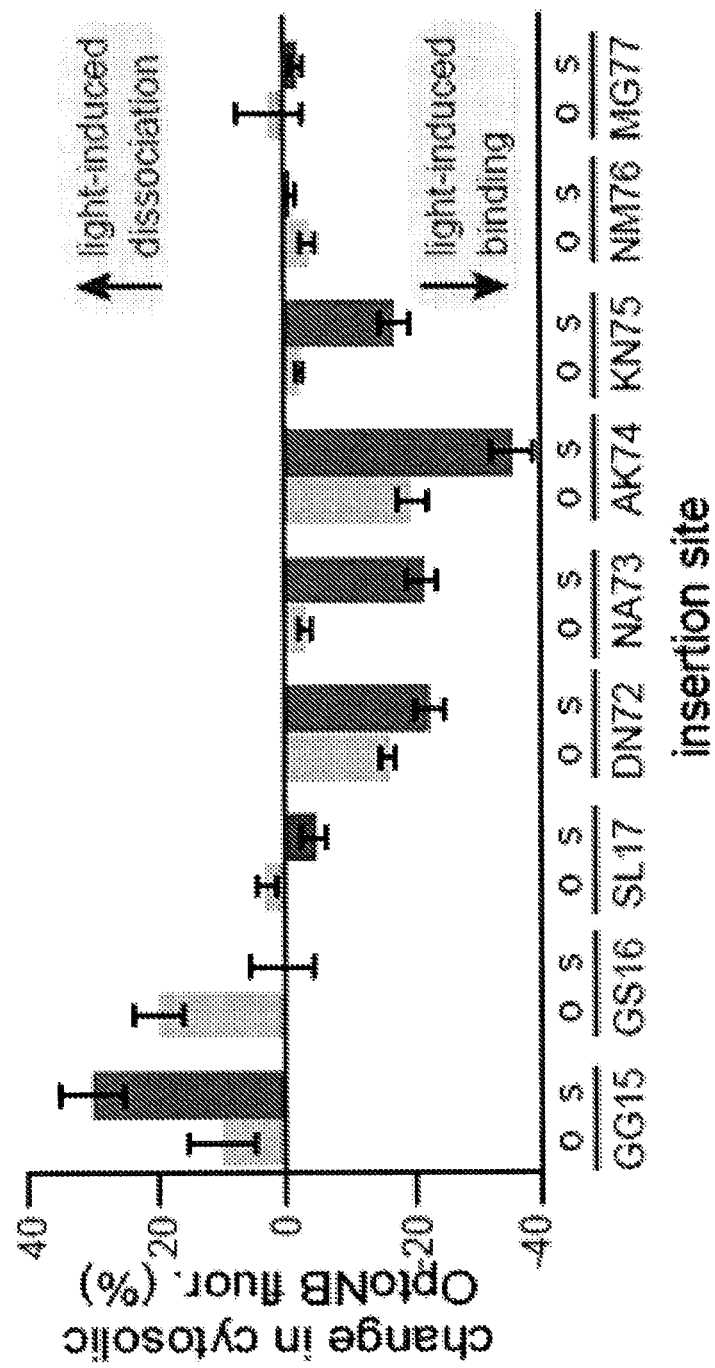
Figure 29C:
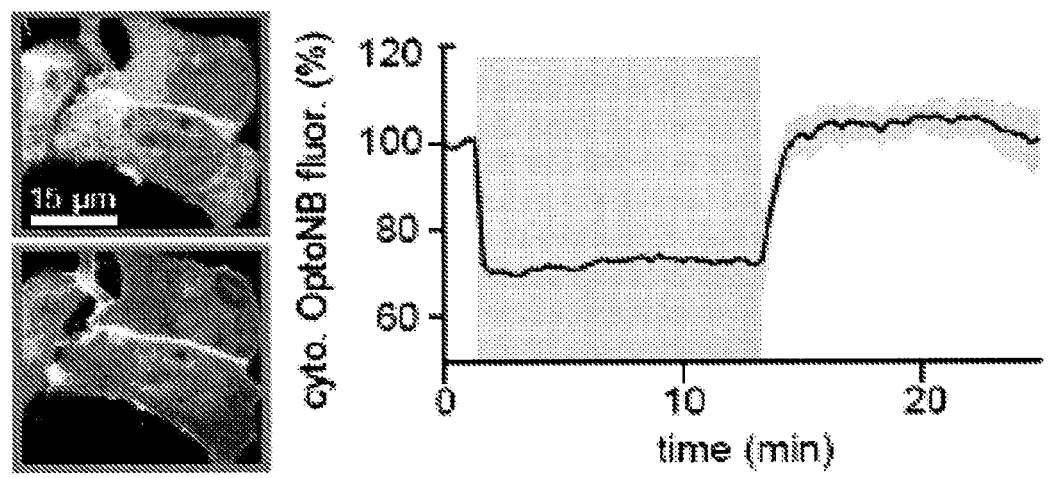
Figure 29D:
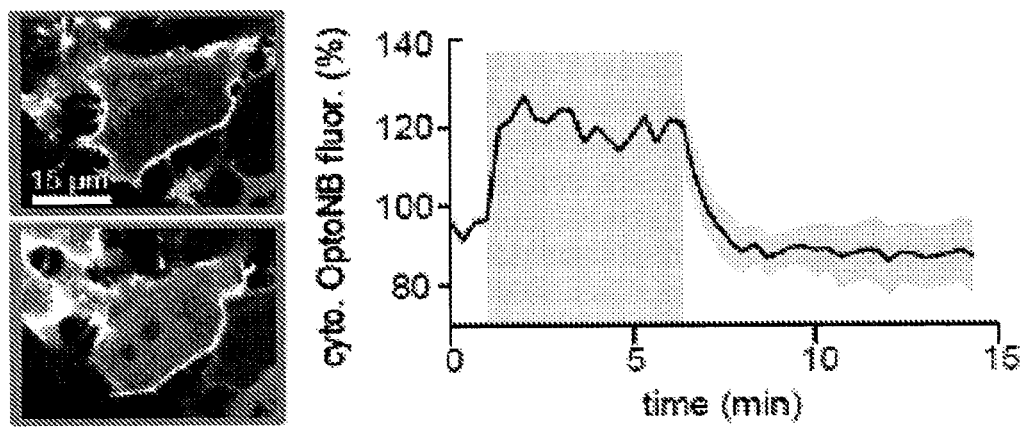

Based on this rationale, a 'short LOV' (sLOV) domain, comprising residues 408-543 of *Avena sativa* Phototropin 1 (versus residues 404-546 in FIG. 28 and 404-547 in Ref 19) was constructed, and insertion sites near the two initial hits were screened (FIG. 29B). Light-dependent nuclear export was no longer observed in any sLOV insertions, consistent with the role of the C-terminal NES in this phenomenon. Additionally, light-induced binding changes were enhanced in 5 of 6 cases (GG15, DN72, NA73, AK74 and KN75) compared to the original AsLOV2 constructs (FIG. 29B). It was confirmed that light-switchable target binding could be reversibly toggled on and off for both light- and dark-inducible OptoNB variants by measuring localization in cycles of darkness and blue light illumination (FIGS. 29C-29D). These results demonstrate that insertion of an optimized LOV domain can eliminate undesired nuclear/cytosolic translocation and generate opto-nanobodies with enhanced photoswitchable binding.

Figure 30A:
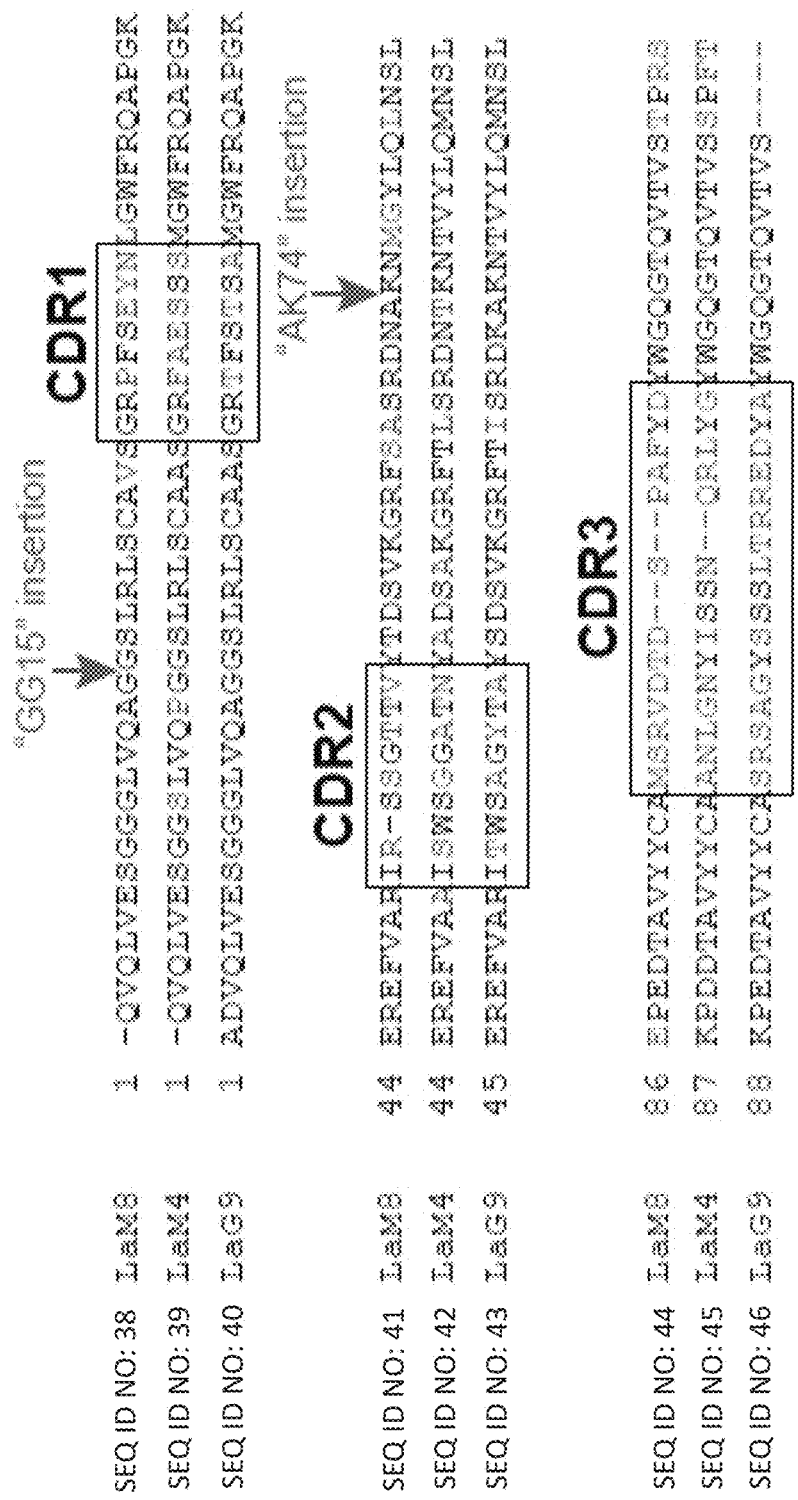
FIGS. 30A-30D show OptoNB design is generalizable and can be used to control intracellular signaling.
Figure 30B:
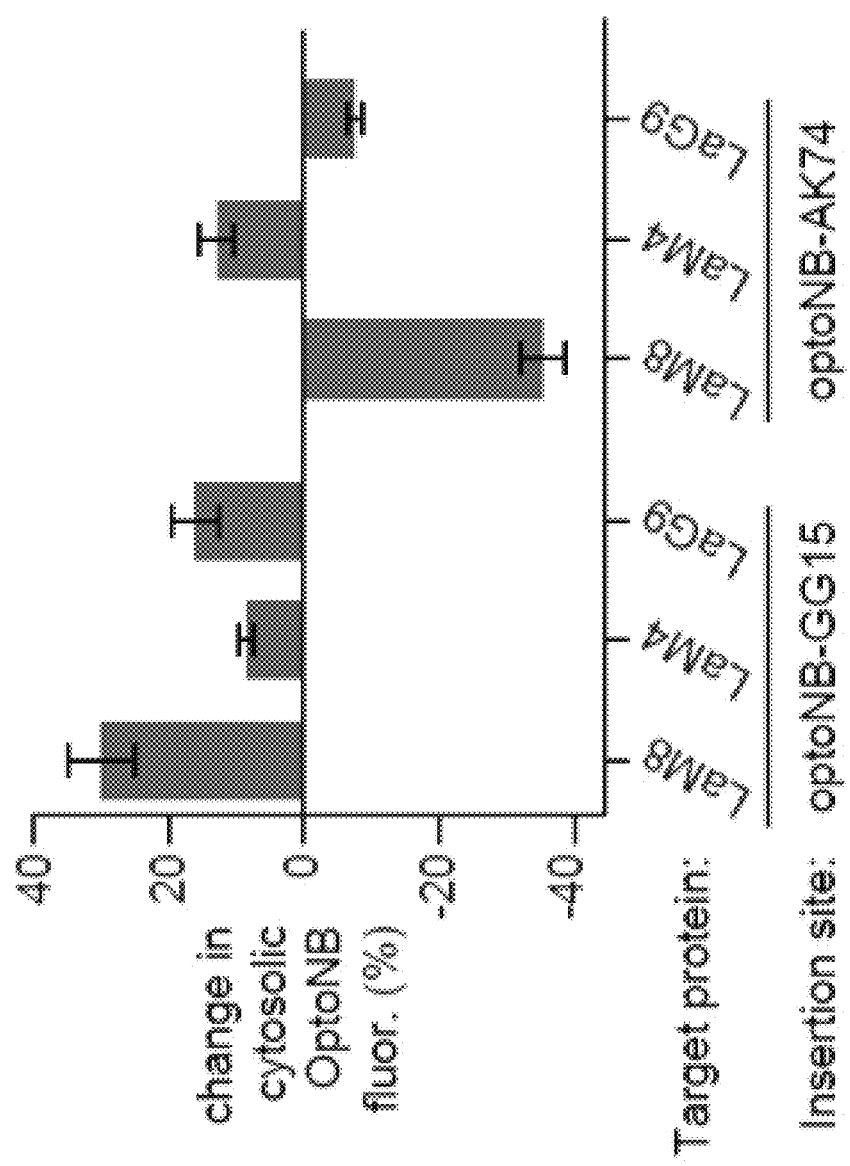

OptoNBs can be constructed for multiple nanobodies and target proteins. The initial OptoNB designs were in the context of a single binding pair: the LaM8 nanobody and its mCherry binding partner. It was next sought to test whether light-induced binding or dissociation generalizes to other nanobodies or targets. Alignment of multiple nanobody sequences (our original LaM8 nanobody, the higher-affinity mCherry nanobody LaM4, and an anti-EGFP nanobody LaG9) indicated that both the AK74 and GG15 insertion sites are located in conserved regions that are distinct from the hypervariable complementarity-determining regions (CDRs) (FIG. 30A)[21]. It was thus hypothesized that similar effects would be elicited upon LOV domain insertion in the same sites of each nanobody.

sLOV insertions at the GG15 and AK74 positions in LaM4-irFP and LaG9-irFP fusion proteins were next generated. Cells were co-transduced with membrane mCherry or EGFP, and cytosolic OptoNB levels monitored during cycles of blue light illumination or darkness (FIG. 30B). It was found that insertion at the GG15 position led to consistent light-inducible dissociation in all three nanobodies, although both LaM4 and LaG9 exhibited weaker dissociation than LaM8, possibly due to their higher-affinity target binding (0.18 and 3.5 nM, respectively, versus 63 nM for LaM8)[21]. In contrast, AK74 insertion led to highly variable results across all three nanobodies: light-induced binding was observed in the cases of LaM8 and LaG9, but light-triggered dissociation for LaM4. The results thus indicate that sLOV insertion at the same sites (GG15 and AK74) confers light-regulated target binding across multiple nanobodies (LaM8, LaM4, LaG9) and/or target proteins (GFP, mCherry). Insertion at the GG15 position appears to generally elicit light-triggered dissociation, whereas AK74 insertion appears to be more variable, with changes in both the sign and magnitude of photoswitchable binding observed between distinct nanobodies. This result is consistent with a model where light-induced destabilization of LOV domain contacts are more likely to disrupt protein function upon light stimulation than to restore it[19], suggesting that the light-induced binding observed in LaM8-AK74 may be a relatively unusual occurrence. The extent of cytosolic translocation from OptoNBs to a gold-standard LOV-based heterodimerization system, the iLID-SSPB system, was also compared, and it was found that LaM8-AK74 switches on a comparable scale to existing optogenetic tools in cells (approximately 40% versus 60% changes in cytosolic intensity between light and dark, respectively).

Coupling OptoNBs to Ras/Erk signaling in vivo. Because the initial screen demonstrated light-directed control over protein binding in live mammalian cells, it was reasoned that it should thus be possible to apply OptoNBs for light-based control over cellular functions without any further modification or optimization. To demonstrate this capability, an OptoNB-based variant of the OptoSOS optogenetic tool was constructed[28]. In this system, membrane localization of the catalytic domain of SOS ($SOS^{cat}$) is used to trigger Ras activity[29], activation of the Erk mitogen activated protein kinase cascade, and eventual responses including cell proliferation and differentiation. Light-induced signaling can also be easily visualized within minutes using the fluorescent Erk kinase translocation reporter (ErkKTR), a synthetic substrate that is exported from the nucleus to the cytosol within minutes of phosphorylation by active Erk[30].

Figure 30C:
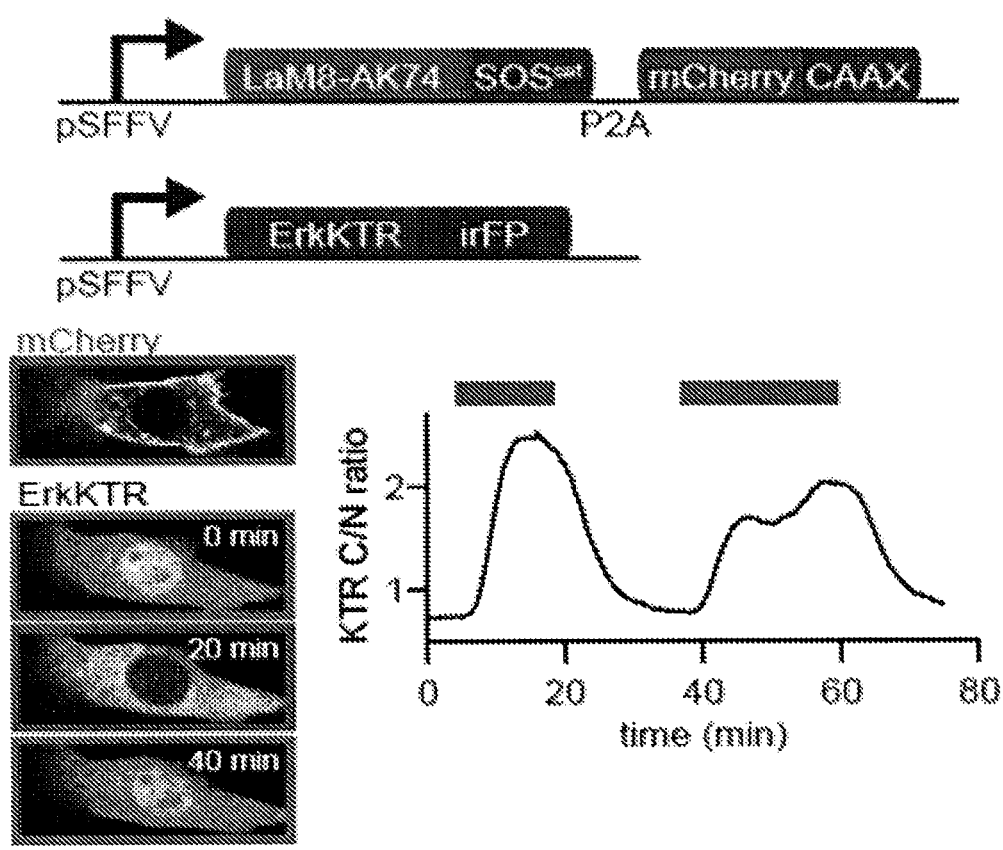
Figure 30D:
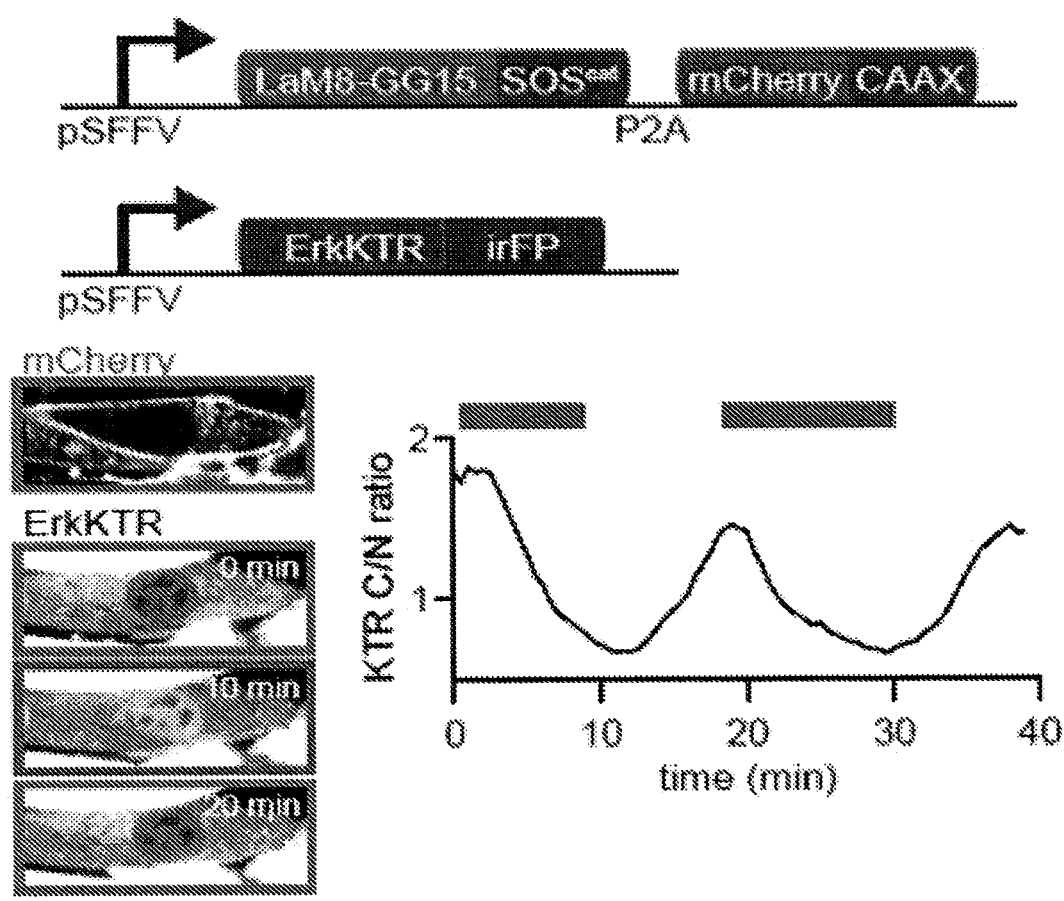

To reversibly trigger OptoSOS activation using nanobody-target binding, NIH3T3 cell lines expressing an OptoNB-SOS$^{cat}$ fusion protein (LaM8-AK74-SOS$^{cat}$ or LaM8-GG15-SOS$^{cat}$), membrane-localized mCherry (mCherry-CAAX) and an infrared fluorescent ErkKTR (ErkKTR-irFP) were generated (FIGS. 30C-30D). It was found that Erk activity could be rapidly toggled on and off with each OptoNB variant (FIGS. 30C-30D). As expected from initial protein-binding results, Erk signaling had opposite responses depending on which OptoNB was used to recruit SOScat to the membrane, with light-induced activation in LaM8-AK74 OptoSOS cells (FIG. 30C) and light-induced inactivation in LaM8-GG15 OptoSOS cells (FIG. 30D). These results demonstrate that OptoNBs can indeed be deployed in cells to manipulate downstream cellular functions (e.g., Ras/Erk signaling) without further optimization.

OptoNBs regulate protein binding in vitro. In addition to controlling intracellular protein-protein interactions, light-controlled nanobodies could be useful in vitro for a variety of applications, including extracellular reagents to modulate receptor-level responses[31], and the ability to decorate light-switchable binders in biochemical purification columns to separate unmodified target proteins based on light stimuli 32. The light-dependent performance of OptoNBs was characterized in vitro in a variety of assays: column-based separation, protein binding to OptoNB-coated agarose beads, and bio-layer interferometry-based measurement of OptoNB-protein binding kinetics.

Figure 31A:
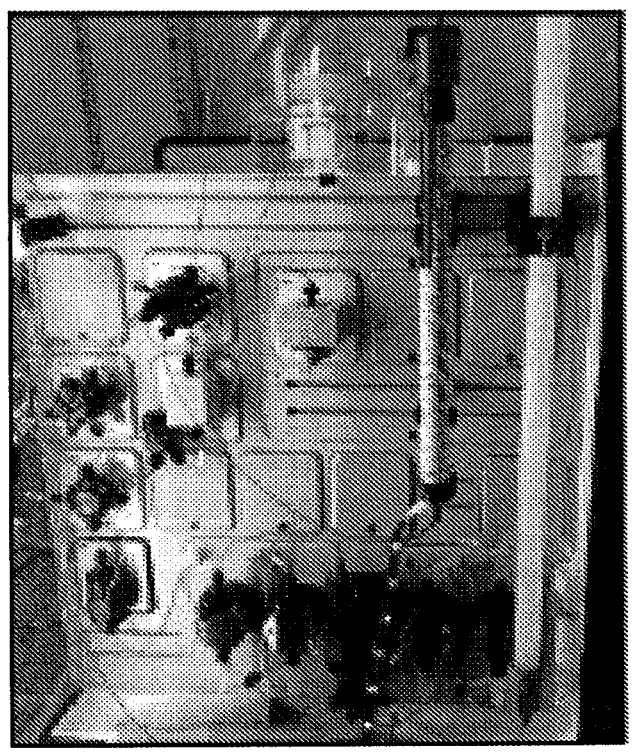
FIGS. 31A-31H show in vitro characterization of OptoNB binding.
Figure 31B:
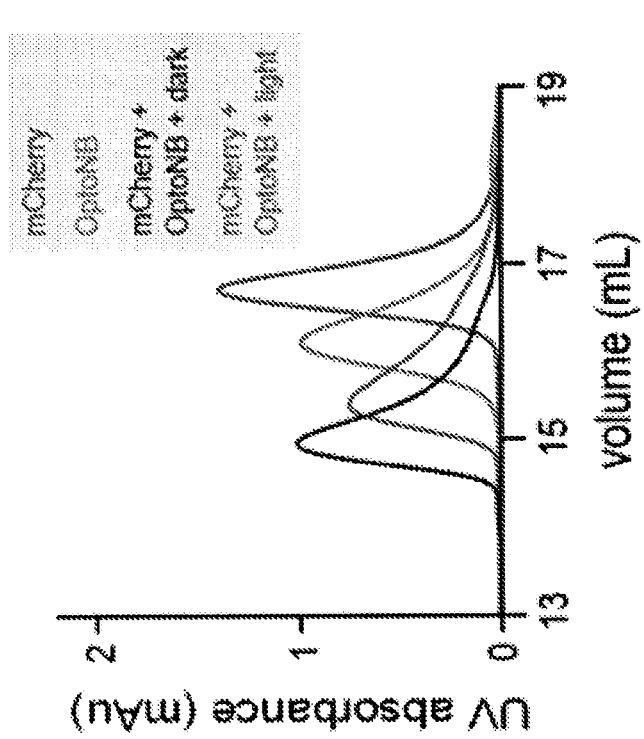
Figure 31C:
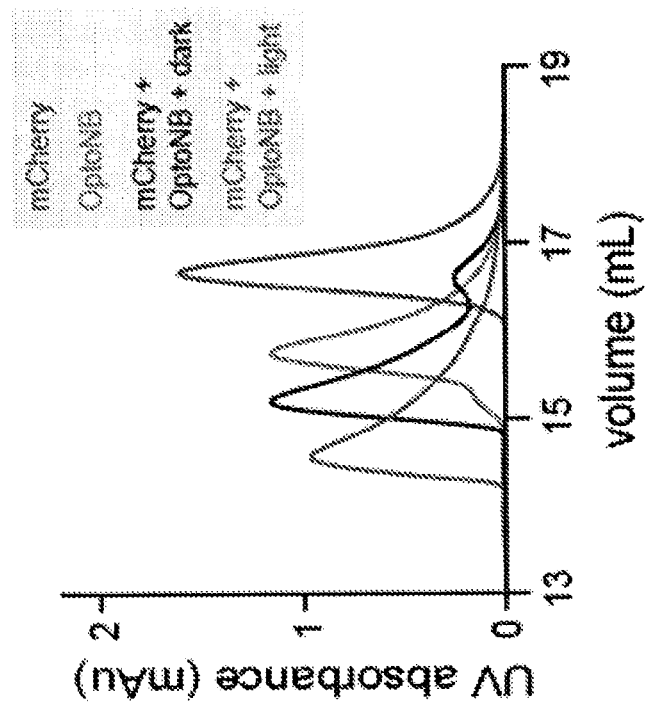

As a first test of their function in vitro, whether purified OptoNBs and their binding partners could be differentially separated in light and darkness using size exclusion chromatography was tested. The dark-inducible binder LaM4-TK74 and the light-inducible binder LaM8-AK74 from E. coli were expressed and purified. A Superdex 200 10/300 GE column with blue light-emitting diodes (LEDs; FIG. 31A) was wrapped in aluminum foil (to keep dark conditions), and solutions containing OptoNB, mCherry, or both were flowed through the column in a 1:1.2 molar ratio of NB to mCherry (FIG. 31B-31C). A strong light-dependent shift in retention time was observed for both OptoNBs. In the case LaM8-AK74, light-induced binding led to a shorter retention time under illumination (FIG. 31B, blue curve), and a longer complex retention time as well as a peak of free mCherry in the dark (FIG. 31B, black curve; compare to red curve for free mCherry). LaM4-TK74 exhibits the converse response, with shorter retention in the dark and longer in the light, indicating light-induced dissociation as previously observed in vivo (FIG. 31C). Nevertheless, under both light and dark conditions, the OptoNB peak exhibited a shorter retention time in the presence of mCherry than when the OptoNB was run alone, indicating an equilibrium between binding and dissociation that was shifted but not eliminated by the change in illumination conditions.

Figure 31D:
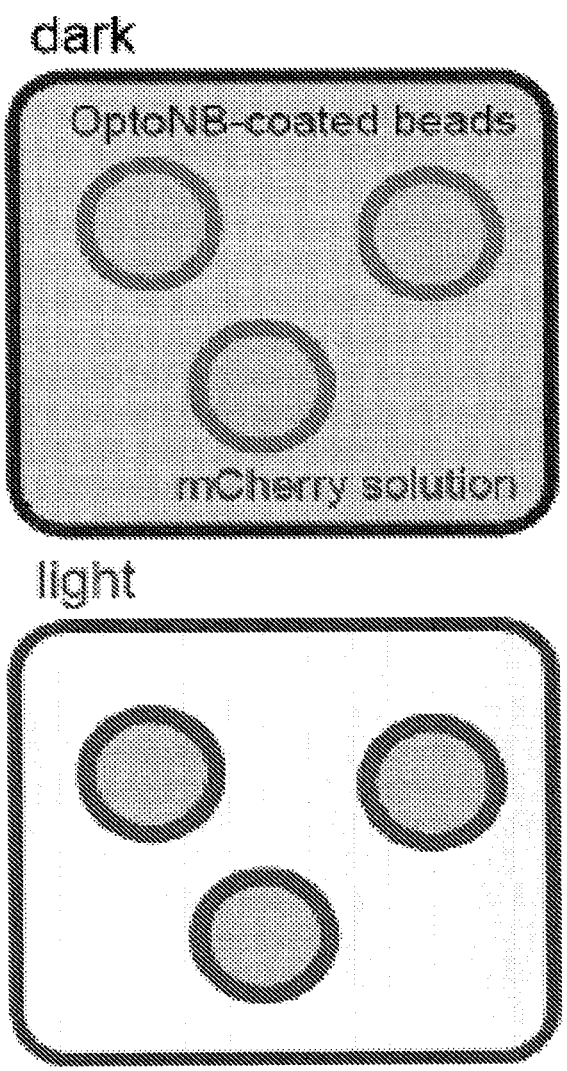

Many in vitro and extracellular applications of protein binders are based on interactions on surfaces (e.g., cell surface receptor binding; affinity-based purification using bead-tethered antibodies). Whether OptoNB-target interactions could be controlled on the surface of agarose beads was thus tested (FIG. 31D). His-tagged OptoNBs (His$_6$ (SEQ ID NO: 49)-LaM8-AK74 and His$_6$ (SEQ ID NO: 49)-LaM8-GG15), as well as His$_6$ (SEQ ID NO: 49)-GFP and His$_6$ (SEQ ID NO: 49)-mCherry from E. coli were purified. To obtain beads with different surface densities of immobilized OptoNBs, nickel-NTA-coated agarose beads were incubated with solutions containing different ratios of anti-mCherry His$_6$ (SEQ ID NO: 49)-OptoNB and His$_6$ (SEQ ID NO: 49)-GFP (where His$_6$ (SEQ ID NO: 49)-GFP was used as a bead surface blocking agent) to achieve different surface densities of OptoNBs.

Figure 31E:
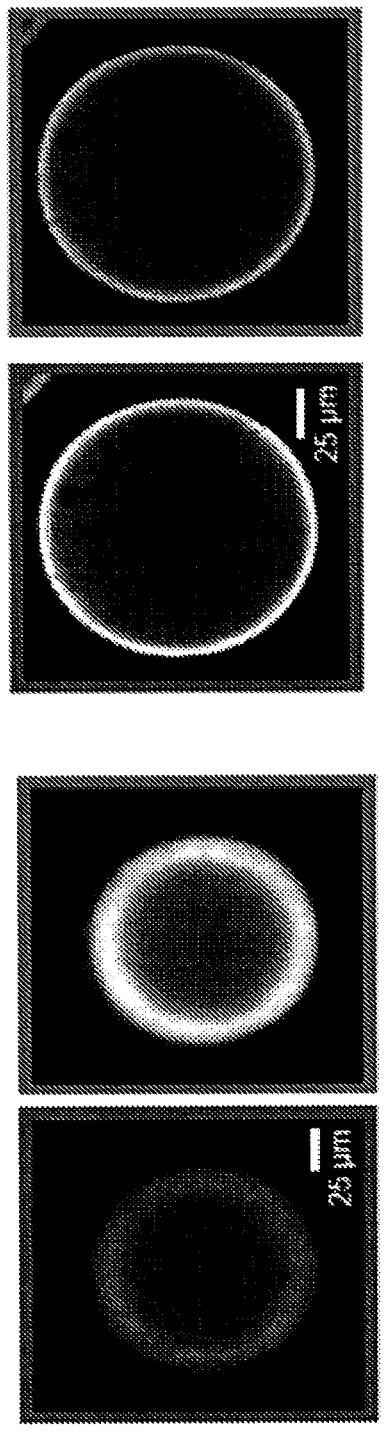
Figure 31F:
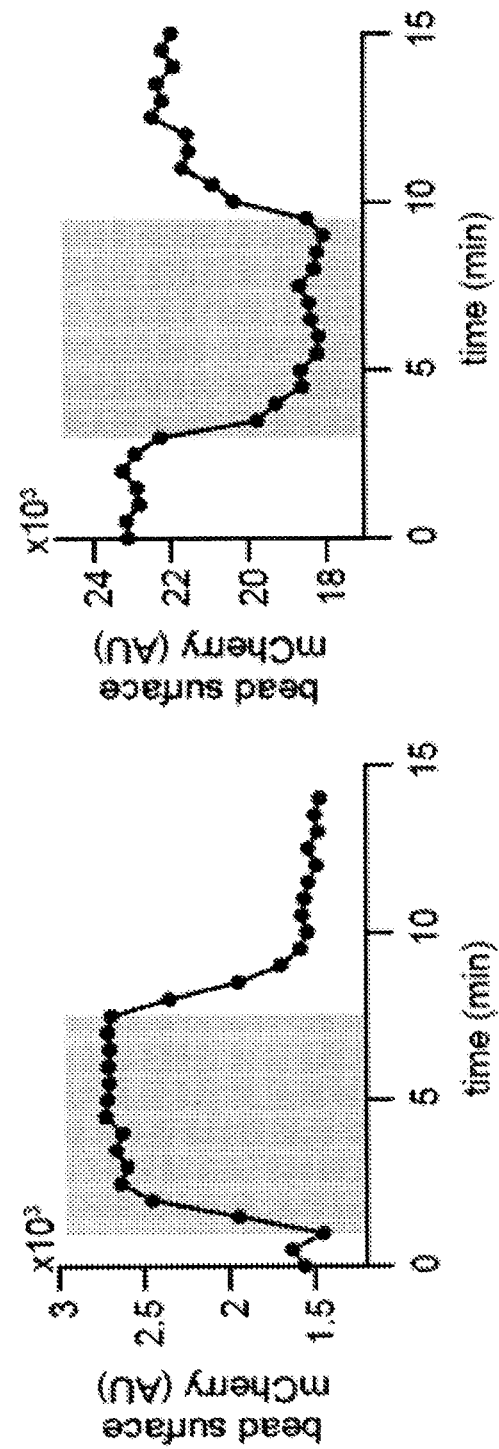

To test for light-dependent mCherry binding, the OptoNB-labeled beads were incubated with soluble mCherry (His$_6$ (SEQ ID NO: 49)-cleaved), and mCherry fluorescence was imaged during cycles of blue light illumination (FIGS. 31E-31F). A light-dependent shift in surface mCherry fluorescence was observed, as expected for AK74- and GG15-based OptoNBs. However, the time required to saturate the beads with bound nanobody upon light activation depended strongly on the density of target protein on the beads. Complete mCherry binding was achieved within 10 seconds when beads were labeled with a 0.5%:99.5% LaM8-AK74:GFP protein ratio. In contrast, beads labeled with 100% LaM8-AK74 were only gradually saturated with mCherry over approximately 1 hour. This phenomenon is likely due to local depletion of mCherry near the illuminated bead's surface at high labeling densities, a picture that is consistent with the approximately linear increase in surface mCherry observed at high OptoNB concentrations[33]. In sum, it was found that OptoNBs exhibit light-switchable binding to their targets across a broad range of contexts, from the mammalian intracellular environment to surface- and solution-based binding in vitro.

Measurement of lit- and dark-state OptoNB binding kinetics. As a final characterization of OptoNB activity, quantitative measurements were performed of their binding affinity and kinetics in the lit and dark states using bio-layer interferometry (BLI). It was reasoned that BLI would be ideal for quantifying light-triggered protein-protein interactions due to its compatibility with sample illumination and accurate quantification of both binding kinetics and affinity. Binding measurements in the dark state can be made by taking advantage of the C450V point mutation in AsLOV2 which prevents photoadduct formation, rendering AsLOV2-based optogenetic tools light-insensitive[34,35]. Although a variety of lit state mutants have been characterized that destabilize docking of the C-terminal Jα and N-terminal A'α helices[36,37], it is unclear whether these mutations fully mimic the lit state when these helices are constrained by being inserted into loops of a chimeric fusion, as in the OptoNBs.

Figure 31G:
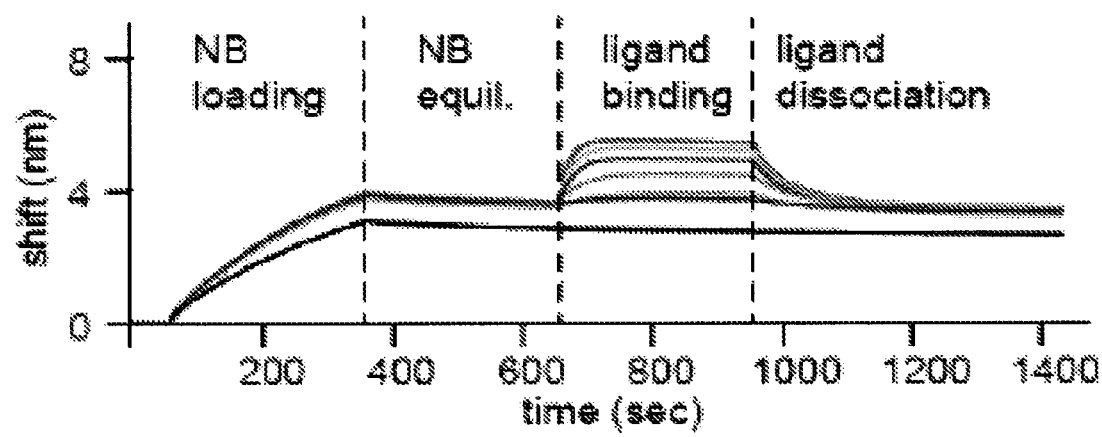
Figure 31H:
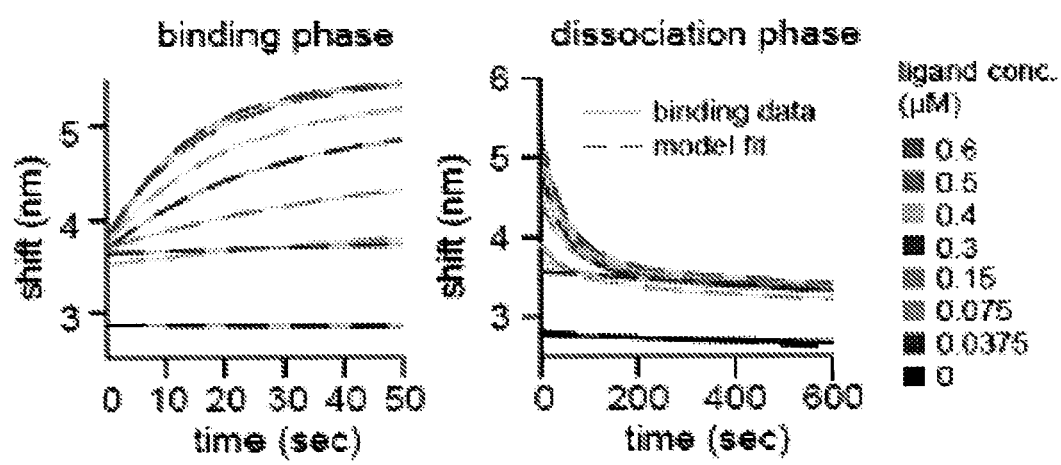

His-tagged variants of the parental LaM8 nanobody, the LaM8-AK74 and LaM8-GG15 OptoNBs were first expressed and purified, and OptoNB mutants that were expected to be light-insensitive and locked in either the dark state (C450V equivalent) or lit state (I532E A536E equivalents)[38]. For each BLI run, one of these nanobody variants was loaded onto Ni-NTA-coated sensors, equilibrated in buffer, exposed to varying concentrations of mCherry to measure the association phase, and finally washed to measure the dissociation phase (FIG. 31G). The binding curves at all mCherry concentrations were then globally fit to a simple mass-action chemical kinetic model of binding and dissociation, from which estimates of $k_{on}$, $k_{off}$ and $K_D$ were obtained (FIG. 31H). The global fitting procedure was able to fit the data well in each case.

The resulting kinetics and affinities are presented in Table 2. An affinity of 230 nM was measured for wild-type LaM8, which differed somewhat from the 63 nM affinity reported previously[21], possibly due to differences in assay design and procedures used to fit binding curves. It was found that the LaM8-GG15 OptoNB also exhibited sub-micromolar affinity for mCherry in its dark state (610 nM) that was weakened to 1.7-2.4 μM in the lit state. In contrast, the LaM8-AK74 variant exhibited weaker affinity for mCherry in its dark state (19.9 µM) than its lit state (3.65-3.79 µM), just as had been observed in vivo and in vitro. All lit state measurements agreed closely between illuminated, photosensitive OptoNBs and lit-state mutants, suggesting that these mutants accurately reflect the nanobody's lit state. Finally, in each case, the affinity change upon illumination was explained primarily by changes in the dissociation rate $k_{off}$, with little change in the association rate $k_{on}$. This observation is consistent with a light-dependent change in the complementarity of the nanobody's binding site for its target protein, decreasing overall affinity by shortening the residence time of the bound complex. In sum, bio-layer interferometry can be used to obtain binding kinetics and affinities for native lit-state optogenetic tools, without relying on mutants that may not perfectly approximate this state for a particular application. Applied to LaM8-GG15 and LaM8-AK74 OptoNBs, BLI reveals a 3- to 5.5-fold change in binding affinity between lit and dark states in vitro.

TABLE 2

Binding kinetic measurements for lit- and dark-state OptoNBs using bio-layer interferometry (BLI). Columns list the nanobody variant used, illumination conditions, and best-fit kinetic rate constants to the raw BLI traces.

| Variant | Illumination | $k_{on}$ ($\mu M^{-1} s^{-1}$) | $k_{off}$ ($s^{-1}$) | $K_D$ ($\mu M$) |
| --- | --- | --- | --- | --- |
| LaM8 | None | 0.076 | 0.018 | 0.23 |
| LaM8-GG15 C450V (pseudo-dark) | None | 0.037 | 0.023 | 0.61 |
| LaM8-GG15 I532E A536E (pseudo-lit) | None | 0.042 | 0.102 | 2.41 |
| LaM8-GG15 | 450 nm light | 0.044 | 0.076 | 1.73 |
| LaM8-AK74 C450V (pseudo-dark) | None | 0.024 | 0.471 | 19.9 |
| LaM8-AK74 I532E A536E (pseudo-lit) | None | 0.036 | 0.13 | 3.65 |
| LaM8-AK74 | 450 nm light | 0.04 | 0.153 | 3.79 |

An actin-binding OptoNB with tight spatiotemporal control in living cells. One major application of light-controlled nanobodies is to modulate binding and unbinding of endogenous protein targets in living cells. Recent efforts have demonstrated substantial progress towards this goal: a split-nanobody strategy has been shown to be efficacious against a variety of endogenous proteins, and chemical dimerization has been successfully applied to a microtubule-binding nanobody. Nevertheless, neither of these current approaches are reversible, and chemical dimerization cannot easily be extended to subcellular spatial control. It was thus sought to test whether this LOV domain insertion strategy could be successfully deployed against an endogenous target. Actin was chosen as a first target as it is abundantly expressed, exhibits well-defined spatial localization in virtually all cells, and because excellent nanobodies are commercially available for its labeling in living cells[42,43].

A set of 13 LOV insertion variants was designed into a TagRFP-fused actin nanobody, including the previously-successful GG15 and AK74 variant equivalents with both long- and short-LOV insertions, as well as long-LOV insertions in all other non-CDR loops where nanobody binding has previously been observed (FIG. 28): Loop 1 (position 16), Loop 3 (positions 40-44), Loop 5 (positions 62-66), and Loop 6 (positions 72-75). Each construct was transiently transfected into NIH3T3 fibroblasts and assayed for localization to the actin cytoskeleton. As a control, the parental actin nanobody lacking a LOV domain insertion, which co-localized to endogenous actin in nanobody-transfected cells, was also assayed.

Figure 32A:
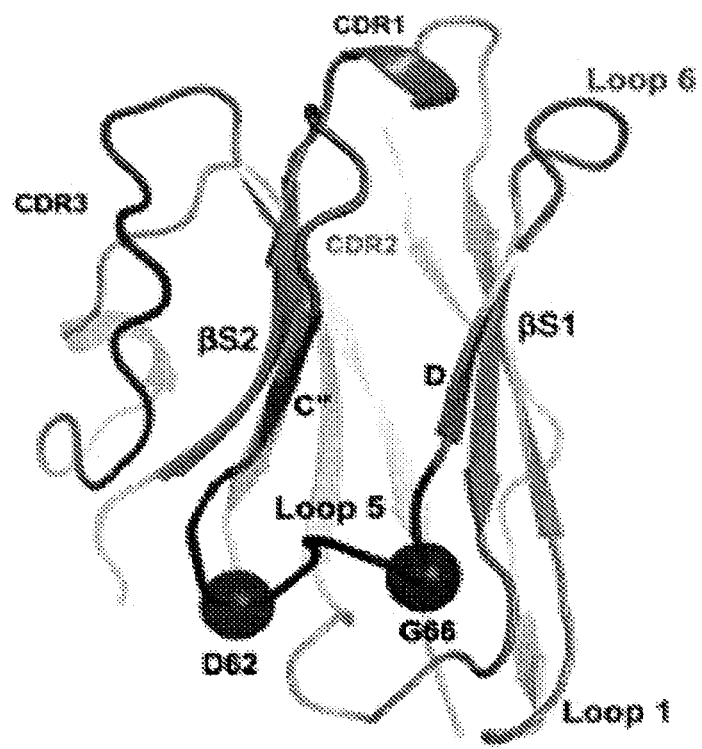
FIGS. 32A-32E show development and characterization of an anti-actin OptoNB.
Figure 32B:
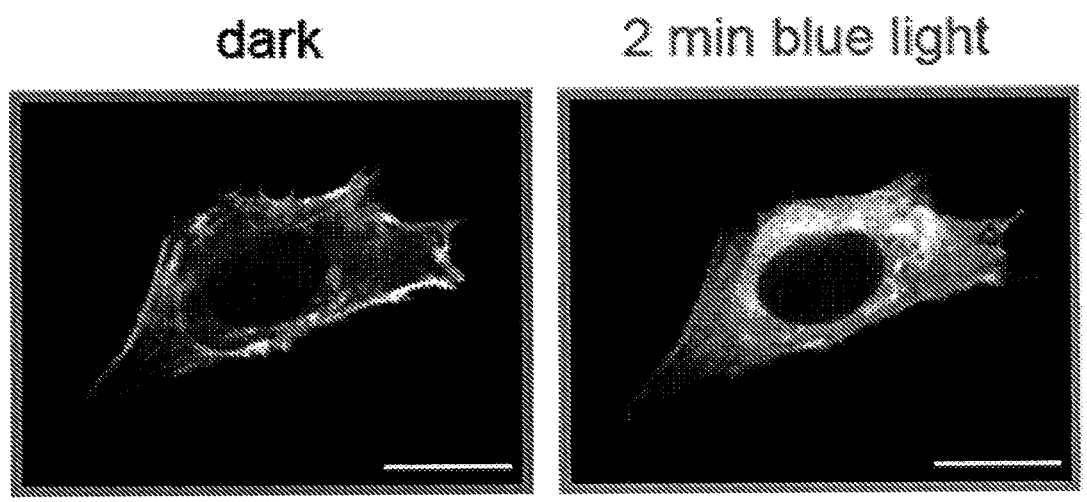
Figure 32C:
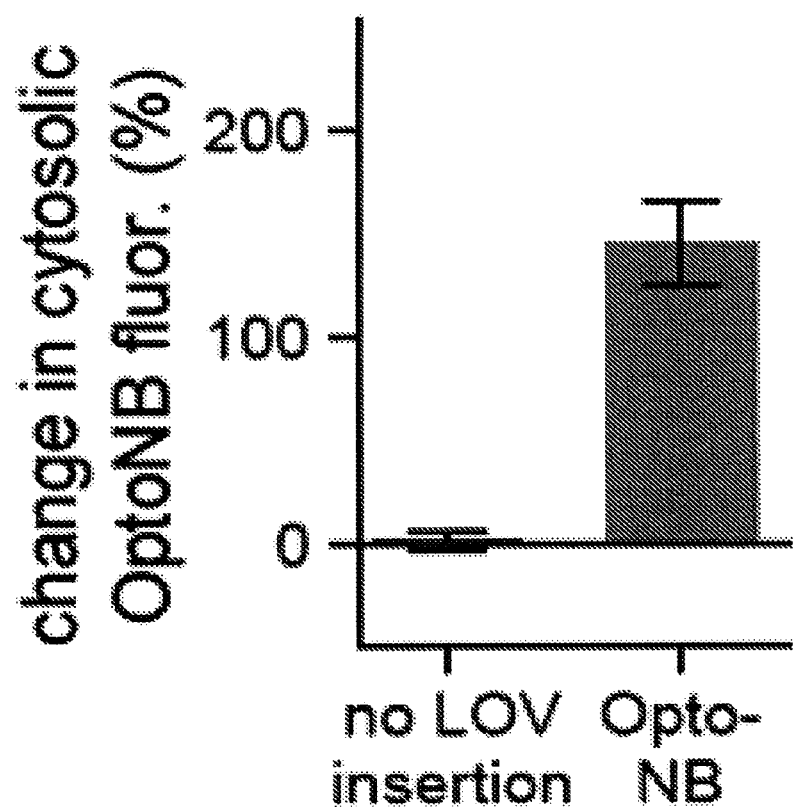
Figure 32D:
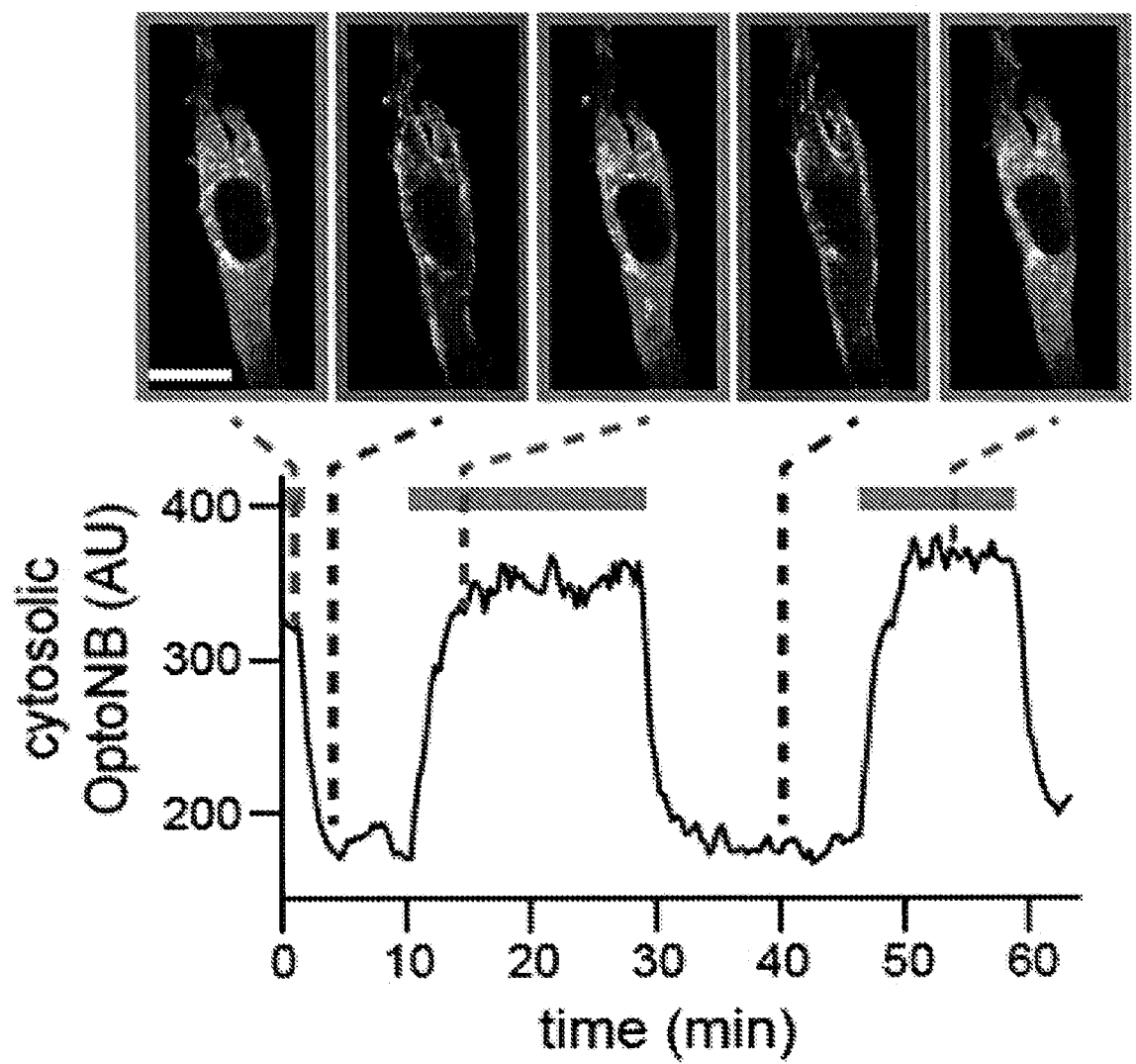

Testing this library revealed nanobody-actin colocalization when LOV domains were inserted in either Loop 3 or 5. Moreover, exceptional light-switchable binding was observed in a single Loop 5 variant in which the original LOV domain insertion was combined with truncation of three nanobody residues (63-65) (FIG. 32A), based on the hypothesis that the length and flexibility of Loop 5 might interfere with allosteric coupling. It was found that this actin-OptoNB undergoes light-induced dissociation, shifting from strong cortical and stress-fiber localization pattern to diffuse, cytosolic localization upon illumination (FIG. 32B). Subsequent quantification across multiple cells revealed a greater than 100% increase in cytosolic OptoNB intensity between dark and lit states (FIG. 32C). Binding and dissociation were rapid and reversible, reaching steady state within approximately 2 minutes, as measured by quantifying changes in intensity of the cytosolic OptoNB pool, and showing no signs of degradation in performance after multiple cycles (FIG. 32D).

Figure 32E:
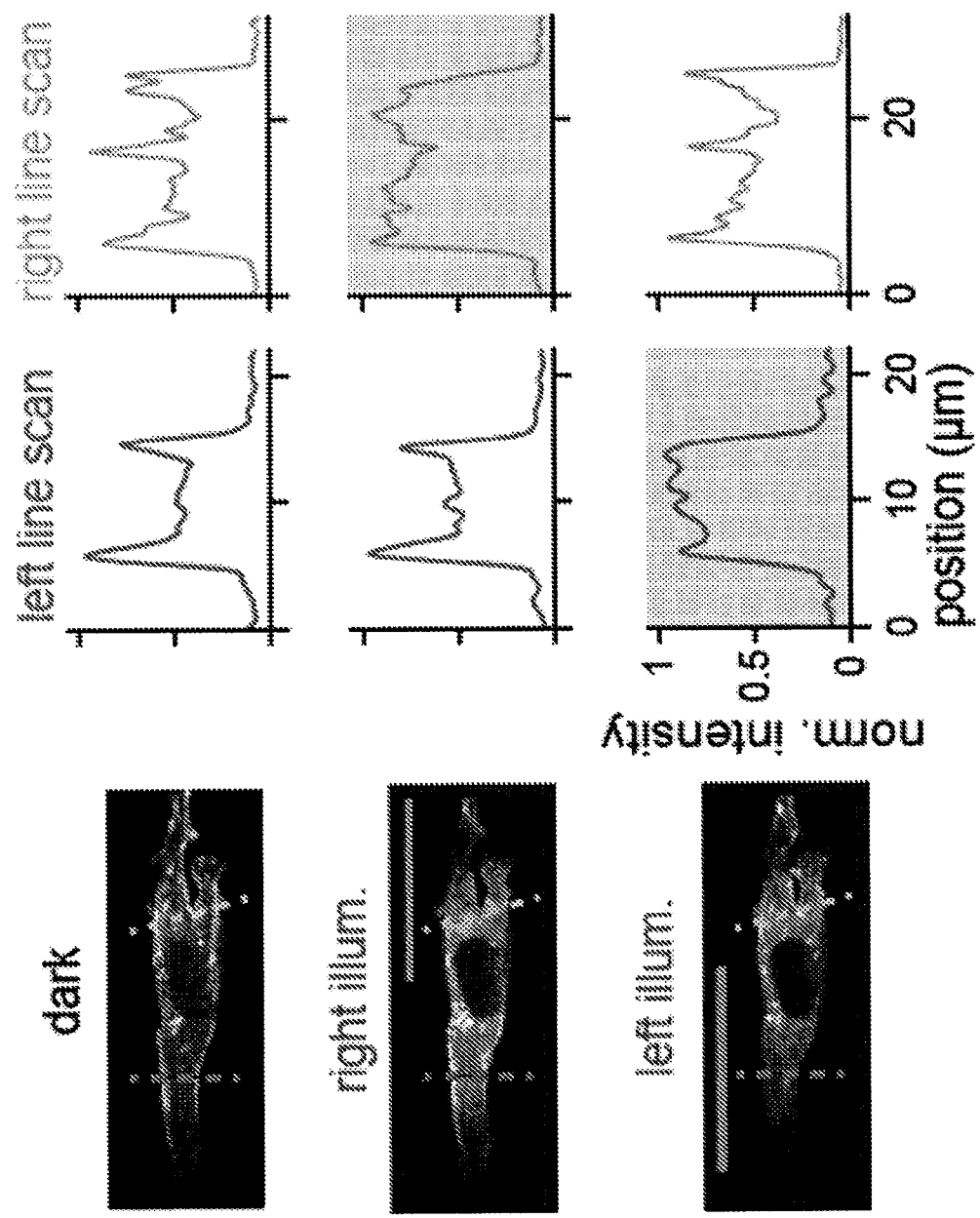

Studies of cell polarization and migration in living cells are currently limited by lack of localized control over the cytoskeleton in specific regions of the cell. As a first step towards direct control over the endogenous cytoskeleton, whether local illumination could give rise to sharp patterns of nanobody-actin binding within individual cells was tested. Subjecting single cells to local blue light stimuli revealed that nanobody binding was suppressed within the illuminated region, as seen previously with whole-cell illumination. Moving the light could also be used to toggle nanobody localization from one side of the cell to the other, labeling of cytoskeletal fibers in the un-illuminated side of the cell (FIG. 32E). These differences were also apparent by quantifying OptoNB intensity through line scans of the cell, revealing loss of cortical enrichment at the cell edges during times of illumination. Together, these data demonstrate the construction of a light-switchable nanobody to an endogenous protein target with reversible, minutes-timescale temporal control and subcellular spatial targeting. This anti-actin OptoNB revealed a third loop in nanobodies in which insertion of a LOV domain can lead to light-switchable binding. Similar to the OptoNBs with LOV domain insertions in Loop 1 (at position GG15), the distance of Loop 5 from the epitope-binding surface of the nanobody suggests an allosteric mechanism of action.

Discussion A strategy for constructing light-sensitive proteins—the insertion of a photoswitchable domain into a target protein—can be used to produce light-sensitive nanobodies (OptoNBs). Nanobodies are a class of proteins with high potential as biological reagents for cell and developmental biology[39,40], biotechnology[32], and therapeutic applications[31,41] because of their small size, ease of expression and purification in both bacterial and eukaryotic cells, and high-affinity binding to a growing list of target proteins. OptoNBs can be produced from multiple nanobody scaffolds, show activity against multiple target proteins, can exhibit either light-inducible or light-dissociable responses, and can be functionally coupled to cell signaling in vivo and column-based assays in vitro. Design variants can be used to optimize OptoNB function, including an optimized, shortened AsLOV2 scaffold that improves photoswitchable binding in 5 of the 6 cases tested and eliminates a side pathway—light-switchable nuclear export—that could be relevant for intracellular applications.

The ability to control nanobody binding with light offers considerable promise for a variety of applications. Nanobodies can be raised against a broad range of target peptides through affinity maturation in immunized camelids, making it easy to envision proteins whose binding can be toggled on and off from a broad range of endogenous protein targets. In many cases, nanobody binding to an endogenous target protein could competitively inhibit the target protein's normal function, opening the door to reversible, specific loss-of-function control. This is particularly intriguing, as most existing optogenetic tools regulate binding between two engineered domains, leaving endogenous processes unaffected. OptoNBs also have high potential for use as light-sensitive reagents outside of cells. Light-switchable binders could in principle be used to reversibly neutralize ligands or cell surface receptors on cells, tissues, or organisms that have not been genetically modified[31]; they could also enable separation of target proteins from complex mixtures without a need for affinity tags that may interfere with the target protein's function[42].

Four conserved loops were identified where a LOV domain insertion can be tolerated without disrupting nanobody-target binding, and cases where insertion in three of these loops (Loops 1, 5, and 6) result in photoswitchable binding is reported. This flexibility may prove advantageous by providing opportunities to "move" the LOV domain insertion site to avoid steric interference with a particular target protein. Furthermore, two opto-nanobodies are reported that can already serve as viable optogenetic tools for intracellular applications: the mCherry-binding LaM8-AK74, and the actin OptoNB. LaM8-AK74 reversibly binds mCherry in mammalian cells to a degree that is comparable to other high-quality optogenetic tools. Similarly, the actin OptoNB exhibits fast, light-switchable translocation that can be toggled on and off with subcellular spatial precision, demonstrating programmable control over binding to an endogenous protein target. It is further demonstrated that localization changes can be harnessed for regulating intracellular processes by constructing an OptoNB-based variant of the OptoSOS system for controlling the Ras/Erk signaling pathway. It should be noted that mCherry is frequently used in intracellular labeling experiments, so LaM8-based OptoNBs could be immediately deployed as a 'backwards-compatible' strategy for altering the intracellular localization of these mCherry-tagged proteins in the cell lines or organisms where they have already been developed.

Analysis of binding affinities in the lit and dark states indicates that LaM8-based OptoNBs exhibit up to a 5.5-fold change between lit and dark states, spanning an overall 30-fold range of affinities between the tightest (610 nM for LaM8-GG15's dark state) and weakest binders (19.9 µM for LaM8-AK74's lit state). Prior studies have designed engineered LOV domains and cognate peptides with up to 50-fold changes in affinity between lit and dark states[4]. Moreover, in the study targeting a monobody against the Abl SH2 domain described herein, it is reported that sLOV insertion chimeras can elicit an approximately 100-fold change in affinity.

In addition, OptoNB function could be supported by the allosteric coupling between the LOV domain's insertion site and nanobody's target-binding surface. Without wishing to be bound by theory, a larger change in binding affinity may thus be achieved by testing additional nanobody insertion sites using the shortened LOV domain sequence or screening additional LOV domain variants with tighter dark-state binding[43]. The apparent discrepancy between the large localization change observed in cells (FIG. 29C) and the in vitro binding assay (Table 2) is noted. It is thus possible that OptoNBs respond differently in these different biochemical environments. For example, nanobodies contain a disulfide bond that may be differentially formed depending on the reducing environment and might alter the nanobody's sensitivity to allosteric control. OptoNBs thus hold considerable promise for delivering programmable, light-controlled binding for broad range of applications inside and outside cells.

Materials and Methods: Plasmid Construction. DNA containing LaM8, LaM4, and LaG9 was kindly gifted by Professor Kole Roybal (UCSF), and a plasmid encoding the anti-actin nanobody was purchased from Chromotek. All DNA was cloned using backbone PCR and inFusion (Clontech). pHR vectors were used for mammalian cell experiments and pBAD vectors were used for bacterial protein overexpression. AsLOV2 404-546 and AsLOV2 408-543 were ordered as gene blocks from IDT and used to insert into the nanobodies using inFusion (Clontech). The BFP-SSPB-SOScat-2A-PuroR-2A-iLID-CAAX plasmid was used to express the iLID/SSPB dimerization system as described previously. All plasmids were cloned by amplifying appropriate sequences by PCR, and performing assembly reactions using the inFusion kit (Clontech). All final plasmids were validated by sequencing (Genewiz). Stellar competent E. coli cells (Clontech) were transformed according to manufacturer's instructions for all plasmid transformations.

Lentivirus Production and Transduction. HEK 293T cells were plated on a 6 or 12 well plate and grown up to 40% confluency. At that point they were co-transfected with desired pHR plasmid and lentiviral packaging plasmids (pMD and CMV) using Fugene HD (Promega). Virus was collected after approximately 48 hours, filtered using 0.45 mm filter and 2 µL of polybrene and 40 µL of HEPES were added to the viral particles. Either HEK 293T or NIH 3T3 cells were plated on a 6-well plate and infected with 200-500 µL of the virus at 40% confluency. Viral media was replaced by growth media 24 hours post infection and imaging was done at least 48 hours post the infection time. For iLID-SSPB translocation experiments, NIH3T3 cells were puromycin-selected after lentiviral transduction and a clonal cell line was established to limit cell-to-cell variability in expression. Media used for all cell culture maintenance contained DMEM, 10% FBS, penicillin, and streptomycin.

Cell transient transfection: NIH 3T3 cells were plated into 96 well plates at 40% confluency 2 days prior to imaging and 1 day prior to transfection. 24 hours after plating cells, 300 ng of DNA encoding actin nanobody variant were transfected into cells. Transfection was done using Lipofectamine LTX reagent (Thermo Fischer Scientific) with 0.5 µL of PLUS reagent, 2.5 µL of LTX reagent, 20 µL of optiMEM. 10 µL of the mix was added into each well and then imaging was done 24 hours after transfection occurred.

Cell imaging. For imaging, 0.17 mm glass-bottomed, black-walled 96-well plates (In Vitro Scientific) were used. Glass was first treated with 10 µg/mL of fibronectin in PBS for 20 min. Cells were then plated and allowed to adhere onto the plate. 50 µL of mineral oil was added on top of the media prior to imaging to limit media evaporation. For RAS/Erk signaling experiments, cells were switched to starvation media prior to imaging (plain DMEM+20 mM HEPES buffer, with no added serum). Cells were washed 3 times with starvation media and then equilibrated in starvation media for at least 3 hours prior to imaging.

The mammalian cells were kept at 37° C. with 5% $CO_2$ for the duration of all imaging experiments. Imaging was done using Nikon Eclipse Ti microscope with a Prior linear motorized stage, a Yokogawa CSU-X1 spinning disk, an Agilent laser line module containing 405, 488, 561 and 650 nm lasers, an iXon DU897 EMCCD camera, and a 40× oil immersion objective lens. A 450 nm LED light source was used for photoexcitation with blue light, which was delivered through a Polygon400 digital micro-mirror device (DMD; Mightex Systems). For all LED illumination experiments, the LED power was adjusted to a final value of ~1 mW/cm$^2$ at the sample plane, as measured by a MQ-510 Quantum light meter with separate sensor (Apogee Instruments) using an equivalent blue LED light source placed above the sample.

Protein Expression. All proteins were expressed using pBAD N-His vector. Nanobody and opto-nanobody plasmids were transformed into Shuffle T7 Express *E. coli* cells (NEB) and eGFP and mCherry plasmids were transformed into One Shot Top 10 cells (Invitrogen). A single colony was used to inoculate a 10 mL 2×YT overnight culture supplemented with 200 μg/mL of Carbenicillin (Carb). The following day the culture was used to inoculate 0.5 L of 2×YT/Carb media that was shaken at 37° C. and 250 rpm until it reached an OD600 of approximately 1.0. Subsequently, the temperature was decreased to 20° C. and protein expression was induced by adding 0.2% Arabinose. The culture was shaken in the dark for approximately 18 hours followed by harvesting the cells by centrifugation at 4° C. and 12000 g. If the protein was not purified right away, the pellets were stored at −80° C.

For the purification, the 0.5 L cell pellet was thawed and resuspended in 25 mL of resuspension buffer (50 mM Tris pH 8.0, 150 mM NaCl) with 0.4 mM phenylmethanesulfphonylfluoride (PMSF) as well as a tablet of cOmplete Mini (Roche) and 14 μL of β-mercapthoethanol. Cells were lysed using a sonicator and the supernatant clarified by centrifugation at 250,000×g for 1 hour. Subsequently, FMN (0.25 mg/mL) was added to the supernatant with approximately 30 minutes incubation to ensure a homogenous distribution of the chromophore. 3-4 mL of Ni-NTA superflow resin (Qiagen) were loaded onto a column and equilibrated with the resuspension buffer. The supernatant was loaded onto the column followed by 100 mL washes with resuspension buffer containing increasing concentrations of imidazole of 10, 20, and 30 mM. The protein was eluted at 250 mM imidazole and dialyzed overnight against resuspension buffer with the protein purity determined by SDS-PAGE. Protein concentrations were determined by recording the Abs$_{280}$ and the following extinction coefficients for eGFP, mCherry, LaM8, and OptoLaM8NBs, 24,995 M$^{-1}$ cm$^{-1}$, 34,380 M$^{-1}$ cm$^{-1}$, 24,535 M$^{-1}$ cm$^{-1}$, and 47,905 M$^{-1}$ cm$^{-1}$, respectively.

Size exclusion chromatography: The size exclusion chromatography was performed on an AKTA Pure system (GE Healthcare) at 4° C. The Superdex 200 Increase 16/300 GL column (GE Healthcare) was equilibrated with 50 mM Tris pH 8.0, 150 mM NaCl and this buffer was used for all subsequent SEC experiments. The purified proteins were assembled in 1:1.2 molar ratio of mCherry:nanobody or mCherry:OptoNB. The final volume of the proteins loaded onto the column was 50-200 μL, depending on the protein concentration. For experiments run in the dark, the lights were turned off, the chromatography refrigerator was covered in a black blanket, and the column was wrapped in aluminum foil. For experiments run in the light the column was wrapped with blue LED string (Grainger). Before loading the proteins onto the column, the mixed samples were incubated for 20 minutes at room temperature, either in blue light or dark, according to the experiment that was being performed.

Agarose Bead Imaging: Ni-NTA agarose resin (Qiagen) was first equilibrated with 50 mM Tris pH 8.0, 150 mM NaCl buffer. To competitively label the resin beads, solutions of 500 μL 1:10, 1:100, and 1:1000 nanobody:eGFP solution was loaded onto 200 μL of resin slurry with the excess protein washed away with the same buffer. 50 μL of 1 μM mCherry (with its His-tag cleaved off using TEV protease) was added onto 0.17 mm glass-bottomed black walled 96 well plate (In Vitro Scientific). 2 μL of the nanobody bead slurry was added to the well with mCherry solution and incubated for at least an hour and up to overnight. The same microscope setup (imaging and blue light excitation) was used to image the beads as previously described for the cell imaging, except for the use of a 20× air objective lens for the beads.

Bio-layer interferometry measurements of binding kinetics: Measurements for the on rates ($k_{on}$), off rates ($k_{off}$), and affinity constants ($K_D$) for LaM8, LaM8 AK74, and LaM8 GG15 nanobodies were performed on Octet RED96e instruments (ForteBio). Ni-NTA sensors (ForteBio) were first equilibrated in 50 mM Tris pH 8.0, 150 mM NaCl buffer for 10 min prior the measurement. Clear 96-well plates were used for the measurements and wells were filled with 200 μL of buffer or sample. During the experimental run the sensors were first immersed in a buffer to record the baseline, then switched to load the His-tagged nanobody onto the sensor and back into the buffer to remove unbound nanobody. To measure the association rate the sensors were subsequently moved into a well with 8 different concentrations of tagless mCherry including a control with 0 mM mCherry. To measure the $k_{off}$ the sensors were then moved into wells with a buffer and the dissociation rate was recorded. In order to measure binding kinetics of the light state, the lid to the Octet remained open during the measurement and a blue LED panel was held above the 96-well plate keeping the protein in the light state for the duration of the experiment. The raw binding and unbinding data were simultaneously fit to models of the binding and unbinding reactions:

$$y_{bind}^i(t) = [a_{on}^i(1 - e^{-(k_{on}[mCh]_i + k_{off})t}) + b_{on}^i] e^{-k_{leak} t}$$

$$y_{unbind}^i(t) = [a_{off}^i e^{-k_{off} t} + b_{off}^i] e^{-k_{leak} t}$$

This model incorporates the following dependent and independent variables:
$y_{bind}^i(t)$ refers to the $i^{th}$ binding curve
$y_{unbind}^i(t)$ the $i^{th}$ unbinding curve
$[mCh]_i$ refers to the concentration of mCherry used for the $i^{th}$ binding curve
t is the time elapsed since the start of the binding/unbinding phase.
It also includes the following parameters
$k_{on}$ is the on-rate (same across all binding and unbinding curves)
$k_{off}$ is the off-rate (same across all binding and unbinding curves)
$k_{leak}$ represents the slow unbinding of His-tagged OptoNB from the probe, leading to a gradual decay of signal.
$a_{on}^i$ is the total change in signal due to mCherry binding for the $i^{th}$ curve
$b_{on}^i$ is the signal baseline during the binding phase
$a_{off}^i$ is the total change in signal due to mCherry unbinding for the $i^{th}$ curve
$b_{off}^i$ is the signal baseline during the unbinding phase
The model thus contains 4*n+3 parameters, where n is the number of distinct mCherry concentrations tested. Fits were performed using nonlinear gradient descent using the MATLAB fmincon function. MATLAB code was used to perform the fits.

REFERENCES

1 Shimizu-Sato, S., Huq, E., Tepperman, J. M. & Quail, P. H. A light-switchable gene promoter system. *Nature biotechnology* 20, 1041-1044, doi:10.1038/nbt734 (2002).
2 Boyden, E. S., Zhang, F., Bamberg, E., Nagel, G. & Deisseroth, K. Millisecond-timescale, genetically targeted optical control of neural activity. *Nat Neurosci* 8, 1263-1268, doi:10.1038/nn1525 (2005).
3 Levskaya, A., Weiner, O. D., Lim, W. A. & Voigt, C. A. Spatiotemporal control of cell signalling using a light-switchable protein interaction. *Nature* 461, 997-1001, doi:10.1038/nature08446 (2009).
4 Guntas, G. et al. Engineering an improved light-induced dimer (iLID) for controlling the localization and activity of signaling proteins. *Proceedings of the National Academy of Sciences of the United States of America* 112, 112-117, doi:10.1073/pnas.1417910112 (2015).
5 Kennedy, M. J. et al. Rapid blue-light-mediated induction of protein interactions in living cells. *Nature methods* 7, 973-975, doi:10.1038/nmeth.1524 (2010).
6 Grusch, M. et al. Spatio-temporally precise activation of engineered receptor tyrosine kinases by light. *The EMBO journal* 33, 1713-1726, doi:10.15252/embj.201387695 (2014).
7 Zhou, X. X., Fan, L. Z., Li, P., Shen, K. & Lin, M. Z. Optical control of cell signaling by single-chain photoswitchable kinases. *Science* 355, 836-842, doi:10.1126/science.aah3605 (2017).
8 Chen, X., Wang, X., Du, Z., Ma, Z. & Yang, Y. Spatiotemporal control of gene expression in mammalian cells and in mice using the LightOn system. *Current protocols in chemical biology* 5, 111-129, doi:10.1002/9780470559277.ch120267 (2013).
9 Motta-Mena, L. B. et al. An optogenetic gene expression system with rapid activation and deactivation kinetics. *Nat Chem Biol* 10, 196-202, doi:10.1038/nchembio.1430 (2014).
10 Renicke, C., Schuster, D., Usherenko, S., Essen, L. O. & Taxis, C. A LOV2 domain-based optogenetic tool to control protein degradation and cellular function. *Chemistry & biology* 20, 619-626, doi:10.1016/j.chembiol.2013.03.005 (2013).
11 Niopek, D. et al. Engineering light-inducible nuclear localization signals for precise spatiotemporal control of protein dynamics in living cells. *Nature communications* 5, 4404, doi:10.1038/ncomms5404 (2014).
12 Niopek, D., Wehler, P., Roensch, J., Eils, R. & Di Ventura, B. Optogenetic control of nuclear protein export. *Nature communications* 7, 10624, doi:10.1038/ncomms10624 (2016).
13 Yumerefendi, H. et al. Control of Protein Activity and Cell Fate Specification via Light-Mediated Nuclear Translocation. *PloS one* 10, e0128443, doi:10.1371/journal.pone.0128443 (2015).
14 Yumerefendi, H. et al. Light-induced nuclear export reveals rapid dynamics of epigenetic modifications. *Nat Chem Biol* 12, 399-401, doi:10.1038/nchembio.2068 (2016).
15 Dine, E., Gil, A. A., Uribe, G., Brangwynne, C. P. & Toettcher, J. E. Protein Phase Separation Provides Long-Term Memory of Transient Spatial Stimuli. *Cell Syst,* doi:10.1016/j.cels.2018.05.002 (2018).
16 Shin, Y. et al. Spatiotemporal Control of Intracellular Phase Transitions Using Light-Activated optoDroplets. *Cell* 168, 159-171 e114, doi:10.1016/j.cell.2016.11.054 (2017).
17 Strickland, D. et al. TULIPs: tunable, light-controlled interacting protein tags for cell biology. *Nature methods* 9, 379-384, doi:10.1038/nmeth.1904 (2012).
18 Muyldermans, S. Nanobodies: natural single-domain antibodies. *Annual review of biochemistry* 82, 775-797, doi:10.1146/annurev-biochem-063011-092449 (2013).
19 Dagliyan, O. et al. Engineering extrinsic disorder to control protein activity in living cells. *Science* 354, 1441-1444, doi:10.1126/science.aah3404 (2016).
20 Dagliyan, O. et al. Rational design of a ligand-controlled protein conformational switch. *Proceedings of the National Academy of Sciences of the United States of America* 110, 6800-6804, doi:10.1073/pnas.1218319110 (2013).
21 Fridy, P. C. et al. A robust pipeline for rapid production of versatile nanobody repertoires. *Nature methods* 11, 1253-1260, doi:10.1038/nmeth.3170 (2014).
22 Bubeck, F. et al. Engineered anti-CRISPR proteins for optogenetic control of CRISPR-Cas9. *Nature methods* 15, 924-927, doi:10.1038/s41592-018-0178-9 (2018).
23 Wang, H. et al. LOVTRAP: an optogenetic system for photoinduced protein dissociation. *Nature methods* 13, 755-758, doi:10.1038/nmeth.3926 (2016).
24 Reis, J. M. et al. Discovering Selective Binders for Photoswitchable Proteins Using Phage Display. *ACS synthetic biology* 7, 2355-2364, doi:10.1021/acssynbio.8b00123 (2018).
25 Tischer, D. K. & Weiner, O. D. Light-based tuning of ligand half-life supports kinetic proofreading model of T cell signaling. *eLife* 8, doi:10.7554/eLife.42498 (2019).
26 Zhao, E. M. et al. Optogenetic regulation of engineered cellular metabolism for microbial chemical production. *Nature* 555, 683-687, doi:10.1038/nature26141 (2018).
27 Zhao, E. M. et al. Light-based control of metabolic flux through assembly of synthetic organelles. *Nat Chem Biol* 15, 589-597, doi:10.1038/s41589-019-0284-8 (2019).
28 Toettcher, J. E., Weiner, O. D. & Lim, W. A. Using optogenetics to interrogate the dynamic control of signal transmission by the Ras/Erk module. *Cell* 155, 1422-1434, doi:10.1016/j.cell.2013.11.004 (2013).
29 Gureasko, J. et al. Membrane-dependent signal integration by the Ras activator Son of sevenless. *Nature structural & molecular biology* 15, 452-461, doi:10.1038/nsmb.1418 (2008).
30 Regot, S., Hughey, J. J., Bajar, B. T., Carrasco, S. & Covert, M. W. High-sensitivity measurements of multiple kinase activities in live single cells. *Cell* 157, 1724-1734, doi:10.1016/j.cell.2014.04.039 (2014).
31 Roovers, R. C. et al. Efficient inhibition of EGFR signaling and of tumour growth by antagonistic anti-EFGR Nanobodies. *Cancer Immunol Immunother* 56, 303-317, doi:10.1007/s00262-006-0180-4 (2007).
32 Pleiner, T., Bates, M. & Gorlich, D. A toolbox of anti-mouse and anti-rabbit IgG secondary nanobodies. *The Journal of cell biology* 217, 1143-1154, doi:10.1083/jcb.201709115 (2018).
33 Schuck, P. & Zhao, H. The role of mass transport limitation and surface heterogeneity in the biophysical characterization of macromolecular binding processes by SPR biosensing. *Methods in molecular biology* 627, 15-54, doi:10.1007/978-1-60761-670-2_2 (2010).
34 Salomon, M., Christie, J. M., Knieb, E., Lempert, U. & Briggs, W. R. Photochemical and mutational analysis of the FMN-binding domains of the plant blue light receptor, phototropin. *Biochemistry* 39, 9401-9410, doi:10.1021/bi000585+ (2000).

35 Gil, A. A. et al. Femtosecond to Millisecond Dynamics of Light Induced Allostery in the *Avena sativa* LOV Domain. *J Phys Chem B* 121, 1010-1019, doi:10.1021/acs.jpcb.7b00088 (2017).

36 Harper, S. M., Christie, J. M. & Gardner, K. H. Disruption of the LOV-Jalpha helix interaction activates phototropin kinase activity. *Biochemistry* 43, 16184-16192, doi:10.1021/bi048092i (2004).

37 Aihara, Y. et al. Mutations in N-terminal flanking region of blue light-sensing light-oxygen and voltage 2 (LOV2) domain disrupt its repressive activity on kinase domain in the *Chlamydomonas* phototropin. *The Journal of biological chemistry* 287, 9901-9909, doi:10.1074/jbc.M111.324723 (2012).

38 Lungu, O. I. et al. Designing photoswitchable peptides using the AsLOV2 domain. *Chemistry & biology* 19, 507-517, doi:10.1016/j.chembiol.2012.02.006 (2012).

39 Bothma, J. P., Norstad, M. R., Alamos, S. & Garcia, H. G. LlamaTags: A Versatile Tool to Image Transcription Factor Dynamics in Live Embryos. *Cell* 173, 1810-1822 e1816, doi:10.1016/j.cell.2018.03.069 (2018).

40 Rothbauer, U. et al. Targeting and tracing antigens in live cells with fluorescent nanobodies. *Nature methods* 3, 887-889, doi:10.1038/nmeth953 (2006).

41 Roybal, K. T. et al. Engineering T Cells with Customized Therapeutic Response Programs Using Synthetic Notch Receptors. *Cell* 167, 419-432 e416, doi:10.1016/j.cell.2016.09.011 (2016).

42 De Meyer, T., Muyldermans, S. & Depicker, A. Nanobody-based products as research and diagnostic tools. *Trends Biotechnol* 32, 263-270, doi:10.1016/j.tibtech.2014.03.001 (2014).

43 Strickland, D. et al. Rationally improving LOV domain-based photoswitches. *Nature methods* 7, 623-626, doi: 10.1038/nmeth.1473 (2010).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A fusion protein comprising a light responsive domain and a heterologous peptide component, wherein the light responsive domain consists of amino acids 408-543 of SEQ ID NO:1, or a variant thereof having a substitution at one or more positions corresponding to V416, G528, or N538 of SEQ ID NO:1.

2. The fusion protein of claim 1, wherein the light responsive domain is flanked by a glycine residue at its N-terminus, C-terminus, or both.

3. The fusion protein of claim 2, comprising SEQ ID NO:47 or SEQ ID NO:48.

4. The fusion protein of claim 2, comprising SEQ ID NO: 9.

5. The fusion protein of claim 1, wherein the light responsive domain comprises a conservative substitution at one or more positions corresponding to V416, G528, or N538 of SEQ ID NO:1.

6. The fusion protein of claim 1, wherein the light responsive domain comprises an isoleucine substitution at a position corresponding to V416 in SEQ ID NO: 1.

7. The fusion protein of claim 1, wherein the light responsive domain comprises a leucine substitution at a position corresponding to V416 in SEQ ID NO: 1.

8. The fusion protein of claim 1, wherein the light responsive domain comprises an alanine substitution at a position corresponding to G528 in SEQ ID NO: 1.

9. The fusion protein of claim 1, wherein the light responsive domain comprises a glutamate substitution at a position corresponding to N538 in SEQ ID NO: 1.

10. The fusion protein of claim 1, wherein the heterologous peptide component is selected from the group consisting of a nanobody, monobody, antibody, designed ankyrin repeat protein (DARPin), and anticalin.

11. The fusion protein of claim 1, wherein the heterologous peptide component is a nanobody, monobody or antibody.

12. The fusion protein of claim 11, wherein the heterologous peptide component is a monobody.

13. The fusion protein of claim 1, wherein the fusion protein is an internal fusion protein, and the light responsive domain is inserted into the heterologous peptide component.

14. The fusion protein of claim 13, wherein the heterologous peptide component has one or more loops, and the light responsive domain is inserted into a loop of the heterologous peptide component.

15. The fusion protein of claim 14, wherein the heterologous peptide component is a monobody and the light responsive domain is inserted into a loop of the monobody that connects a first β-sheet to a second β-sheet.

16. The fusion protein of claim 15, wherein the heterologous peptide component is a HA4 monobody.

17. The fusion protein of claim 1, wherein the fusion protein is immobilized on chromatography resin.

18. A method of purifying a target protein from a cell lysate, the method comprising:
providing a substrate comprising an immobilized fusion protein intended to bind a target protein, the fusion protein comprising a light responsive domain and a heterologous peptide component, wherein the light responsive domain consists of amino acids 408-543 of SEQ ID NO:1, or a variant thereof having a substitution at V416, G528, or N538 of SEQ ID NO:1, or a combination thereof, wherein exposure of the fusion protein to light induces a conformational change that alters its ability to bind the target protein; and
exposing the substrate to the cell lysate in the presence of light under conditions sufficient to induce binding of the target protein and the fusion protein; and
eluting the target protein in the absence of light, wherein the fusion protein binds the target protein upon exposure to light and dissociates from the target protein in the absence of light, thereby purifying the target protein; or
exposing the substrate to the cell lysate in the absence of light under conditions sufficient to induce binding of the target protein and the fusion protein;
and eluting the target protein in the presence of light, wherein the fusion protein binds the target protein in the absence of light and dissociates from the target protein upon exposure to light, thereby purifying the target protein.

19. The method of claim 18, wherein the fusion protein is covalently attached to the substrate.

20. The method of claim 18, wherein the fusion protein is non-covalently attached to the substrate.

* * * * *